(12) United States Patent
Vianello et al.

(10) Patent No.: US 10,183,952 B2
(45) Date of Patent: Jan. 22, 2019

(54) THIENOPYRROLES AS HISTONE DEMETHYLASE INHIBITORS

(71) Applicant: ISTITUTO EUROPEO DI ONCOLOGIA S.R.L., Milan (IT)

(72) Inventors: Paola Vianello, Milan (IT); Luca Sartori, Brunate (IT); Mario Varasi, Milan (IT); Ciro Mercurio, Legnano (IT); Elisa Zagarri, Castellanza (IT); Anna Cappa, Visso (IT); Alessia Romussi, Milan (IT); Manuela Villa, Luraga d'Erba (IT); Giuseppe Meroni, Milan (IT); Loris Moretti, Milan (IT)

(73) Assignee: Istituto Europeo di Oncologia S.r.l., Milan (IT)

( * ) Notice: Subject to any disclaimer, the term of this patent is extended or adjusted under 35 U.S.C. 154(b) by 20 days.

(21) Appl. No.: 15/508,816

(22) PCT Filed: Sep. 4, 2015

(86) PCT No.: PCT/IB2015/001953
§ 371 (c)(1),
(2) Date: Mar. 3, 2017

(87) PCT Pub. No.: WO2016/034946
PCT Pub. Date: Mar. 10, 2016

(65) Prior Publication Data
US 2017/0260197 A1    Sep. 14, 2017

(30) Foreign Application Priority Data

Sep. 5, 2014    (EP) .................................. 14183755

(51) Int. Cl.
| | | |
|---|---|---|
| *C07D 495/04* | (2006.01) |
| *A61K 31/407* | (2006.01) |
| *A61K 31/438* | (2006.01) |
| *A61K 31/4439* | (2006.01) |
| *A61K 31/454* | (2006.01) |
| *A61K 31/496* | (2006.01) |
| *A61K 31/5377* | (2006.01) |
| *A61K 31/55* | (2006.01) |
| *C07D 519/00* | (2006.01) |

(52) U.S. Cl.
CPC .......... *C07D 495/04* (2013.01); *A61K 31/407* (2013.01); *A61K 31/438* (2013.01); *A61K 31/4439* (2013.01); *A61K 31/454* (2013.01); *A61K 31/496* (2013.01); *A61K 31/5377* (2013.01); *A61K 31/55* (2013.01); *C07D 519/00* (2013.01)

(58) Field of Classification Search
CPC ................................................... C07D 495/04
See application file for complete search history.

(56) References Cited

FOREIGN PATENT DOCUMENTS

| EP | 2740474 A1 | 6/2014 |
| WO | WO 2006/077412 A1 | 7/2006 |
| WO | WO 2013/025805 A1 | 2/2013 |

OTHER PUBLICATIONS emedicinehealth. "Leukemia." © 2017. Available from: < https://www.emedicinehealth.com/leukemia-health/page7.htm >.*
Mayo Clinic. "Lung cancer." © 2017. Available from: < https://www.mayoclinic.org/diseases-conditions/lung-cancer/symptoms-causes/syc-20374620?p=1 >.*
Mayo Clinic. "Liver cancer." © 2017. Available from: < https://www.mayoclinic.org/diseases-conditions/liver-cancer/symptoms-causes/syc-20353659?p=1 >.*
Florida Hospital. "Glioma." © 2017. Available from: < https://www.floridahospital.com/glioma/prevention-glioma >.*
Centers for Disease Control. "Strategies to Prevent Obesity." © 2017. Available from: < https://www.cdc.gov/obesity/strategies/ >.*
Binda C. et al "Insights into the mode of inhibition of human mitochondrial monoamine oxidase B from high-resolution crystal structures" *Proc. Natl. Acad. Sci. USA*, 2003, pp. 9750-9755.
CAS 1204944-60-4, Feb. 9, 2010.
CAS 1204935-35-2, Feb. 9, 2010.
CAS 1205349-51-4, Feb. 10, 2010.
CAS 1205627-53-7, Feb. 10, 2010.
CAS 1205797-86-9, Feb. 11, 2010.
CAS 1206030-07-0, Feb. 11, 2010.
CAS 1204934-97-3, Feb. 9, 2010.

(Continued)

*Primary Examiner* — Andrew D Kosar
*Assistant Examiner* — John S Kenyon
(74) *Attorney, Agent, or Firm* — Cooley LLP; Heidi A. Erlacher; Thomas J. Paxton

(57) ABSTRACT

The present application relates to thienopyrrole derivatives, compounds of Formulas (I) and (Ia), wherein R, $R^1$, $R^2$ and $R^3$ are as defined in the specification, pharmaceutical compositions containing such compounds and to their use in therapy. The compounds of the application can be useful for inhibiting KDM1 and the prevention and/or treatment of cancer, infectious disease, or a disease characterized by aberration of cellular energy metabolism, e.g., obesity.

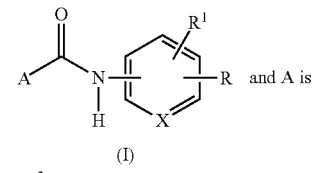

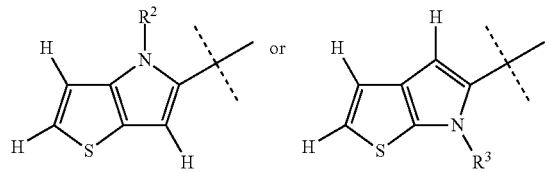

28 Claims, No Drawings

(56) References Cited

OTHER PUBLICATIONS

CAS 1205463-37-1, Feb. 10, 2010.
CAS 1206029-55-1, Feb. 11, 2010.
CAS 1374527-29-3, May 25, 2012.
CAS 1374629-24-9, May 27, 2012.
Forneris, F. et al. "LSD1: oxidative chemistry for multifaceted functions in chromatin regulation" *Trends Biochem. Sci.*, 2008, 33, pp. 181-189.
Forneris, F. et al. "Structural Basis of LSD1-CoREST Selectivity in Histone H3 Recognition" *J. Biol. Chem.*, 2007, 282, pp. 20070-20074.
Hitchin, J. et al. "Development and evaluation of selective, reversible LSD1 inhibitors derived from fragments" *Med Chem. Commun.*, 2013, 4, pp. 1513-1522.
Yee Y. et al. "$N^2$-Aroylanthranilamide inhibitors of human factor Xa" *J. Med Chem.*, 2000, 43, pp. 873-882.
Sorna, V. et al. "High-Throughput Virtual Screening Identifies Novel N'-(1-Phenylethylidene)-benzohydrazides as Potent, Specific, and Reversible LSD1 Inhibitors" *J. Med Chem.*, 2013, 56, pp. 9496-9508.

\* cited by examiner

THIENOPYRROLES AS HISTONE DEMETHYLASE INHIBITORS

CROSS-REFERENCE TO RELATED APPLICATIONS

This application is a U.S. National Phase application, filed under 35 U.S.C. § 371(c), of International Application No. PCT/IB2015/001953, filed Sep. 4, 2015, which claims priority to, and the benefit of, European Patent Application No. 14183755.9, filed Sep. 5, 2014, the contents of each of which are incorporated herein by reference in their entireties.

FIELD OF THE APPLICATION

The present application relates to thienopyrrole derivatives, pharmaceutical compositions containing such compounds and to their use in therapy.

BACKGROUND

Alterations in the structural and functional states of chromatin, mainly determined by post-translational modifications of histone components, are involved in the pathogenesis of a variety of diseases. The enzymatic processes, which govern these post-translational modifications on the nucleosomes, have become potential targets for the so-called epigenetic therapies (Portela, A. et al. Nat. Biotechnol. 2010, 28, 1057-1068).

The discovery of an increasing number of histone lysine demethylases has highlighted the dynamic nature of the regulation of histone methylation, a key chromatin modification that is involved in eukaryotic genome and gene regulation. Histone lysine demethylases represent attractive targets for epigenetic drugs, since their expression and/or activities are often misregulated in cancer (Varier, R. A. et al. Biochim. Biophys. Acta. 2011, 1815, 75-89). A lysine can be mono-, di-, and tri-methylated and each modification, even on the same amino acid, can have different biological effects.

Histone lysine demethylases exert their activity through two different type of mechanism (Anand, R. et al. J. Biol. Chem. 2007, 282, 35425-35429; Metzger, E. et al. Nat. Struct. Mol. Biol. 2007, 14, 252-254). While the Jumonji domain-containing histone demethylases, which are iron and 2-oxoglutarate dependent oxygenases, act on mono-, di- and trimethylated lysines, the flavin-dependent (FAD) histone demethylases catalyse the cleavage of mono and dimethylated lysine residues. Currently, two FAD dependent demethylases have been identified: LSD1, also known as KDM1A, and LSD2, also known as KDM1B. (Culhane, J. C. et al. Curr. Opin. Chem. Biol. 2007, 11, 561-568, Ciccone, D. N. et al. Nature 2009, 461, 415-418).

KDM1A is a constituent in several chromatin-remodeling complexes and is often associated with the co-repressor protein CoREST. KDM1A specifically removes the methyl groups from mono- and di-methyl Lys4 of histone H3, which is a well-characterized gene activation mark. KDM1A represents an interesting target for epigenetic drugs due to its over-expression in solid and hematological tumors (Schulte, J. H. et al. Cancer Res. 2009, 69, 2065-2071; Lim, S. et al. Carcinogenesis 2010, 31, 512-520; Hayami, S. et al. Int. J. Cancer 2011, 128, 574-586; Schildhaus, H. U. et al. Hum. Pathol. 2011, 42, 1667-1675; Bennani-Baiti, I. M. et al. Hum. Pathol. 2012, 43, 1300-1307). Its over-expression correlates to tumor recurrence in prostate cancer (Kahl, P. et al. Cancer Res. 2006, 66, 11341-11347), and KDM1A has a role in various differentiation processes, such as adipogenesis (Musri, M. M. et al. J. Biol. Chem. 2010, 285, 30034-30041), muscle skeletal differentiation (Choi, J. et al. Biochem. Biophys. Res. Commun. 2010, 401, 327-332), and hematopoiesis (Hu, X. et al. Proc. Natl. Acad. Sci. USA 2009, 106, 10141-10146; Li, Y. et al. Oncogene. 2012, 31, 5007-5018). KDM1A is further involved in the regulation of cellular energy expenditure (Hino S. Et al. Nat Commun. 2012, doi: 10.1038/ncomms1755), in the regulation of thermogenesis and oxidative metabolism in adipose tissue (Duteil et al. Nat Commun. 2014 Jun. 10; 5:4093. doi: 10.1038/ncomms5093.), in the control of checkpoints of viral gene expression in productive and latent infections (Roizman, B. J. Virol. 2011, 85, 7474-7482), and more specifically in the control of herpes virus infection (Gu, H. J. Virol. 2009, 83, 4376-4385) and HIV transcription (Sakane, N. et al. PLoS Pathog. 2011, 7(8):e1002184). The role of KDM1A in the regulation of neural stem cell proliferation (Sun, G. et al. Mol. Cell Biol. 2010, 30, 1997-2005) and in the control of neuritis morphogenesis (Zibetti, C. et al. J. Neurosci. 2010, 30, 2521-2532) suggests its possible involvement in neurodegenerative diseases.

Furthermore, KDM1A has been found to be relevant in the control of other important cellular processes, such as DNA methylation (Wang, J. et al. Nat. Genet. 2009, 41(1): 125-129), cell proliferation (Scoumanne, A. et al. J. Biol. Chem. 2007, 282, 15471-15475; Cho, H. S. et al. Cancer Res. 2011, 71, 655-660), epithelial mesenchimal transition (Lin, T. et al. Oncogene. 2010, 29, 4896-4904) and chromosome segregation (Lv, S. et al. Eur. J. Cell Biol. 2010, 89, 557-563). Moreover, KDM1A inhibitors were able to reactivate silenced tumor suppressor genes (Huang, Y. et al. Proc. Natl. Acad. Sci. USA. 2007, 104, 8023-8028; Huang, Y. et al. Clin. Cancer Res. 2009, 15, 7217-7228), to target selectively cancer cells with pluripotent stem cell properties (Wang, J. et al. Cancer Res. 2011, 71, 7238-7249), as well as to reactivate the all-trans-retinoic acid differentiation pathway in acute myeloid leukemia (Schenk, T. et al. Nat Med. 2012, 18, 605-611). Moreover, KDM1A has a clear role in sustaining the oncogenic potential of MLL-AF9 translocation in leukaemia stem cells (Harris et al. Cancer Cell, 21 (2012), 473-487), as well as in the stem-like tumor propagating cells of human glioblastoma (Suva et al. Cell 2014, 157, 580-594).

The more recently discovered demethylase KDM1B (LSD2) displays similarly to KDM1A specificity for mono- and di-methylated Lys4 of histone H3. KDM1B, differently from KDM1A, does not bind CoREST and it has not been found up to now in any of KDM1A-containing protein complexes (Karytinos, A. et al. J. Biol. Chem. 2009, 284, 17775-17782). On the contrary, KDM1B forms active complexes with euchromatic histone methyltransferases G9a and NSD3 as well as with cellular factors involved in transcription elongation. KDM1B has been reported to have a role as regulator of transcription elongation rather than that of a transcriptional repressor as proposed for KDM1A (Fang, R. et al. Mol. Cell 2010, 39, 222-233).

KDM1A and KDM1B are both flavo amino oxidase dependent proteins sharing a FAD coenzyme-binding motif, a SWIRM domain and an amine oxidase domain, all of which are integral to the enzymatic activity of KDM1 family members. Moreover, both KDM1A and KDM1B show a structural similarity with the monoamine oxidases MAO-A and MAO-B. Indeed, tranylcypromine, a MAO inhibitor used as antidepressant agent, was found to be also able to inhibit KDM1A. The compound acts as an irreversible inhibitor forming a covalent adduct with the FAD cofactor.

(Lee, M. G. et al. Chem. Biol. 2006, 13, 563; Schmidt, D. M. Z. et al. Biochemistry 2007, 46, 4408). Tranylcypromine analogs and their KDM1A inhibitory activity have been described in Bioorg. Med. Chem. Lett. 2008, 18, 3047-3051, in Bioorg. Med. Chem. 2011, 19, 3709-3716, and in J. Am. Chem. Soc 2011, 132, 6827-6833. Further arylcyclopropylamine and heteroarylcyclopropylamine derivatives as KDM1A, MAO-A and/or MAO-B enzyme inhibitors are disclosed in US2010/324147, in WO2012/045883, in WO2013/022047 and in WO2011/131576.

Reversible KDM1A inhibitors are not so common and no clinical data for them are so far available. Examples of reversible inhibitors are aminothiazoles as described in Med. Chem. Commun. 2013, 4, 1513-1522 or a N'-(1-phenylethylidene)-benzohydrazide series (J. Med. Chem. 2013, 56, 9496-9508, WO2013025805). Thus, there is still a need for further reversible inhibitors having useful antitumor properties, adequate selectivity and stability of action, and possibly showing a higher activity with respect to specific subclasses thereof.

N-(4-benzyloxyphenyl)-4-methyl-thieno[3,2-b]pyrrole-5-carboxamide (CAS 1204944-60-4), N-(4-benzyloxyphenyl)-4-ethyl-thieno[3,2-b]pyrrole-5-carboxamide (CAS 1204935-35-2), N-(4-benzyloxyphenyl)-4-isopropyl-thieno[3,2-b]pyrrole-5-carboxamide (CAS 1205349-51-4), N-[3-(phenoxymethyl)phenyl]-4-methyl-thieno[3,2-b]pyrrole-5-carboxamide (CAS 1205627-53-7), N-[3-(phenoxymethyl)phenyl]-4-ethyl-thieno[3,2-b]pyrrole-5-carboxamide (CAS 1205797-86-9) and N-[3-(phenoxymethyl)phenyl]-4-isopropyl-thieno[3,2-b]pyrrole-5-carboxamide (CAS 1206030-07-0) are disclosed in the Aurora Screening Library, but no use has been associated to them.

SUMMARY

Compounds of the application may have highly potent inhibitory activities of the KDM1 family of enzymes, e.g., the KDM1A enzyme, and may selectively inhibit KDM1 enzymes over monoamine oxidases (MAOs). Further the compounds of the application may be useful in the treatment and/or prevention of diseases and conditions associated with the activity of the histone demethylases.

In a first aspect, the compounds of the application relate to compounds of Formula (I) and (Ia):

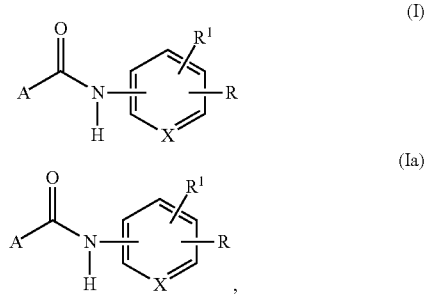

or a stereoisomer or pharmaceutically acceptable salt thereof, wherein each of the variables in Formula (I) and (Ia) are defined and exemplified herein.

In one aspect, the present application relates to a compound of Formula (I) or (Ia) for use as a medicament.

In one aspect, the present application relates to a method of inhibiting KDM1 comprising administering to a subject a therapeutically effective amount of a compound of Formula (I) or (Ia).

In one aspect, the present application relates to a method of treating and/or preventing a cancer, infectious disease, or a disease characterized by aberration of cellular energy metabolism, comprising administering to a subject a therapeutically effective amount of a compound of Formula (I) or (Ia).

In one aspect, the present application relates to the use of a compound of Formula (I) or (Ia), for treating and/or preventing a cancer, infectious disease, or a disease characterized by aberration of cellular energy metabolism.

In one aspect, the present application relates to the use of a compound of Formula (I) or (Ia) in the manufacture of a medicament for treating and/or preventing a cancer, infectious disease, or a disease characterized by aberration of cellular energy metabolism.

In one aspect, the present application relates to a pharmaceutical composition comprising a compound of Formula (I) or (Ia) together with a pharmaceutically acceptable excipient and/or diluent.

In one aspect, the present application relates to a pharmaceutical composition comprising a compound of Formula (I) or (Ia) together with a pharmaceutically acceptable excipient and/or diluent, in the form of tablets, capsules, oral preparations, powders, granules, pills, injectable or infusible liquid, solutions, suspensions, emulsions, suppositories, ointments, creams, lotions, gels, pastes, transdermal delivery devices.

In one aspect, the present application relates to a pharmaceutical composition comprising a compound of Formula (I) or (Ia) together with a pharmaceutically acceptable excipient and/or diluent, further comprising at least one therapeutic agent selected from the group consisting of histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, Selective COX-2 inhibitors and a chemotherapeutic agent.

DETAILED DESCRIPTION

The present application relates to substituted thienopyrrole derivatives, i.e., compounds of Formula (I) or (Ia) or compounds of the application, which may have highly potent inhibitory activities of the KDM1 family of enzymes, e.g., the KDM1A enzyme, and may selectively inhibit KDM1 enzymes over monoamine oxidases (MAOs). Further the compounds of the application may be useful in the treatment and/or prevention of diseases or conditions associated with the activity of the histone demethylases. It should be understood that designations such as "compounds of Formula (I) or (Ia)" or "compounds of the application" are intended to encompass not only the above general Formula (I) and (Ia) in its stated aspects, but also each and every embodiment discussed herein.

In one embodiment, the KDM1 family of enzymes includes both the KDM1A and KDM1B enzymes.

In one embodiment, the present application relates to compounds of formula (I)

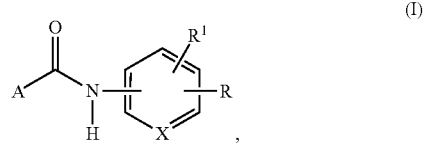

wherein:
A is

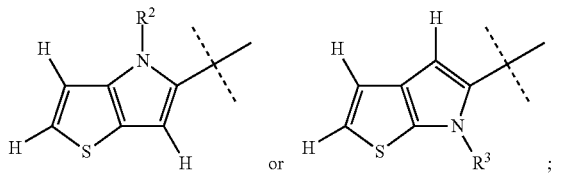

X is CH or N;
R is $L^1$-$R^4$;
$R^1$ is H, halogen, $C_1$-$C_6$-alkyl, $C_1$-$C_6$-alkoxy, —$CH_2$—Z—$R^5$, or —Z—$CH_2$—$R^6$;
$R^2$ and $R^3$ are $C_1$-$C_4$-alkyl;
$L^1$ is —$(CH_2)_j$—Y—, —Y—$(CH_2)_k$—, —$CH_2$—$CH_2$— or —CO—NH—;
j and k are, independently, each an integer from 1 to 6;
Y is oxygen, sulphur, NH, or N($C_1$-$C_6$-alkyl);
Z is a bond, oxygen, sulphur, NH or N($C_1$-$C_6$-alkyl);
$R^4$, $R^5$, and $R^6$ are, independently, $C_1$-$C_6$-alkyl, aryl, heteroaryl, wherein the aryl or heteroaryl are optionally substituted by halogen, $C_1$-$C_6$-alkyl, or $L^2$-$R^7$; or heterocyclyl, wherein the heterocyclyl is optionally substituted by $C_1$-$C_6$-alkyl;
$L^2$ is —$(CH_2)_m$— or —$(CH_2)_n$—W—$(CH_2)_o$—;
$R^7$ is $C_1$-$C_6$-alkylamino, $C_3$-$C_7$ cycloalkyl or heterocyclyl, wherein the $C_3$-$C_7$ cycloalkyl or heterocyclyl are optionally substituted by $C_1$-$C_6$-alkyl, or $NH_2$; or guanidine;
m, n, and o are, independently, each zero or an integer from 1 to 6;
W is oxygen, sulphur, NH, or $CH_2$;
wherein aryl is a mono or bicyclic aromatic ring system of 6 or 9 or 10 atoms; heteroaryl is a mono or bicyclic heteroaromatic ring system of 5 to 10 members, which contains one, two, three or four heteroatoms selected from nitrogen, oxygen and sulphur, and one to nine carbon atoms; and heterocyclyl is a mono, bicyclic or a spirocyclic saturated or partially saturated non-aromatic ring system of 4 to 12 members, which contains one, two, or three heteroatoms selected from nitrogen, oxygen, and sulphur, and three to eleven carbon atoms.

In one embodiment, for the compound of formula (I), A is

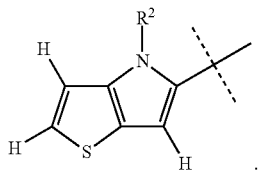

In one embodiment, for the compound of formula (I), A is

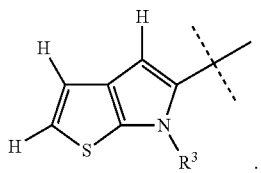

In one embodiment, for the compound of formula (I), $R^2$ and $R^3$ are methyl or ethyl.

In one embodiment, for the compound of formula (I), X is CH.

In one embodiment, for the compound of formula (I), $R^4$ is aryl substituted by $L^2$-$R^7$.

In one embodiment, for the compound of formula (I), $L^1$ is —$CH_2$—O—, —$CH_2$—NH—, —O—$CH_2$, —$CH_2$—$CH_2$— or —CO—NH—. In one embodiment, $L^1$ is —$CH_2$—O—, —$CH_2$—NH—, or —O—$CH_2$. In one embodiment, $L^1$ is —$CH_2$—O—. In one embodiment, $L^1$ is —$CH_2$—NH—. In one embodiment, $L^1$ is —O—$CH_2$.

In one embodiment, $L^2$ is —$(CH_2)_m$—. In one embodiment, $L^2$ is —$(CH_2)_n$—W—$(CH_2)_o$—.

In one embodiment, W is oxygen. In one embodiment, W is sulphur. In one embodiment, W is NH. In one embodiment, for the compound of formula (I), W is $CH_2$.

In one embodiment, for the compound of formula (I), A is

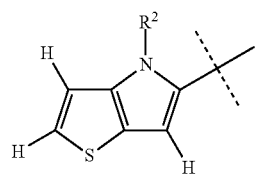

$R^2$ is methyl or ethyl, X is CH, and $R^4$ is aryl substituted by $L^2$-$R^7$.

In one embodiment, for the compound of formula (I), A is

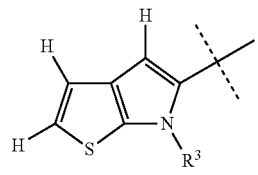

$R^3$ is methyl or ethyl, X is CH, and $R^4$ is aryl substituted by $L^2$-$R^7$.

In one embodiment, for the compound of formula (I), A is

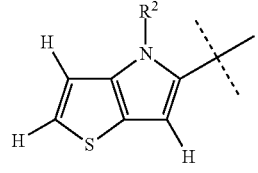

$R^2$ is methyl or ethyl, X is CH, $R^4$ is aryl substituted by $L^2$-$R^7$, and $L^1$ is —$CH_2$—O—, —$CH_2$—NH—, —O—$CH_2$, —$CH_2$—$CH_2$— or —CO—NH—.

In one embodiment, for the compound of formula (I), A is

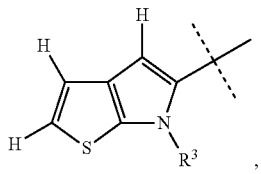

$R^3$ is methyl or ethyl, X is CH, $R^4$ is aryl substituted by $L^2$-$R^7$, and $L^1$ is —$CH_2$—O—, —$CH_2$—NH—, —O—$CH_2$—, —$CH_2$—$CH_2$— or —CO—NH—.

In one embodiment, for the compound of formula (I), A is

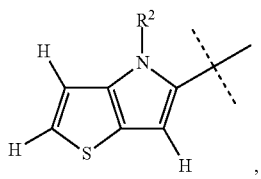

$R^2$ is methyl or ethyl, X is CH, $R^4$ is aryl substituted by $L^2$-$R^7$, $L^1$ is —$CH_2$—O—, —$CH_2$—NH—, —O—$CH_2$—, —$CH_2$—$CH_2$— or —CO—NH—, and $L^2$ is —$(CH_2)_m$—.

In one embodiment, for the compound of formula (I), A is

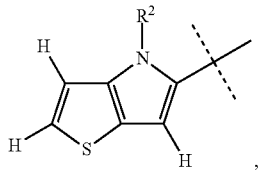

$R^2$ is methyl or ethyl, X is CH, $R^4$ is aryl substituted by $L^2$-$R^7$, $L^1$ is —$CH_2$—O—, —$CH_2$—NH—, —O—$CH_2$—, —$CH_2$—$CH_2$— or —CO—NH—, and $L^2$ is —$(CH_2)_n$—W—$(CH_2)_o$—.

In one embodiment, for the compound of formula (I), A is

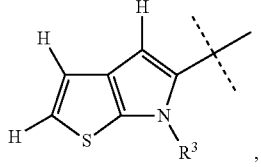

$R^3$ is methyl or ethyl, X is CH, $R^4$ is aryl substituted by $L^2$-$R^7$, $L^1$ is —$CH_2$—O—, —$CH_2$—NH—, —O—$CH_2$—, —$CH_2$—$CH_2$— or —CO—NH—, and $L^2$ is —$(CH_2)_m$—.

In one embodiment, for the compound of formula (I), A is

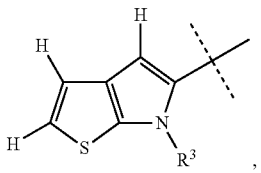

$R^3$ is methyl or ethyl, X is CH, $R^4$ is aryl substituted by $L^2$-$R^7$, $L^1$ is —$CH_2$—O—, —$CH_2$—NH—, —O—$CH_2$—, —$CH_2$—$CH_2$— or —CO—NH—, and $L^2$ is —$(CH_2)_n$—W—$(CH_2)_o$—.

In one embodiment, for the compound of formula (I), A is

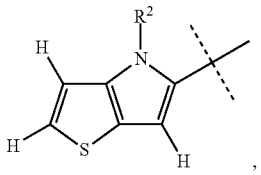

$R^2$ is methyl or ethyl, X is CH, $R^4$ is aryl substituted by $L^2$-$R^7$, $L^1$ is —$CH_2$—O—, —$CH_2$—NH—, —O—$CH_2$—, —$CH_2$—$CH_2$— or —CO—NH—, $L^2$ is —$(CH_2)_n$—W—$(CH_2)_o$—, and W is oxygen.

In one embodiment, for the compound of formula (I), A is

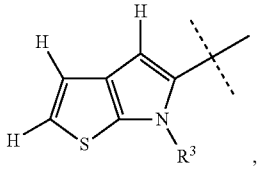

$R^3$ is methyl or ethyl, X is CH, $R^4$ is aryl substituted by $L^2$-$R^7$, $L^1$ is —$CH_2$—O—, —$CH_2$—NH—, —O—$CH_2$—, —$CH_2$—$CH_2$— or —CO—NH—, $L^2$ is —$(CH_2)_n$—W—$(CH_2)_o$—, and W is oxygen.

In one embodiment, for the compound of formula (I), A is

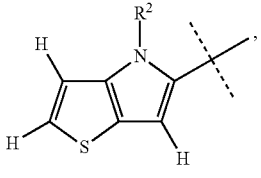

$R^2$ is methyl or ethyl, X is CH, $R^4$ is aryl substituted by $L^2$-$R^7$, $L^1$ is —$CH_2$—O—, —$CH_2$—NH—, —O—$CH_2$—, —$CH_2$—$CH_2$— or —CO—NH—, $L^2$ is —$(CH_2)_n$—W—$(CH_2)_o$—, and W is sulphur.

In one embodiment, for the compound of formula (I), A is

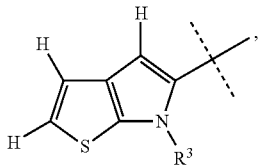

$R^3$ is methyl or ethyl, X is CH, $R^4$ is aryl substituted by $L^2$-$R^7$, $L^1$ is —$CH_2$—O—, —$CH_2$—NH—, —O—$CH_2$—, —$CH_2$—$CH_2$— or —CO—NH—, $L^2$ is —$(CH_2)_n$—W—$(CH_2)_o$—, and W is sulphur.

In one embodiment, for the compound of formula (I), A is

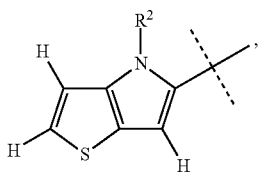

$R^2$ is methyl or ethyl, X is CH, $R^4$ is aryl substituted by $L^2$-$R^7$, $L^1$ is —$CH_2$—O—, —$CH_2$—NH—, —O—$CH_2$—, —$CH_2$—$CH_2$— or —CO—NH—, $L^2$ is —$(CH_2)_n$—W—$(CH_2)_o$—, and W is NH.

In one embodiment, for the compound of formula (I), A is

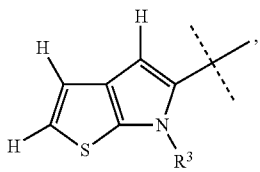

$R^3$ is methyl or ethyl, X is CH, $R^4$ is aryl substituted by $L^2$-$R^7$, $L^1$ is —$CH_2$—O—, —$CH_2$—NH—, —O—$CH_2$—, —$CH_2$—$CH_2$— or —CO—NH—, $L^2$ is —$(CH_2)_n$—W—$(CH_2)_o$—, and W is NH.

In one embodiment, for the compound of formula (I), A is

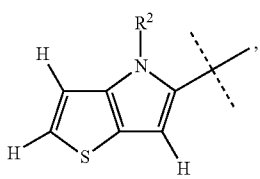

$R^2$ is methyl or ethyl, X is CH, $R^4$ is aryl substituted by $L^2$-$R^7$, $L^1$ is —$CH_2$—O—, —$CH_2$—NH—, —O—$CH_2$—, —$CH_2$—$CH_2$— or —CO—NH—, $L^2$ is —$(CH_2)_n$—W—$(CH_2)_o$—, and W is $CH_2$.

In one embodiment, for the compound of formula (I), A is

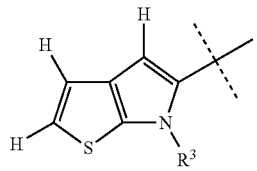

$R^3$ is methyl or ethyl, X is CH, $R^4$ is aryl substituted by $L^2$-$R^7$, $L^1$ is —$CH_2$—O—, —$CH_2$—NH—, —O—$CH_2$—, —$CH_2$—$CH_2$— or —CO—NH—, $L^2$ is —$(CH_2)_n$—W—$(CH_2)_o$—, and W is $CH_2$.

In one embodiment, the compound of formula (I) is selected from:
4-Methyl-N-[2-[[4-(4-piperidyloxy)phenoxy]methyl]phenyl]thieno[3,2-b]pyrrole-5-carboxamide;
4-methyl-N-[2-[[4-(4-piperidylmethoxy)phenoxy]methyl]phenyl]thieno-[3,2-b]pyrrole-5-carboxamide;
N-[2-[[4-[(1-ethyl-4-piperidyl)oxy]phenoxy]methyl]phenyl]-4-methyl-thieno[3,2-b]pyrrole-5-carboxamide;
4-methyl-N-[2-[[4-[[(3R)-pyrrolidin-3-yl]methoxy]phenoxy]methyl]phenyl]thieno[3,2-b]pyrrole-5-carboxamide;
4-methyl-N-[2-[[4-(pyrrolidin-3-ylmethoxy)phenoxy]methyl]phenyl]thieno[3,2-b]pyrrole-5-carboxamide;
4-ethyl-N-[3-[[4-(4-piperidyloxy)phenoxy]methyl]phenyl]thieno[3,2-b]pyrrole-5-carboxamide;
N-[2-[[4-(azepan-4-yloxy)phenoxy]methyl]phenyl]-4-methyl-thieno[3,2-b]pyrrole-5-carboxamide;
4-ethyl-N-[2-[[4-(4-piperidyloxy)phenoxy]methyl]phenyl]thieno[3,2-b]pyrrole-5-carboxamide;
N-[2-[[4-(cis-4-aminocyclohexoxy)phenoxy]methyl]phenyl]-4-methyl-thieno[3,2-b]pyrrole-5-carboxamide;
4-methyl-N-[3-[[4-(4-piperidyloxy)phenoxy]methyl]phenyl]thieno[3,2-b]pyrrole-5-carboxamide;
4-methyl-N-[2-[[4-[[(3 S)-pyrrolidin-3-yl]methoxy]phenoxy]methyl]phenyl]thieno[3,2-b]pyrrole-5-carboxamide;
4-ethyl-N-[2-[[4-[(1-methyl-4-piperidyl)oxy]phenoxy]methyl]phenyl]thieno[3,2-b]pyrrole-5-carboxamide;
4-methyl-N-[2-[[4-[(1-methyl-4-piperidyl)oxy]phenoxy]methyl]phenyl]thieno[3,2-b]pyrrole-5-carboxamide;
N-[2-[[4-(trans-4-aminocyclohexoxy)phenoxy]methyl]phenyl]-4-methyl-thieno[3,2-b]pyrrole-5-carboxamide;
4-methyl-N-[3-[[4-[(1-methyl-4-piperidyl)oxy]phenoxy]methyl]phenyl]thieno[3,2-b]pyrrole-5-carboxamide;
4-methyl-N-[2-[(4-pyrrolidin-3-yloxyphenoxy)methyl]phenyl]thieno[3,2-b]pyrrole-5-carboxamide;
4-methyl-N-[2-[[3-[(1-methyl-4-piperidyl)oxy]phenoxy]methyl]phenyl]thieno[3,2-b]pyrrole-5-carboxamide;
4-methyl-N-[2-[[3-(4-piperidyloxy)phenoxy]methyl]phenyl]thieno[3,2-b]pyrrole-5-carboxamide;
4-methyl-N-[3-[(1-methyl-3-piperidyl)methoxy]phenyl]thieno[3,2-b]pyrrole-5-carboxamide;
4-methyl-N-[2-[[4-[(4-methylpiperazin-1-yl)methyl]phenoxy]methyl]phenyl]thieno[3,2-b]pyrrole-5-carboxamide;
4-methyl-N-[3-(4-pyridylmethoxy)phenyl]thieno[3,2-b]pyrrole-5-carboxamide;
4-methyl-N-[3-(4-pyridyloxymethyl)phenyl]thieno[3,2-b]pyrrole-5-carboxamide;
4-methyl-N-[4-[[4-[(1-methyl-4-piperidyl)oxy]phenoxy]methyl]phenyl]thieno[3,2-b]pyrrole-5-carboxamide;
N-[2-[[4-[[(1 S,5R)-8-azabicyclo[3.2.1]octan-3-yl]oxy]phenoxy]methyl]phenyl]-4-methyl-thieno[3,2-b]pyrrole-5-carboxamide;

N-[3-[[4-[[(1S,5R)-8-azabicyclo[3.2.1]octan-3-yl]oxy]phenoxy]methyl]phenyl]-4-methyl-thieno[3,2-b]pyrrole-5-carboxamide;
4-methyl-N-[3-[[4-(4-piperidylmethoxy)phenoxy]methyl]phenyl]thieno[3,2-b]pyrrole-5-carboxamide;
4-methyl-N-[2-[[4-(3-piperidyloxy)phenoxy]methyl]phenyl]thieno[3,2-b]pyrrole-5-carboxamide;
4-methyl-N-[3-[[4-(3-piperidyloxy)phenoxy]methyl]phenyl]thieno[3,2-b]pyrrole-5-carboxamide;
N-[3-[[4-(trans-4-aminocyclohexoxy)phenoxy]methyl]phenyl]-4-methyl-thieno[3,2-b]pyrrole-5-carboxamide;
N-[3-[[4-(azetidin-3-ylmethoxy)phenoxy]methyl]phenyl]-4-methyl-thieno[3,2-b]pyrrole-5-carboxamide;
4-methyl-N-[2-[[4-(3-methylaminopropoxy)phenoxy]methyl]phenyl]thieno[3,2-b]pyrrole-5-carboxamide;
4-methyl-N-[3-[(4-pyrrolidin-3-yloxyphenoxy)methyl]phenyl]thieno[3,2-b]pyrrole-5-carboxamide;
N-[3-[[4-(azepan-4-yloxy)phenoxy]methyl]phenyl]-4-methyl-thieno[3,2-b]pyrrole-5-carboxamide;
N-[3-[[4-(cis-4-aminocyclohexoxy)phenoxy]methyl]phenyl]-4-methyl-thieno[3,2-b]pyrrole-5-carboxamide;
4-methyl-N-[3-[[4-(pyrrolidin-3-ylmethoxy)phenoxy]methyl]phenyl]thieno[3,2-b]pyrrole-5-carboxamide;
4-methyl-N-[2-[[4-(4-piperidyloxy)phenyl]carbamoyl]phenyl]thieno[3,2-b]pyrrole-5-carboxamide;
4-methyl-N-[2-[(4-piperazin-1-ylphenoxy)methyl]phenyl]thieno[3,2-b]pyrrole-5-carboxamide;
4-methyl-N-[2-[[4-[(1-methyl-4-piperidyl)oxy]phenyl]methoxy]phenyl]thieno[3,2-b]pyrrole-5-carboxamide;
4-methyl-N-[2-[[4-(4-piperidylamino)phenoxy]methyl]phenyl]thieno[3,2-b]pyrrole-5-carboxamide;
N-[2-[[4-(azetidin-3-ylmethoxy)phenoxy]methyl]phenyl]-4-methyl-thieno[3,2-b]pyrrole-5-carboxamide;
N-[2-[[4-(2,8-diazaspiro[4.5]decan-2-ylmethyl)phenoxy]methyl]phenyl]-4-methyl-thieno[3,2-b]pyrrole-5-carboxamide;
N-[3-(methoxymethyl)-2-[[4-[[(3R)-pyrrolidin-3-yl]methoxy]phenoxy]methyl]phenyl]-4-methyl-thieno[3,2-b]pyrrole-5-carboxamide;
N-[3-(methoxymethyl)-2-[[4-(4-piperidyloxy)phenoxy]methyl]phenyl]-4-methyl-thieno[3,2-b]pyrrole-5-carboxamide;
N-[2-[[4-(azepan-4-yloxy)phenoxy]methyl]-3-(methoxymethyl)phenyl]-4-methyl-thieno[3,2-b]pyrrole-5-carboxamide;
4-ethyl-N-[3-(methoxymethyl)phenyl]thieno[3,2-b]pyrrole-5-carboxamide;
4-methyl-N-[3-(methylsulfanylmethyl)phenyl]thieno[3,2-b]pyrrole-5-carboxamide;
4-methyl-N-[3-(methoxymethyl)phenyl]thieno[3,2-b]pyrrole-5-carboxamide;
N-[3-(methoxymethyl)phenyl]-6-methyl-thieno[2,3-b]pyrrole-5-carboxamide;
N-[3-(methoxymethyl)-2-[[4-[[(3S)-pyrrolidin-3-yl]methoxy]phenoxy]methyl]phenyl]-4-methyl-thieno[3,2-b]pyrrole-5-carboxamide;
N-[3-(ethoxymethyl)-2-[[4-(4-piperidyloxy)phenoxy]methyl]phenyl]-4-methyl-thieno[3,2-b]pyrrole-5-carboxamide;
N-[3-(isopropoxymethyl)-2-[[4-(4-piperidyloxy)phenoxy]methyl]phenyl]-4-methyl-thieno[3,2-b]pyrrole-5-carboxamide;
N-[3-(ethoxymethyl)-2-[[4-[[(3R)-pyrrolidin-3-yl]methoxy]phenoxy]methyl]phenyl]-4-methyl-thieno[3,2-b]pyrrole-5-carboxamide;
4-ethyl-N-[3-(methoxymethyl)-2-[[4-[[(3R)-pyrrolidin-3-yl]methoxy]phenoxy]methyl]phenyl]thieno[3,2-b]pyrrole-5-carboxamide;
4-methyl-N-[3-(morpholinomethyl)-2-[[4-(4-piperidyloxy)phenoxy]methyl]phenyl]thieno[3,2-b]pyrrole-5-carboxamide;
4-methyl-N-[5-methyl-2-[[4-(pyrrolidin-3-ylmethoxy)phenoxy]methyl]phenyl]thieno[3,2-b]pyrrole-5-carboxamide;
4-methyl-N-[2-[[5-(4-piperidyloxy)-2-pyridyl]oxymethyl]phenyl]thieno[3,2-b]pyrrole-5-carboxamide;
4-methyl-N-[2-(4-piperidylmethoxy)phenyl]thieno[3,2-b]pyrrole-5-carboxamide;
4-methyl-N-[3-[[3-(4-piperidyloxy)phenoxy]methyl]phenyl]thieno[3,2-b]pyrrole-5-carboxamide;
N-[3-[[4-(guanidinomethyl)phenoxy]methyl]phenyl]-4-methyl-thieno[3,2-b]pyrrole-5-carboxamide;
N-[2-[[4-(guanidinomethyl)phenoxy]methyl]phenyl]-4-methyl-thieno[3,2-b]pyrrole-5-carboxamide;
4-methyl-N-[2-[2-[4-(4-piperidyloxy)phenyl]ethyl]phenyl]thieno[3,2-b]pyrrole-5-carboxamide;
4-methyl-N-[3-[2-[4-(4-piperidyloxy)phenyl]ethyl]phenyl]thieno[3,2-b]pyrrole-5-carboxamide;
4-methyl-N-[2-[[4-(4-piperidyloxy)anilino]methyl]phenyl]thieno[3,2-b]pyrrole-5-carboxamide;
6-methyl-N-[2-[[3-(4-piperidyloxy)phenoxy]methyl]phenyl]thieno[2,3-b]pyrrole-5-carboxamide;
6-ethyl-N-[2-[[3-(4-piperidyloxy)phenoxy]methyl]phenyl]thieno[2,3-b]pyrrole-5-carboxamide;
6-ethyl-N-[2-[[4-(4-piperidyloxy)phenoxy]methyl]phenyl]thieno[2,3-b]pyrrole-5-carboxamide;
6-methyl-N-[2-[[4-(4-piperidyloxy)phenoxy]methyl]phenyl]thieno[2,3-b]pyrrole-5-carboxamide;
6-methyl-N-[2-[[4-(pyrrolidin-3-ylmethoxy)phenoxy]methyl]phenyl]thieno[2,3-b]pyrrole-5-carboxamide;
4-methyl-N-[4-[[4-(4-piperidyloxy)phenyl]carbamoyl]-2-pyridyl]thieno[3,2-b]pyrrole-5-carboxamide;
and stereoisomers or pharmaceutically acceptable salts thereof.

In one embodiment, the present application relates to a compound of formula (I) for use as a medicament.

In one embodiment, the present application relates to a method of inhibiting KDM1 comprising administering to a subject a therapeutically effective amount of a compound of formula (I). In one embodiment, the compound of formula (I) is a KDM1A inhibitor. In one embodiment the compound of formula (I) is a KDM1B inhibitor.

In one embodiment, the present application relates to a method of inhibiting KDM1 comprising administering to a subject a therapeutically effective amount of a compound of formula (I), wherein the compound of formula (I) is a reversible KDM1 inhibitor. In one embodiment, the compound of formula (I) is a reversible KDM1A inhibitor. In one embodiment the compound of formula (I) is a reversible KDM1B inhibitor.

In one embodiment, the present application relates to a method of treating and/or preventing a cancer, infectious disease, or a disease characterized by aberration of cellular energy metabolism, comprising administering to a subject a therapeutically effective amount of a compound of formula (I).

In one embodiment, the present application relates to a method of treating and/or preventing a cancer, comprising administering to a subject a therapeutically effective amount of a compound of formula (I).

In one embodiment, the present application relates to a method of treating and/or preventing a cancer, comprising administering to a subject a therapeutically effective amount of a compound of formula (I), wherein the cancer is leukemia, non-small cell lung cancer, hepatocellular carcinoma, or glioblastoma.

In one embodiment, the present application relates to a method of treating and/or preventing glioblastoma, wherein the glioblastoma is giant cell glioblastoma or gliosarcoma.

In one embodiment, the present application relates to a method of treating and/or preventing an infectious disease, comprising administering to a subject a therapeutically effective amount of a compound of formula (I).

In one embodiment, the present application relates to a method of treating and/or preventing a disease characterized by aberration of cellular energy metabolism, comprising administering to a subject a therapeutically effective amount of a compound of formula (I).

In one embodiment, the present application relates to a method of treating and/or preventing a disease characterized by aberration of cellular energy metabolism, comprising administering to a subject a therapeutically effective amount of a compound of formula (I), wherein the disease characterized by aberration of cellular energy metabolism is obesity.

In one embodiment, the present application relates to a compound of formula (I) for use in the treatment and/or prevention of cancer, infectious disease, or a disease characterized by aberration of cellular energy metabolism.

In one embodiment, the present application relates to a compound of formula (I) for use in the treatment and/or prevention of cancer.

In one embodiment, the present application relates to a compound of formula (I) for use in the treatment and/or prevention of cancer, wherein the cancer is leukemia, non-small cell lung cancer, hepatocellular carcinoma, or glioblastoma.

In one embodiment, the present application relates to a compound of formula (I) for use in the treatment and/or prevention of glioblastoma, wherein the glioblastoma is giant cell glioblastoma or gliosarcoma.

In one embodiment, the present application relates to a compound of formula (I) for use in the treatment and/or prevention of an infectious disease.

In one embodiment, the present application relates to a compound of formula (I) for use in the treatment and/or prevention of a disease characterized by aberration of cellular energy metabolism.

In one embodiment, the present application relates to a compound of formula (I) for use in the treatment and/or prevention of a disease characterized by aberration of cellular energy metabolism, wherein the disease characterized by aberration of cellular energy metabolism is obesity.

In one embodiment, the present application relates to the use of a compound of formula (I) in the manufacture of a medicament for treating and/or preventing a cancer, infectious disease, or a disease characterized by aberration of cellular energy metabolism.

In one embodiment, the present application relates to the use of a compound of formula (I) in the manufacture of a medicament for treating and/or preventing a cancer.

In one embodiment, the present application relates to the use of a compound of formula (I) in the manufacture of a medicament for treating and/or preventing a cancer, wherein the cancer is leukemia, non-small cell lung cancer, hepatocellular carcinoma, or glioblastoma.

In one embodiment, the present application relates to the use of a compound of formula (I) in the manufacture of a medicament for treating and/or preventing glioblastoma, wherein the glioblastoma is giant cell glioblastoma or gliosarcoma.

In one embodiment, the present application relates to the use of a compound of formula (I) in the manufacture of a medicament for treating and/or preventing an infectious disease.

In one embodiment, the present application relates to the use of a compound of formula (I) in the manufacture of a medicament for treating and/or preventing a disease characterized by aberration of cellular energy metabolism.

In one embodiment, the present application relates to the use of a compound of formula (I) in the manufacture of a medicament for treating and/or preventing a disease characterized by aberration of cellular energy metabolism, wherein the disease characterized by aberration of cellular energy metabolism is obesity.

In one embodiment, the present application relates to a method of treating a cancer, infectious disease, or a disease characterized by aberration of cellular energy metabolism, comprising administering to a subject a therapeutically effective amount of a compound of formula (I).

In one embodiment, the present application relates to a method of treating a cancer, comprising administering to a subject a therapeutically effective amount of a compound of formula (I).

In one embodiment, the present application relates to a method of treating a cancer, comprising administering to a subject a therapeutically effective amount of a compound of formula (I), wherein the cancer is leukemia, non-small cell lung cancer, hepatocellular carcinoma, or glioblastoma.

In one embodiment, the present application relates to a method of treating glioblastoma, wherein the glioblastoma is giant cell glioblastoma or gliosarcoma.

In one embodiment, the present application relates to a method of treating an infectious disease, comprising administering to a subject a therapeutically effective amount of a compound of formula (I).

In one embodiment, the present application relates to a method of treating a disease characterized by aberration of cellular energy metabolism, comprising administering to a subject a therapeutically effective amount of a compound of formula (I).

In one embodiment, the present application relates to a method of treating a disease characterized by aberration of cellular energy metabolism, comprising administering to a subject a therapeutically effective amount of a compound of formula (I), wherein the disease characterized by aberration of cellular energy metabolism is obesity.

In one embodiment, the present application relates to the use of a compound of formula (I), for treating a cancer, infectious disease, or a disease characterized by aberration of cellular energy metabolism.

In one embodiment, the present application relates to the use of a compound of formula (I), for treating a cancer.

In one embodiment, the present application relates to the use of a compound of formula (I), for treating a cancer, wherein the cancer is leukemia, non-small cell lung cancer, hepatocellular carcinoma, or glioblastoma.

In one embodiment, the present application relates to the use of a compound of formula (I), for treating glioblastoma, wherein the glioblastoma is giant cell glioblastoma or gliosarcoma.

In one embodiment, the present application relates to the use of a compound of formula (I), for treating an infectious disease.

In one embodiment, the present application relates to the use of a compound of formula (I), for treating a disease characterized by aberration of cellular energy metabolism.

In one embodiment, the present application relates to the use of a compound of formula (I), for treating a disease characterized by aberration of cellular energy metabolism, wherein the disease characterized by aberration of cellular energy metabolism is obesity.

In one embodiment, the present application relates to the use of a compound of formula (I) in the manufacture of a medicament for treating a cancer, infectious disease, or a disease characterized by aberration of cellular energy metabolism.

In one embodiment, the present application relates to the use of a compound of formula (I) in the manufacture of a medicament for treating a cancer.

In one embodiment, the present application relates to the use of a compound of formula (I) in the manufacture of a medicament for treating a cancer, wherein the cancer is leukemia, non-small cell lung cancer, hepatocellular carcinoma, or glioblastoma.

In one embodiment, the present application relates to the use of a compound of formula (I) in the manufacture of a medicament for treating glioblastoma, wherein the glioblastoma is giant cell glioblastoma or gliosarcoma.

In one embodiment, the present application relates to the use of a compound of formula (I) in the manufacture of a medicament for treating an infectious disease.

In one embodiment, the present application relates to the use of a compound of formula (I) in the manufacture of a medicament for treating a disease characterized by aberration of cellular energy metabolism.

In one embodiment, the present application relates to the use of a compound of formula (I) in the manufacture of a medicament for treating a disease characterized by aberration of cellular energy metabolism, wherein the disease characterized by aberration of cellular energy metabolism is obesity.

In one embodiment, the present application relates to a pharmaceutical composition comprising a compound of formula (I) together with a pharmaceutically acceptable excipient and/or diluent.

In one embodiment, the present application relates to a pharmaceutical composition comprising a compound of formula (I) together with a pharmaceutically acceptable excipient and/or diluent, in the form of tablets, capsules, oral preparations, powders, granules, pills, injectable or infusible liquid, solutions, suspensions, emulsions, suppositories, ointments, creams, lotions, gels, pastes, transdermal delivery devices.

In one embodiment, the present application relates to a pharmaceutical composition comprising a compound of formula (I) together with a pharmaceutically acceptable excipient and/or diluent, further comprising at least one therapeutic agent, selected from the group consisting of histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, Selective COX-2 inhibitors or a chemotherapeutic agent.

In one embodiment, the present application relates to a pharmaceutical composition comprising a compound of formula (I) together with a pharmaceutically acceptable excipient and/or diluent, further comprising at least one therapeutic agent, selected from the group consisting of histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, Selective COX-2 inhibitors or a chemotherapeutic agent, in the form of tablets, capsules, oral preparations, powders, granules, pills, injectable or infusible liquid, solutions, suspensions, emulsions, suppositories, ointments, creams, lotions, gels, pastes, transdermal delivery devices.

In one embodiment, the present application relates to compounds of formula (Ia)

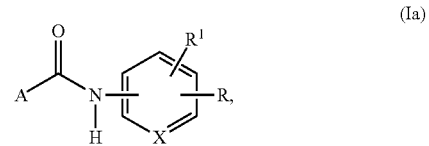

(Ia)

or a stereoisomer or pharmaceutically acceptable salt thereof,
wherein:
A is

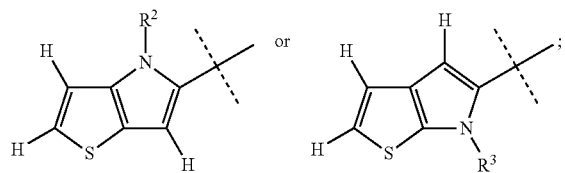

X is CH or N;
R is $L^1$-$R^4$;
$R^1$ is H, halogen, $C_1$-$C_6$-alkyl, $C_1$-$C_6$-alkoxy, —$CH_2$—Z—$R^5$, or —Z—$CH_2$—$R^6$;
$R^2$ and $R^3$ are $C_1$-$C_4$-alkyl;
$L^1$ is —$(CH_2)_j$—Y—, —Y—$(CH_2)_k$—, —$CH_2$—$CH_2$— or —CO—NH—;
j and k are, independently, each an integer from 1 to 6;
Y is oxygen, sulphur, NH or N($C_1$-$C_6$-alkyl);
Z is a bond, oxygen, sulphur, NH or N($C_1$-$C_6$-alkyl);
$R^4$ is aryl, or heteroaryl, wherein the aryl or heteroaryl are optionally substituted by halogen, $C_1$-$C_6$-alkyl, or $L^2$-$R^7$; or heterocyclyl, wherein the heterocyclyl is optionally substituted by $C_1$-$C_6$-alkyl;
$R^5$ and $R^6$ are, independently, $C_1$-$C_6$-alkyl; aryl, or heteroaryl, wherein the aryl or heteroaryl are optionally substituted by halogen, $C_1$-$C_6$-alkyl, or $L^2$-$R^7$; or heterocyclyl, wherein the heterocyclyl is optionally substituted by $C_1$-$C_6$-alkyl;
$L^2$ is —$(CH_2)_m$— or —$(CH_2)_n$—W—$(CH_2)_o$—;
$R^7$ is $C_1$-$C_6$-alkylamino, $C_3$-$C_7$ cycloalkyl or heterocyclyl, wherein the $C_3$-$C_7$ cycloalkyl or heterocyclyl are optionally substituted by $C_1$-$C_6$-alkyl, or $NH_2$; or guanidine;
m, n, o are, independently, each zero or an integer from 1 to 6;
W is oxygen, sulphur, NH, or $CH_2$;
wherein aryl is a mono or bicyclic aromatic ring system of 6 or 9 or 10 atoms; heteroaryl is a mono or bicyclic heteroaromatic ring system of 5 to 10 members, which contains one, two, three or four heteroatoms selected from nitrogen, oxygen and sulphur, and one to nine carbon atoms; and heterocyclyl is a mono, bicyclic or a spirocyclic saturated or partially saturated non-aromatic ring system of 4 to 12 members, which contains one, two, or three heteroatoms selected from nitrogen, oxygen, and sulphur, and three to eleven carbon atoms;

provided that when A is 4H-thieno[3,2-b]pyrrole-5-yl, $R^2$ is methyl, ethyl or isopropyl, and X is CH, then R is other than 4-benzyloxy or 3-phenoxymethylene.

In one embodiment, when A is 4H-thieno[3,2-b]pyrrole-5-yl, $R^2$ is methyl, ethyl or isopropyl, and X is CH, then R is substituted 2-phenoxymethylene or substituted 3-phenoxymethylene.

In one embodiment, for the compound of formula (Ia), A is

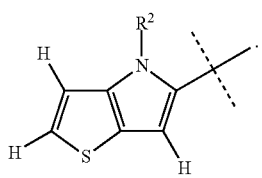

In one embodiment, for the compound of formula (Ia), A is

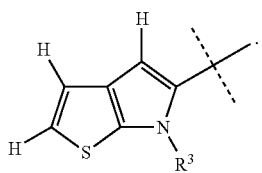

In one embodiment, for the compound of formula (Ia), $R^2$ and $R^3$ are methyl or ethyl.

In one embodiment, for the compound of formula (Ia), X is CH.

In one embodiment, for the compound of formula (Ia), $R^4$ is aryl substituted by $L^2$-$R^7$.

In one embodiment, for the compound of formula (Ia), $L^1$ is —CH$_2$—O—, —CH$_2$—NH—, —O—CH$_2$, —CH$_2$—CH$_2$— or —CO—NH—. In one embodiment, $L^1$ is —CH$_2$—O—, —CH$_2$—NH—, or —O—CH$_2$. In one embodiment, $L^1$ is —CH$_2$—O—. In one embodiment, $L^1$ is —CH$_2$—NH—. In one embodiment, $L^1$ is —O—CH$_2$—.

In one embodiment, $L^2$ is —(CH$_2$)$_m$—. In one embodiment, $L^2$ is —(CH$_2$)$_n$—W—(CH$_2$)$_o$—.

In one embodiment, W is oxygen. In one embodiment, W is sulphur. In one embodiment, W is NH. In one embodiment, for the compound of formula (Ia), W is CH$_2$.

In one embodiment, for the compound of formula (Ia), A is

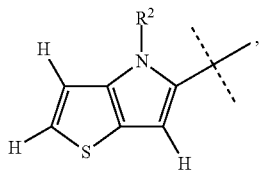

$R^2$ is methyl or ethyl, X is CH, and $R^4$ is aryl substituted by $L^2$-$R^7$.

In one embodiment, for the compound of formula (Ia), A is

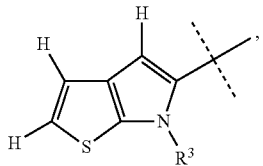

$R^3$ is methyl or ethyl, X is CH, and $R^4$ is aryl substituted by $L^2$-$R^7$.

In one embodiment, for the compound of formula (Ia), A is

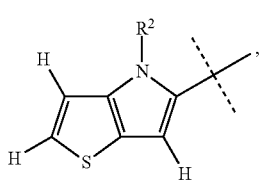

$R^2$ is methyl or ethyl, X is CH, $R^4$ is aryl substituted by $L^2$-$R^7$, and Li is —CH$_2$—O—, —CH$_2$—NH—, —O—CH$_2$, —CH$_2$—CH$_2$— or —CO—NH—.

In one embodiment, for the compound of formula (Ia), A is

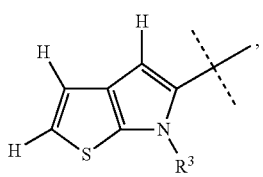

$R^3$ is methyl or ethyl, X is CH, $R^4$ is aryl substituted by $L^2$-$R^7$, and Li is —CH$_2$—O—, —CH$_2$—NH—, —O—CH$_2$, —CH$_2$—CH$_2$— or —CO—NH—.

In one embodiment, for the compound of formula (Ia), A is

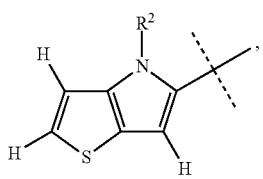

$R^2$ is methyl or ethyl, X is CH, $R^4$ is aryl substituted by $L^2$-$R^7$, Li is —CH$_2$—O—, —CH$_2$—NH—, —O—CH$_2$, —CH$_2$—CH$_2$— or —CO—NH—, and $L^2$ is —(CH$_2$)$_m$—.

In one embodiment, for the compound of formula (Ia), A is

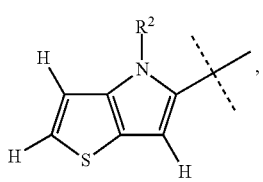

$R^2$ is methyl or ethyl, X is CH, $R^4$ is aryl substituted by $L^2$-$R^7$, $L^1$ is —CH$_2$—O—, —CH$_2$—NH—, —O—CH$_2$, —CH$_2$—CH$_2$— or —CO—NH—, and $L^2$ is —(CH$_2$)$_n$—W—(CH$_2$)$_o$—.

In one embodiment, for the compound of formula (Ia), A is

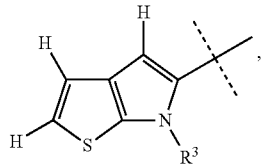

$R^3$ is methyl or ethyl, X is CH, $R^4$ is aryl substituted by $L^2$-$R^7$, $L^1$ is —CH$_2$—O—, —CH$_2$—NH—, —O—CH$_2$, —CH$_2$—CH$_2$— or —CO—NH—, and $L^2$ is —(CH$_2$)$_m$—.

In one embodiment, for the compound of formula (Ia), A is

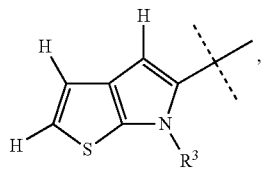

$R^3$ is methyl or ethyl, X is CH, $R^4$ is aryl substituted by $L^2$-$R^7$, $L^1$ is —CH$_2$—O—, —CH$_2$—NH—, —O—CH$_2$, —CH$_2$—CH$_2$— or —CO—NH—, and $L^2$ is —(CH$_2$)$_n$—W—(CH$_2$)$_o$—.

In one embodiment, for the compound of formula (Ia), A is

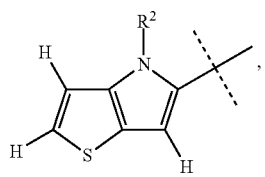

$R^2$ is methyl or ethyl, X is CH, $R^4$ is aryl substituted by $L^2$-$R^7$, $L^1$ is —CH$_2$—O—, —CH$_2$—NH—, —O—CH$_2$, —CH$_2$—CH$_2$— or —CO—NH—, $L^2$ is —(CH$_2$)$_n$—W—(CH$_2$)$_o$—, and W is oxygen.

In one embodiment, for the compound of formula (Ia), A is

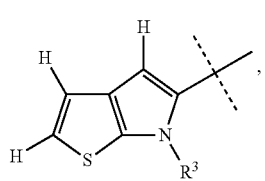

$R^3$ is methyl or ethyl, X is CH, $R^4$ is aryl substituted by $L^2$-$R^7$, $L^1$ is —CH$_2$—O—, —CH$_2$—NH—, —O—CH$_2$, —CH$_2$—CH$_2$— or —CO—NH—, $L^2$ is —(CH$_2$)$_n$—W—(CH$_2$)$_o$—, and W is oxygen.

In one embodiment, for the compound of formula (Ia), A is

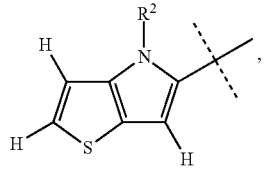

$R^2$ is methyl or ethyl, X is CH, $R^4$ is aryl substituted by $L^2$-$R^7$, $L^1$ is —CH$_2$—O—, —CH$_2$—NH—, —O—CH$_2$, —CH$_2$—CH$_2$— or —CO—NH—, $L^2$ is —(CH$_2$)$_n$—W—(CH$_2$)$_o$—, and W is sulphur.

In one embodiment, for the compound of formula (Ia), A is

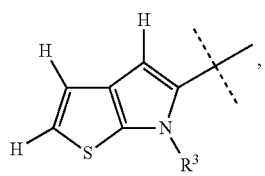

$R^3$ is methyl or ethyl, X is CH, $R^4$ is aryl substituted by $L^2$-$R^7$, $L^1$ is —CH$_2$—O—, —CH$_2$—NH—, —O—CH$_2$, —CH$_2$—CH$_2$— or —CO—NH—, $L^2$ is —(CH$_2$)$_n$—W—(CH$_2$)$_o$—, and W is sulphur.

In one embodiment, for the compound of formula (Ia), A is

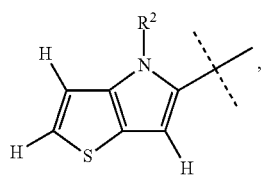

$R^2$ is methyl or ethyl, X is CH, $R^4$ is aryl substituted by $L^2$-$R^7$, $L^1$ is —CH$_2$—O—, —CH$_2$—NH—, —O—CH$_2$, —CH$_2$—CH$_2$— or —CO—NH—, $L^2$ is —(CH$_2$)$_n$—W—(CH$_2$)$_o$—, and W is NH.

In one embodiment, for the compound of formula (Ia), A is

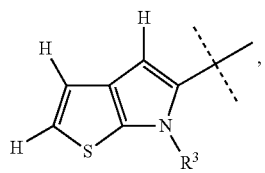

$R^3$ is methyl or ethyl, X is CH, $R^4$ is aryl substituted by $L^2$-$R^7$, $L^1$ is —CH$_2$—O—, —CH$_2$—NH—, —O—CH$_2$, —CH$_2$—CH$_2$— or —CO—NH—, $L^2$ is —(CH$_2$)$_n$—W—(CH$_2$)$_o$—, and W is NH.

In one embodiment, for the compound of formula (Ia), A is

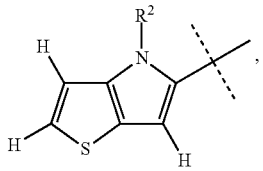

$R^2$ is methyl or ethyl, X is CH, $R^4$ is aryl substituted by $L^2$-$R^7$, $L^1$ is —$CH_2$—O—, —$CH_2$—NH—, —O—$CH_2$, —$CH_2$—$CH_2$— or —CO—NH—, $L^2$ is —$(CH_2)_n$—W—$(CH_2)_o$—, and W is $CH_2$.

In one embodiment, for the compound of formula (Ia), A is

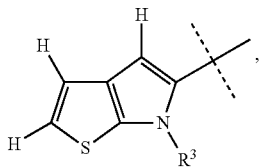

$R^3$ is methyl or ethyl, X is CH, $R^4$ is aryl substituted by $L^2$-$R^7$, $L^1$ is —$CH_2$—O—, —$CH_2$—NH—, —O—$CH_2$, —$CH_2$—$CH_2$— or —CO—NH—, $L^2$ is —$(CH_2)_n$—W—$(CH_2)_o$—, and W is $CH_2$.

In one embodiment, the compound of formula (Ia) is selected from:

4-Methyl-N-[2-[[4-(4-piperidyloxy)phenoxy]methyl]phenyl]thieno[3,2-b]pyrrole-5-carboxamide;
4-methyl-N-[2-[[4-(4-piperidylmethoxy)phenoxy]methyl]phenyl]thieno-[3,2-b]pyrrole-5-carboxamide;
N-[2-[[4-[(1-ethyl-4-piperidyl)oxy]phenoxy]methyl]phenyl]-4-methyl-thieno[3,2-b]pyrrole-5-carboxamide;
4-methyl-N-[2-[[4-[[(3R)-pyrrolidin-3-yl]methoxy]phenoxy]methyl]phenyl]thieno[3,2-b]pyrrole-5-carboxamide;
4-methyl-N-[2-[[4-(pyrrolidin-3-ylmethoxy)phenoxy]methyl]phenyl]thieno[3,2-b]pyrrole-5-carboxamide;
4-ethyl-N-[3-[[4-(4-piperidyloxy)phenoxy]methyl]phenyl]thieno[3,2-b]pyrrole-5-carboxamide;
N-[2-[[4-(azepan-4-yloxy)phenoxy]methyl]phenyl]-4-methyl-thieno[3,2-b]pyrrole-5-carboxamide;
4-ethyl-N-[2-[[4-(4-piperidyloxy)phenoxy]methyl]phenyl]thieno[3,2-b]pyrrole-5-carboxamide;
N-[2-[[4-(cis-4-aminocyclohexoxy)phenoxy]methyl]phenyl]-4-methyl-thieno[3,2-b]pyrrole-5-carboxamide;
4-methyl-N-[3-[[4-(4-piperidyloxy)phenoxy]methyl]phenyl]thieno[3,2-b]pyrrole-5-carboxamide;
4-methyl-N-[2-[[4-[[(3 S)-pyrrolidin-3-yl]methoxy]phenoxy]methyl]phenyl]thieno[3,2-b]pyrrole-5-carboxamide;
4-ethyl-N-[2-[[4-[(1-methyl-4-piperidyl)oxy]phenoxy]methyl]phenyl]thieno[3,2-b]pyrrole-5-carboxamide;
4-methyl-N-[2-[[4-[(1-methyl-4-piperidyl)oxy]phenoxy]methyl]phenyl]thieno[3,2-b]pyrrole-5-carboxamide;
N-[2-[[4-(trans-4-aminocyclohexoxy)phenoxy]methyl]phenyl]-4-methyl-thieno[3,2-b]pyrrole-5-carboxamide;
4-methyl-N-[3-[[4-[(1-methyl-4-piperidyl)oxy]phenoxy]methyl]phenyl]thieno[3,2-b]pyrrole-5-carboxamide;
4-methyl-N-[2-[(4-pyrrolidin-3-yloxyphenoxy)methyl]phenyl]thieno[3,2-b]pyrrole-5-carboxamide;
4-methyl-N-[2-[[3-[(1-methyl-4-piperidyl)oxy]phenoxy]methyl]phenyl]thieno[3,2-b]pyrrole-5-carboxamide;
4-methyl-N-[2-[[3-(4-piperidyloxy)phenoxy]methyl]phenyl]thieno[3,2-b]pyrrole-5-carboxamide;
4-methyl-N-[3-[(1-methyl-3-piperidyl)methoxy]phenyl]thieno[3,2-b]pyrrole-5-carboxamide;
4-methyl-N-[2-[[4-[(4-methylpiperazin-1-yl)methyl]phenoxy]methyl]phenyl]thieno[3,2-b]pyrrole-5-carboxamide;
4-methyl-N-[3-(4-pyridylmethoxy)phenyl]thieno[3,2-b]pyrrole-5-carboxamide;
4-methyl-N-[3-(4-pyridyloxymethyl)phenyl]thieno[3,2-b]pyrrole-5-carboxamide;
4-methyl-N-[4-[[4-[(1-methyl-4-piperidyl)oxy]phenoxy]methyl]phenyl]thieno[3,2-b]pyrrole-5-carboxamide;
N-[2-[[4-[[(1 S,5R)-8-azabicyclo[3.2.1]octan-3-yl]oxy]phenoxy]methyl]phenyl]-4-methyl-thieno[3,2-b]pyrrole-5-carboxamide;
N-[3-[[4-[[(1 S,5R)-8-azabicyclo[3.2.1]octan-3-yl]oxy]phenoxy]methyl]phenyl]-4-methyl-thieno[3,2-b]pyrrole-5-carboxamide;
4-methyl-N-[3-[[4-(4-piperidylmethoxy)phenoxy]methyl]phenyl]thieno[3,2-b]pyrrole-5-carboxamide;
4-methyl-N-[2-[[4-(3-piperidyloxy)phenoxy]methyl]phenyl]thieno[3,2-b]pyrrole-5-carboxamide;
4-methyl-N-[3-[[4-(3-piperidyloxy)phenoxy]methyl]phenyl]thieno[3,2-b]pyrrole-5-carboxamide;
N-[3-[[4-(trans-4-aminocyclohexoxy)phenoxy]methyl]phenyl]-4-methyl-thieno[3,2-b]pyrrole-5-carboxamide;
N-[3-[[4-(azetidin-3-ylmethoxy)phenoxy]methyl]phenyl]-4-methyl-thieno[3,2-b]pyrrole-5-carboxamide;
4-methyl-N-[2-[[4-(3-methylaminopropoxy)phenoxy]methyl]phenyl]thieno[3,2-b]pyrrole-5-carboxamide;
4-methyl-N-[3-[(4-pyrrolidin-3-yloxyphenoxy)methyl]phenyl]thieno[3,2-b]pyrrole-5-carboxamide;
N-[3-[[4-(azepan-4-yloxy)phenoxy]methyl]phenyl]-4-methyl-thieno[3,2-b]pyrrole-5-carboxamide;
N-[3-[[4-(cis-4-aminocyclohexoxy)phenoxy]methyl]phenyl]-4-methyl-thieno[3,2-b]pyrrole-5-carboxamide;
4-methyl-N-[3-[[4-(pyrrolidin-3-ylmethoxy)phenoxy]methyl]phenyl]thieno[3,2-b]pyrrole-5-carboxamide;
4-methyl-N-[2-[[4-(4-piperidyloxy)phenyl]carbamoyl]phenyl]thieno[3,2-b]pyrrole-5-carboxamide;
4-methyl-N-[2-[(4-piperazin-1-ylphenoxy)methyl]phenyl]thieno[3,2-b]pyrrole-5-carboxamide;
4-methyl-N-[2-[[4-[(1-methyl-4-piperidyl)oxy]phenyl]methoxy]phenyl]thieno[3,2-b]pyrrole-5-carboxamide;
4-methyl-N-[2-[[4-(4-piperidylamino)phenoxy]methyl]phenyl]thieno[3,2-b]pyrrole-5-carboxamide;
N-[2-[[4-(azetidin-3-ylmethoxy)phenoxy]methyl]phenyl]-4-methyl-thieno[3,2-b]pyrrole-5-carboxamide;
N-[2-[[4-(2,8-diazaspiro[4.5]decan-2-ylmethyl)phenoxy]methyl]phenyl]-4-methyl-thieno[3,2-b]pyrrole-5-carboxamide;
N-[3-(methoxymethyl)-2-[[4-[[(3R)-pyrrolidin-3-yl]methoxy]phenoxy]methyl]phenyl]-4-methyl-thieno[3,2-b]pyrrole-5-carboxamide;
N-[3-(methoxymethyl)-2-[[4-(4-piperidyloxy)phenoxy]methyl]phenyl]-4-methyl-thieno[3,2-b]pyrrole-5-carboxamide;
N-[2-[[4-(azepan-4-yloxy)phenoxy]methyl]-3-(methoxymethyl)phenyl]-4-methyl-thieno[3,2-b]pyrrole-5-carboxamide;
N-[3-(methoxymethyl)-2-[[4-[[(3S)-pyrrolidin-3-yl]methoxy]phenoxy]methyl]phenyl]-4-methyl-thieno[3,2-b]pyrrole-5-carboxamide;
N-[3-(ethoxymethyl)-2-[[4-(4-piperidyloxy)phenoxy]methyl]phenyl]-4-methyl-thieno[3,2-b]pyrrole-5-carboxamide;

N-[3-(isopropoxymethyl)-2-[[4-(4-piperidyloxy)phenoxy]methyl]phenyl]-4-methyl-thieno[3,2-b]pyrrole-5-carboxamide;
N-[3-(ethoxymethyl)-2-[[4-[[(3R)-pyrrolidin-3-yl]methoxy]phenoxy]methyl]phenyl]-4-methyl-thieno[3,2-b]pyrrole-5-carboxamide;
4-ethyl-N-[3-(methoxymethyl)-2-[[4-[[(3R)-pyrrolidin-3-yl]methoxy]phenoxy]methyl]phenyl]thieno[3,2-b]pyrrole-5-carboxamide;
4-methyl-N-[3-(morpholinomethyl)-2-[[4-(4-piperidyloxy)phenoxy]methyl]phenyl]thieno[3,2-b]pyrrole-5-carboxamide;
4-methyl-N-[5-methyl-2-[[4-(pyrrolidin-3-ylmethoxy)phenoxy]methyl]phenyl]thieno[3,2-b]pyrrole-5-carboxamide;
4-methyl-N-[2-[[5-(4-piperidyloxy)-2-pyridyl]oxymethyl]phenyl]thieno[3,2-b]pyrrole-5-carboxamide;
4-methyl-N-[2-(4-piperidylmethoxy)phenyl]thieno[3,2-b]pyrrole-5-carboxamide;
4-methyl-N-[3-[[3-(4-piperidyloxy)phenoxy]methyl]phenyl]thieno[3,2-b]pyrrole-5-carboxamide;
N-[3-[[4-(guanidinomethyl)phenoxy]methyl]phenyl]-4-methyl-thieno[3,2-b]pyrrole-5-carboxamide;
N-[2-[[4-(guanidinomethyl)phenoxy]methyl]phenyl]-4-methyl-thieno[3,2-b]pyrrole-5-carboxamide;
4-methyl-N-[2-[2-[4-(4-piperidyloxy)phenyl]ethyl]phenyl]thieno[3,2-b]pyrrole-5-carboxamide;
4-methyl-N-[3-[2-[4-(4-piperidyloxy)phenyl]ethyl]phenyl]thieno[3,2-b]pyrrole-5-carboxamide;
4-methyl-N-[2-[[4-(4-piperidyloxy)anilino]methyl]phenyl]thieno[3,2-b]pyrrole-5-carboxamide;
6-methyl-N-[2-[[3-(4-piperidyloxy)phenoxy]methyl]phenyl]thieno[2,3-b]pyrrole-5-carboxamide;
6-ethyl-N-[2-[[3-(4-piperidyloxy)phenoxy]methyl]phenyl]thieno[2,3-b]pyrrole-5-carboxamide;
6-ethyl-N-[2-[[4-(4-piperidyloxy)phenoxy]methyl]phenyl]thieno[2,3-b]pyrrole-5-carboxamide;
6-methyl-N-[2-[[4-(4-piperidyloxy)phenoxy]methyl]phenyl]thieno[2,3-b]pyrrole-5-carboxamide;
6-methyl-N-[2-[[4-(pyrrolidin-3-ylmethoxy)phenoxy]methyl]phenyl]thieno[2,3-b]pyrrole-5-carboxamide;
4-methyl-N-[4-[[4-(4-piperidyloxy)phenyl]carbamoyl]-2-pyridyl]thieno[3,2-b]pyrrole-5-carboxamide;
and stereoisomers or pharmaceutically acceptable salts thereof.

In one embodiment, the present application relates to a compound of formula (Ia) for use as a medicament.

In one embodiment, the present application relates to a method of inhibiting KDM1 comprising administering to a subject a therapeutically effective amount of a compound of formula (Ia). In one embodiment, the compound of formula (Ia) is a KDM1A inhibitor. In one embodiment the compound of formula (Ia) is a KDM1B inhibitor.

In one embodiment, the present application relates to a method of inhibiting KDM1 comprising administering to a subject a therapeutically effective amount of a compound of formula (Ia), wherein the compound of formula (Ia) is a reversible KDM1 inhibitor. In one embodiment, the compound of formula (Ia) is a reversible KDM1A inhibitor. In one embodiment the compound of formula (Ia) is a reversible KDM1B inhibitor.

In one embodiment, the present application relates to a method of treating and/or preventing a cancer, infectious disease, or a disease characterized by aberration of cellular energy metabolism, comprising administering to a subject a therapeutically effective amount of a compound of formula (Ia).

In one embodiment, the present application relates to a method of treating and/or preventing a cancer, comprising administering to a subject a therapeutically effective amount of a compound of formula (Ia).

In one embodiment, the present application relates to a method of treating and/or preventing a cancer, comprising administering to a subject a therapeutically effective amount of a compound of formula (Ia), wherein the cancer is leukemia, non-small cell lung cancer, hepatocellular carcinoma, or glioblastoma.

In one embodiment, the present application relates to a method of treating and/or preventing glioblastoma, wherein the glioblastoma is giant cell glioblastoma or gliosarcoma.

In one embodiment, the present application relates to a method of treating and/or preventing an infectious disease, comprising administering to a subject a therapeutically effective amount of a compound of formula (Ia).

In one embodiment, the present application relates to a method of treating and/or preventing a disease characterized by aberration of cellular energy metabolism, comprising administering to a subject a therapeutically effective amount of a compound of formula (Ia).

In one embodiment, the present application relates to a method of treating and/or preventing a disease characterized by aberration of cellular energy metabolism, comprising administering to a subject a therapeutically effective amount of a compound of formula (Ia), wherein the disease characterized by aberration of cellular energy metabolism is obesity.

In one embodiment, the present application relates to the use of a compound of formula (Ia), for treating and/or preventing a cancer, infectious disease, or a disease characterized by aberration of cellular energy metabolism.

In one embodiment, the present application relates to the use of a compound of formula (Ia), for treating and/or preventing a cancer.

In one embodiment, the present application relates to the use of a compound of formula (Ia), for treating and/or preventing a cancer, wherein the cancer is leukemia, non-small cell lung cancer, hepatocellular carcinoma, or glioblastoma.

In one embodiment, the present application relates to the use of a compound of formula (Ia), for treating and/or preventing glioblastoma, wherein the glioblastoma is giant cell glioblastoma or gliosarcoma.

In one embodiment, the present application relates to the use of a compound of formula (Ia), for treating and/or preventing an infectious disease.

In one embodiment, the present application relates to the use of a compound of formula (Ia), for treating and/or preventing a disease characterized by aberration of cellular energy metabolism.

In one embodiment, the present application relates to the use of a compound of formula (Ia), for treating and/or preventing a disease characterized by aberration of cellular energy metabolism, wherein the disease characterized by aberration of cellular energy metabolism is obesity.

In one embodiment, the present application relates to the use of a compound of formula (Ia) in the manufacture of a medicament for treating and/or preventing a cancer, infectious disease, or a disease characterized by aberration of cellular energy metabolism.

In one embodiment, the present application relates to the use of a compound of formula (Ia) in the manufacture of a medicament for treating and/or preventing a cancer.

In one embodiment, the present application relates to the use of a compound of formula (Ia) in the manufacture of a medicament for treating and/or preventing a cancer, wherein the cancer is leukemia, non-small cell lung cancer, hepatocellular carcinoma, or glioblastoma.

In one embodiment, the present application relates to the use of a compound of formula (Ia) in the manufacture of a medicament for treating and/or preventing glioblastoma, wherein the glioblastoma is giant cell glioblastoma or gliosarcoma.

In one embodiment, the present application relates to the use of a compound of formula (Ia) in the manufacture of a medicament for treating and/or preventing glioblastoma, wherein the glioblastoma is giant cell glioblastoma or gliosarcoma.

In one embodiment, the present application relates to the use of a compound of formula (Ia) in the manufacture of a medicament for treating and/or preventing an infectious disease.

In one embodiment, the present application relates to the use of a compound of formula (Ia) in the manufacture of a medicament for treating and/or preventing a disease characterized by aberration of cellular energy metabolism.

In one embodiment, the present application relates to the use of a compound of formula (Ia) in the manufacture of a medicament for treating and/or preventing a disease characterized by aberration of cellular energy metabolism, wherein the disease characterized by aberration of cellular energy metabolism is obesity.

In one embodiment, the present application relates to a method of treating a cancer, infectious disease, or a disease characterized by aberration of cellular energy metabolism, comprising administering to a subject a therapeutically effective amount of a compound of formula (Ia).

In one embodiment, the present application relates to a method of treating a cancer, comprising administering to a subject a therapeutically effective amount of a compound of formula (Ia).

In one embodiment, the present application relates to a method of treating a cancer, comprising administering to a subject a therapeutically effective amount of a compound of formula (Ia), wherein the cancer is leukemia, non-small cell lung cancer, hepatocellular carcinoma, or glioblastoma.

In one embodiment, the present application relates to a method of treating glioblastoma, wherein the glioblastoma is giant cell glioblastoma or gliosarcoma.

In one embodiment, the present application relates to a method of treating an infectious disease, comprising administering to a subject a therapeutically effective amount of a compound of formula (Ia).

In one embodiment, the present application relates to a method of treating a disease characterized by aberration of cellular energy metabolism, comprising administering to a subject a therapeutically effective amount of a compound of formula (Ia).

In one embodiment, the present application relates to a method of treating a disease characterized by aberration of cellular energy metabolism, comprising administering to a subject a therapeutically effective amount of a compound of formula (Ia), wherein the disease characterized by aberration of cellular energy metabolism is obesity.

In one embodiment, the present application relates to the use of a compound of formula (Ia), for treating a cancer, infectious disease, or a disease characterized by aberration of cellular energy metabolism.

In one embodiment, the present application relates to the use of a compound of formula (Ia), for treating a cancer.

In one embodiment, the present application relates to the use of a compound of formula (Ia), for treating a cancer, wherein the cancer is leukemia, non-small cell lung cancer, hepatocellular carcinoma, or glioblastoma.

In one embodiment, the present application relates to the use of a compound of formula (Ia), for treating glioblastoma, wherein the glioblastoma is giant cell glioblastoma or gliosarcoma.

In one embodiment, the present application relates to the use of a compound of formula (Ia), for treating an infectious disease.

In one embodiment, the present application relates to the use of a compound of formula (Ia), for treating a disease characterized by aberration of cellular energy metabolism.

In one embodiment, the present application relates to the use of a compound of formula (Ia), for treating a disease characterized by aberration of cellular energy metabolism, wherein the disease characterized by aberration of cellular energy metabolism is obesity.

In one embodiment, the present application relates to the use of a compound of formula (Ia) in the manufacture of a medicament for treating a cancer, infectious disease, or a disease characterized by aberration of cellular energy metabolism.

In one embodiment, the present application relates to the use of a compound of formula (Ia) in the manufacture of a medicament for treating a cancer.

In one embodiment, the present application relates to the use of a compound of formula (Ia) in the manufacture of a medicament for treating a cancer, wherein the cancer is leukemia, non-small cell lung cancer, hepatocellular carcinoma, or glioblastoma.

In one embodiment, the present application relates to the use of a compound of formula (Ia) in the manufacture of a medicament for treating glioblastoma, wherein the glioblastoma is giant cell glioblastoma or gliosarcoma.

In one embodiment, the present application relates to the use of a compound of formula (Ia) in the manufacture of a medicament for treating an infectious disease.

In one embodiment, the present application relates to the use of a compound of formula (Ia) in the manufacture of a medicament for treating a disease characterized by aberration of cellular energy metabolism.

In one embodiment, the present application relates to the use of a compound of formula (Ia) in the manufacture of a medicament for treating a disease characterized by aberration of cellular energy metabolism, wherein the disease characterized by aberration of cellular energy metabolism is obesity.

In one embodiment, the present application relates to a pharmaceutical composition comprising a compound of formula (Ia) together with a pharmaceutically acceptable excipient and/or diluent.

In one embodiment, the present application relates to a pharmaceutical composition comprising a compound of formula (Ia) together with a pharmaceutically acceptable excipient and/or diluent, in the form of tablets, capsules, oral preparations, powders, granules, pills, injectable or infusible liquid, solutions, suspensions, emulsions, suppositories, ointments, creams, lotions, gels, pastes, transdermal delivery devices.

In one embodiment, the present application relates to a pharmaceutical composition comprising a compound of formula (Ia) together with a pharmaceutically acceptable excipient and/or diluent, further comprising at least one therapeutic agent, selected from the group consisting of histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, Selective COX-2 inhibitors or a chemotherapeutic agent.

In one embodiment, the present application relates to a pharmaceutical composition comprising a compound of formula (Ia) together with a pharmaceutically acceptable excipient and/or diluent, further comprising at least one therapeutic agent, selected from the group consisting of histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, Selective COX-2 inhibitors or a chemotherapeutic agent, in the form of tablets, capsules, oral preparations, powders, granules, pills, injectable or infusible liquid, solutions, suspensions, emulsions, suppositories, ointments, creams, lotions, gels, pastes, transdermal delivery devices.

In one embodiment, the above mentioned compounds of the application are for medical use.

In one embodiment, the application provides the compounds of general formula (I) or (Ia) for use as KDM1 inhibitors.

In one embodiment, the compounds of the application of formula (I) or (Ia) are reversible KDM1 inhibitors. In another embodiment, the application provides the compounds of general formula (I) or (Ia) for the use in the treatment and/or prevention of cancer, infectious diseases or a disease characterized by aberration of cellular energy metabolism, such as obesity. In one embodiment, the compounds of general formula (I) or (Ia) are for the use in the treatment and/or prevention of leukemia, non-small cell lung cancer, hepatocellular carcinoma, or glioblastoma.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human.

In the present application, and as it relates to the compounds of the application, "aryl" represents a mono or bicyclic aromatic ring system of, respectively, 6, 9 or 10 atoms, examples of such an aryl are phenyl, indenyl, indanyl and naphthyl and tetrahydronaphthalenyl. Substituted aryl means that at least one hydrogen atom on a carbon atom is replaced by a substituent as defined herein.

"Heteroaryl" represents a mono or bicyclic heteroaromatic ring system of, respectively, 5 to 10 members, which contains one, two, three or four heteroatoms selected from nitrogen, oxygen or sulphur and one to nine carbon atoms. Examples of said heteroaryls include, but are not limited to: pyrrolyl, furyl, thienyl, pyrazolyl, imidazolyl, oxazolyl, thiazolyl, 1,2,3-oxadiazolyl, 1,3,4-thiadiazolyl, tetrazolyl, pyridyl, pyridazinyl, pyrimidinyl, pyrazinyl, indolyl, isoindolyl, benzo[b]furanyl, benzo[b]thienyl, benzopyranyl, indazolyl, benzimidazolyl, purinyl, quinolyl, isoquinolyl, quinazolinyl, and quinoxalinyl. Substituted heteroaryl means that at least one hydrogen atom on a carbon atom or heteroatom is replaced by a substituent as defined herein.

"Heterocyclyl" represents a mono, bicyclic or a spirocyclic saturated or partially saturated non-aromatic ring system of, respectively, 4 to 12 members, which contains one, two, or three heteroatoms selected from nitrogen, oxygen, and sulphur and three to eleven carbon atoms. Examples of such heterocycles include, but are not limited to: pyrrolidyl, pyrrolidinyl, piperidyl, piperidinyl, piperazinyl, tetrahydrofuranyl, tetrahydropyranyl, morpholinyl, thiomorpholinyl, tetrahydroquinolinyl, tetrahydroisoquinolinyl, tetrahydroquinoxalinyl, benzodioxolyl, 2,3-dihydro-benzodioxinyl, benzoxazolyl, azetidyl, azepinyl, and diazapinyl. Examples of bicyclic ring systems include, but are not limited to, 2-aza-bicyclo[2.2.1]heptanyl, 2,5-diaza-bicyclo[2.2.1]hept-2-yl or 8-azabicyclo[3.2.1]octanyl. Examples of spirocyclic ring systems include, but are not limited to, 3,8-diazaspiro [4.5]decane. Substituted heterocyclyl means that one or two hydrogen atoms on a carbon atom or heteroatom is replaced by a substituent as defined herein.

The term "$C_1$-$C_6$ alkyl" refers to a straight or branched hydrocarbon chain radical, consisting solely of carbon and hydrogen atoms, having from one to six carbon atoms. In one embodiment, the "$C_1$-$C_6$ alkyl" group is a linear or branched $C_1$-$C_4$ alkyl group. In one embodiment, a $C_1$-$C_2$ alkyl group. Suitable examples of $C_1$-$C_6$ alkyl include methyl, ethyl, n-propyl, isopropyl, butyl, tert-butyl, pentyl, and hexyl. The term "$C_1$-$C_4$ alkyl" refers to a straight or branched hydrocarbon chain radical, consisting solely of carbon and hydrogen atoms, having from one to four carbon atoms.

The term "$C_{3-7}$ cycloalkyl" refers to a saturated monocyclic hydrocarbon ring system having three to seven carbon atoms. Suitable examples of $C_{3-6}$-cycloalkyl groups include cyclopropyl, cyclobutyl, cyclopentyl, and cyclohexyl.

Substituted $C_{3-7}$ cycloalkyl means that one or two hydrogen atoms on independently each carbon atom may be independently replaced by a substituent as defined herein.

The term "$C_1$-$C_6$ alkoxy" refers to a straight or branched O—$C_1$-$C_6$ alkyl, where alkyl is as defined herein. In one embodiment, the "$C_1$-$C_6$ alkoxy" group is a linear or branched $C_1$-$C_4$ alkoxy group. In one embodiment, a $C_1$-$C_2$ alkoxy group.

The term "$C_1$-$C_6$-alkylamino" refers to a straight or branched —NH—$C_1$-$C_6$ alkyl, where $C_1$-$C_6$ alkyl is as defined herein.

The term "halogen" refers to fluoro, chloro, bromo, or iodo. In one embodiment, "halogens" include fluoro, chloro or bromo. In one embodiment, halogen is fluoro or chloro.

"Leaving group" refers to halogen, In one embodiment, chloride, bromide or iodide.

"Reversible inhibitor" is an inhibiting molecular entity that interacts with an enzyme by non-covalent interactions and is able to associate/dissociate to the enzyme.

Pharmaceutically acceptable salts refers to those compounds, materials, compositions, and/or carriers which are, within the scope of sound medical judgment, suitable for use in contact with the tissues of human beings and animals without excessive toxicity, irritation, allergic response, or other problem or complication, commensurate with a reasonable benefit/risk ratio and comprise conventional non-toxic salts obtained by salification of a compound of formula (I) or (Ia) with inorganic acids (e.g. hydrochloric, hydrobromic, sulphuric, or phosphoric acids), or with organic acids (e.g. acetic, propionic, succinic, benzoic, sulfanilic, 2-acetoxy-benzoic, cinnamic, mandelic, salicylic, glycolic, lactic, oxalic, malic, maleic, malonic, fumaric, tartaric, citric, p-toluenesulfonic, methanesulfonic, ethanesulfonic, or naphthalensulfonic acids). For reviews on suitable pharmaceutical salts see Berge S. M. et al., J. Pharm. Sci. 1977, 66, 1-19; Gould P. L. Int. J. Pharm 1986, 33, 201-217; and Bighley et al. Encyclopedia of Pharmaceutical Technology, Marcel Dekker Inc, New York 1996, Volume 13, page 453-497. Other salts, which are not pharmaceutically acceptable, for example the trifluoroacetate salt, may be useful in the preparation of compounds of this application and these form a further aspect of the application. The application includes within its scope all possible stoichiometric and non-stoichiometric forms of the salts of the compounds of formula (I) or (Ia).

In addition, the compounds of formula (I) or (Ia) may exist in unsolvated as well as in solvated forms with pharmaceutically acceptable solvents such as water, EtOH and the like.

Certain compounds of formula (I) or (Ia) may exist in stereoisomeric forms (e.g. they may contain one or more asymmetric carbon atoms). The individual stereoisomers (enantiomers and diastereomers) and mixtures of these are included within the scope of the present application. The present application also covers the individual isomers of the compounds represented by formula (I) or (Ia) as mixtures with isomers thereof in which one or more chiral centres are inverted.

The application also includes all suitable isotopic variations of a compound of the application. Examples of isotopes that can be incorporated into compounds of the application include isotopes such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the application, for example, those in which a radioactive isotope such as $^3H$ or $^{14}C$ is incorporated, are useful in drug and/or substrate tissue distribution studies. Further, substitution with isotopes such as deuterium $^2H$, may afford certain therapeutic advantages resulting from greater metabolic stability. Isotopic variations of the compounds of the application can generally be prepared by conventional procedures such as by the illustrative methods or by the preparations described in the examples hereafter using appropriate isotopic variations of suitable reagents.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$.

Combinations of substituents and/or variables are permissible, but only if such combinations result in stable compounds.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

A3 or A4 by reaction of a compound of formula A1 or A2 with $R^2$-LG or $R^3$-LG, where $R^2$ and $R^3$ are as defined herein and LG is a leaving group, for example bromide or iodide, and in presence of a base, the hydrolysis of a compound of formula A3 or A4 to the carboxylic acids of formula A5 or A6, and the condensation of a compound of formula A5 or A6 with an amine A7 to obtain a compound of formula (Ia), as represented in Scheme A below:

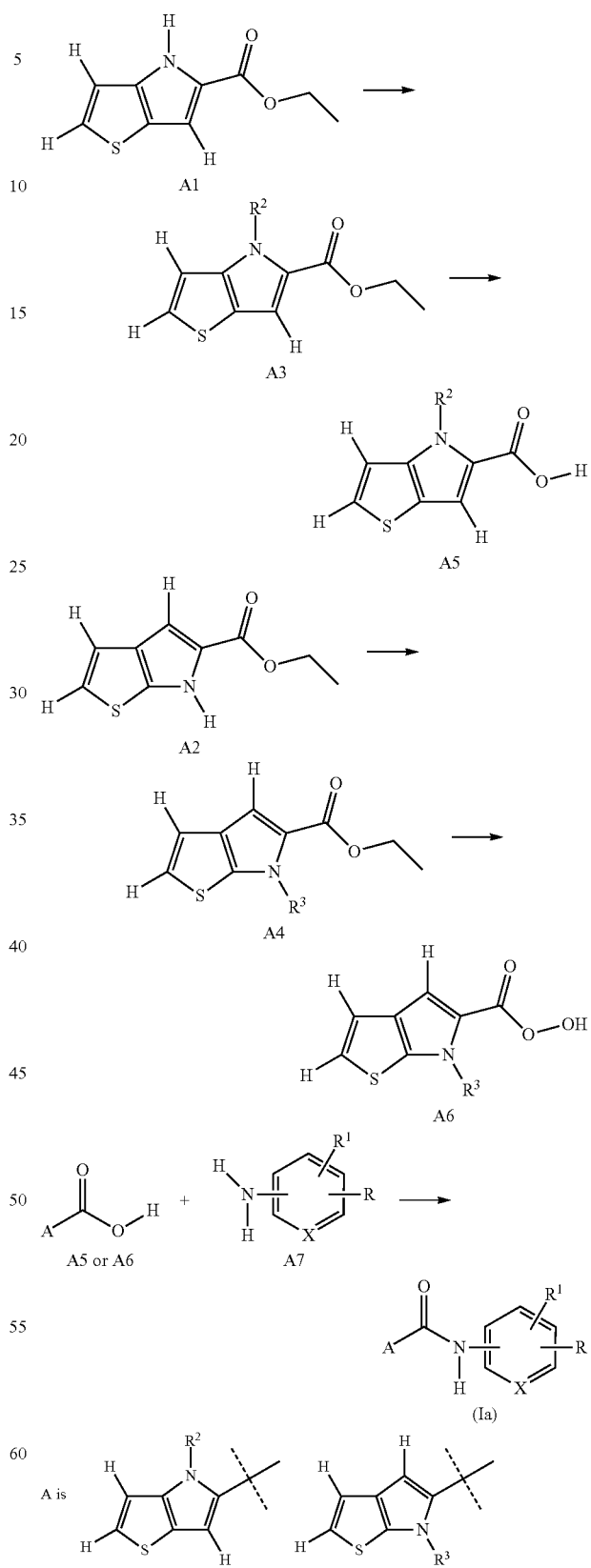

wherein X, R, $R^1$, $R^2$, and $R^3$ are as defined herein.

Ethyl 4H-thieno[3,2-b]pyrrole-5-carboxylate (compound A1, Fluorochem, Cat No. 067104) and ethyl 6H-thieno[2,3-b]pyrrole-5-carboxylate (compound A2, Sigma Aldrich, cat. number PH011284) are commercially available. Compound A1 or A2 can be alkylated with a suitable alkylhalide $R^2$-LG or $R^3$-LG, where $R^2$ and $R^3$ are as defined herein and LG is a leaving group, for example bromide or iodide, in presence of a suitable base, such as NaH, in a suitable solvent, such as DMF, at a temperature ranging from about 0° C. to about 50° C.

The ethyl ester group of a compound of formula A3 or A4 can be hydrolysed into a carboxylic acid of formula A5 or A6 according to known methods, e.g., by treatment with a base, such as LiOH or NaOH, in a suitable solvent, for example in ethanol, in THF, in an ethanol/water or in a dioxane/water mixture. The hydrolysis of the ethyl ester can be carried out at a temperature ranging from 0° C. to the boiling point of the solvent.

The reaction of a compound of formula A5 or A6 with a compound of formula A7 can be carried out according to methods well known to a person skilled in the art for the preparation of carboxamido derivatives. For example, the carboxylic acid of formula A5 or A6 is converted into a suitable acylating agent, such as an acyl chloride, which is then treated with a compound of formula A7. The coupling reaction is carried out in a suitable solvent such as polar aprotic solvents, for instance, tetrahydrofuran, 1,4-dioxane, dimethylformamide, dichloromethane, or mixtures thereof, at a temperature ranging from about 0° C. to reflux and for a time varying from about 30 minutes up to 96 hours, if needed in the presence of a suitable base, such as triethylamine, N,N'-diisopropylethylamine or pyridine.

Alternatively, a compound of formula (Ia), wherein R is $L^1$-$R^4$, L as defined herein, $R^4$ is aryl or heteroaryl substituted by $L^2$-$R^7$, $L^2$ is —$(CH_2)_n$—W—$(CH_2)_o$—; W is oxygen, n is zero and o and $R^7$ are as defined herein, can be obtained by the condensation of a compound of formula A5 or A6 with an amine B1 to obtain a hydroxyl derivative B2, which is then treated with an alcohol B3 to obtain a compound of formula (Ia), as represented in Scheme B below:

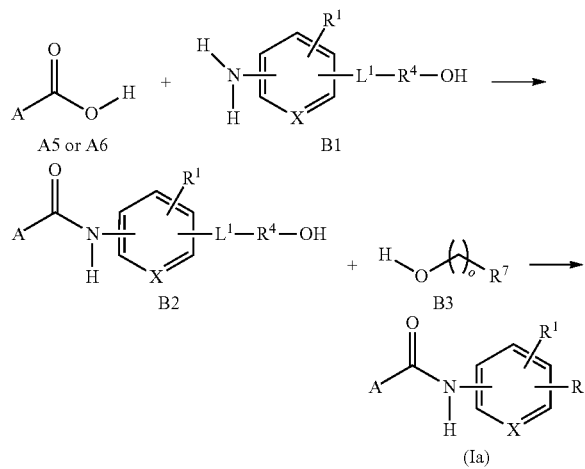

wherein A, o, X, $R^1$, and $R^7$ are as defined herein and $R^4$ is aryl or heteroaryl.

The reaction of a carboxylic acid of formula A5 or A6 with a compound of formula B1 can be carried out as described herein for the reaction a compound of formula A5 or A6 with a compound of formula A7. The reaction of a compound of formula B2 with an alcohol B3 can be carried out under the standard conditions of the Mitsunobu reaction, for instance by reaction with triphenylphosphine and diethylazodicarboxylate, at a temperature ranging from about 0° C. to 80° C., in a suitable solvent, such as tetrahydrofuran or toluene, for a time varying from about 30 min up to 72 h.

Compounds of formula A7, B1, and B3 are known compounds or can be prepared by known methods.

For instance, a compound of formula B1, wherein X is as defined herein, $L^1$ is —$(CH_2)_j$—Y—, j is 1, Y is oxygen and $R^4$ is phenyl, can be obtained by reaction of a compound of formula C1 with a diol derivative of formula C2 providing a nitro derivative of formula C3, which can be reduced to a compound of formula B1, as represented in Scheme C below:

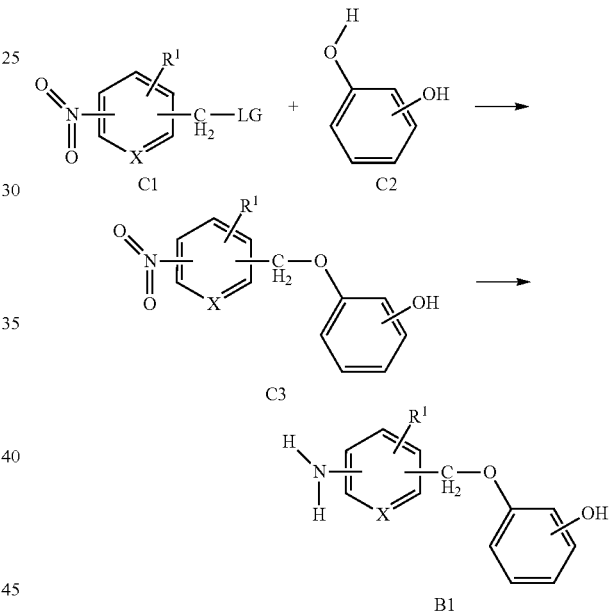

wherein $R^1$ and LG are as defined herein.

Compounds of formula C1 are known compounds or can be prepared by known methods. Reaction between a of formula C1 with a diol derivative of formula C2 can be carried out at a temperature ranging from about 0° C. to the boiling temperature of the solvent, in a suitable solvent, such as acetone, for a time varying from about 30 min up to 48 h. Reduction of the nitro group of a compound of formula C3 can be carried out in an appropriate organic solvent, such as an alcohol, in the presence of a catalyst, for example Pd/C or $PtO_2$ at a pressure ranging from atmospheric pressure to 100 bars at a temperature ranging from RT to the boiling temperature of the solvent.

In the case it is necessary to protect a chemical group of a compound of the present application and/or an intermediate thereof, before carrying out one of the reactions described herein, said chemical group can be protected and deprotected according to known methods. A thorough discussion for protection/deprotection steps is provided for example in Greene and Wuts (Greene, T. W.; Wuts, P. G. M.

"Protective Groups in Organic Synthesis", John Wiley & Sons Inc., 2006) or in Kocienski (Kocienski, P. J. "Protecting Groups", George Thieme Verlag, 2005).

Salification of the compounds of formula (I) or (Ia), and preparation of compounds of formula (I) or (Ia), free of their salts, can be carried out by known conventional methods.

The KDM1A inhibiting activity of the compounds of the application was determined using a TR-FRET assay (time resolved fluorescence resonance energy transfer, Lance® Ultra Demethylase technology (Perkin Elmer, Waltham, Mass., USA)), which comprises a Europium chelate donor dye (TRF0404, Perkin Elmer, Waltham, Mass., USA) together with ULight™ (TR0102, Perkin Elmer, Waltham, Mass., USA), a small molecular weight acceptor dye with a red-shifted fluorescent emission, and a biotinylated 21 amino acids histone H3-derived monomethylated peptide (H3K4me) [Lys(Mel)4]-Histone H3 (1-21)-GGK(biotin), (64355, Anaspec, Fremont, Calif., USA) as substrate. The intensity of the light emission is proportional to the level of biotinylated reaction product. The complex of human recombinant KDM1A/CoREST protein was produced in *E. coli* as separate proteins and co-purified as previously described. (Forneris, F. et al. Trends Biochem, Sci, 2008, 33, 181-189) (Forneris, F. et al. J. Biol. Chem. 2007, 282, 20070-20074). Compounds 1-46, 49-55, and 58-68 exhibit $IC_{50}$ values of less than 10 µM, examples 47, 48, and 56 exhibit $IC_{50}$ values of less than 25 µM, example 57 exhibits an $IC_{50}$ value of less than 50 M.

The CellTiter-Fluor™ Cell Viability Assay measures the conserved and constitutive protease activity within live cells and therefore acts as a marker for cell viability. Compounds 1-21, 49-55 and 61-63 exhibit $IC_{50}$ values of less than 10 µM against human leukemia MV4-11 cells and $IC_{50}$ values of less than 20 µM against human leukemia NB4 cells.

The MAO Glo Assay from Promega (cat. V1402, Promega, Madison, Wis.) was used to measure the effect of inhibitors on MAO A and MAO B activity. Compounds 1-17, 19, 22, 26, 38, 42-45, 50, 52-53, 55, 61-62, 66 and 68 were at least 10 times more active against KDM1A (LSD1) compared to both MAO A and MAO B, compounds 18, 20-21, 30, 35, 46-48 were at least 5 times more active against KDM1A (LSD1) compared to both MAO A and MAO B.

In view of the above described mechanisms of action, the compounds of the present application may be useful in the prevention or treatment of tumor type diseases, including but not limited to: acute and chronic myeloid leukaemia, acute and chronic lymphoblastic leukaemia, myelodysplastic syndromes, multiple myeloma, Hodgkin's disease, non-Hodgkin's lymphomas, cutaneous and peripheral T-cell lymphoma, adult T-cell leukemia, large B-cell lymphoma; mammary tumors; pulmonary tumors and pleural mesotheliomas, adenocarcinoma, non-small lung cancer, small-cell lung cancer; skin tumors including basal cell carcinomas (basaliomas), melanomas, squamous cell carcinoma, Kaposi's sarcoma, keratocanthomas, osteosarcomas, fibrosarcomas, rhabdomyosarcomas, neuroblastomas, glioblastomas, cerebral tumors, head and neck cancer, testicular and ovarian tumors, cervical carcinoma, endometrial and prostate tumors (for example advanced prostate cancer), thyroid carcinomas (for example thyroid follicular cancer), colon cancers (for example colon adenocarcinoma, colon adenoma), gastric tumors and gastrointestinal adenocarcinomas, hepatocellular carcinomas, pancreatic carcinomas (for example exocrine pancreatic carcinoma), renal tumors, teratocarcinomas and embryonic carcinomas.

In one embodiment, the compounds of the application may be useful in the prevention or treatment of infections, including, but not limited to, infections caused by protozoa, fungi, phytotoxic agents, viruses and parasites, for example HIV or herpes virus infections.

In one embodiment, the compounds of the application may be useful in the prevention or treatment of obesity.

The compounds of formula (I) or (Ia), can also be used in combination with additional agents, in particular anti-tumor and differentiating agents, either by separate administrations, or by including the two active agents in the same pharmaceutical formulation. Non-exhaustive examples of suitable additional agents include:

a) histone deacetylase inhibitors (for example, but not limited to SAHA, PXD101, JNJ-26481585, SB939, ITF-2357, LBH589, PCI-24781, valproic acid, butyric acid, MS-275, MGCD0103 and FK-228);

b) retinoid receptor modulators such as 13-cis-retinoic acid, 9-cis-retinoic acid, bexarotene, alitretinoin, or tretinoin; vitamin D;

c) antiproliferative/antineoplastic drugs and combinations thereof, as used in medical oncology, such as alkylating agents (for example platin derivatives like cis-platin, carboplatin, oxaliplatin, lobaplatin, satraplatin, nedaplatin, heptaplatin; nitrogen mustard such as chlorambucil, melphalan, chlormethine, cyclophosphamide, ifosfamide, trofosfamide, uramustine, bendamustine, estramustine; busulphan, temozolomide or nitrosoureas); antimetabolites (for example antifolates such as aminopterin, methotrexate, pemetrexed, raltitrexed); purines such as cladribine, clofarabine, fludarabine, mercaptopurine, pentostatin, thioguanine; pyrimidines like capecitabine, cytarabine, fluorouracil, floxuridine, gemcitabine; azacitidine, decitabine; cytosine arabinoside or hydroxyurea; antitumour antibiotics (for example anthracyclines like aclarubicin, amrubicin, daunomycin, doxorubicin, epirubicin, idarabicin, valrubicin, zorubicine; mitoxantrone; or antibiotics from *streptomyces* like actinomycin, bleomycin, mitomycin, or plicamycin); antimitotic agents (for example vinca alkaloids like vincristine, vinblastine, vindesine or vinorelbine; taxoids like docetaxel, paclitaxel or tesetaxel; epothilones like ixabepilone) and topoisomerase inhibitors (for example epipodophyllotoxins like etoposide and teniposide; amsacrine, camptothecin, irinotecan, rubitecan, and topotecan);

d) cytostatic agents such as antioestrogens (for example but not limited to tamoxifen, toremifene, raloxifene, droloxifene and idoxifene), oestrogen receptor down regulators (for example but not limited to fulvestrant), antiandrogens (for example but not limited to bicalutamide, flutamide, nilutamide, liarozole or cyproterone acetate), LHRH antagonists or LHRH agonists (for example but not limited to goserelin, leuprorelin or buserelin), progestogens (for example but not limited to megestrol acetate), aromatase inhibitors (for example but not limited to anastrozole, letrozole, vorazole and exemestane) and inhibitors of 5-alpha-reductase such as finasteride;

e) agents which inhibit cancer cell invasion (for example metalloproteinase inhibitors and inhibitors of urokinase plasminogen activator receptor function);

f) inhibitors of growth factor function, for example growth factor antibodies, growth factor receptor antibodies (for example but not limited to the anti-erbb2 antibody trastuzumab, the anti-erbb1 antibody cetuximab and panitumumab, the anti IGF1R antibody figitumumab), famesyl transferase inhibitors, MEK inhibitors, tyrosine kinase inhibitors and serine/threonine kinase inhibitors, for example enzastaurin, dasatinib, erlotinib, gefitinib, imatinib, lapatinib, nilotinib, sorafenib, sunitinib, everolimus, sirolimus or temsirolimus;

g) antiangiogenic agents such as those which inhibit the effects of vascular endothelial growth factor, for example the anti-vascular endothelial cell growth factor antibody bevacizumab, lenalidomide or thalidomide;

h) cell cycle inhibitors including for example CDK inhibitors (for example but not limited to flavopiridol, roscovitine) and other inhibitors of cell cycle checkpoints; inhibitors of aurora kinase and other kinases involved in mitosis and cytokinesis regulation;

i) proteasome inhibitors (for example but not limited to lactacystin, bortezomib, epoxomicin);

j) HSP90 inhibitors (for example but not limited to AT-13387, KOS-953, KOS-1022, CNF-1010, CNF-2024, SNX 5422, STA-9090, NVP-HSP990, NVP-AUY922, PU-H17 and XL-888)

k) Selective COX-2 inhibitors (for example but not limited to celecoxib), or non selective NSAIDs (for example but not limited to diclofenac, flurbiprofen, ibuprofen, ketoprofen, or naproxen).

In another aspect, a compound of general formula (I) can be used in combination with radiation therapy. In yet another aspect, a compound of general formula (I) may be administered in combination with standard chemotherapy combinations such as, but not restricted to, CMF (cyclophosphamide, methotrexate and 5-fluorouracil), CAF (cyclophosphamide, doxorubicin and 5-fluorouracil), AC (doxorubicin and cyclophosphamide), FEC (5-fluorouracil, epirubicin, and cyclophosphamide), ACT or ATC (doxorubicin, cyclophosphamide, and paclitaxel), or CMFP (cyclophosphamide, methotrexate, 5-fluorouracil and prednisone).

The application also provides pharmaceutical compositions comprising one or more compounds of formula (I) or (Ia), and one or more pharmaceutically acceptable excipients and/or diluents. The type of pharmaceutical composition can be chosen on the basis of the treatment requirements. Such compositions are prepared by blending and are suitably adapted to oral or parenteral administration, and as such can be administered in the form of tablets, capsules, oral preparations, powders, granules, pills, injectable or infusible liquid, solutions, suspensions, emulsions, suppositories, ointments, creams, lotions, gels, pastes, transdermal delivery devices.

Tablets and capsules for oral administration are normally presented in unit dose form and contain conventional excipients such as binders, fillers (including cellulose, mannitol, lactose), diluents, tableting agents, lubricants (including magnesium stearate), detergents, disintegrants (e.g. polyvinylpyrrolidone and starch derivatives such as sodium glycolate starch), coloring agents, flavoring agents, and wetting agents (for example sodium lauryl sulfate).

The oral solid compositions can be prepared by conventional methods of blending, filling or tableting. The blending operation can be repeated to distribute the active principle throughout compositions containing large quantities of fillers. Such operations are conventional.

Oral liquid preparations can be in the form of, for example, aqueous or oily suspensions, solutions, emulsions, syrups or elixirs, or can be presented as a dry product for reconstitution with water or with a suitable vehicle before use. Such liquid preparations can contain conventional additives such as suspending agents, for example sorbitol, syrup, methyl cellulose, gelatin, hydroxyethyl cellulose, carboxymethyl cellulose, aluminium stearate gel, or hydrogenated edible fats; emulsifying agents, such as lecithin, sorbitan monooleate, or acacia; non-aqueous vehicles (which can include edible oils), such as almond oil, fractionated coconut oil, oily esters such as esters of glycerine, propylene glycol, or ethyl alcohol; preservatives, such as methyl or propyl p-hydroxybenzoate or sorbic acid, and if desired, conventional flavoring or coloring agents. Oral formulations also include conventional slow-release formulations such as enterically coated tablets or granules.

Pharmaceutical preparation for administration by inhalation can be delivered from an insufflator or a nebulizer pressurized pack.

For parenteral administration fluid unit dosages can be prepared, containing the compound and a sterile vehicle. The compound can be either suspended or dissolved, depending on the vehicle and concentration. The parenteral solutions are normally prepared by dissolving the compound in a vehicle, sterilising by filtration, filling suitable vials and sealing. Advantageously, adjuvants such as local anaesthetics, preservatives and buffering agents can also be dissolved in the vehicle. To increase the stability, the composition can be frozen after having filled the vials and removed the water under vacuum. Parenteral suspensions are prepared in substantially the same manner, except that the compound can be suspended in the vehicle instead of being dissolved, and sterilized by exposure to ethylene oxide before suspending in the sterile vehicle. Advantageously, a surfactant or wetting agent can be included in the composition to facilitate uniform distribution of the compound of the application.

For buccal or sublingual administration the compositions may be tablets, lozenges, pastilles, or gel.

The compounds can be pharmaceutically formulated as suppositories or retention enemas, e.g. containing conventional suppositories bases such as cocoa butter, polyethylene glycol, or other glycerides, for a rectal administration.

Another means of administering the compounds of the application regards topical treatment. Topical formulations can contain for example ointments, creams, lotions, gels, solutions, pastes and/or can contain liposomes, micelles and/or microspheres. Examples of ointments include oleaginous ointments such as vegetable oils, animal fats, semisolid hydrocarbons, emulsifiable ointments such as hydroxystearin sulfate, anhydrous lanolin, hydrophilic petrolatum, cetyl alcohol, glycerol monostearate, stearic acid, water soluble ointments containing polyethylene glycols of various molecular weights. Creams, as known to formulation experts, are viscous liquids or semisolid emulsions, and contain an oil phase, an emulsifier and an aqueous phase. The oil phase generally contains petrolatum and an alcohol such as cetyl or stearic alcohol. Formulations suitable for topical administration to the eye also include eye drops, wherein the active ingredient is dissolved or suspended in a suitable carrier, especially an aqueous solvent for the active ingredient.

A further method of administering the compounds of the application regards transdermal delivery. Typical transdermal formulations comprise conventional aqueous and non-aqueous vectors, such as creams, oils, lotions or pastes or can be in the form of membranes or medicated patches.

A reference for the formulations is the book by Remington ("Remington: The Science and Practice of Pharmacy", Lippincott Williams & Wilkins, 2000).

The compounds of the present application may be employed alone as a sole therapy or in combination with other therapeutic agents for the treatment of the above-mentioned conditions. The combination can be administered as separate compositions (simultaneous, sequential) of the individual components of the treatment or as a single dosage form containing both agents. When the compounds of this application are in combination with others active ingredients, the active ingredients may be separately formulated into single-ingredient preparations of one of the above-described forms and then provided as combined preparations, which are given at the same time or different times, or may be formulated together into a two- or more-ingredient preparation.

As is common practice, the compositions are normally accompanied by written or printed instructions for use in the treatment in question.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The application having now been described by way of written description, those of skill in the art will recognize that the application can be practiced in a variety of embodiments and that the foregoing description and examples below are for purposes of illustration and not limitation of the claims that follow.

The following examples and biological data are presented in order to further illustrate the application.

EXAMPLES

Example 1: Chemical Synthesis

Unless otherwise indicated, commercially available reagents and solvents (HPLC grade) were used without further purification. (R)-1-Boc-3-pyrrolidinemethanol was obtained from Alfa Aesar (Cat. No. H57217), (S)-1-Boc-3-pyrrolidinemethanol from Alfa Aesar (Cat. No. H57753), 1-Boc-3-pyrrolidinemethanol was from Sigma Aldrich (Cat. No. ADE000016), 1-Boc-4-hydroxypiperidine from Sigma Aldrich (Cat. No. 495484), 1-Boc-3-hydroxypiperidine from Fluorochem (Cat. No. 021286), 1-Boc-4-piperidinemethanol from Sigma Aldrich (Cat. No. 556017), 1-Boc-4-hydroxyazepane from Enamine Ltd. (Cat. No. EN300-154246), trans-4-Boc-aminocyclohexanol from Fluorochem (Cat. No. 024189), cis-4-Boc-aminocyclohexanol from Alfa Aesar (Cat. No. H62238), tert-butyl 3-endo-3-hydroxy-8-azabicyclo[3.2.1]octane-8-carboxylate from Fluorochem (Cat. No. 215197), 3-(4-pyridylmethoxy)aniline from Enamine Ltd. (Cat. No. EN300-68966), 3-(methoxymethyl)aniline from Enamine Ltd. (Cat. No. EN300-31924), ethyl 4H-thieno[3,2-b]pyrrole-5-carboxylate from Fluorochem (Cat. No. 067104).

Specifically, the following abbreviations may have been used in the descriptions of the experimental methods:

| | |
|---|---|
| NMR (Nuclear Magnetic Resonance) | $^1$H (proton) |
| MHz (Megahertz) | Hz (Hertz) |
| HPLC (High Performance Liquid Chromatography) | LC-MS (Liquid Chromatography Mass Spectrum) |
| s (seconds) | min (minutes) |
| h (hours) | mg (milligrams) |
| g (grams) | μL (microliters) |
| mL (milliliters) | mmol (millimoles) |
| nm (nanometers) | μM (micromolar) |
| M (molarity) | RT (room temperature) |
| BOC or boc (tert-butyloxycarbonyl) | (BOC)$_2$O (di-tert-butyl dicarbonate) |
| CBr$_4$ (carbon tetrabromide) | CH$_2$Cl$_2$ (dichloromethane) |
| CH$_3$CN (acetonitrile) | DIAD (diisopropyl azodicarboxylate) |
| DMA (dimethylacetamide) | DMAP (dimethylaminopyridine) |
| DMF (dimethylformamide) | DMSO (dimethyl sulfoxide) |
| DMSO-d$_6$ (deuterated dimethyl sulfoxide) | DTT (dithiothreitol) |
| Et$_2$O (diethyl ether) | EtOAc (ethyl acetate) |
| EtOH (ethanol) | HCl (hydrochloric acid) |
| LiHMDS ([bis(trimethylsilyl)amino]lithium) | LiOH (lithium hydroxide) |
| K$_2$CO$_3$ (potassium carbonate) | MAO A (monoamine oxidase A) |
| MAO B (monoamine oxidase B) | MeOH (methanol) |
| NaBH$_4$ (sodium borohydride) | NaBH(OAc)$_3$ (sodium triacetoxyborohydride) |
| NaH (sodium hydride) | NBS (1-bromopyrrolidine-2,5-dione)_ |
| NaCl (sodium chloride) | NaHCO$_3$ (sodium bicarbonate) |
| Na$_2$SO$_4$ (sodium sulphate) | NH$_3$ (ammonia) |
| NH$_4$Cl (ammonium chloride) | PPh$_3$ (triphenylphosphine) |
| TEA (triethylamine) | THF (tetrahydrofuran) |
| Tris (tris(hydroxymethyl)aminomethane) | Pd(dba)$_2$ (bis(dibenzylideneacetone)palladium(0)) |

Except where indicated otherwise, all temperatures are expressed in ° C. (degrees centigrade) or K (Kelvin).

The $^1$H-NMR spectra were acquired with a Varian 500 MHz instrument. The chemical shifts are expressed in parts per million (ppm, δ units). The coupling constants are expressed in Hertz (Hz) and the splitting patterns are described as s (singlet), bs (broad signal), d (doublet), t (triplet), q (quartet), quint (quintet), m (multiplet).

The LC-MS analyses were carried out on a Waters Acquity UPLC or Waters Acquity UPLC H-Class linked to with a SQD Single quadrupole (Waters) using an Acquity UPLC BEH C18 (50×2.1 mm, 1.7 m) or Acquity UPLC HSS T3 (50×2.1 mm, 1.8 μm) column. Phase A was composed by either Milli-Q water/CH$_3$CN 95/5+0.07% formic acid or Milli-Q water+0.07% formic acid; Phase B by CH$_3$CN+0.05% formic acid; flow rate: 0.6 mL/min; UV detection (DIODE array) from 210 to 400 nm; ESI+ detection in the 100-2000 m/z range. The yields were calculated assuming that products were 100% pure if not stated otherwise.

Intermediate 1: 4-Methylthieno[3,2-b]pyrrole-5-carboxylic acid

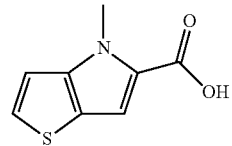

Ethyl 4-methylthieno[3,2-b]pyrrole-5-carboxylate 1.5 g (7.7 mmol) of ethyl 4H-thieno[3,2-b]pyrrole-5-carboxylate (Fluorochem, Cat No. 067104) was added at RT portion wise to a suspension of 0.46 g (12 mmol) of NaH in 35 mL of dry DMF. After stirring for 20 min at RT 3.3 g (23 mmol) of CH$_3$I was added in one portion and the mixture was stirred for additional 30 min. The reaction mixture was then poured into a saturated NH$_4$Cl solution and extracted with Et$_2$O. The combined organic layers were dried over Na$_2$SO$_4$, filtered and the solvent evaporated to give 1.6 g of ethyl 4-methylthieno[3,2-b]pyrrole-5-carboxylate (99%) as a brown oil. $^1$H NMR (CDCl$_3$) δ (ppm): 7.34 (d, J=5.4 Hz, 1H), 7.20 (s, 1H), 6.95 (d, J=5.4 Hz, 1H), 4.34 (q, J=7.3 Hz, 2H), 4.07 (s, 3H), 1.39 (t, J=7.1 Hz, 3H); MS (ESI): m/z: 210 [M+H]$^+$

4-Methylthieno[3,2-b]pyrrole-5-carboxylate 0.92 g (38 mmol) of LiOH in 11 mL of H$_2$O was added at RT to a solution of 1.6 g (7.7 mmol) of ethyl 4-methyl-thieno[3,2-b]pyrrole-5-carboxylate in 11 mL of EtOH. The mixture was stirred for 30 min at reflux. The solvent was evaporated, then H$_2$O was added and the solution was brought to a pH value of about 2 with 2 M HCl. The mixture was extracted with EtOAc, the combined organic layers were dried over Na$_2$SO$_4$ and the solvent was evaporated to give 1.39 g of 4-methylthieno[3,2-b]pyrrole-5-carboxylate (99%) as a beige solid. $^1$H NMR (CDCl$_3$) δ (ppm): 12.45 (bs, 1H), 7.54 (d, J=5.4 Hz, 1H), 7.20 (d, J=5.4 Hz, 1H), 7.12 (s, 1H), 3.99 (s, 3H); MS (ESI): m/z: 182 [M+H]$^+$

Intermediate 2: 4-Ethylthieno[3,2-b]pyrrole-5-carboxylic acid

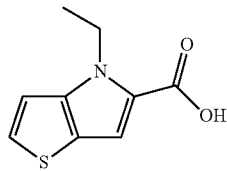

Ethyl 4-ethylthieno[3,2-b]pyrrole-5-carboxylate 1.00 g (5.12 mmol) of ethyl 4H-thieno[3,2-b]pyrrole-5-carboxylate was added at RT to a suspension of 0.31 g (7.7 mmol) of NaH in 50 mL of dry DMF. After stirring for 20 min at RT 2.39 g (15.4 mmol) of ethyliodide was added and the mixture was stirred for further 30 min at RT. The reaction mixture was then poured into a saturated NH$_4$Cl solution and extracted with Et$_2$O. The combined organic layers were dried over Na$_2$SO$_4$ and the solvent evaporated to give 1.10 g (96%) of ethyl 4-ethylthieno[3,2-b]pyrrole-5-carboxylate as a brown oil. $^1$H NMR (CDCl$_3$) δ (ppm): 7.34 (d, J=5.4 Hz, 1H), 7.20 (s, 1H), 6.96 (d, J=5.4 Hz, 1H), 4.56 (q, J=7.3 Hz, 2H), 4.34 (q, J=7.3 Hz, 2H), 1.46-1.34 (m, 6H); MS (ESI): m/z: 224 [M+H]$^+$.

4-Ethylthieno[3,2-b]pyrrole-5-carboxylic acid 0.21 g (9.0 mmol) of LiOH in 4 mL of H$_2$O was added at RT to a solution of 0.40 g (1.8 mmol) of ethyl 4-ethylthieno[3,2-b]pyrrole-5-carboxylate in 4 mL of EtOH. The mixture was stirred for 30 min at reflux, then EtOH was evaporated, water was added and the pH was brought to about 2 with 2 M HCl. The mixture extracted with EtOAc, the combined organic layers dried over Na$_2$SO$_4$ and the solvent evaporated to give 0.35 g (quantitative) of 4-ethylthieno[3,2-b]pyrrole-5-carboxylic acid as a beige solid. $^1$H NMR (DMSO-d$_6$) δ (ppm): 12.47 (bs, 1H), 7.56 (d, J=5.4 Hz, 1H), 7.24 (d, J=5.4 Hz, 1H), 7.13 (s, 1H), 4.51 (q, J=7.3 Hz, 2H), 1.28 (t, J=7.3 Hz, 3H); MS (ESI): m/z: 196 [M+H]$^+$.

Intermediate 3: tert-Butyl 4-[4-[(2-aminophenyl)methoxy]phenoxy]piperidine-1-carboxylate

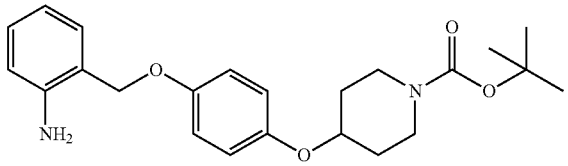 [SMILES: CC(C)(C)OC(=O)N1CCC(Oc2ccc(OCc3ccccc3N)cc2)CC1]

4-[(2-nitrophenyl)methoxy]phenol

A mixture of 6.6 g (30 mmol) of 1-(bromomethyl)-2-nitro-benzene (Fluorochem, Cat No. 002679) 16.5 g (150 mmol) hydroquinone and 6.2 g (45 mmol) K$_2$CO$_3$ in 110 mL acetone was heated at reflux until disappearance of the starting material. After 7 h, the mixture was cooled down to RT, K$_2$CO$_3$ was filtered off and the solvent was concentrated. The crude mixture was taken up in CH$_2$Cl$_2$, triturated, and the filtrate was concentrated and purified on a silica pad eluting with CH$_2$Cl$_2$ to give 4.87 g (66%) of 4-[(2-nitrophenyl)methoxy]phenol as a beige solid. $^1$H NMR (CDCl$_3$) δ (ppm): 8.20-8.14 (m, 1H), 7.95-7.88 (m, 1H), 7.72-7.66 (m, 1H), 7.53-7.45 (m, 1H), 6.92-6.76 (m, 4H), 5.44 (s, 2H), 4.44 (s, 1H); MS (ESI): m/z: 268 [M+Na]$^+$.

tert-butyl 4-[4-[(2-nitrophenyl)methoxy]phenoxy]piperidine-1-carboxylate 0.85 g (4.0 mmol) of DIAD was added dropwise to a solution of 0.49 g (2.0 mmol) of 4-[(2-nitrophenyl)methoxy]phenol, 0.83 g (4.0 mmol) of tert-butyl 4-hydroxypiperidine-1-carboxylate and 1.1 g (4.0 mmol) of PPh$_3$ in 20 mL of dry THF cooled down to 0° C. and under a N$_2$ atmosphere. The mixture was allowed to reach RT and stirred overnight. Then, the solvent was evaporated and the crude mixture was purified by flash chromatography (eluent hexane/acetone, 0% of acetone to 10% of acetone) to give 0.71 g (83%) of tert-butyl 4-[4-[(2-nitrophenyl)methoxy]phenoxy]piperidine-1-carboxylate as a yellow oil. $^1$H NMR (CDCl$_3$) δ (ppm): 8.22-8.13 (m, 1H), 7.96-7.87 (m, 1H), 7.74-7.65 (m, 1H), 7.54-7.44 (m, 1H), 6.99-6.82 (m, 4H), 5.45 (s, 2H), 4.41-4.28 (m, 1H), 3.78-3.65 (m, 2H), 3.37-3.24 (m, 2H), 1.96-1.85 (m, 2H), 1.79-1.68 (m, 2H), 1.48 (s, 9H); MS (ESI): m/z: 373 [M+H−56]$^+$.

tert-butyl 4-[4-[(2-aminophenyl)methoxy]phenoxy]piperidine-1-carboxylate 642 mg (1.50 mmol) of tert-butyl 4-[4-[(2-nitrophenyl)methoxy]phenoxy]piperidine-1-carboxylate was dissolved in 60 mL of EtOH. The solution was hydrogenated in an H-Cube apparatus (PtO$_2$ cartridge, atmospheric pressure, 70° C., flow 0.5 mL/min). The solvent was evaporated to give 587 mg (98%) of tert-butyl 4-[4-[(2-aminophenyl)methoxy]phenoxy]piperidine-1-carboxylate as a yellow oil. $^1$H NMR (CDCl$_3$) δ (ppm): 7.22-7.15 (m, 2H), 6.97-6.83 (m, 4H), 6.82-6.75 (m, 2H), 5.00 (s, 2H), 4.39-4.26 (m, 1H), 3.78-3.62 (m, 2H), 3.36-3.21 (m, 2H), 1.97-1.82 (m, 2H), 1.79-1.67 (m, 2H), 1.48 (s, 9H); MS (ESI): m/z: 399 [M+H]$^+$.

Intermediate 4: tert-butyl 4-[4-[(3-aminophenyl) methoxy]phenoxy]piperidine-1-carboxylate

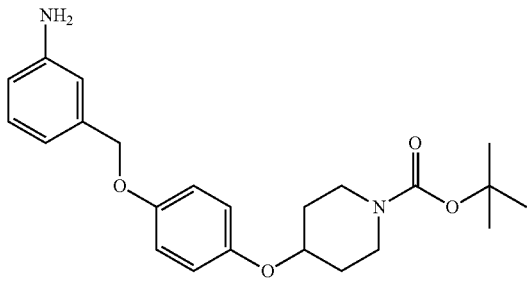 [SMILES: CC(C)(C)OC(=O)N1CCC(Oc2ccc(OCc3cccc(N)c3)cc2)CC1]

tert-butyl 4-[4-[(3-aminophenyl)methoxy]phenoxy]piperidine-1-carboxylate was prepared according to the procedure for Intermediate 3, step 2, starting from 4-[(3-nitrophenyl)methoxy]phenol and tert-butyl 4-hydroxypiperidine-1-carboxylate, providing tert-butyl 4-[4-[(3-nitrophenyl)methoxy]phenoxy]piperidine-1-carboxylate intermediate. $^1$H NMR (DMSO-$d_6$) δ (ppm): 8.29 (s, 1H), 8.22-8.15 (m, 1H), 7.93-7.86 (m, 1H), 7.75-7.66 (m, 1H), 7.01-6.86 (m, 4H), 5.19 (s, 2H), 4.45-4.34 (m, 1H), 3.70-3.57 (m, 2H), 3.21-3.01 (m, 2H), 1.89-1.77 (m, 2H), 1.55-1.42 (m, 2H), 1.39 (s, 9H); MS (ESI): m/z: 373 [M+H−56]+. Reduction of tert-butyl 4-[4-[(3-nitrophenyl)methoxy]phenoxy]piperidine-1-carboxylate to tert-butyl 4-[4-[(3-aminophenyl)methoxy]phenoxy]piperidine-1-carboxylate was carried out according to the procedure described for Intermediate 3, step 3. $^1$H NMR (DMSO-$d_6$) δ (ppm): 7.03-6.95 (m, 1H), 6.92-6.84 (m, 4H), 6.60 (s, 1H), 6.55-6.51 (m, 1H), 6.50-6.45 (m, 1H), 5.09 (s, 2H), 4.86 (s, 2H), 4.44-4.30 (m, 1H), 3.68-3.58 (m, 2H), 3.18-3.07 (m, 2H), 1.90-1.78 (m, 2H), 1.51-1.42 (m, 2H), 1.39 (s, 9H); MS (ESI): m/z: 399 [M+H]+.

Intermediate 5: 3-[[4-[(1-methyl-4-piperidyl)oxy]phenoxy]methyl]aniline

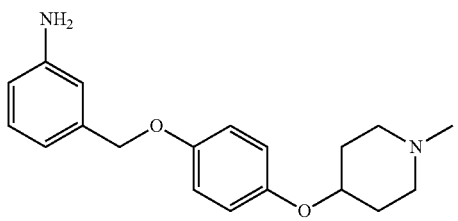 [SMILES: CN1CCC(Oc2ccc(OCc3cccc(N)c3)cc2)CC1]

4-[4-[(3-nitrophenyl)methoxy]phenoxy]piperidine 5 mL of 4 M HCl in 1,4-dioxane was added to a solution of 0.655 g (1.53 mmol) tert-butyl 4-[4-[(3-nitrophenyl)methoxy]phenoxy]piperidine-1-carboxylate (Intermediate 4, step 2) in 4 mL of dry 1,4-dioxane and the mixture was stirred at RT for 90 min. The reaction mixture was then concentrated, the residue was taken up in saturated NaHCO$_3$ solution and extracted with EtOAc. The combined organic phases were dried over Na$_2$SO$_4$ and concentrated to afford 4-[4-[(3-nitrophenyl)methoxy]phenoxy]piperidine as a yellow oil (490 mg, 98%).

$^1$H NMR (DMSO-$d_6$) δ (ppm): 8.29 (s, 1H), 8.22-8.14 (m, 1H), 7.92-7.83 (m, 1H), 7.73-7.66 (m, 1H), 6.99-6.82 (m, 4H), 5.19 (s, 2H), 4.29-4.16 (m, 1H), 2.97-2.84 (m, 2H), 2.57-2.50 (m, 2H), 1.85 (td, J=3.9, 8.9 Hz, 2H), 1.47-1.33 (m, 2H); MS (ESI): m/z: 329 [M+H]+.

1-methyl-4-[4-[(3-nitrophenyl)methoxy]phenoxy] piperidine 0.13 mL (1.788 mmol) of formaldehyde (37% in H$_2$O), 0.085 mL (1.5 mmol) of glacial acetic acid and 0.118 g (1.788 mmol) of NaBH$_3$CN were added to 0.49 g (1.492 mmol) of 4-[4-[(3-nitrophenyl)methoxy]phenoxy]piperidine in 15 mL of MeOH. The reaction mixture was stirred at RT until disappearance of the starting material. Then, the solvent was removed and the crude mixture was partitioned between H$_2$O and CH$_2$Cl$_2$. The organic phase was dried over Na$_2$SO$_4$, filtered off and concentrated to afford a yellow oil. The crude product was purified by column chromatography (eluent CH$_2$Cl$_2$/MeOH/NH$_3$, 96:4:0.4 v:v:v) to afford 407 mg (80%) of 1-methyl-4-[4-[(3-nitrophenyl)methoxy]phenoxy]piperidine as a yellow oil. $^1$H NMR (DMSO-$d_6$) S (ppm): 8.29 (s, 1H), 8.22-8.13 (m, 1H), 7.94-7.83 (m, 1H), 7.74-7.65 (m, 1H), 7.03-6.80 (m, 4H), 5.20 (s, 2H), 4.38 (bs, 1H), 3.11-2.64 (m, 4H), 2.55 (bs, 3H), 2.04-1.65 (m, 4H); MS (ESI): m/z: 343 [M+H]+.

3-[[4-[(1-methyl-4-piperidyl)oxy]phenoxy]methyl] aniline 0.257 g (0.751 mmol) of 1-methyl-4-[4-[(3-nitrophenyl)methoxy]phenoxy]piperidine was dissolved in 30 mL of EtOH. The solution was hydrogenated in an H-Cube apparatus (PtO$_2$ cartridge, atmospheric pressure, 70° C., flow 0.5 mL/min). The solvent was evaporated to give 147 mg (63%) of 3-[[4-[(1-methyl-4-piperidyl)oxy]phenoxy]methyl]aniline as a pale yellow solid. $^1$H NMR (DMSO-$d_6$) δ (ppm): 7.03-6.95 (m, 1H), 6.94-6.83 (m, 4H), 6.60 (s, 1H), 6.55-6.44 (m, 2H), 5.09 (bs, 2H), 4.86 (s, 2H), 4.31 (bs, 1H), 2.91 (bs, 2H), 2.62 (bs, 2H), 2.45 (bs, 3H), 1.92 (bs, 2H), 1.71 (bs, 2H); MS (ESI): m/z: 313 [M+H]+.

Intermediate 6: 4-[[4-[(1-methyl-4-piperidyl)oxy] phenoxy]methyl]aniline

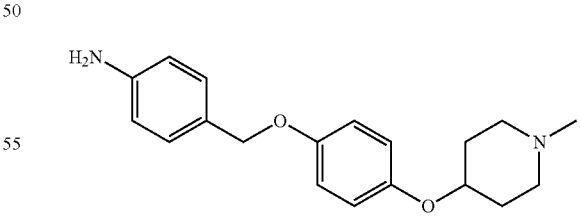

4-[[4-[(1-methyl-4-piperidyl)oxy]phenoxy]methyl]aniline was prepared according to the procedure for Intermediate 5 except for step 1, which was carried out with TFA in CH$_2$Cl$_2$. $^1$H NMR (CDCl$_3$) δ (ppm): 7.25-7.18 (m, 2H), 6.93-6.82 (m, 4H), 6.74-6.66 (m, 2H), 4.89 (s, 2H), 4.22 (bs, 1H), 3.72 (bs, 2H), 2.81-2.71 (m, 2H), 2.43-2.27 (m, 5H), 2.10-1.96 (m, 2H), 1.92-1.79 (m, 2H); MS (ESI): m/z: 313 [M+H]+.

Intermediate 7: 4-[(2-aminophenyl)methoxy]phenol

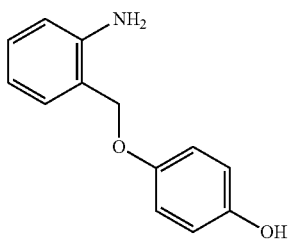 [SMILES: Nc1ccccc1COc1ccc(O)cc1]

A solution 1.34 g (5.45 mmol) of 4-[(2-nitrophenyl)methoxy]phenol (Intermediate 3, step 1) in 200 mL of EtOH was hydrogenated in the H-Cube apparatus at atmospheric pressure and 70° C., using a $PtO_2$ cartridge and a flow of 0.5 mL/min. The solvent was removed under vacuum to give 1.1 g (98%) 4-[(2-aminophenyl)methoxy]phenol as a pale yellow oil. $^1$H NMR (CDCl$_3$) δ (ppm): 7.22-7.14 (m, 2H), 6.93-6.85 (m, 2H), 6.82-6.72 (m, 4H), 4.99 (s, 2H), 4.32 (bs, 3H); MS (ESI): m/z: 238 [M+Na]$^+$.

Intermediate 8: 4-[(3-aminophenyl)methoxy]phenol

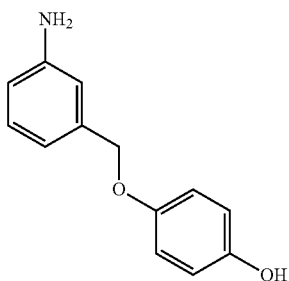 [SMILES: Nc1cccc(COc2ccc(O)cc2)c1]

4-[(3-aminophenyl)methoxy]phenol was prepared as described for 4-[(2-aminophenyl)methoxy]phenol (Intermediate 7) starting from 3-(bromomethyl)-2-nitro-benzene (Sigma Aldrich, Cat No. N4131) and hydroquinone and subsequent reduction of the nitro group to give 4-[(3-aminophenyl)methoxy]phenol as a pale yellow solid. $^1$H NMR (DMSO-d$_6$) δ (ppm): 4.81 (s, 2H) 5.07 (s, 2H) 6.47 (dd, J=7.83, 1.47 Hz, 1H) 6.51 (d, J=7.34 Hz, 1H) 6.59 (s, 1H) 6.63-6.67 (m, 2H) 6.75-6.80 (m, 2H) 6.98 (t, J=7.58 Hz, 1H) 8.89 (s, 1H); MS (ESI): m/z: 216 [M+H]$^+$.

Intermediate 9: N-[2-[(4-hydroxyphenoxy)methyl]phenyl]-4-methyl-thieno[3,2-b]pyrrole-5-carboxamide

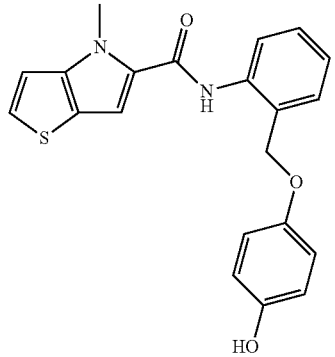 [SMILES: Cn1c(C(=O)Nc2ccccc2COc2ccc(O)cc2)cc2sccc21]

0.31 g (2.6 mmol, 0.19 mL) of $SOCl_2$ and 3 drops of dry DMF were added at RT to a solution of 0.360 g (2.00 mmol) of 4-methylthieno[3,2-b]pyrrole-5-carboxylic acid (Intermediate 1) in 8 mL of dry THF. The mixture was stirred for 2 h at reflux. The reaction mixture was then cooled down to RT and poured into a solution of 0.384 g (1.78 mmol) of 4-[(2-aminophenyl)methoxy]phenol (Intermediate 7) in 6 mL of pyridine. The mixture was stirred for 10 min at RT, then quenched with water and concentrated. The residue was dissolved in $CH_2Cl_2$, washed with brine, dried over $Na_2SO_4$, filtered and the solvent evaporated to give an oil which was purified by column chromatography (hexane/acetone, 0% of acetone to 20% of acetone) to give 416 mg (62%) of N-[2-[(4-hydroxyphenoxy)methyl]phenyl]-4-methyl-thieno[3,2-b]pyrrole-5-carboxamide as a white solid. $^1$H NMR (DMSO-d$_6$) δ (ppm): 9.72 (s, 1H), 8.93 (s, 1H), 7.57-7.47 (m, 3H), 7.39-7.31 (m, 1H), 7.27-7.20 (m, 3H), 6.82-6.76 (m, 2H), 6.67-6.59 (m, 2H), 5.05 (s, 2H), 4.00 (s, 3H); MS (ESI): m/z: 379 [M+H]$^+$.

Intermediate 10: N-[3-[(4-hydroxyphenoxy)methyl]phenyl]-4-methyl-thieno[3,2-b]pyrrole-5-carboxamide

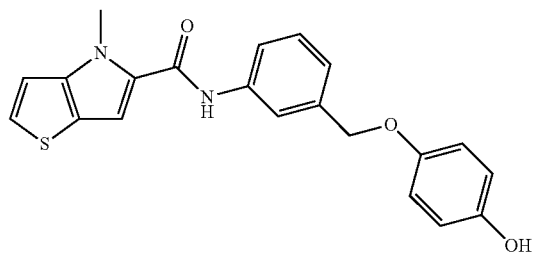 [SMILES: Cn1c(C(=O)Nc2cccc(COc3ccc(O)cc3)c2)cc2sccc21]

N-[3-[(4-hydroxyphenoxy)methyl]phenyl]-4-methyl-thieno[3,2-b]pyrrole-5-carboxamide was prepared as described for Intermediate 9 starting from 4-methylthieno[3,2-b]pyrrole-5-carboxylic acid (Intermediate 1) and 4-[(3-aminophenyl)methoxy]phenol (Intermediate 8). $^1$H NMR (DMSO-d$_6$) δ (ppm): 10.04 (s, 1H), 8.94 (s, 1H), 7.83 (s, 1H), 7.68 (d, J=8.31 Hz, 1H), 7.52 (d, J=5.38 Hz, 1H), 7.30-7.35 (m, 2H), 7.24 (d, J=5.38 Hz, 1H), 7.11 (d, J=7.34

Hz, 1H), 6.80-6.85 (m, 2H), 6.64-6.70 (m, 2H), 4.98 (s, 2H), 4.02 (s, 3H); MS (ESI): m/z: 379 [M+H]⁺.

Intermediate 11: tert-butyl 4-[4-[(2-aminobenzoyl)amino]phenoxy]piperidine-1-carboxylate

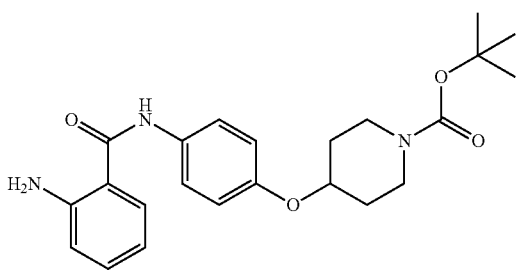 [SMILES: CC(C)(C)OC(=O)N1CCC(Oc2ccc(NC(=O)c3ccccc3N)cc2)CC1]

tert-butyl 4-[4-[(2-nitrobenzoyl)amino]phenoxy]piperidine-1-carboxylate 0.094 g (0.62 mmol) 1-hydroxybenzotriazole hydrate, 0.15 g (0.51 mmol) tert-butyl 4-(4-aminophenoxy)piperidine-1-carboxylate (Sigma Aldrich, cat. no. CDS017851) and 0.11 mL (0.77 mmol) TEA were added to a solution of 0.086 g (0.51 mmol) of 2-nitrobenzoic acid (Sigma Aldrich, cat. no. 127698) and 0.12 g (0.62 mmol) of 3-(ethyliminomethyleneamino)-N,N-dimethyl-propan-1-amine hydrochloride in 2 mL dry $CH_2Cl_2$. The mixture was stirred for 5 h at RT and then the solution was washed with water and brine, dried over $Na_2SO_4$ and concentrated. The crude mixture was purified by column chromatography (hexane/EtOAc, from 5% to 60% of EtOAc) to give 0.20 g (88%) of tert-butyl 4-[4-[(2-nitrobenzoyl)amino]phenoxy]piperidine-1-carboxylate as a yellow solid. ¹H NMR ($CDCl_3$) δ (ppm): 8.20-8.11 (m, 1H), 7.80-7.32 (m, 5H), 7.02-6.83 (m, 2H), 4.52-4.42 (m, 1H), 3.76-3.64 (m, 2H), 3.40-3.30 (m, 2H), 1.98-1.70 (m, 4H), 1.61-1.41 (m, 9H); MS (ESI): m/z: 440 [M+H]⁺.

tert-butyl 4-[4-[(2-aminobenzoyl)amino]phenoxy]piperidine-1-carboxylate 0.12 g (0.27 mmol) of tert-butyl 4-[4-[(2-nitrobenzoyl)amino]phenoxy]piperidine-1-carboxylate was dissolved in 4.5 mL of EtOH. The solution was hydrogenated in an H-Cube apparatus (10% Pd/C cartridge, atmospheric pressure, 50° C., flow 0.5 mL/min). The solvent was evaporated to give 113 mg (quantitative) of tert-butyl 4-[4-[(2-aminobenzoyl)amino]phenoxy]piperidine-1-carboxylate as a brown solid. ¹H NMR (DMSO-$d_6$) δ (ppm): 9.87 (s, 1H), 7.64-7.53 (m, 3H), 7.23-7.14 (m, 1H), 7.00-6.87 (m, 2H), 6.80-6.67 (m, 1H), 6.62-6.52 (m, 1H), 6.28 (bs, 2H), 4.55-4.43 (m, 1H), 3.71-3.59 (m, 2H), 3.25-3.05 (m, 2H), 1.94-1.76 (m, 2H), 1.57-1.45 (m, 2H), 1.40 (s, 9H); MS (ESI): m/z: 412 [M+H]⁺.

Intermediate 12: tert-butyl 4-[4-[(2-aminophenyl)methoxy]phenyl]piperazine-1-carboxylate

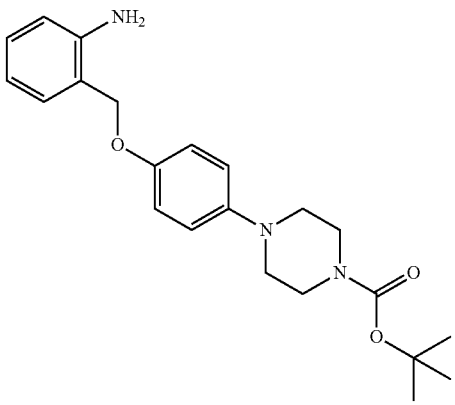 [SMILES: CC(C)(C)OC(=O)N1CCN(c2ccc(OCc3ccccc3N)cc2)CC1]

tert-butyl 4-[4-[(2-nitrophenyl)methoxy]phenyl]piperazine-1-carboxylate 0.37 g (2.7 mmol) of $K_2CO_3$ and 0.48 g (2.2 mmol) 1-(bromomethyl)-2-nitro-benzene were added to a solution of 0.50 g (1.8 mmol) tert-butyl 4-(4-hydroxyphenyl)piperazine-1-carboxylate (Sigma Aldrich, cat. no. CDS004430) in 14 mL of dry $CH_3CN$ under inert atmosphere. The suspension was heated to 110° C. under microwave irradiation for 2.5 h. The solid was filtered off and rinsed with $CH_3CN$. The mother liquor was brought to dryness and purified by flash chromatography (eluent hexane/EtOAc, from 10% to 50% of EtOAc) obtaining 0.321 g (43%) of tert-butyl 4-[4-[(2-nitrophenyl)methoxy]phenyl]piperazine-1-carboxylate as orange solid. ¹H NMR ($CDCl_3$) δ (ppm): 8.18 (d, J=7.83 Hz, 1H), 7.91 (d, J=7.83 Hz, 1H), 7.69 (s, 1H), 7.54-7.45 (m, 1H), 7.04-6.81 (m, 4H), 5.47 (s, 2H), 3.70-3.48 (m, 4H), 3.16-2.92 (m, 4H), 1.50 (s, 9H); MS (ESI): m/z: 414 [M+H]⁺.

tert-butyl 4-[4-[(2-aminophenyl)methoxy]phenyl]piperazine-1-carboxylate 0.32 g (0.77 mmol) tert-butyl 4-[4-[(2-nitrophenyl)methoxy]phenyl]piperazine-1-carboxylate was hydrogenated according to the procedure for Intermediate 5, last step, providing 0.287 g (97%) of tert-butyl 4-[4-[(2-aminophenyl)methoxy]phenyl]piperazine-1-carboxylate as off white solid. ¹H NMR ($CDCl_3$) δ (ppm): 7.21-7.14 (m, 2H), 7.03-6.85 (m, 4H), 6.80-6.71 (m, 2H), 5.00 (s, 2H), 4.10 (bs, 2H), 3.71-3.48 (m, 4H), 3.14-2.93 (m, 4H), 1.50 (s, 9H); MS (ESI): m/z: 384 [M+H]⁺.

Intermediate 13: tert-butyl 4-[N-tert-butoxycarbonyl-4-[[2-[(4-methylthieno[3,2-b]pyrrole-5-carbonyl)amino]phenyl]methoxy]anilino]piperidine-1-carboxylate

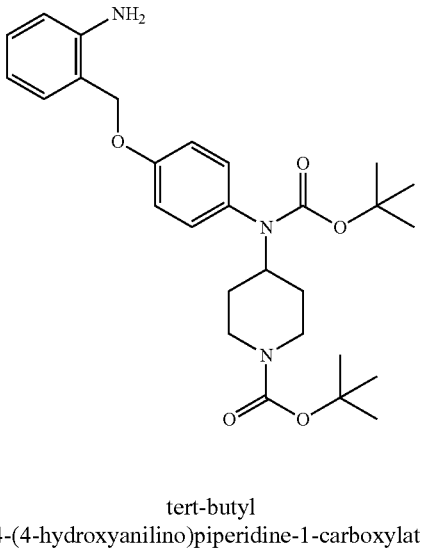

tert-butyl 4-(4-hydroxyanilino)piperidine-1-carboxylate

A solution of 0.365 g (1.83 mmol) of tert-butyl 4-oxopiperidine-1-carboxylate (Sigma Aldrich, cat. no. 461350), 0.20 g (1.8 mmol) of 4-aminophenol (Sigma Aldrich, cat. no. A71328) and 0.105 mL (1.83 mmol) glacial acetic acid in 10 mL of dry $CH_2Cl_2$ was treated with 0.777 g (3.67 mmol) $NaBH(OAc)_3$ at 0° C. The suspension was brought to RT and stirred for 20 h. Then, the mixture was quenched with water and extracted with $CH_2Cl_2$. The combined organic layers were washed with brine, dried over $Na_2SO_4$, filtered and evaporated to afford a pale yellow oily residue, which was purified by column chromatography (eluent hexane/EtOAc, from 15% to 100% EtOAc) providing 0.451 g (84%) of tert-butyl 4-(4-hydroxyanilino)piperidine-1-carboxylate as a white solid.
$^1$H NMR ($CDCl_3$) δ (ppm): 6.76-6.67 (m, 2H), 6.62-6.53 (m, 2H), 4.41-3.74 (m, 4H), 3.37-3.28 (m, 1H), 2.97-2.82 (m, 2H), 2.08-1.97 (m, 2H), 1.47 (s, 9H), 1.37-1.24 (m, 2H); MS (ESI): m/z: 293 [M+H]$^+$.

tert-Butyl 4-(N-tert-butoxycarbonyl-4-hydroxy-anilino)piperidine-1-carboxylate 0.645 g (2.96 mmol) of tert-butoxycarbonyl tert-butyl carbonate, 0.16 mL (1.2 mmol) TEA and 0.14 g (1.2 mmol) of N,N-dimethylpyridin-4-amine was added to a solution of 0.288 g (0.985 mmol) tert-butyl 4-(4-hydroxyanilino)piperidine-1-carboxylate in 4 mL dry $CH_2Cl_2$ and the reaction mixture was stirred overnight at RT. The mixture was partitioned between $CH_2Cl_2$ and brine, the organic layer was dried over $Na_2SO_4$, filtered and concentrated. The obtained crude product was purified by column chromatography (eluent hexane/EtOAc from 10% to 80% EtOAc) providing 0.256 g (66%) of tert-butyl 4-(N-tert-butoxycarbonyl-4-hydroxy-anilino)piperidine-1-carboxylate as a white solid.
$^1$H NMR ($CDCl_3$) δ (ppm): 7.03-6.94 (m, 2H), 6.71-6.54 (m, 2H), 4.14-3.94 (m, 2H), 3.44-3.32 (m, 1H), 2.99-2.81 (m, 2H), 2.08-1.99 (m, 2H), 1.55 (s, 9H), 1.47 (s, 9H), 1.40-1.27 (m, 2H); MS (ESI): m/z: 393 [M+H]f.

tert-butyl 4-[N-tert-butoxycarbonyl-4-[(2-nitrophenyl)methoxy]anilino]piperidine-1-carboxylate 0.106 g (0.764 mmol) of $K_2CO_3$ and 0.112 g (0.510 mmol) 1-(bromomethyl)-2-nitro-benzene were added to a solution of 0.50 g (1.8 mmol) tert-butyl 4-(N-tert-butoxycarbonyl-4-hydroxy-anilino)piperidine-1-carboxylate in 1 mL of dry $CH_3CN$ under inert atmosphere. The suspension was heated to 80° C. overnight. The mixture was then diluted with $CH_3CN$, filtered, concentrated and purified by column chromatography (eluent hexane/EtOAc, 1:5, v:v) giving 0.091 g (34%) of tert-butyl 4-[N-tert-butoxycarbonyl-4-[(2-nitrophenyl)methoxy]anilino]piperidine-1-carboxylate as a pale yellow solid. $^1$H NMR ($CDCl_3$) δ (ppm): 8.17-8.07 (m, 1H), 7.70-7.51 (m, 2H), 7.45-7.39 (m, 1H), 7.01 (d, J=8.8 Hz, 2H), 6.75-6.58 (m, 2H), 4.80 (bs, 2H), 4.31-4.15 (m, 2H), 3.93-3.82 (m, 1H), 2.86-2.71 (m, 2H), 1.92-1.79 (m, 2H), 1.55 (s, 9H), 1.45 (s, 9H), 1.42-1.25 (m, 2H). MS (ESI): m/z: 528 [M+H]$^+$.

tert-butyl 4-[4-[(2-aminophenyl)methoxy]-N-tert-butoxycarbonyl-anilino]piperidine-1-carboxylate 0.089 g (0.17 mmol) of tert-butyl 4-[N-tert-butoxycarbonyl-4-[(2-nitrophenyl)methoxy]anilino]piperidine-1-carboxylate in 5 mL of THF was hydrogenated in the H-Cube apparatus at atmospheric pressure and 65° C., using a $PtO_2$ cartridge and a flow of 0.5 ml/min. The pale yellow solution was concentrated providing 0.084 g (quantitative) tert-butyl 4-[4-[(2-aminophenyl)methoxy]-N-tert-butoxycarbonyl-anilino]piperidine-1-carboxylate, which was used without any further purification in the next step. MS (ESI): m/z: 498 [M+H]$^+$.

Intermediate 14: tert-butyl 3-[[4-[(2-aminophenyl)methoxy]phenoxy]methyl]azetidine-1-carboxylate

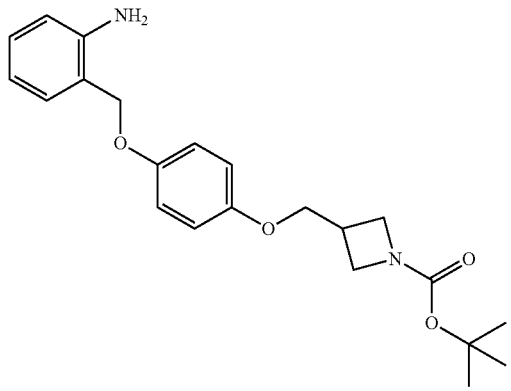 [SMILES: CC(C)(C)OC(=O)N1CC(COc2ccc(OCc3ccccc3N)cc2)C1]

tert-butyl 3-[[4-[(2-nitrophenyl)methoxy]phenoxy]methyl]azetidine-1-carboxylate 0.237 g (57%) tert-butyl 3-[[4-[(2-nitrophenyl)methoxy]phenoxy]methyl]azetidine-1-carboxylate was obtained as a yellow oil according to the procedure described for Intermediate 3, Step 2, starting from 0.25 g (1.0 mmol) (4-[(2-nitrophenyl)methoxy]phenol (Intermediate 3, Step 1) and 0.28 g (1.5 mmol) tert-butyl 3-(hydroxymethyl)azetidine-1-carboxylate (Fluorochem, cat. no. 040532). $^1$H NMR ($CDCl_3$) δ (ppm): 8.22-8.14 (m, 1H), 7.96-7.88 (m, 1H), 7.75-7.65 (m, 1H), 7.55-7.45 (m, 1H), 6.99-6.82 (m, 4H), 5.46 (s, 2H), 4.15-4.00 (m, 4H), 3.84-3.71 (m, 2H), 3.03-2.88 (m, 1H), 1.46 (s, 9H). MS (ESI): m/z: 415 [M+H]$^+$.

tert-butyl 3-[[4-[(2-aminophenyl)methoxy]phenoxy]methyl]azetidine-1-carboxylate 0.236 g (0.570 mmol) tert-butyl 3-[[4-[(2-nitrophenyl)methoxy]phenoxy]methyl]azetidine-1-carboxylate was hydrogenated according to the procedure for Intermediate 5, last step, providing 0.218 g (quantitative) of tert-butyl 3-[[4-[(2-aminophenyl)methoxy]phenoxy]methyl]azetidine-1-carboxylate as off white solid. $^1$H NMR (CDCl$_3$) δ (ppm): 7.25-7.16 (m, 2H), 6.98-6.91 (m, 2H), 6.89-6.76 (m, 4H), 5.03 (s, 2H), 4.12-3.99 (m, 4H), 3.82-3.75 (m, 2H), 3.01-2.88 (m, 1H), 1.46 (s, 9H); MS (ESI): m/z: 385 [M+H]$^+$.

Intermediate 15: tert-butyl 3-[[4-[(2-aminophenyl)methoxy]phenyl]methyl]-3,8-diazaspiro[4.5]decane-8-carboxylate

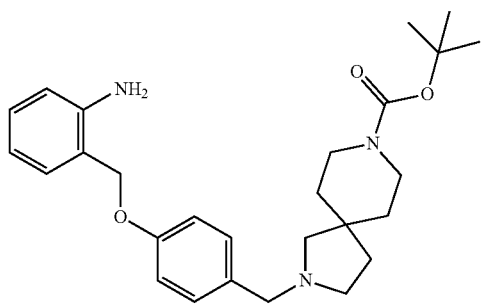 [SMILES: CC(C)(C)OC(=O)N1CCC2(CCN(Cc3ccc(OCc4ccccc4N)cc3)C2)CC1]

tert-butyl 3-[[4-[(2-nitrophenyl)methoxy]phenyl]methyl]-3, 8-diazaspiro[4.5]decane-8-carboxylate 0.119 g (0.495 mmol) of tert-butyl 3,8-diazaspiro[4.5]decane-8-carboxylate (Fluorochem, cat. no. 091348) and 0.140 g (0.544 mmol) of 4-[(2-nitrophenyl)methoxy]benzaldehyde (Vitas-M Lab, cat. no. BBL024967) were dissolved in 6 mL of dry THF. After 30 min of stirring, the reaction mixture was treated with 0.276 g (1.236 mmol) of NaBH(OAc)$_3$ and stirred overnight. The reaction was quenched with 10 mL of saturated aqueous NaHCO$_3$. The aqueous phase was extracted with EtOAc, the combined organic layers were washed with brine, dried over Na$_2$SO$_4$, filtered and evaporated to afford a residue, which was purified by column chromatography (eluent hexane/acetone, from 0% to 15% acetone) providing 0.217 g (91%) of tert-butyl 3-[[4-[(2-nitrophenyl)methoxy]phenyl]methyl]-3,8-diazaspiro[4.5]decane-8-carboxylate as yellow oil. $^1$H NMR (DMSO-d$_6$) δ (ppm): 8.15-8.07 (m, 1H), 7.82-7.74 (m, 2H), 7.66-7.57 (m, 1H), 7.29-7.13 (m, 2H), 6.99-6.89 (m, 2H), 5.42 (s, 2H), 3.45 (s, 2H), 3.31-3.25 (m, 2H), 3.23-3.12 (m, 2H), 2.46 (t, J=6.8 Hz, 2H), 2.29 (s, 2H), 1.55 (t, J=6.8 Hz, 2H), 1.43-1.34 (m, 13H). MS (ESI): m/z: 482 [M+H]$^+$.

tert-butyl 3-[[4-[(2-aminophenyl)methoxy]phenyl]methyl]-3,8-diazaspiro[4.5]decane-8-carboxylate 0.213 g (0.442 mmol) of tert-butyl 3-[[4-[(2-nitrophenyl)methoxy]phenyl]methyl]-3,8-diazaspiro[4.5]decane-8-carboxylate dissolved in 18 mL of EtOH was hydrogenated according to the procedure described for Intermediate 3, last step, providing 0.199 g (quantitative) of tert-butyl 3-[[4-[(2-aminophenyl)methoxy]phenyl]methyl]-3,8-diazaspiro[4.5]decane-8-carboxylate as a yellow sticky oil. $^1$H NMR (DMSO-d$_6$) δ (ppm): 7.24-7.13 (m, 3H), 7.05-6.99 (m, 1H), 6.98-6.91 (m, 2H), 6.70-6.64 (m, 1H), 6.57-6.49 (m, 1H), 5.02 (s, 2H), 4.93 (s, 2H), 3.44 (s, 2H), 3.31-3.25 (m, 2H), 3.23-3.13 (m, 2H), 2.47 (t, J=6.8 Hz, 2H), 2.28 (s, 2H), 1.54 (t, J=6.8 Hz, 2H), 1.43-1.33 (m, 13H); MS (ESI): m/z: 452 [M+H]$^+$.

Intermediate 16: 4-[[2-(methoxymethyl)-6-nitrophenyl]methoxy]phenol

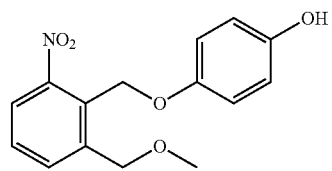 [SMILES: COCc1cccc([N+](=O)[O-])c1COc1ccc(O)cc1]

methyl 2-(methoxymethyl)-6-nitro-benzoate 1.62 g (9.05 mmol) of 7-nitro-3H-isobenzofuran-1-one (J. Org. Chem, 1987, 129-134) was dissolved in THF (5 mL) and 9.5 mL of 1 M NaOH (9.5 mmol) was added. The mixture was heated at 50° C. for 45 min until complete disappearance of the starting material. The solution was then concentrated to give sodium 2-(hydroxymethyl)-6-nitro-benzoate. The crude product was suspended in dry DMA (23 mL) under N$_2$ atmosphere and 0.43 g (11 mmol) of NaH (60% dispersion in mineral oil) were added at 0° C. Temperature was brought to RT in 30 min; then 3.85 g of iodomethane (1.69 mL, 27.2 mmol) were added at 0° C. The mixture was then stirred overnight at RT, then the reaction was stopped by adding H$_2$O and the product was extracted with EtOAc. The combined organic layers were washed with brine and dried over Na$_2$SO$_4$. After filtration the solvent was removed under vacuum and the crude product was purified by column chromatography on silica gel (eluent hexane/EtOAc, from 5% to 40% of EtOAc) to give 0.971 g (48%) of methyl 2-(methoxymethyl)-6-nitro-benzoate as white powder. 1H NMR (DMSO-d$_6$) δ (ppm): 8.15-7.71 (m, 3H), 4.51 (s, 2H), 3.84 (s, 3H), 3.26 (s, 3H). MS (ESI): m/z: 248 [M+H]$^+$.

[2-(methoxymethyl)-6-nitro-phenyl]methanol

A solution of 0.837 g (3.72 mmol) of methyl 2-(methoxymethyl)-6-nitro-benzoate in dry THF (3 mL) was added to a 2 M suspension of lithium borohydride (9.29 mL, 18.6 mmol) in dry THF at 0° C. under inert atmosphere. Then, 2 mL of dry MeOH was added, the mixture was allowed to reach RT and was stirred for 3 h. The reaction was cooled down again to 0° C. and quenched with a saturated solution of NH$_4$Cl. The product was extracted with EtOAc and the combined organic layers were dried over Na$_2$SO$_4$, filtered and evaporated. The crude product was purified by column chromatography on silica gel (eluent hexane/EtOAc, from 7% to 60% of EtOAc) to give 0.589 g (80%) of [2-(methoxymethyl)-6-nitro-phenyl]methanol as white solid. $^1$H NMR (DMSO-d$_6$) δ (ppm): 7.75-7.63 (m, 2H), 7.52-7.45 (m, 1H), 5.29-5.24 (m, 1H), 4.64-4.61 (m, 2H), 4.58 (s, 2H), 3.33 (s, 3H). MS (ESI): m/z: 198 [M+H]⁺.

2-(bromomethyl)-1-(methoxymethyl)-3-nitro-benzene 1.4 g (4.2 mmol) of CBr$_4$ and 1.3 g (5.1 mmol) of PPh$_3$ were added to a solution of 0.556 g (2.82 mmol) of [2-(methoxymethyl)-6-nitro-phenyl]methanol in CH$_3$CN. After stirring 5 h at RT the mixture was quenched with H$_2$O, concentrated and the aqueous phase was extracted with CH$_2$Cl$_2$. The combined organic layers were dried over Na$_2$SO$_4$, filtered and evaporated and the crude product was purified by column chromatography on silica gel (eluent hexane/EtOAc, from 2% to 20% of EtOAc) to give 0.623 g (85%) of 2-(bromomethyl)-1-(methoxymethyl)-3-nitro-benzene as yellow oil. $^1$H NMR (DMSO) δ (ppm): 7.98-7.75 (m, 2H), 7.65-7.59 (m, 1H), 4.81 (s, 2H), 4.66 (s, 2H), 3.33 (s, 3H). MS (ESI): m/z: 261 [M+H]⁺.

4-[[2-(methoxymethyl)-6-nitro-phenyl]methoxy]phenol 0.620 g (79%) 4-[[2-(methoxymethyl)-6-nitro-phenyl]methoxy]phenol was prepared according to the procedure for Intermediate 3, step 1, starting from 0.519 g (0.752 mmol) 2-(bromomethyl)-1-(methoxymethyl)-3-nitro-benzene. $^1$H NMR (DMSO-d$_6$) δ (ppm): 9.01 (s, 1H), 7.87-7.71 (m, 2H), 7.65-7.54 (m, 1H), 6.81-6.62 (m, 4H), 5.11 (s, 2H), 4.60 (s, 2H), 3.32 (s, 3H); MS (ESI): m/z: 290 [M+H]⁺.

Intermediate 17: tert-butyl (3R)-3-[[4-[[2-amino-6-(methoxymethyl)phenyl]methoxy]phenoxy]methyl]pyrrolidine-1-carboxylate

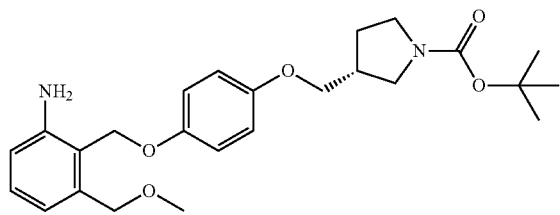 [SMILES: COCc1cccc(N)c1COc1ccc(OC[C@@H]2CCN(C(=O)OC(C)(C)C)C2)cc1]

0.080 g (49%) tert-butyl (3R)-3-[[4-[[2-amino-6-(methoxymethyl)phenyl]methoxy]phenoxy]methyl]pyrrolidine-1-carboxylate was prepared according to the procedure for Intermediate 3, step 2, starting from 0.10 g (0.35 mmol) 4-[[2-(methoxymethyl)-6-nitro-phenyl]methoxy]phenol (Intermediate 16) and 0.157 g (0.778 mmol) tert-butyl (3R)-3-(hydroxymethyl)pyrrolidine-1-carboxylate. $^1$H NMR (DMSO-d$_6$) δ (ppm): 7.89-7.55 (m, 3H), 6.91-6.85 (m, 4H), 5.15 (s, 2H), 4.61 (s, 2H), 3.93-3.79 (m, 2H), 3.51-2.80 (m, 7H), 2.43-1.47 (m, 3H), 1.38 (s, 9H) MS (ESI): m/z: 473 [M+H]⁺.

Reduction of 0.078 g (0.17 mmol) tert-butyl (3R)-3-[[4-[[2-(methoxymethyl)-6-nitro-phenyl]methoxy]phenoxy]methyl]pyrrolidine-1-carboxylate providing 0.069 g (95%) of tert-butyl (3R)-3-[[4-[[2-amino-6-(methoxymethyl)phenyl]methoxy]phenoxy]methyl]pyrrolidine-1-carboxylate was carried out according to the procedure described for Intermediate 3, step 3. $^1$H NMR (DMSO-d$_6$) δ (ppm): 7.06-6.52 (m, 7H), 5.07 (s, 2H), 4.93 (s, 2H), 4.36 (s, 2H), 3.94-3.79 (m, 2H), 3.50-2.81 (m, 7H), 2.40-1.46 (m, 3H), 1.39 (s, 9H); MS (ESI): m/z: 443 [M+H]⁺.

Intermediate 18: tert-butyl 4-[4-[[2-amino-6-(methoxymethyl)phenyl]methoxy]phenoxy]piperidine-1-carboxylate

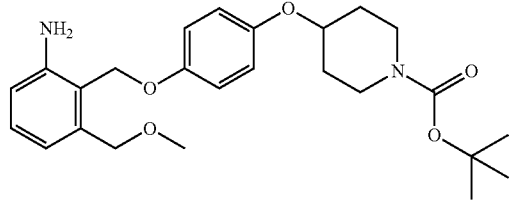 [SMILES: COCc1cccc(N)c1COc1ccc(OC2CCN(C(=O)OC(C)(C)C)CC2)cc1]

tert-butyl 4-[4-[[2-amino-6-(methoxymethyl)phenyl]methoxy]phenoxy]piperidine-1-carboxylate was prepared according to the procedure for Intermediate 3, step 2, starting from 4-[[2-(methoxymethyl)-6-nitro-phenyl]methoxy]phenol (Intermediate 16) and tert-butyl 4-hydroxypiperidine-1-carboxylate, providing tert-butyl 4-[4-[[2-(methoxymethyl)-6-nitro-phenyl]methoxy]phenoxy]piperidine-1-carboxylate intermediate. $^1$H NMR (DMSO-d$_6$) δ (ppm): 7.88-7.59 (m, 3H), 6.96-6.81 (m, 4H), 5.15 (s, 2H), 4.62 (s, 2H), 4.46-4.37 (m, 1H), 3.69-3.57 (m, 2H), 3.29 (s, 3H), 3.22-3.09 (m, 2H), 1.92-1.44 (2m, 4H), 1.40 (s, 9H) MS (ESI): m/z: 473 [M+H]⁺.

Reduction of tert-butyl 4-[4-[[2-(methoxymethyl)-6-nitro-phenyl]methoxy]phenoxy]piperidine-1-carboxylate to tert-butyl 4-[4-[[2-amino-6-(methoxymethyl)phenyl]methoxy]phenoxy]piperidine-1-carboxylate was carried out according to the procedure described for Intermediate 3, step 3. $^1$H NMR (DMSO-d$_6$) δ (ppm): 7.05-6.98 (m, 1H), 6.98-6.85 (m, 4H), 6.70-6.53 (m, 2H), 5.07 (s, 2H), 4.93 (s, 2H), 4.45-4.33 (m, s, 3H), 3.68-3.55 (m, 2H), 3.22 (s, 3H), 3.19-3.09 (m, 2H), 1.91-1.79 (m, 2H), 1.54-1.43 (m, 2H), 1.40 (s, 9H); MS (ESI): m/z: 443 [M+H]⁺.

Intermediate 19: tert-butyl 4-[4-[[2-amino-6-(methoxymethyl)phenyl]methoxy]phenoxy]azepane-1-carboxylate

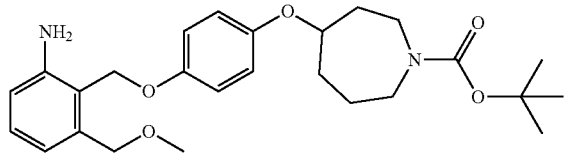 [SMILES: COCc1cccc(N)c1COc1ccc(OC2CCCN(C(=O)OC(C)(C)C)CC2)cc1]

tert-butyl 4-[4-[[2-amino-6-(methoxymethyl)phenyl]methoxy]phenoxy]azepane-1-carboxylate was prepared according to the procedure for Intermediate 3, step 2, starting from 4-[[2-(methoxymethyl)-6-nitro-phenyl]methoxy]phenol (Intermediate 16) and tert-butyl 4-hydroxyazepane-1-carboxylate. $^1$H NMR (DMSO-d$_6$) δ (ppm): 7.88-7.52 (m, 3H), 6.90-6.82 (m, 4H), 5.15 (s, 2H), 4.61 (s, 2H), 4.38 (m, 1H), 3.44-3.20 (m, 4H), 3.33 (s, 3H), 1.99-1.50 (m, 6H), 1.40 (s, 9H). MS (ESI): m/z: 487 [M+H]⁺.

Reduction of tert-butyl 4-[4-[[2-(methoxymethyl)-6-nitro phenyl]methoxy]phenoxy]azepane-1-carboxylate to tert-butyl 4-[4-[[2-amino-6-(methoxymethyl)phenyl]methoxy]phenoxy]azepane-1-carboxylate was carried out according to the procedure described for Intermediate 3, step 3. $^1$H NMR (DMSO-d₆) δ (ppm): =7.04-6.54 (m, 7H), 5.06 (s, 2H), 4.92 (s, 2H), 4.41-4.35 (m, 1H), 4.36 (s, 3H), 3.43-3.24 (m, 4H), 3.21 (s, 3H), 2.03-1.49 (m, 6H), 1.40 (s, 9H). MS (ESI): m/z: 457 [M+H]⁺.

Intermediate 20: 6-methylthieno[2,3-b]pyrrole-5-carboxylic acid

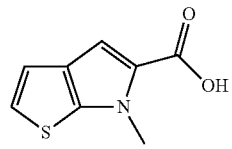

Ethyl 6-methylthieno[2,3-b]pyrrole-5-carboxylate

Ethyl 6-methylthieno[2,3-b]pyrrole-5-carboxylate was obtained as yellow solid starting from ethyl 6H-thieno[2,3-b]pyrrole-5-carboxylate (Eras J. et al. J. Het. Chemistry 1984, 21, 215-217) according to the procedure for Intermediate 1, Step 1. ¹H NMR (CDCl₃) δ (ppm): 7.34 (d, J=5.4 Hz, 1H), 7.20 (s, 1H), 6.95 (d, J=5.4 Hz, 1H), 4.34 (q, J=7.3 Hz, 2H), 4.07 (s, 3H), 1.39 (t, J=-7.1 Hz, 3H); MS (ESI): m/z: 210 [M+H]⁺

6-Methylthieno[2,3-b]pyrrole-5-carboxylic acid 6-methylthieno[2,3-b]pyrrole-5-carboxylic acid was obtained as a white solid from ethyl 6-methylthieno[2,3-b]pyrrole-5-carboxylate according to the procedure for Intermediate 1, Step 2. ¹H NMR (DMSO-d₆ δ (ppm): 12.49 (bs, 1H), 7.17 (d, J=5.4 Hz, 1H), 7.08-7.00 (m, 2H), 3.95 (s, 3H); MS (ESI): m/z: 182 [M+H]⁺

Intermediate 21: tert-Butyl (3S)-3-[[4-[[2-amino-6-(methoxymethyl)phenyl]methoxy]phenoxy]methyl]pyrrolidine-1-carboxylate

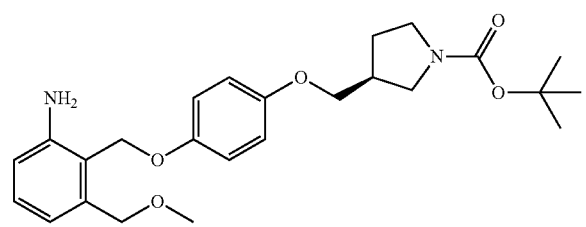 [SMILES: COCc1cccc(N)c1COc1ccc(OC[C@H]2CCN(C(=O)OC(C)(C)C)C2)cc1]

tert-Butyl (3 S)-3-[[4-[[2-nitro-6-(methoxymethyl)phenyl]methoxy]phenoxy]methyl]pyrrolidine-1-carboxylate was prepared according to the procedure for Intermediate 3, step 2, starting from 4-[[2-(methoxymethyl)-6-nitro-phenyl]methoxy]phenol (Intermediate 16) and tert-butyl (3S)-3-(hydroxymethyl)pyrrolidine-1-carboxylate. ¹H NMR (DMSO-d₆) δ (ppm): 7.87-7.55 (m, 3H), 6.91-6.84 (m, 4H), 5.15 (s, 2H), 4.61 (s, 2H), 3.93-3.82 (m, 2H), 3.49-2.98 (m, 4H), 3.31 (s, 3H), 2.66-2.51 (m, 1H), 2.03-1.60 (m, 2H), 1.39 (s, 9H); MS (ESI): m/z: 473 [M+H]⁺.

Reduction of tert-butyl (3S)-3-[[4-[[2-(methoxymethyl)-6-nitro-phenyl]methoxy]phenoxy]methyl]pyrrolidine-1-carboxylate providing tert-butyl (3S)-3-[[4-[[2-amino-6-(methoxymethyl)phenyl]methoxy]phenoxy]methyl]pyrrolidine-1-carboxylate was carried out according to the procedure described for Intermediate 3, step 3. ¹H NMR (DMSO-d₆) δ (ppm): 7.05-6.52 (m, 7H), 5.07 (s, 2H), 4.92 (s, 2H), 4.35 (s, 2H), 3.93-3.81 (m, 2H), 3.50-3.00 (m, 4 H), 3.21 (s, 3H), 2.66-2.52 (m, 1H), 2.05-1.60 (m, 2H), 1.39 (s, 9H); MS (ESI): m/z: 443 [M+H]⁺.

Intermediate 22: tert-Butyl (3R)-3-[[4-[[2-amino-6-(ethoxymethyl)phenyl]methoxy]phenoxy]methyl]pyrrolidine-1-carboxylate

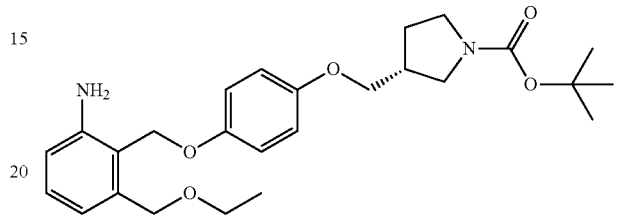

Ethyl 2-(ethoxymethyl)-6-nitro-benzoate 0.131 g (46%) of ethyl 2-(ethoxymethyl)-6-nitro-benzoate were prepared by first hydrolyzing 0.20 g (1.1 mmol) of 7-nitro-3H-isobenzofuran-1-one (J. Org. Chem, 1987, 129-134) with NaOH and then reacting the formed alcohol with iodoethane following the procedure for Intermediate 16, step 1. ¹H NMR (DMSO-d₆) δ (ppm): 8.14-7.70 (m, 3H), 4.55 (s, 2H), 4.34-4.27 (m, 2H), 3.46-3.40 (m, 2H), 1.31-1.06 (m, 6H).

[2-(Ethoxymethyl)-6-nitro-phenyl]methanol 0.048 g (45%) of [2-(ethoxymethyl)-6-nitro-phenyl]methanol were synthesized by reduction of 0.129 g (0.509 mmol) ethyl 2-(ethoxymethyl)-6-nitro-benzoate and with lithium borohydride according to the procedure described for Intermediate 16, step 2. ¹H NMR (DMSO-d₆) δ (ppm): 7.75-7.45 (m, 3H), 5.28-3.23 (m, 1H), 4.67-4.57 (m, 4H), 3.55-3.49 (m, 2H), 1.19-1.13 (m, 3H).

2-(Bromomethyl)-1-(ethoxymethyl)-3-nitro-benzene 0.041 g (67%) of 2-(bromomethyl)-1-(ethoxymethyl)-3-nitro-benzene were prepared starting from 0.047 g (0.22 mmol) [2-(ethoxymethyl)-6-nitro-phenyl]methanol and CBr₄ according to the procedure described for Intermediate 16, step 3. ¹H NMR (DMSO-d₆) δ (ppm): 7.96-7.56 (m, 3H), 4.81 (s, 2H), 4.69 (s, 2H), 3.59-3.52 (m, 2H), 1.21-1.16 (m, 3H).

4-[[2-(Ethoxymethyl)-6-nitro-phenyl]methoxy]phenol 0.024 g (55%) of 4-[[2-(ethoxymethyl)-6-nitro-phenyl]methoxy]phenol were obtained as a yellow oil by reacting 0.040 g (0.15 mmol) 2-(bromomethyl)-1-(ethoxymethyl)-3-nitro-benzene and 0.08 g (0.73 mmol) benzene-1,4-diol according to the procedure for Intermediate 3, step 1. ¹H NMR (DMSO-d₆) δ (ppm): 9.01 (s, 1H), 7.88-7.53 (m, 3H), 6.79-6.61 (m, 4H), 5.11 (s, 2H), 4.63 (s, 2H), 3.46-3.54 (m, 2H), 1.17-1.11 (m, 3H).

tert-Butyl (3R)-3-[[4-[[2-amino-6-(ethoxymethyl) phenyl]methoxy]phenoxy]methyl]-pyrrolidine-1-carboxylate 0.021 g (56%) tert-butyl (3R)-3-[[4-[[2-amino-6-(ethoxymethyl)phenyl]methoxy]phenoxy]-methyl]pyrrolidine-1-carboxylate was prepared according to the procedure described for Intermediate 3, step 2, starting from 0.023 g (0.076 mmol) 4-[[2-(ethoxymethyl)-6-nitro-phenyl] methoxy]phenol and 0.011 g (0.057 mmol) tert-butyl (3R)-3-(hydroxymethyl)pyrrolidine-1-carboxylate. $^1$H NMR (DMSO-d$_6$) δ (ppm): 7.86-7.54 (m, 3H), 6.90-6.84 (m, 4H), 5.16 (s, 2H), 4.64 (s, 2H), 3.93-3.82 (m, 2H), 3.53-3.47 (m, 2H), 3.47-3.17 (m, 4H), 2.65-2.52 (m, 1H), 2.03-1.61 (m, 2H), 1.38 (s, 9H), 1.16-1.11 (m, 3H); MS (ESI): m/z: 487 [M+H]$^+$.

tert-butyl (3R)-3-[[4-[[2-amino-6-(ethoxymethyl) phenyl]methoxy]phenoxy]methyl]-pyrrolidine-1-carboxylate Reduction of 0.019 g (0.039 mmol) of tert-butyl (3R)-3-[[4-[[2-(ethoxymethyl)-6-nitro-phenyl]methoxy]phenoxy] methyl]pyrrolidine-1-carboxylate providing 0.018 g (99%) of tert-butyl (3R)-3-[[4-[[2-amino-6-(ethoxymethyl)phenyl] methoxy]phenoxy]methyl]-pyrrolidine-1-carboxylate was carried out according to the procedure described for Intermediate 3, step 3. $^1$H NMR (DMSO-d$_6$) δ (ppm): 7.06-6.52 (m, 7H), 5.11-5.01 (bs, 2H), 4.93 (s, 2H), 4.39 (s, 2H), 3.93-3.81 (m, 2H), 3.47-3.02 (m, 6H), 2.66-2.52 (m, 1H), 2.04-1.59 (m, 2H), 1.39 (s, 9H), 1.09-1.04 (m, 3H); MS (ESI): m/z: 457 [M+H]$^+$.

Intermediate 23: tert-butyl 4-[4-[[2-amino-6-[(1-methyl-1-trimethylsilyl-ethoxy)methyl]phenyl] methoxy]phenoxy]piperidine-1-carboxylate

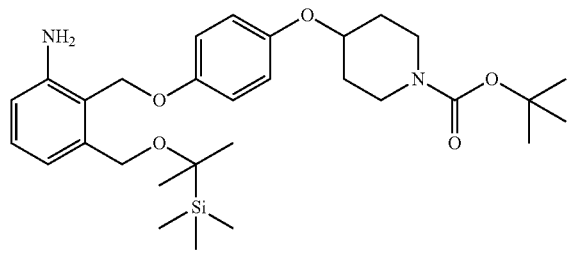 [SMILES: CC(C)(C)OC(=O)N1CCC(Oc2ccc(OCc3c(N)cccc3COC(C)(C)[Si](C)(C)C)cc2)CC1]

Isopropyl 2-(hydroxymethyl)-6-nitro-benzoate 0.60 g (3.3 mmol) of 7-nitro-3H-isobenzofuran-1-one (J. Org. Chem, 1987, 129-134) suspended in 3.5 mL of 1 M NaOH and 1.5 mL THF was heated at 50° C. for 30 min. Then, the solution was concentrated and the residue was suspended in 3 mL of DMA and 0.6 g (3.52 mmol) of 2-iodopropane was added. The reaction was carried out for 12 h at RT, then a further portion of 0.114 g (0.67 mmol) of 2-iodopropane was added to the mixture. After 16 h the reaction was quenched with water and it was extracted with EtOAc, the organic layers were dried over Na$_2$SO$_4$, filtered and concentrated. The residue was then purified by column chromatography (eluent: EtOAc/hexane, from 5% to 40% of EtOAc) providing 388 mg (48%) of isopropyl 2-(hydroxymethyl)-6-nitro-benzoate. $^1$H NMR (DMSO-d$_6$) δ (ppm): 8.11-7.67 (m, 3H), 5.59 (bs, 1H), 5.22-5.09 (m, 1H), 4.58 (m, 2H), 1.28 (m, 6H).

Isopropyl 2-[[tert-butyl(dimethyl)silyl]oxymethyl]-6-nitro-benzoate 0.27 g (1.8 mmol) of tert-butyl-chloro-dimethyl-silane dissolved in 1 mL of CH$_2$Cl$_2$ was added under nitrogen atmosphere at 0° C. to a solution of 0.387 g (1.62 mmol) of isopropyl 2-(hydroxymethyl)-6-nitro-benzoate and 0.14 g (2.1 mmol) of imidazole in 1 ml of dry CH$_2$Cl$_2$. The mixture was stirred for 15 min; the white precipitate was filtered off and rinsed with CH$_2$Cl$_2$ providing 0.572 g (quantitative) isopropyl 2-[[tert-butyl(dimethyl)silyl]oxymethyl]-6-nitro-benzoate. $^1$H NMR (DMSO-d$_6$) δ (ppm): 8.11-7.73 (m, 3H), 5.21-5.11 (m, 1H), 4.77 (s, 2H), 1.31-1.27 (m, 6H), 0.87 (s, 9H), 0.06 (s, 6H); MS (ESI): m/z: 354 [M+H]$^+$.

[2-[[tert-Butyl(dimethyl)silyl]oxymethyl]-6-nitro-phenyl]methanol 0.594 g (1.68 mmol) of isopropyl 2-[[tert-butyl(dimethyl) silyl]oxymethyl]-6-nitro-benzoate dissolved in 1.7 mL of THF was added under nitrogen atmosphere to a 2 M suspension of LiBH$_4$ in THF (2.7 mL, 5.4 mmol) at 0° C. Then, 0.24 mL of dry MeOH was added and the mixture was stirred at 60° C. for 30 min. The mixture was then cooled down to 0° C. and it was quenched with a saturated aqueous NH$_4$Cl solution; it was extracted with EtOAc and the combined organic layers were dried over Na$_2$SO$_4$, filtered and evaporated to afford a residue, which was purified by column chromatography (eluent: EtOAc/hexane, from 1% to 10% EtOAc) providing 0.303 g (61%) of [2-[[tert-butyl (dimethyl)silyl]oxymethyl]-6-nitro-phenyl]methanol as a pale yellow oil. $^1$H NMR (DMSO-d$_6$) δ (ppm): 7.77-7.44 (m, 3H), 5.28-5.23 (m, 1H), 4.88 (s, 2H), 4.63-4.59 (m, 2H), 0.90 (s, 9H), 0.09 (s, 6H); MS (ESI): m/z: 298 [M+H]$^+$.

[2-[[tert-Butyl(dimethyl)silyl]oxymethyl]-6-nitro-phenyl]methyl methanesulfonate 0.17 mL (1.2 mmol) of TEA was added under nitrogen atmosphere to a solution of 0.28 g (0.94 mmol) of [2-[[tert-butyl(dimethyl)silyl]oxymethyl]-6-nitro-phenyl]methanol in 3 mL of CH$_2$Cl$_2$ cooled down to −15° C.; then 0.087 mL (1.1 mmol) of methanesulfonyl chloride was added After stirring the mixture for 20 min at −15° C., the reaction was stopped by adding an aqueous saturated NaHCO$_3$ solution and the product was extracted with CH$_2$Cl$_2$. The combined organic layers were dried over Na$_2$SO$_4$, filtered and evaporated to afford 0.35 g (quantitative) of 2-[[tert-butyl(dimethyl)silyl]oxymethyl]-6-nitro-phenyl]methyl methanesulfonate. $^1$H NMR (DMSO-d$_6$) δ (ppm): 7.95-7.65 (m, 3H), 5.43 (s, 2H), 4.93 (s, 2H), 3.23 (s, 3H), 0.90 (s, 9H), 0.1 (s, 6H).

4-[[2-[[tert-Butyl(dimethyl)silyl]oxymethyl]-6-nitro-phenyl]methoxy]phenol 0.354 g (0.942 mmol) of [2-[[tert-butyl(dimethyl)silyl] oxymethyl]-6-nitro-phenyl]methyl methanesulfonate dissolved in 4 mL of acetone was added dropwise to a suspension of 0.519 g (4.71 mmol) of benzene-1,4-diol and 0.33 g (2.4 mmol) of K₂CO₃ in 1 mL of acetone. The mixture was stirred overnight at RT and then for 45 min at 60° C. Then the solvent was removed and the residue was extracted with CH₂Cl₂. The combined organic layers were dried over Na₂SO₄, filtered and evaporated to afford a residue, which was purified by column chromatography (eluent: EtOAc/hexane, from 3% to 30% EtOAc) providing 0.218 g (59%) of 4-[[2-[[tert-butyl(dimethyl)silyl]oxymethyl]-6-nitro-phenyl]methoxy]phenol. $^1$H NMR (DMSO-d₆) δ (ppm): 9.02 (s, 1H), 7.82-7.55 (m, 3H), 6.78-6.62 (m, 4H), 5.10 (s, 2H), 4.88 (s, 2H), 0.87 (s, 9H), 0.06 (s, 6H); MS (ESI): m/z: 390 [M+H]⁺.

tert-Butyl 4-[4-[[2-[[tert-butyl(dimethyl)silyl]oxymethyl]-6-nitro-phenyl]methoxy]phenoxy]-piperidine-1-carboxylate 0.04 g (0.15 mmol) of PPh₃ was added at 0° C. and under nitrogen atmosphere to a solution of 0.04 g (0.10 mmol) 4-[[2-[[tert-butyl(dimethyl)silyl]oxymethyl]-6-nitro-phenyl]methoxy]phenol and 0.031 g (0.15 mmol) of tert-butyl 4-hydroxypiperidine-1-carboxylate in 0.6 mL of THF. 0.031 g (0.15 mmol) of DIAD was slowly added and the mixture was stirred overnight at RT. The solvent was then removed and the residue was purified by column chromatography (eluent: EtOAc/hexane, from 2% to 20% of EtOAc) providing 0.0355 g (60%) of tert-butyl 4-[4-[[2-[[tert-butyl(dimethyl)silyl]oxymethyl]-6-nitro-phenyl]methoxy]phenoxy]piperidine-1-carboxylate [$^1$H NMR (DMSO-d₆) δ (ppm): 7.85-7.55 (m, 3H), 6.94-6.81 (m, 4H), 5.14 (s, 2H), 4.89 (s, 2H), 4.45-4.34 (m, 1H), 3.68-3.55 (m, 2H), 3.21-3.02 (m, 2H), 1.89-1.43 (m, 4H), 1.39 (s, 9H), 0.87 (s, 9H), 0.06 (s, 6H); MS (ESI): m/z: 573 [M+H]⁺], tert-Butyl 4-[4-[[2-amino-6-[(1-methyl-1-trimethylsilyl-ethoxy)methyl]phenyl]methoxy]-phenoxy]piperidine-1-carboxylate 0.034 g (0.059 mmol) of tert-butyl 4-[4-[[2-[[tert-butyl(dimethyl)silyl]oxymethyl]-6-nitro-phenyl]methoxy]phenoxy]piperidine-1-carboxylate were reduced to tert-butyl 4-[4-[[2-amino-6-[[tert-butyl(dimethyl)silyl]oxymethyl]phenyl]methoxy]phenoxy]piperidine-1-carboxylate (yield: 94%) according to the procedure of Intermediate 3, step 3. $^1$H NMR (DMSO-d₆) δ (ppm): 7.04-6.56 (m, 7H), 5.05 (bs, 2H), 4.93 (s, 2H), 4.65 (s, 2H), 4.44-4.36 (m, 1H), 3.67-3.54 (m, 2H), 3.24-3.03 (m, 2H), 1.89-1.43 (m, 4H), 1.39 (s, 9H), 0.83 (s, 9H), 0.01 (s, 6H); MS (ESI): m/z: 543 [M+H]⁺.

Intermediate 24: tert-Butyl 4-[4-[[2-(methylsulfonyloxymethyl)-6-[(4-methylthieno[3,2-b]pyrrole-5-carbonyl)amino]phenyl]methoxy]phenoxy]-piperidine-1-carboxylate

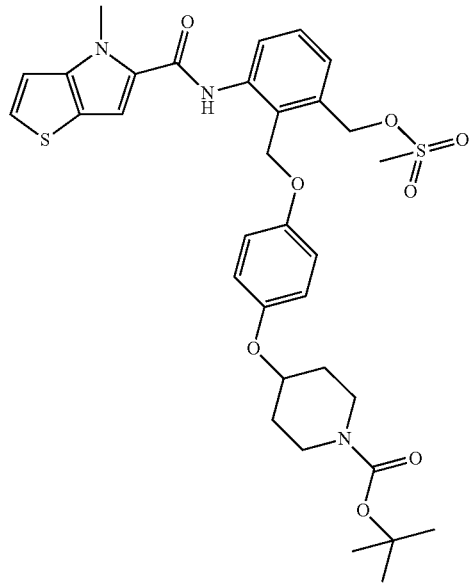 [SMILES: Cn1c(C(=O)Nc2cccc(COS(C)(=O)=O)c2COc2ccc(OC3CCN(C(=O)OC(C)(C)C)CC3)cc2)cc2sccc21]

tert-Butyl 4-[4-[[2-[[tert-butyl(dimethyl)silyl]oxymethyl]-6-[(4-methylthieno[3,2-b]pyrrole-5-carbonyl)amino]phenyl]methoxy]phenoxy]piperidine-1-carboxylate 0.031 mg (67%) of tert-butyl 4-[4-[[2-[[tert-butyl(dimethyl)silyl]oxymethyl]-6-[(4-methylthieno[3,2-b]pyrrole-5-carbonyl)amino]phenyl]methoxy]phenoxy]piperidine-1-carboxylate were obtained starting from 0.012 g (0.066 mmol) of 4-methylthieno[3,2-b]pyrrole-5-carboxylic acid (Intermediate 1) and 0.030 g (0.060 mmol) of tert-butyl 4-[4-[[2-amino-6-[(1-methyl-1-trimethylsilyl-ethoxy) methyl]phenyl]methoxy]phenoxy]-piperidine-1-carboxylate (Intermediate 23) according to the procedure of Example 1, step 1. $^1$H NMR (DMSO-d₆) δ (ppm): 9.80 (s, 1H), 7.84-7.50 (m, 1H), 7.41-7.36 (m, 3H), 7.23-7.20 (m, 1H), 7.19 (s, 1H), 6.85-6.87 (m, 4H), 5.05 (s, 2H), 4.85 (s, 2H), 4.43-4.29 (m, 1H), 3.98 (s, 3H), 3.65-3.54 (m, 2H), 3.20-3.02 (m, 2H), 1.87-1.74 (m, 2H), 1.51-1.41 (m, 2H), 1.38 (s, 9H), 0.88 (s, 9H), 0.05 (s, 6H); MS (ESI): m/z: 707 [M+H]⁺.

4-[4-[[2-(Hydroxymethyl)-6-[(4-methylthieno[3,2-b]pyrrole-5-carbonyl)amino]phenyl]-methoxy]phenoxy]piperidine-1-carboxylate 0.047 mL of 1 M tetrabutylammonium fluoride in THF was added to a solution of 0.03 g (0.042 mmol) of tert-butyl 4-[4-[[2-[[tert-butyl(dimethyl)silyl]oxymethyl]-6-[(4-methylthieno[3,2-b]pyrrole-5-carbonyl)amino]phenyl]methoxy] phenoxy]piperidine-1-carboxylate in 0.2 mL THF. The mixture was stirred for 45 min at RT, then the solvent was removed and the residue was extracted with EtOAc, the combined organic layers were dried over Na₂SO₄, filtered and evaporated to afford a residue, which was purified by column chromatography (eluent: EtOAc/hexane, from 12% to 100% EtOAc) providing 0.019 g (76%) of tert-4-[4-[[2-(hydroxymethyl)-6-[(4-methylthieno[3,2-b]pyrrole-5-carbonyl)amino]phenyl]methoxy]phenoxy]piperidine-1-carboxylate as a white sticky solid. $^1$H NMR (DMSO-$d_6$) δ (ppm): 9.78 (s, 1H), 7.50-7.48 (m, 1H), 7.40-7.35 (m, 3H), 7.23-6.20 (m, 1H), 7.17 (s, 1H), 6.91-6.83 (m, 4H), 5.24 (m, 1H), 5.04 (s, 2H), 4.66-4.62 (m, 2H), 4.41-4.32 (m, 1H), 3.97 (s, 3H), 3.66-3.56 (m, 2H), 3.20-3.04 (m, 2H), 1.86-1.75 (m, 2H), 1.49-1.43 (m, 2H), 1.39 (s, 9H); MS (ESI): m/z: 592 [M+H]$^+$.

tert-Butyl 4-[4-[[2-(methylsulfonyloxymethyl)-6-[(4-methylthieno[3,2-b]pyrrole-5-carbonyl)amino]phenyl]methoxy]phenoxy]piperidine-1-carboxylate 0.016 mL (0.11 mmol) of TEA was added under N$_2$ atmosphere to a solution of 0.040 g (0.068 mmol) of tert-butyl 4-[4-[[2-(hydroxymethyl)-6-[(4-methylthieno[3,2-b]pyrrole-5-carbonyl)amino]phenyl]methoxy]phenoxy]piperidine-1-carboxylate in 0.4 mL of CH$_2$Cl$_2$ cooled down to −15° C. Then, 0.011 g (0.095 mmol) of methanesulfonyl chloride was added and the mixture was stirred for 25 min at −15° C. The reaction was quenched with a saturated NaHCO$_3$ solution and the product was extracted with CH$_2$Cl$_2$. The combined organic layers were dried over Na$_2$SO$_4$, filtered and concentrated to give 49.7 mg (quantitative) of tert-butyl 4-[4-[[2-(methylsulfonyloxymethyl)-6-[(4-methylthieno[3,2-b]pyrrole-5-carbonyl)amino]phenyl]methoxy]phenoxy]piperidine-1-carboxylate. $^1$H NMR (DMSO-$d_6$) δ (ppm): 9.91 (s, 1H), 7.55-7.13 (m, 6H), 6.93-6.78 (m, 4H), 5.44 (s, 2H), 5.09 (s, 2H), 4.41-4.31 (m, 1H), 3.98 (s, 3H), 3.66-3.55 (m, 2H), 3.20 (s, 3H), 3.14-3.06 (m, 2H), 1.87-1.75 (m, 2H), 1.51-1.40 (m, 2H), 1.39 (s, 9H); MS (ESI): m/z: 670 [M+H]$^+$.

Intermediate 25: N-[2-[(4-hydroxyphenoxy)methyl]-5-methyl-phenyl]-4-methyl-thieno[3,2-b]pyrrole-5-carboxamide

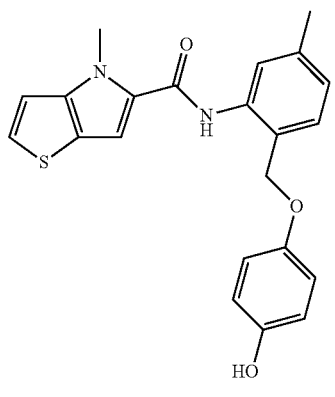 [SMILES: Cc1ccc(COc2ccc(O)cc2)c(NC(=O)c2cc3sccc3n2C)c1]

3-(Bromomethyl)-2-nitro-benzene 1.5 g (9.0 mmol) of 4-methyl-2-nitro-phenyl)methanol (Fluorochem, Cat No. 390234) was dissolved in 40 mL of CH$_2$Cl$_2$. The solution was cooled down to 0° C. and 3.7 g (21 mmol) of NBS and 2.6 g (9.9 mmol) of PPh$_3$ were added. The reaction mixture was allowed to reach RT. After stirring overnight at RT, the solvent was evaporated and the orange oily residue was purified by column chromatography (eluent: EtOAc/hexane, from 5% to 20% EtOAc) providing 1.52 g (74%) of 3-(bromomethyl)-2-nitro-benzene as a pale orange oil. $^1$H NMR (CDCl$_3$) δ (ppm): 7.87 (s, 1H), 7.48-7.38 (m, 2H), 4.82 (s, 2H), 2.46 (s, 3H).

4-[(2-Amino-4-methyl-phenyl)methoxy]phenol

4-[(2-amino-4-methyl-phenyl)methoxy]phenol was prepared as described for 4-[(2-aminophenyl)methoxy]phenol (Intermediate 7) starting from 3-(bromomethyl)-2-nitro-benzene and hydroquinone and subsequent reduction of the nitro group to give 4-[(2-amino-4-methyl-phenyl)methoxy]phenol as a white solid. $^1$H NMR (CDCl$_3$) δ (ppm): 7.05 (d, J=7.3 Hz, 1H), 6.89 (d, J=9.3 Hz, 2H), 6.76 (d, J=9.3 Hz, 2H), 6.62-6.53 (m, 2H), 4.95 (s, 2H), 4.43 (bs, 1H), 4.04 (bs, 2H), 2.28 (s, 3H); MS (ESI): m/z: 230 [M+H]$^+$.

N-[2-[(4-Hydroxyphenoxy)methyl]-5-methyl-phenyl]-4-methyl-thieno[3,2-b]pyrrole-5-carboxamide N-[2-[(4-hydroxyphenoxy)methyl]-5-methyl-phenyl]-4-methyl-thieno[3,2-b]pyrrole-5-carboxamide was prepared as described for Intermediate 9 starting from 4-methylthieno[3,2-b]pyrrole-5-carboxylic acid (Intermediate 1) and 4-[(2-amino-4-methyl-phenyl)methoxy]phenol.

$^1$H NMR (DMSO-$d_6$) δ (ppm): 9.65 (s, 1H), 8.92 (s, 1H), 7.51 (d, J=5.4 Hz, 1H), 7.41-7.33 (m, 2H), 7.27-7.19 (m, 2H), 7.05 (d, J=7.8 Hz, 1H), 6.78 (d, J=8.8 Hz, 2H), 6.63 (d, J=8.8 Hz, 2H), 5.01 (s, 2H), 4.00 (s, 3H), 2.32 (s, 3H); MS (ESI): m/z: 393 [M+H]$^+$.

Intermediate 26: tert-Butyl 4-[[6-[(2-aminophenyl)methoxy]-3-pyridyl]oxy]piperidine-1-carboxylate

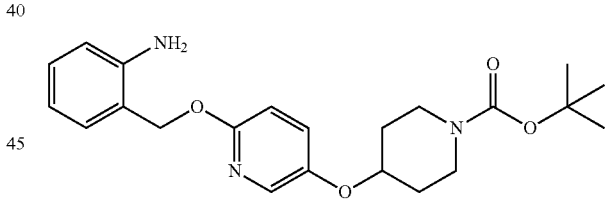

tert-Butyl 4-[(6-chloro-3-pyridyl)oxy]piperidine-1-carboxylate tert-butyl 4-[(6-chloro-3-pyridyl)oxy]piperidine-1-carboxylate was prepared according to the procedure for Intermediate 3, step 2, starting from 2-chloro-5-hydroxypyridine (Apollo Scientific, Cat No. OR8994) and tert-butyl 4-hydroxypiperidine-1-carboxylate. $^1$H NMR (CDCl$_3$) δ (ppm): 7.99-8.13 (m, 1H), 7.11-7.31 (m, 2H), 4.38-4.55 (m, 1H), 3.61-3.76 (m, 2H), 3.23-3.41 (m, 2H), 1.68-2.00 (m, 4H), 1.48 (s, 9H); MS (ESI): m/z: 257 [M+H]$^+$.

tert-Butyl 4-[(6-hydroxy-3-pyridyl)oxy]piperidine-1-carboxylate 3 mL of dioxan was added under argon atmosphere to a mixture of 0.23 g (0.74 mmol) of tert-butyl 4-[(6-chloro-3- pyridyl)oxy]piperidine-1-carboxylate, 0.007 g (0.007 mmol) of Pd(dba)$_2$, 0.01 g (0.02 mmol) of ditert-butyl-[2,3,4,5-tetramethyl-6-(2,4,6-triisopropylphenyl)phenyl]phosphane and 0.124 g (2.21 mmol) of KOH in 0.4 mL of H$_2$O and the reaction was carried out under argon atmosphere for 24 h at 106° C. The solution was then allowed to cool down to RT, brought to a pH value of 4-5 with 0.1 M HCl and the product was extracted with CH$_2$Cl$_2$. The combined organic phases were washed with brine, dried over Na$_2$SO$_4$, filtered, concentrated and purified by column chromatography (eluent: CH$_2$Cl$_2$/MeOH, from 1% to 10% MeOH) providing 0.152 g (70%) of tert-butyl 4-[(6-hydroxy-3-pyridyl)oxy]piperidine-1-carboxylate as a beige solid. $^1$H NMR (DMSO-d$_6$) δ (ppm): 11.15 (bs, 1H), 7.33 (dd, J=9.78, 3.42 Hz, 1H), 7.12-7.23 (m, 1H), 6.32 (m, 1H), 4.19 (bs, 1H), 3.55-3.69 (m, 2H), 3.10 (bs, 2H), 1.71-1.89 (m, 2H), 1.29-1.52 (m, 11H); MS (ESI): m/z: 239 [M+H−56]$^+$.

tert-Butyl 4-[[6-[(2-nitrophenyl)methoxy]-3-pyridyl]oxy]piperidine-1-carboxylate A mixture of 0.138 g (0.469 mmol) of tert-butyl 4-[(6-hydroxy-3-pyridyl)oxy]piperidine-1-carboxylate, 0.11 g (0.52 mmol) and of 0.16 g (1.2 mmol) 1-(bromomethyl)-2-nitro-benzene and K$_2$CO$_3$ in 1 mL of DMF was stirred at RT for 5 h. Water was then added to the mixture and the product was extracted with CH$_2$Cl$_2$. The combined organic phases were washed with brine, dried over Na$_2$SO$_4$, filtered, concentrated and purified by column chromatography (eluent: hexane/acetone, 3:1, v:v) providing 0.170 g (84%) of tert-butyl 4-[[6-[(2-nitrophenyl)methoxy]-3-pyridyl]oxy]piperidine-1-carboxylate. $^1$H NMR (DMSO-d$_6$) δ (ppm): 8.11 (m, 1H), 7.37-7.76 (m, 4H), 6.93 (m, 1H), 6.44 (m, 1H), 5.35 (s, 2H), 4.07-4.22 (m, 1H), 3.53-3.67 (m, 2H), 3.10 (bs, 2H), 1.84 (bs, 2H), 1.32-1.54 (m, 11H); MS (ESI): m/z: 430 [M+H]$^+$.

tert-Butyl 4-[[6-[(2-aminophenyl)methoxy]-3-pyridyl]oxy]piperidine-1-carboxylate A mixture of 0.11 g (0.26 mmol) of tert-butyl 4-[[6-[(2-nitrophenyl)methoxy]-3-pyridyl]oxy]piperidine-1-carboxylate, 0.072 g (1.3 mmol) of iron and 0.034 g (0.64 mmol) of NH$_4$Cl in 5 mL of a water/EtOH mixture (1:2, v:v) was heated to reflux for 1 h. Then, the solution was allowed to cold down to RT, filtered through a celite pad and rinsed with CH$_2$Cl$_2$. Water was added and the two phases were separated. The organic layer was dried over Na$_2$SO$_4$, filtered and concentrated to provide 0.087 g (85%) of tert-butyl 4-[[6-[(2-aminophenyl)methoxy]-3-pyridyl]oxy]piperidine-1-carboxylate. $^1$H NMR (DMSO-d$_6$) δ (ppm): 7.49 (m, 1H), 7.39 (m, 1H), 6.92-7.16 (m, 2H), 6.92-7.16 (m, 2H), 6.32-6.65 (m, 3H), 5.47 (s, 2H), 4.12-4.23 (m, 1H), 4.90 (s, 2H), 3.54-3.67 (m, 2H), 3.10 (bs, 2H), 1.69-1.87 (m, 2H), 1.31-1.51 (m, 11H); MS (ESI): m/z: 400 [M+H]$^+$.

Intermediate 27: tert-Butyl 4-[3-[(3-aminophenyl)methoxy]phenoxy]piperidine-1-carboxylate

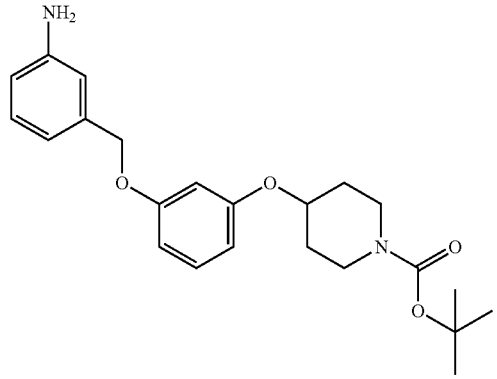 [SMILES: CC(C)(C)OC(=O)N1CCC(Oc2cccc(OCc3cccc(N)c3)c2)CC1]

3-[(3-Nitrophenyl)methoxy]phenol

3-[(3-nitrophenyl)methoxy]phenol was obtained starting from 1-(bromomethyl)-3-nitro-benzene (Fluorochem, Cat. No. 002721) and resorcinol according to the procedure for Intermediate 3, step 1 (75%). $^1$H NMR (CDCl$_3$) δ (ppm): 8.36-8.30 (m, 1H), 8.25-8.15 (m, 1H), 7.81-7.74 (m, 1H), 7.62-7.55 (m, 1H), 7.21-7.13 (m, 1H), 6.62-6.54 (m, 1H), 6.53-6.44 (m, 2H), 5.15 (s, 2H), 4.74 (bs, 1H); MS (ESI): m/z: 244 [M−H]$^-$.

tert-Butyl 4-[3-[(3-nitrophenyl)methoxy]phenoxy]piperidine-1-carboxylate tert-Butyl 4-[3-[(3-nitrophenyl)methoxy]phenoxy]piperidine-1-carboxylate was prepared according to the procedure described for Intermediate 3, step 2, starting from 4-[(3-nitrophenyl)methoxy]phenol and tert-butyl 4-hydroxypiperidine-1-carboxylate (45%). $^1$H NMR (CDCl$_3$) δ (ppm): 8.37-8.31 (m, 1H), 8.25-8.17 (m, 1H), 7.81-7.74 (m, 1H), 7.62-7.54 (m, 1H), 7.25-7.17 (m, 1H), 6.63-6.53 (m, 3H), 5.14 (s, 2H), 4.52-4.41 (m, 1H), 3.77-3.65 (m, 2H), 3.39-3.30 (m, 2H), 1.99-1.87 (m, 2H), 1.82-1.68 (m, 2H), 1.48 (s, 9H); MS (ESI): m/z: 373 [M+H−56]$^+$.

tert-Butyl 4-[3-[(3-aminophenyl)methoxy]phenoxy]piperidine-1-carboxylate

Reduction of tert-butyl 4-[3-[(3-nitrophenyl)methoxy]phenoxy]piperidine-1-carboxylate to tert-butyl 4-[3-[(3-aminophenyl)methoxy]phenoxy]piperidine-1-carboxylate was carried out according to the procedure described for Intermediate 3, step 3 (70%). $^1$H NMR (CDCl$_3$) δ (ppm): 7.26-7.21 (m, 1H), 7.21-7.14 (m, 1H), 6.97-6.92 (m, 2H), 6.86-6.80 (m, 1H), 6.60-6.50 (m, 3H), 4.98 (s, 2H), 4.48-4.38 (m, 1H), 3.75-3.65 (m, 2H), 3.36-3.27 (m, 2H), 1.97-1.85 (m, 2H), 1.79-1.68 (m, 2H), 1.47 (s, 9H); MS (ESI): m/z: 399 [M+H]$^+$

Intermediate 28: tert-Butyl N-[[4-[(3-aminophenyl)methoxy]phenyl]methyl]-N-[(Z)—N,N,N'-tris(tert-butoxycarbonyl)carbamimidoyl]carbamate

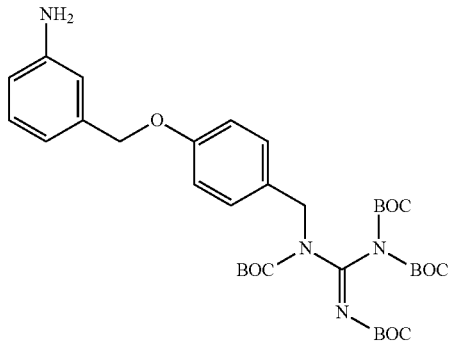 [SMILES: CC(C)(C)OC(=O)/N=C(/N(Cc1ccc(OCc2cccc(N)c2)cc1)C(=O)OC(C)(C)C)N(C(=O)OC(C)(C)C)C(=O)OC(C)(C)C]

[4-[(3-Nitrophenyl)methoxy]phenyl]methanol 0.29 g (7.8 mmol) of NaBH₄ was added in portions to a solution of 2.0 g (7.8 mmol) of 4-[(3-nitrobenzyl)oxy]benzaldehyde (Helv. Chim. Acta, 1993, 76, 1361-1378) in 30 mL of MeOH. After stirring for 1 h at RT the solution was poured into an ice/water mixture and the product was extracted with CH₂Cl₂. The combined organic layers were dried over Na₂SO₄, filtered and evaporated providing 1.967 g (97%) of [4-[(3-nitrophenyl)methoxy]phenyl]methanol as a yellow solid. ¹H NMR (DMSO-d₆) δ (ppm): ¹H NMR (DMSO-d₆) δ (ppm): 8.30 (s, 1H), 8.19 (d, J=7.8 Hz, 1H), 7.90 (d, J=7.3 Hz, 1H), 7.73-7.66 (m, 1H), 7.24 (d, J=8.3 Hz, 2H), 6.99 (d, J=8.3 Hz, 2H), 5.26 (s, 2H), 5.06 (t, J=5.6 Hz, 1H), 4.41 (d, J=5.4 Hz, 2H); MS (ESI): m/z: 242 [M+H-H₂O]⁺.

tert-Butyl N-[(E)-N'-tert-butoxycarbonylcarbamimidoyl]-N-[[4-[(3-nitrophenyl)methoxy]-phenyl]methyl]carbamate 0.92 g (3.4 mmol) of PPh₃ and 0.60 g (2.4 mmol) of [4-[(3-nitrophenyl)methoxy]phenyl]methanol was added to a solution of 0.60 g (2.4 mmol) of tert-butyl (NE)-N-[amino-(tert-butoxycarbonylamino)methylene]carbamate in 22 mL of dry toluene. 0.74 g (3.5 mmol) of DIAD was slowly added to the solution cooled down to 0° C. and the mixture was then stirred overnight at RT. Water was then added and the solvents were evaporated. The obtained orange oil was purified by column chromatography (eluent: hexane/EtOAc, from 5% to 30% of EtOAc) providing 0.40 g (35%) of tert-butyl N-[(E)-N'-tert-butoxycarbonylcarbamimidoyl]-N-[[4-[(3-nitrophenyl)methoxy]phenyl]methyl]carbamate as a colourless oil. ¹H NMR (DMSO-d₆) δ (ppm): 9.13 (bs, 2H), 8.28 (s, 1H), 8.18 (d, J=8.3 Hz, 1H), 7.89 (d, J=7.3 Hz, 1H), 7.69 (t, J=7.8 Hz, 1H), 7.14 (d, J=8.8 Hz, 2H), 7.01 (d, J=8.3 Hz, 2H), 5.26 (s, 2H), 4.96 (s, 2H), 1.53-1.13 (m, 18H); MS (ESI): m/z: 501 [M+H]⁺.

tert-Butyl N-[(Z)—N,N'-bis(tert-butoxycarbonyl)-N-[[4-[(3-nitrophenyl)methoxy]phenyl]-methyl]carbamimidoyl]-N-tert-butoxycarbonyl-carbamate 2.84 g (13.0 mmol) of (BOC)₂O and 0.032 g (0.26 mmol) of DMAP were added to a solution of 0.43 g (0.86 mmol) of tert-butyl N-[(E)-N'-tert-butoxycarbonylcarbamimidoyl]-N-[[4-[(3-nitrophenyl)methoxy]phenyl]methyl]carbamate in 13 mL of dry ACN under nitrogen atmosphere. The mixture was heated to reflux for 22 h, then the solvent was evaporated and the oil residue was purified by column chromatography (eluent: hexane/EtOAc, from 5% to 30% of EtOAc) providing 0.379 g (63%) of tert-butyl N-[(Z)—N,N'-bis(tert-butoxycarbonyl)-N-[[4-[(3-nitrophenyl)methoxy]phenyl]methyl]carbamimidoyl]-N-tert-butoxycarbonyl-carbamate. ¹H NMR (DMSO-d₆) δ (ppm): 8.29 (s, 1H), 8.18 (d, J=9.3 Hz, 1H), 7.89 (d, J=7.8 Hz, 1H), 7.71-7.66 (m, 1H), 7.25 (d, J=8.3 Hz, 2H), 6.99 (d, J=8.3 Hz, 2H), 5.27 (s, 2H), 4.86 (s, 2H), 1.63-0.98 (m, 36H); MS (ESI): m/z: 701 [M+H]⁺.

tert-Butyl N-[[4-[(3-aminophenyl)methoxy]phenyl]methyl]-N-[(Z)—N,N,N'-tris(tert-butoxycarbonyl)carbamimidoyl]carbamate Reduction of tert-butyl N-[[4-[(3-nitrophenyl)methoxy]phenyl]methyl]-N-[(Z)—N,N,N'-tris(tert-butoxycarbonyl)carbamimidoyl]carbamate to tert-butyl N-[[4-[(3-aminophenyl)methoxy]phenyl]methyl]-N-[(Z)—N,N,N'-tris(tert-butoxycarbonyl)-carbamimidoyl]carbamate was carried out according to the procedure described for Intermediate 3, step 3. ¹H NMR (DMSO-d₆) δ (ppm): 7.23 (d, J=8.3 Hz, 2H), 7.01-6.96 (m, 1H), 6.91 (d, J=8.3 Hz, 2H), 6.60 (s, 1H), 6.55-6.46 (m, 2H), 5.10 (s, 2H), 4.90 (s, 2H), 4.85 (s, 2H), 1.44-1.29 (m, 36H); MS (ESI): m/z: 671 [M+H]⁺.

Intermediate 29: tert-Butyl N-[[4-[(2-aminophenyl)methoxy]phenyl]methyl]-N-[(Z)—N,N'-bis(tert-butoxycarbonyl)carbamimidoyl]carbamate

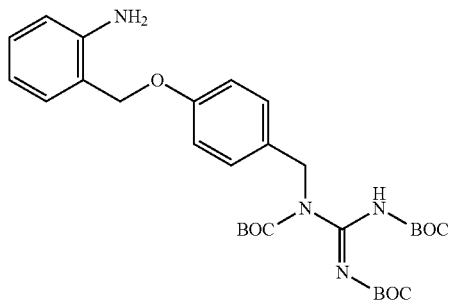 [SMILES: CC(C)(C)OC(=O)/N=C(\NC(=O)OC(C)(C)C)N(Cc1ccc(OCc2ccccc2N)cc1)C(=O)OC(C)(C)C]

tert-Butyl N-[[4-[(2-aminophenyl)methoxy]phenyl]methyl]-N-[(Z)—N,N'-bis(tert-butoxycarbonyl)carbamimidoyl]carbamate was prepared starting from 4-[(2-nitrobenzyl)oxy]benzaldehyde (Vitas-M Lab, cat. no. STL286541) according to the procedure described for Intermediate 27. ¹H NMR (DMSO-d₆) δ (ppm): 10.28 (bs, 1H), 7.21 (d, J=8.8 Hz, 2H), 7.16 (d, J=7.3 Hz, 1H), 7.04-6.93 (m, 3H), 6.66 (d, J=7.8 Hz, 1H), 6.53 (t, J=7.3 Hz, 1H), 5.02 (s, 2H), 4.94 (s, 2H), 4.65 (s, 2H), 1.46-1.28 (m, 27H); MS (ESI): m/z: 571 [M+H]⁺.

Intermediate 30: tert-Butyl 4-[4-[2-(2-aminophenyl)ethyl]phenoxy]piperidine-1-carboxylate

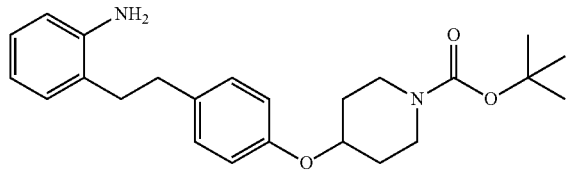 [SMILES: CC(C)(C)OC(=O)N1CCC(Oc2ccc(CCc3ccccc3N)cc2)CC1]

tert-Butyl 4-[4-[(E)-2-(2-nitrophenyl)vinyl]phenoxy]piperidine-1-carboxylate 1.1 mL of a 1 M solution of LiHMDS in THF was added dropwise at 0° C. to a solution of 0.27 g (1.0 mmol) of 1-(diethoxyphosphorylmethyl)-2-nitro-benzene (Org. Lett. 2013, 15, 824-827) in 5 mL of dry THF. After stirring for 10 min at 0° C., 0.31 g (1.0 mmol) of tert-butyl 4-(4-formylphenoxy)piperidine-1-carboxylate (WO2010/11657) in 1 mL of THF was added in one portion and stirring was continued for 20 min at 0° C. and then 2 h at RT. Then, a further portion of 0.3 mL of 1 M LiHMDS in THF was added and the mixture was stirred for 1 h at RT. The solution was then diluted with $Et_2O$, washed with brine and dried over $Na_2SO_4$. The solution was filtered off, concentrated and the residue was purified by column chromatography (eluent: hexane/acetone, from 0% to 15% of acetone) providing 0.313 g (74%) of tert-butyl 4-[4-[(E)-2-(2-nitrophenyl)vinyl]phenoxy]piperidine-1-carboxylate as a yellow oil. $^1H$ NMR ($CDCl_3$) δ (ppm): 7.99-7.93 (m, 1H), 7.80-7.74 (m, 1H), 7.63-7.57 (m, 1H), 7.52-7.44 (m, 3H), 7.42-7.36 (m, 1H), 7.06 (d, J=15.7 Hz, 1H), 6.96-6.90 (m, 2H), 4.59-4.47 (m, 1H), 3.77-3.66 (m, 2H), 3.43-3.29 (m, 2H), 2.00-1.89 (m, 2H), 1.85-1.71 (m, 2H), 1.49 (s, 9H); MS (ESI): m/z: 369 [M+H−56]$^+$.

tert-Butyl 4-[4-[2-(2-aminophenyl)ethyl]phenoxy]piperidine-1-carboxylate 0.24 g (0.57 mmol) of tert-butyl 4-[4-[(E)-2-(2-nitrophenyl)vinyl]phenoxy]piperidine-1-carboxylate was dissolved in 23 mL of EtOH and the solution was hydrogenated in an H-Cube apparatus (Pd/C 10% cartridge, flow 0.5 mL/min, atmospheric pressure, 30° C.). The colourless solution was concentrated to afford 214 mg (95%) of tert-butyl 4-[4-[2-(2-aminophenyl)ethyl]phenoxy]piperidine-1-carboxylate as a pale yellow solid. $^1H$ NMR (DMSO-$d_6$) δ (ppm): 7.25-7.11 (m, 2H), 6.93-6.84 (m, 4H), 6.64-6.56 (m, 1H), 6.50-6.41 (m, 1H), 4.83 (s, 2H), 4.54-4.43 (m, 1H), 3.69-3.58 (m, 2H), 3.23-3.09 (m, 2H), 2.77-2.59 (m, 4H), 1.93-1.80 (m, 2H), 1.55-1.44 (m, 2H), 1.40 (s, 9H); MS (ESI): m/z: 397 [M+H]$^+$.

Intermediate 31: tert-Butyl 4-[4-[2-(3-aminophenyl)ethyl]phenoxy]piperidine-1-carboxylate

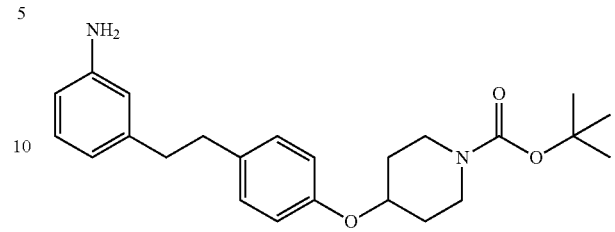

tert-Butyl 4-[4-[2-(3-aminophenyl)ethyl]phenoxy]piperidine-1-carboxylate was prepared starting from 1-(diethoxyphosphorylmethyl)-3-nitro-benzene (WO2014/70859) following the procedure described for Intermediate 29. $^1H$ NMR (DMSO-$d_6$) δ (ppm): 7.16-7.08 (m, 3H), 6.88-6.80 (m, 2H), 6.72-6.61 (m, 3H), 4.48-4.38 (m, 1H), 3.76-3.66 (m, 2H), 3.39-3.28 (m, 2H), 2.91-2.74 (m, 4H), 1.98-1.86 (m, 2H), 1.81-1.70 (m, 2H), 1.48 (s, 9H); MS (ESI): m/z: 397 [M+H]$^+$.

Intermediate 32: tert-butyl 4-[4-[(2-aminophenyl)methyl-tert-butoxycarbonyl-amino]phenoxy]piperidine-1-carboxylate

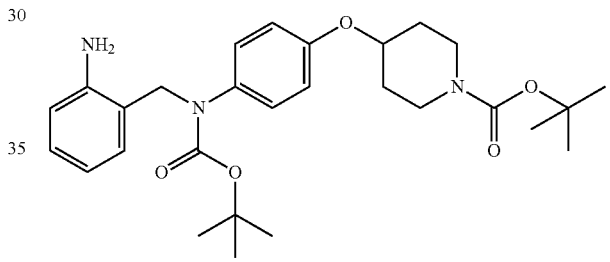

tert-Butyl 4-[4-[(2-nitrophenyl)methylamino]phenoxy]piperidine-1-carboxylate 0.62 g (2.8 mmol) of NaBH(OAc)$_3$ was added in portions to a stirred solution of 0.28 g (1.9 mmol) 2-nitrobenzaldehyde, 0.54 g (1.9 mmol) of tert-butyl 4-(4-aminophenoxy)piperidine-1-carboxylate (Sigma Aldrich, Cat No. CDS017851) and 0.53 mL (9.3 mmol) of acetic acid in 12 mL of 1,2-dichloroethane. After stirring at RT overnight, the solution was diluted with $CH_2Cl_2$, washed with an aqueous $NaHCO_3$ solution and brine and dried over $Na_2SO_4$. The solution was filtered off, concentrated and the residue was purified by column chromatography (eluent: hexane/EtOAc, from 7% to 50% of EtOAc) providing 0.681 g (86%) of tert-butyl 4-[4-[(2-nitrophenyl)methylamino]phenoxy]piperidine-1-carboxylate as a orange oil. $^1H$ NMR ($CDCl_3$) δ (ppm): 8.11-8.03 (m, 1H), 7.77-7.68 (m, 1H), 7.63-7.55 (m, 1H), 7.49-7.40 (m, 1H), 6.84-6.73 (m, 2H), 6.69-6.54 (m, 2H), 4.68 (s, 2H), 4.33-4.22 (m, 1H), 3.76-3.62 (m, 2H), 3.33-3.20 (m, 2H), 1.94-1.80 (m, 2H), 1.77-1.63 (m, 2H), 1.47 (s, 9H); MS (ESI): m/z: 372 [M+H−56]+.

tert-Butyl 4-[4-[tert-butoxycarbonyl-[(2-nitrophenyl)methyl]amino]phenoxy]piperidine-1-carboxylate 0.57 mL (4.1 mmol) of TEA, 0.17 g (1.4 mmol) of DMAP and 0.89 g (4.1 mmol) of tert-butoxycarbonyl tert-butyl carbonate were added to 0.58 g (1.36 mmol) of tert-butyl 4-[4-[(2-nitrophenyl)methylamino]phenoxy]piperidine-1-carboxylate in 12 mL of dry CH$_2$Cl$_2$. After stirring at 40° C. for 36 h the mixture was partitioned between water and CH$_2$Cl$_2$, and the combined organic layers were dried over Na$_2$SO$_4$. The solution was filtered off, concentrated and the residue was purified by column chromatography (eluent: hexane/acetone, from 0% to 15% of acetone) providing 0.158 g (24%) of tert-butyl 4-[4-[tert-butoxycarbonyl-[(2-nitrophenyl)methyl]amino]phenoxy]piperidine-1-carboxylate as a orange oil. $^1$H NMR (CDCl$_3$) δ (ppm): 8.10-7.98 (m, 1H), 7.70-7.58 (m, 2H), 7.49-7.39 (m, 1H), 7.21-7.02 (m, 2H), 6.89-6.76 (m, 2H), 5.19 (s, 2H), 4.46-4.35 (m, 1H), 3.75-3.59 (m, 2H), 3.40-3.26 (m, 2H), 1.96-1.82 (m, 2H), 1.79-1.66 (m, 2H), 1.48 (s, 9H), 1.40 (s, 9H); MS (ESI): m/z: 528 [M+H]$^+$.

tert-Butyl 4-[4-[(2-aminophenyl)methyl-tert-butoxycarbonyl-amino]phenoxy]piperidine-1-carboxylate tert-butyl 4-[4-[(2-aminophenyl)methyl-tert-butoxycarbonyl-amino]phenoxy]piperidine-1-carboxylate was prepared starting from tert-butyl 4-[4-[tert-butoxycarbonyl-[(2-nitrophenyl)methyl]amino]phenoxy]piperidine-1-carboxylate according to the procedure described for Intermediate 3, step 3. $^1$H NMR (DMSO-d$_6$) δ (ppm): 7.04-6.96 (m, 2H), 6.94-6.88 (m, 1H), 6.87-6.81 (m, 2H), 6.74-6.65 (m, 1H), 6.63-6.57 (m, 1H), 6.45-6.36 (m, 1H), 5.02 (bs, 2H), 4.59 (s, 2H), 4.50-4.43 (m, 1H), 3.68-3.60 (m, 2H), 3.17-3.08 (m, 2H), 1.90-1.81 (m, 2H), 1.49-1.43 (m, 2H), 1.43-1.29 (m, 18H); MS (ESI): m/z: 498 [M+H]$^+$.

Intermediate 33: N-(2-hydroxyphenyl)-4-methyl-thieno[3,2-b]pyrrole-5-carboxamide

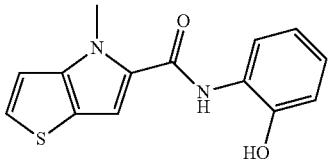 [SMILES: Cn1c(C(=O)Nc2ccccc2O)cc2sccc21]

N-(2-hydroxyphenyl)-4-methyl-thieno[3,2-b]pyrrole-5-carboxamide was obtained starting from 4-methylthieno[3,2-b]pyrrole-5-carboxylic acid (Intermediate 1) and 2-aminophenol according to the procedure described for Intermediate 9. The reaction mixture was quenched with water and concentrated. The residue was dissolved in CH$_2$Cl$_2$, washed with brine, dried over Na$_2$SO$_4$, filtered and the solvent evaporated to give a brown solid (61%). $^1$H NMR (CDCl$_3$) δ (ppm): =8.71 (bs, 1H), 7.91 (s, 1H), 7.37 (d, J=5.4 Hz, 1H), 7.21-7.12 (m, 2H), 7.11-7.06 (m, 1H), 7.03 (s, 1H), 6.99 (d, J=5.4 Hz, 1H), 6.96-6.88 (m, 1H), 4.12 (s, 3H); MS (ESI): m/z: 273 [M+H]$^+$.

Intermediate 34: 6-ethylthieno[2,3-b]pyrrole-5-carboxylic acid

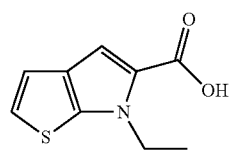

Ethyl 6-ethylthieno[2,3-b]pyrrole-5-carboxylate

Ethyl 6-ethylthieno[2,3-b]pyrrole-5-carboxylate was obtained as yellow solid starting from ethyl 6H-thieno[2,3-b]pyrrole-5-carboxylate (Eras J. et al. J. Het. Chemistry 1984, 21, 215-217) and ethyl iodide according to the procedure for Intermediate 1, Step 1. $^1$H NMR (CDCl$_3$) δ (ppm): 7.17 (s, 1H), 7.00 (d, J=5.4 Hz, 1H), 6.92 (d, J=5.4 Hz, 1H), 4.51 (q, J=7.2 Hz, 2H), 4.33 (q, J=7.3 Hz, 2H), 1.49-1.35 (m, 6H); MS (ESI): m/z: 224 [M+H]$^+$

6-ethylthieno[2,3-b]pyrrole-5-carboxylic acid 6-ethylthieno[2,3-b]pyrrole-5-carboxylic acid was obtained as a white solid from ethyl 6-ethylthieno[2,3-b]pyrrole-5-carboxylate according to the procedure for Intermediate 1, Step 2. $^1$H NMR (DMSO-d$_6$ δ (ppm): 12.47 (bs, 1H), 7.17 (d, J=5.4 Hz, 1H), 7.08-7.00 (m, 2H), 4.44 (q, J=7.2 Hz, 2H), 1.32 (t, J=7.2 Hz, 3H); MS (ESI): m/z: 196 [M+H].

Intermediate 35: tert-Butyl 4-[4-[[2-[(4-methylthieno[3,2-b]pyrrole-5-carbonyl)amino]pyridine-4-carbonyl]amino]phenoxy]piperidine-1-carboxylate

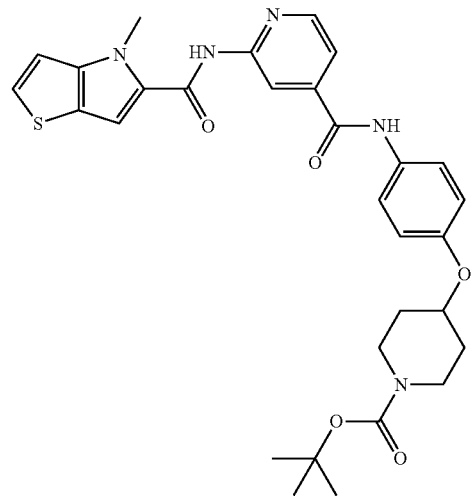 [SMILES: Cn1c(C(=O)Nc2cc(C(=O)Nc3ccc(OC4CCN(C(=O)OC(C)(C)C)CC4)cc3)ccn2)cc2sccc21]

Ethyl 2-[(4-methylthieno[3,2-b]pyrrole-5-carbonyl)amino]pyridine-4-carboxylate Ethyl 2-[(4-methylthieno[3,2-b]pyrrole-5-carbonyl)amino]pyridine-4-carboxylate was obtained as white solid starting from 200 mg (1.10 mmol) of 4-methylthieno[3,2-b]pyrrole-5-carboxylic acid (Intermediate 1) and 183 mg (1.10 mmol) of ethyl 2-aminoisonicotinate (Apollo Scientific, Cat No. OR5579) according to the procedure described for Example 1, step 1. (0.204 g, yield 56%). $^1$H NMR (DMSO-D$_6$) δ (ppm): 10.80 (s, 1H), 8.69-8.65 (m, 1H), 8.56 (d, J=4.9 Hz, 1H), 7.59 (s, 1H), 7.58-7.55 (m, 2H), 7.26 (d, J=4.9 Hz, 1H), 4.38 (q, J=7.1 Hz, 2H), 4.05 (s, 3H), 1.35 (t, J=7.1 Hz, 3H); MS (ESI): m/z: 330 [M+H]$^+$.

2-[(4-Methylthieno[3,2-b]pyrrole-5-carbonyl)amino]pyridine-4-carboxylic acid 0.203 g (0.616 mmol) of ethyl 2-[(4-methylthieno[3,2-b]pyrrole-5-carbonyl)amino]pyridine-4-carboxylate and 0.0738 g (3.08 mmol) of LiOH in ethanol/water was heated to 50° C. for 30 min. Then, the solution was concentrated, brought to pH 2 with 2 M HCl. The yellow precipitate was filtered and then washed with $H_2O$ and dried under vacuum to give 168 g (90%) of 2-[(4-methylthieno[3,2-b]pyrrole-5-carbonyl)amino]pyridine-4-carboxylic acid. $^1$H NMR (DMSO-$d_6$) δ (ppm): 13.85-13.34 (bs, 1H), 10.75 (s, 1H), 8.68-8.65 (m, 1H), 8.55-8.51 (m, 1H), 7.59 (s, 1H), 7.58-7.53 (m, 2H), 7.26 (d, J=5.4 Hz, 1H), 4.05 (s, 3H); MS (ESI): m/z: 302 [M+H]$^+$.

tert-Butyl 4-[4-[[2-[(4-methylthieno[3,2-b]pyrrole-5-carbonyl)amino]pyridine-4-carbonyl]amino]phenoxyl]piperidine-1-carboxylate 0.066 g (28%) of tert-butyl 4-[4-[[2-[(4-methylthieno[3,2-b]pyrrole-5-carbonyl)amino]pyridine-4-carbonyl]amino]phenoxy]piperidine-1-carboxylate was obtained as white powder starting from 0.04 g (0.13 mmol) of 42-[(4-methylthieno[3,2-b]pyrrole-5-carbonyl)amino]pyridine-4-carboxylic acid and 0.043 g (0.15 mmol) of tert-butyl 4-(4-aminophenoxy)piperidine-1-carboxylate (Sigma Aldrich, Cat No. CDS017851) according to the procedure described for Example 1, step 1. $^1$H NMR (DMSO-$d_6$) δ (ppm): 10.72 (s, 1H), 10.41 (s, 1H), 8.59-8.57 (m, 1H), 8.55-8.52 (m, 1H), 7.69-7.64 (m, 2H), 7.60 (s, 1H), 7.56-7.55 (m, 1H), 7.56 (d, J=5.4 Hz, 1H), 7.26 (d, J=5.4 Hz, 2H), 7.02-6.96 (m, 2H), 4.59-4.45 (m, 1H), 4.05 (s, 3H), 3.72-3.57 (m, 2H), 3.24-3.09 (m, 2H), 1.95-1.83 (m, 2H), 1.58-1.46 (m, 2H), 1.40 (s, 9H); MS (ESI): m/z: 576 [M+H]$^+$.

The preparation of 3-[(1-methyl-3-piperidyl)methoxy]aniline, of tert-butyl 4-[3-[(2-aminophenyl)methoxy]phenoxy]piperidine-1-carboxylate, of 2-[[3-[(1-methyl-4-piperidyl)oxy]phenoxy]methyl]aniline, of 2-[[4-[(1-methyl-4-piperidyl)oxy]phenoxy]methyl]aniline and of 2-[[4-[(4-methylpiperazin-1-yl)methyl]phenoxy]methyl]aniline were carried out as disclosed in WO2010/049768, the preparation of tert-butyl N-(3-hydroxypropyl)-N-methyl-carbamate as described in Tetrahedron Lett. 2008, 49, 2527-2532 and the synthesis of ethyl 6H-thieno[2,3-b]pyrrole-5-carboxylate as described in J. Het. Chemistry 1984, 21, 215-217.

Example 1: 4-Methyl-N-[2-[[4-(4-piperidyloxy)phenoxy]methyl]phenyl]thieno[3,2-b]pyrrole-5-carboxamide

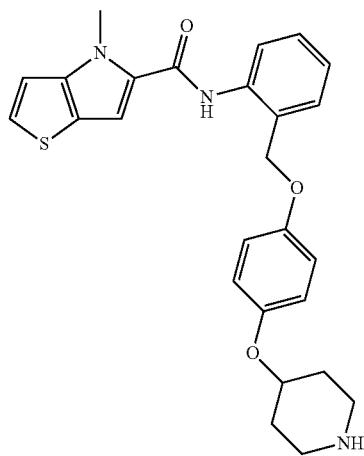 [SMILES: Cn1c(C(=O)Nc2ccccc2COc2ccc(OC3CCNCC3)cc2)cc2sccc21]

tert-butyl 4-[4-[[2-[(4-methylthieno[3,2-b]pyrrole-5-carbonyl)amino]phenyl]methoxy]phenoxy]piperidine-1-carboxylate 0.24 g (2.0 mmol, 0.15 mL) of $SOCl_2$ and 3 drops of dry DMF were added at RT to a solution of 0.277 g (1.53 mmol) of 4-methylthieno[3,2-b]pyrrole-5-carboxylic acid (Intermediate 1) in 9 mL of dry THF. The mixture was stirred for 2 h under reflux. The reaction mixture was then cooled down to RT and added to a solution of 0.52 g (1.3 mmol) tert-butyl 4-[4-[(2-aminophenyl)methoxy]phenoxy]piperidine-1-carboxylate (Intermediate 3) in 7 mL of pyridine.

The mixture was stirred for 30 min at RT and for further 45 min at 60° C. Then, the mixture was diluted with $CH_2Cl_2$, washed with a saturated $NaHCO_3$ solution and brine, dried over $Na_2SO_4$, filtered and concentrated to give an oil which was purified by flash column chromatography (hexane/acetone, from 0% of acetone to 15% of acetone). Trituration in $Et_2O$ provided 426 mg (58%) of tert-butyl 4-[4-[[2-[(4-methylthieno[3,2-b]pyrrole-5-carbonyl)amino]phenyl]methoxy]phenoxy]piperidine-1-carboxylate as a white solid. $^1$H NMR (DMSO-$d_6$) δ (ppm): 9.72 (s, 1H), 7.55-7.47 (m, 3H), 7.40-7.32 (m, 1H), 7.29-7.19 (m, 3H), 6.94-6.83 (m, 4H), 5.10 (s, 2H), 4.42-4.32 (m, 1H), 4.00 (s, 3H), 3.68-3.55 (m, 2H), 3.22-3.05 (m, 2H), 1.88-1.75 (m, 2H), 1.49-1.40 (m, 2H), 1.39 (s, 9H); MS (ESI): m/z: 584 [M+Na]$^+$.

4-methyl-N-[2-[[4-(4-piperidyloxy)phenoxy]methyl]phenyl]thieno[3,2-b]pyrrole-5-carboxamide 407 mg (0.725 mmol) of tert-butyl 4-[4-[[2-[(4-methylthieno[3,2-b]pyrrole-5-carbonyl)amino]phenyl]methoxy]phenoxy]piperidine-1-carboxylate was dissolved in a mixture of 3 mL of dry 1,4-dioxane and 3 mL of dry MeOH. 4.17 mL of 4 M HCl in 1,4-dioxane was added and the mixture was stirred at RT for 3 h. The reaction mixture was then concentrated and the residue was taken up in a saturated $NaHCO_3$ solution and extracted with EtOAc. The combined organic phases were dried over $Na_2SO_4$, concentrated and triturated in $Et_2O$ give 309 mg (92%) of 4-methyl-N-[2-[[4-(4-piperidyloxy)phenoxy]methyl]phenyl]thieno[3,2-b]pyrrole-5-carboxamide as a white solid. $^1$H NMR (DMSO-$d_6$) δ (ppm): 9.72 (s, 1H), 7.57-7.46 (m, 3H), 7.40-7.31 (m, 1H), 7.29-7.17 (m, 3H), 6.93-6.79 (m, 4H), 5.09 (s, 2H), 4.27-4.13 (m, 1H), 4.00 (s, 3H), 2.94-2.84 (m, 2H), 2.49-2.42 (m, 2H), 1.89-1.73 (m, 2H), 1.43-1.30 (m, 2H); MS (ESI): m/z: 462 [M+H]$^+$.

Example 2: 4-methyl-N-[2-[[4-(4-piperidylmethoxy)
phenoxy]methyl]phenyl]thieno-[3,2-b]pyrrole-5-
carboxamide

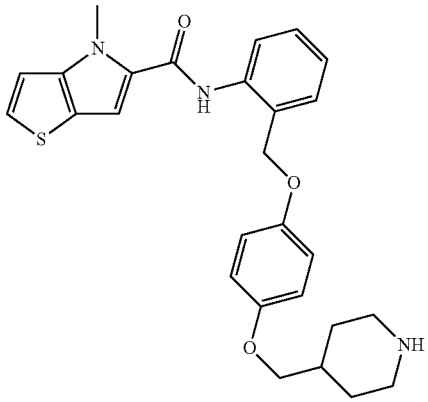 [SMILES: Cn1c(C(=O)Nc2ccccc2COc2ccc(OCC3CCNCC3)cc2)cc2sccc21]

tert-butyl 4-[[4-[[2-[(4-methylthieno[3,2-b]pyrrole-
5-carbonyl)amino]phenyl]methoxy]-phenoxy]
methyl]piperidine-1-carboxylate 75 mg (0.35 mmol) of DIAD was added dropwise to a solution of 89 mg (0.24 mmol) of N-[2-[(4-hydroxyphenoxy)methyl]phenyl]-4-methyl-thieno[3,2-b]pyrrole-5-carboxamide (Intermediate 9), 76 mg (0.35 mmol) of tert-butyl 4-(hydroxymethyl)piperidine-1-carboxylate (Sigma aldrich, Cat No. 556017) and 94 mg (0.35 mmol) of $PPh_3$ in 3 mL of dry THF cooled down to 0° C. and under $N_2$ atmosphere. The reaction mixture was allowed to reach RT and was stirred overnight. The solvent was evaporated and the crude mixture was purified by column chromatography (eluent hexane/acetone, from 0% of acetone to 11% of acetone). Trituration in $Et_2O$ provided 80 mg (59%) of tert-butyl 4-[[4-[[2-[(4-methylthieno[3,2-b]pyrrole-5-carbonyl)amino]phenyl]methoxy]phenoxy]methyl]piperidine-1-carboxylate as a white solid. $^1$H NMR (DMSO-$d_6$) δ (ppm): 9.07 (s, 1H), 8.34-8.18 (m, 1H), 7.46-7.39 (m, 1H), 7.34-7.28 (m, 2H), 7.16-7.10 (m, 1H), 7.01-6.95 (m, 3H), 6.88-6.80 (m, 3H), 5.14 (s, 2H), 4.21-4.10 (m, 5H), 3.77 (d, J=6.4 Hz, 2H), 2.81-2.70 (m, 2H), 2.01-1.89 (m, 1H), 1.87-1.79 (m, 2H), 1.47 (s, 9H), 1.26-1.19 (m, 2H); MS (ESI): m/z: 576 [M+H]$^+$.

4-methyl-N-[2-[[4-(4-piperidylmethoxy)phenoxy]
methyl]phenyl]thieno[3,2-b]pyrrole-5-carboxamide 79 mg (0.14 mmol) of tert-butyl 4-[[4-[[2-[(4-methylthieno[3,2-b]pyrrole-5-carbonyl)amino]phenyl]methoxy]phenoxy]methyl]piperidine-1-carboxylate was dissolved in 1 mL of dry 1,4-dioxane. 0.80 mL of 4 M HCl in 1,4-dioxane was added and the mixture was stirred at RT for 2 h. The mixture was then concentrated and the residue was taken up in a saturated $NaHCO_3$ solution and extracted with $CH_2Cl_2$. The combined organic phases were dried over $Na_2SO_4$, concentrated and the product was purified by flash chromatography (eluent $CH_2Cl_2$/MeOH/$NH_3$, 94:6:0.6, v:v:v). Trituration in $Et_2O$ provided 41 mg (63%) of 4-methyl-N-[2-[[4-(4-piperidylmethoxy)phenoxy]methyl]phenyl]thieno[3,2-b]pyrrole-5-carboxamide as a white solid. $^1$H NMR (DMSO-$d_6$) δ (ppm): 9.72 (s, 1H), 7.56-7.46 (m, 3H), 7.39-7.31 (m, 1H), 7.29-7.18 (m, 3H), 6.93-6.77 (m, 4H), 5.09 (s, 2H), 4.00 (s, 3H), 3.68 (d, J=6.4 Hz, 2H), 2.96-2.85 (m, 2H), 2.46-2.39 (m, 2H), 1.80-1.68 (m, 1H), 1.67-1.58 (m, 2H), 1.16-1.01 (m, 2H); MS (ESI): m/z: 476 [M+H]$^+$.

Example 3: N-[2-[[4-[(1-ethyl-4-piperidyl)oxy]phenoxy]methyl]phenyl]-4-methyl-thieno[3,2-b]pyrrole-5-carboxamide

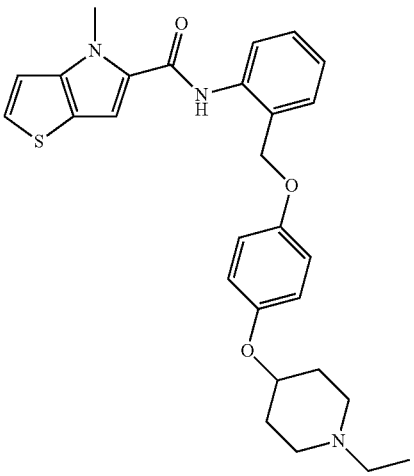 [SMILES: CCN1CCC(Oc2ccc(OCc3ccccc3NC(=O)c3cc4sccc4n3C)cc2)CC1]

8.9 mg (0.20 mmol) of acetaldehyde was added under inert atmosphere to a solution of 0.078 g (0.17 mmol) of 4-methyl-N-[2-[[4-(4-piperidyloxy)phenoxy]methyl]phenyl]thieno[3,2-b]pyrrole-5-carboxamide (Example 1) in 1.3 mL of 1,2-dichloroethane. The mixture was stirred at RT for 2 h, then 0.060 g (0.27 mmol) of NaBH(OAc)$_3$ was added and the mixture was stirred overnight. The reaction was stopped by addition of a saturated $NaHCO_3$ solution and the product was extracted with $CH_2Cl_2$. The organic layers were dried over $Na_2SO_4$ and filtered and the solvent was removed in vacuo. The crude mixture was purified by column chromatography (eluent $CH_2Cl_2$/MeOH/$NH_3$ 96:4:0.4, v:v:v) to afford 21 mg (25%) of N-[2-[[4-[(1-ethyl-4-piperidyl)oxy]phenoxy]methyl]phenyl]-4-methyl-thieno[3,2-b]pyrrole-5-carboxamide as a beige solid. $^1$H NMR (DMSO-$d_6$) δ (ppm): 8.99 (s, 1H), 8.36-8.22 (m, 1H), 7.47-7.39 (m, 1H), 7.36-7.29 (m, 2H), 7.18-7.11 (m, 1H), 7.04-6.96 (m, 3H), 6.91-6.85 (m, 2H), 6.81 (s, 1H), 5.14 (s, 2H), 4.60 (bs, 1H), 4.13 (s, 3H), 3.41 (bs, 2H), 3.09 (bs, 4H), 2.60 (bs, 2H), 2.19 (bs, 2H), 1.47 (bs, 3H); MS (ESI): m/z: 490 [M+H]$^+$.

The following compounds (see Table 1) were prepared starting from 4-methylthieno[3,2-b]pyrrole-5-carboxylic acid (Intermediate 1: Examples 10, 13, 15, 17-23, 36-44, 49, 52, 56, 58-63, and 69) or 4-ethylthieno[3,2-b]pyrrole-5-carboxylic acid (Intermediate 2: Examples 6, 8, 12 and 53), 6-methylthieno[2,3-b]pyrrole-5-carboxylic acid (Intermediate 20: Examples 48, 64, 67 and 68) or 6-ethylthieno[2,3-b]pyrrole-5-carboxylic acid (Intermediate 34: Examples 65-66) and the appropriate anilines according to the procedure described for Example 1; or starting from N-[2-[(4-hydroxyphenoxy)methyl]phenyl]-4-methyl-thieno[3,2-b]pyrrole-5-carboxamide (Intermediate 9) (Examples 4, 5, 7, 9, 11, 14, 16, 24, 27 and 31), N-[3-[(4-hydroxyphenoxy)methyl]phenyl]-4-methyl-thieno[3,2-b]pyrrole-5-carboxamide (Intermediate 10) (Examples 25, 26, 28, 29, 30, 32-35), N-[2-[(4-hydroxyphenoxy)methyl]-5-methyl-phenyl]-4-methyl-thieno[3,2-b]pyrrole-5-carboxamide (Intermediate 25: Example 55) or N-(2-hydroxyphenyl)-4-methyl-thieno[3,2-b]pyrrole-5-carboxamide (Intermediate 33: Example 57) and the appropriate hydroxy derivatives under the standard conditions of the Mitsunobu reaction according to the procedure described for Intermediate 3, step 2; or reacting Intermediate 24 at 0° C. with NaH in EtOH (Example 50) or isopropanol (Example 51), or with morpholine in presence of TEA in $CH_2Cl_2$ (Example 54) and purification of the BOC intermediates by column chromatography (eluent EtOAc/hexane).

In case of the Examples 4-11, 14, 16, 18, 24-37 39-44, and 49-68 the formed BOC intermediate was deprotected as described for Example 2, step 2 (Table 2). Examples 7, 31, 32 and 35 were evaluated without any purification with column chromatography. Examples 64, 65, and 67 were purified by preparative HPLC, the collected fractions were neutralized with $KHCO_3$, and the product was extracted with EtOAc and dried.

Example 45 (Vitas-M Laboratory Ltd., Cat No. STK942407), example 46 (Vitas-M Laboratory Ltd., Cat No. STK943529) and example 47 (Vitas-M Laboratory Ltd., Cat No. STK942407) are commercially available.

TABLE 1

BOC Intermediates

| Name | Structure | Analytical Data |
| --- | --- | --- |
| tert-butyl (3R)-3-[[4-[[2-[(4-methylthieno[3,2-b]pyrrole-5-carbonyl)amino]phenyl]methoxy]phenoxy]methyl]pyrrolidine-1-carboxylate | 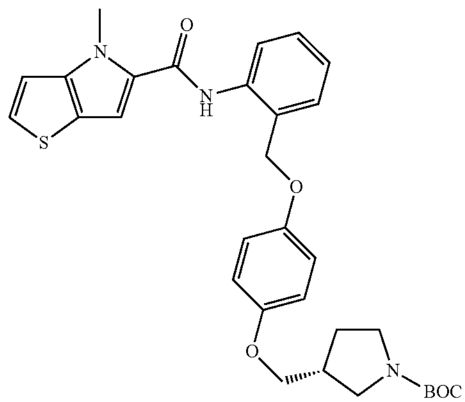 [SMILES: Cn1c(C(=O)Nc2ccccc2COc2ccc(OC[C@@H]3CCN(C(=O)OC(C)(C)C)C3)cc2)cc2sccc21] | MS (ESI): m/z: 562 [M + H]$^+$ |
| tert-butyl 3-[[4-[[2-[(4-methylthieno[3,2-b]pyrrole-5-carbonyl)amino]phenyl]methoxy]phenoxy]methyl]pyrrolidine-1-carboxylate | 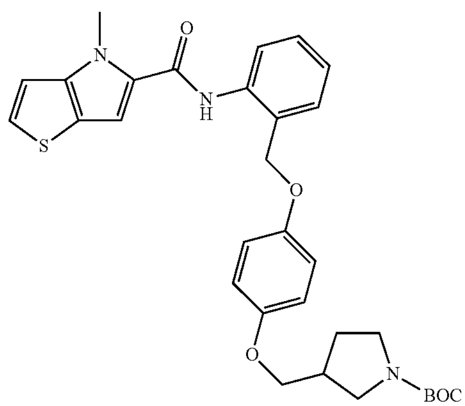 [SMILES: Cn1c(C(=O)Nc2ccccc2COc2ccc(OCC3CCN(C(=O)OC(C)(C)C)C3)cc2)cc2sccc21] | $^1$H NMR (CDCl$_3$) δ (ppm): 9.05 (s, 1 H), 8.34-8.17 (m, 1 H), 7.45-7.40 (m, 1 H), 7.34-7.29 (m, 2 H), 7.16-7.11 (m, 1 H), 7.02-6.95 (m, 3 H), 6.89-6.84 (m, 2 H), 6.82 (s, 1 H), 5.14 (s, 2 H), 4.13 (s, 3 H), 3.94-3.82 (m, 2 H), 3.65-3.55 (m, 1 H), 3.54-3.43 (m, 1 H), 3.42-3.32 (m, 1 H), 3.27-3.16 (m, 1 H), 2.74-2.60 (m, 1 H), 2.13-2.02 (m, 1 H), 1.86-1.74 (m, 1 H), 1.48 (s, 9 H); MS (ESI): m/z: 462 [M + H]$^+$ |
| tert-butyl 4-[4-[[3-[(4-ethylthieno[3,2-b]pyrrole-5-carbonyl)amino]phenyl]methoxy]phenoxy]piperidine-1-carboxylate | 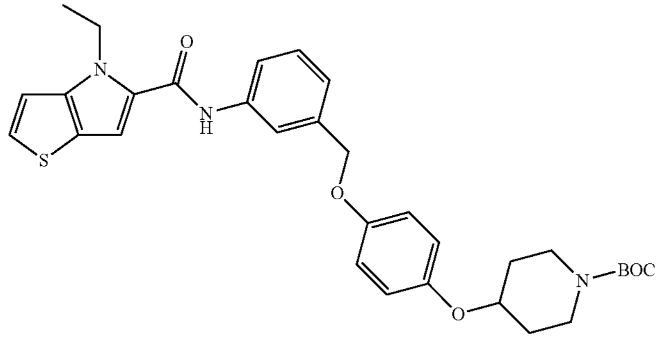 [SMILES: CCn1c(C(=O)Nc2cccc(COc3ccc(OC4CCN(C(=O)OC(C)(C)C)CC4)cc3)c2)cc2sccc21] | $^1$H NMR (CDCl$_3$) δ (ppm): 7.73 (s, 1 H), 7.70-7.68 (m, 1 H), 7.59-7.54 (m, 1 H), 7.42-7.36 (m, 1 H), 7.33 (d, J = 5.4 Hz, 1 H), 7.23-7.19 (m, 1 H), 7.00 (d, J = 5.4 Hz, 1 H), 6.95-6.83 (m, 5 H), 5.05 (s, 2 H), 4.60 (q, J = 6.8 Hz, 2 H), 4.39-4.29 (m, 1 H), 3.76-3.68 (m, 2 H), 3.35-3.25 (m, 2 H), 1.95-1.85 (m, 2H), 1.77-1.67 (m, 2 H), 1.51-1.43 (m, 12 H); MS (ESI): m/z: 598 [M + Na]$^+$ |

TABLE 1-continued

BOC Intermediates

| Name | Structure | Analytical Data |
|---|---|---|
| tert-butyl 4-[4-[[2-[(4-methylthieno[3,2-b]pyrrole-5-carbonyl)amino]phenyl]methoxy]phenoxy]azepane-1-carboxylate | 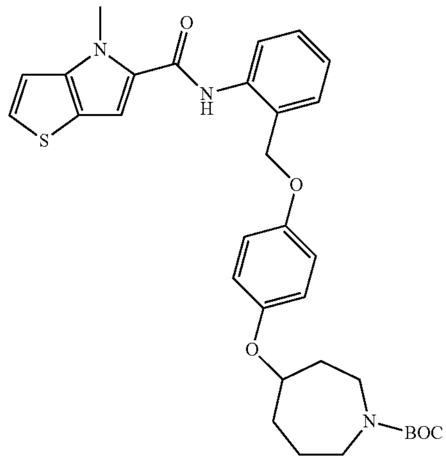 [SMILES: Cn1c(C(=O)Nc2ccccc2COc2ccc(OC3CCCN(C(=O)OC(C)(C)C)CC3)cc2)cc2sccc21] | $^1$H NMR (CDCl$_3$) δ (ppm): 9.07 (s, 1 H), 8.28 (d, J = 7.3 Hz, 1 H), 7.46-7.39 (m, 1 H), 7.34-7.29 (m, 2 H), 7.16-7.11 (m, 1 H), 7.00-6.96 (m, 3 H), 6.88-6.82 (m, 3 H), 5.14 (s, 2 H), 4.39-4.31 (m, 1 H), 4.13 (s, 3 H), 3.64-3.25 (m, 4 H), 2.10-1.84 (m, 5 H), 1.70-1.59 (m, 1 H), 1.48 (s, 9 H); MS (ESI): m/z: 598 [M + Na]$^+$ |
| tert-butyl 4-[4-[[2-[(4-ethylthieno[3,2-b]pyrrole-5-carbonyl)amino]phenyl]methoxy]phenoxy]piperidine-1-carboxylate | 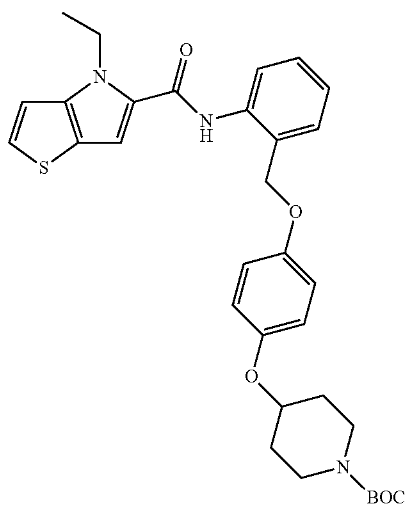 [SMILES: CCn1c(C(=O)Nc2ccccc2COc2ccc(OC3CCN(C(=O)OC(C)(C)C)CC3)cc2)cc2sccc21] | MS (ESI): m/z: 576 [M + H]$^+$ |
| tert-butyl N-[cis-4-[4-[[2-[(4-methylthieno[3,2-b]pyrrole-5-carbonyl)amino]phenyl]methoxy]phenoxy]cyclohexyl]carbamate | 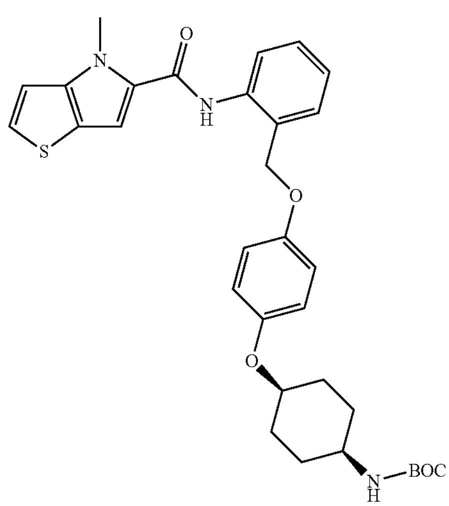 [SMILES: Cn1c(C(=O)Nc2ccccc2COc2ccc(O[C@H]3CC[C@@H](NC(=O)OC(C)(C)C)CC3)cc2)cc2sccc21] | MS (ESI): m/z: 576 [M + H]$^+$ |

TABLE 1-continued

BOC Intermediates

| Name | Structure | Analytical Data |
|---|---|---|
| tert-butyl 4-[4-[[3-[(4-methylthieno[3,2-b]pyrrole-5-carbonyl)amino]phenyl]methoxy]phenoxy]piperidine-1-carboxylate | 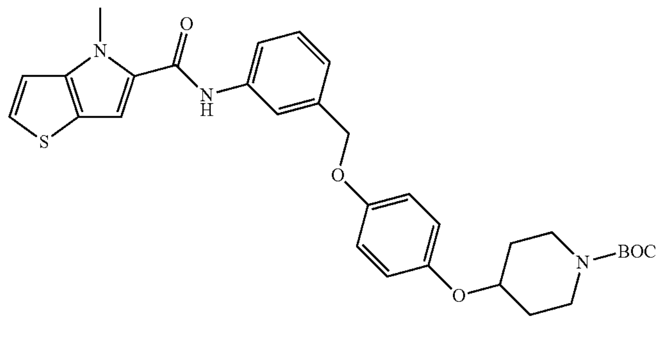 [SMILES: Cn1c(C(=O)Nc2cccc(COc3ccc(OC4CCN(C(=O)OC(C)(C)C)CC4)cc3)c2)cc2sccc21] | $^1$H NMR (DMSO-d$_6$) δ (ppm): 10.04 (s, 1 H), 7.88-7.82 (m, 1 H), 7.71-7.65 (m, 1 H), 7.52 (d, J = 5.4 Hz, 1 H), 7.37-7.30 (m, 2 H), 7.24 (d, J = 5.4 Hz, 1 H), 7.16-7.09 (m, 1 H), 6.97-6.85 (m, 4 H), 5.03 (s, 2 H), 4.46-4.32 (m, 1 H), 4.01 (s, 3 H), 3.67-3.59 (m, 2 H), 3.23-3.05 (m, 2 H), 1.91-1.78 (m, 2 H), 1.54-1.43 (m, 2 H), 1.39 (s, 9 H); MS (ESI): m/z: 584 [M + Na]$^+$ |
| tert-butyl (3S)-3-[[4-[[2-[(4-methylthieno[3,2-b]pyrrole-5-carbonyl)amino]phenyl]methoxy]phenoxy]methyl]pyrrolidine-1-carboxylate | 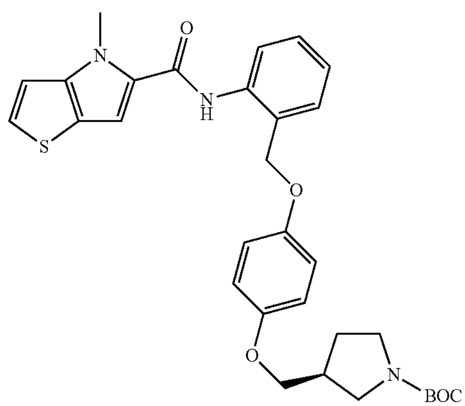 [SMILES: Cn1c(C(=O)Nc2ccccc2COc2ccc(OC[C@H]3CCN(C(=O)OC(C)(C)C)C3)cc2)cc2sccc21] | MS (ESI): m/z: 562 [M + H]$^+$ |
| tert-butyl N-[trans-4-[4-[[2-[(4-methylthieno[3,2-b]pyrrole-5-carbonyl)amino]phenyl]methoxy]phenoxy]cyclohexyl]carbamate | 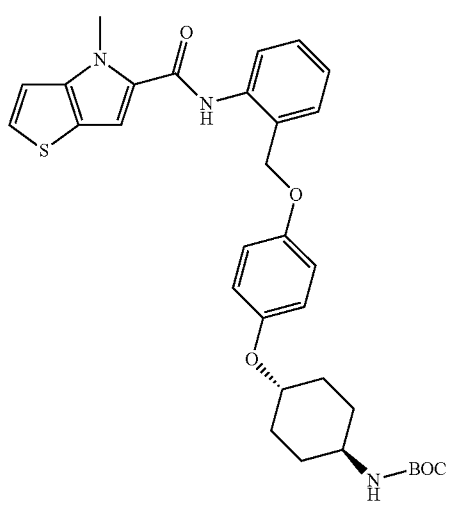 [SMILES: Cn1c(C(=O)Nc2ccccc2COc2ccc(O[C@H]3CC[C@H](NC(=O)OC(C)(C)C)CC3)cc2)cc2sccc21] | MS (ESI): m/z: 576 [M + H]$^+$ |

TABLE 1-continued

| Name | Structure | Analytical Data |
|---|---|---|
| tert-butyl 3-[4-[[2-[(4-methylthieno[3,2-b]pyrrole-5-carbonyl)amino]phenyl]methoxy]phenoxy]pyrrolidine-1-carboxylate | 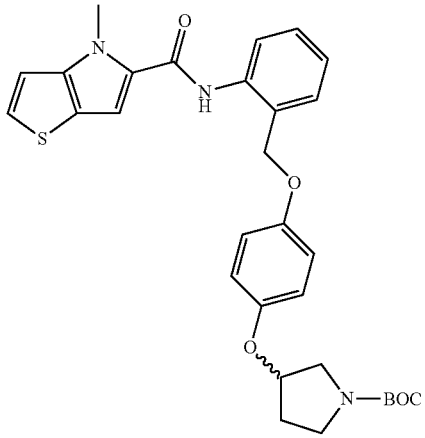 [SMILES: Cn1c(C(=O)Nc2ccccc2COc2ccc(OC3CCN(C(=O)OC(C)(C)C)C3)cc2)cc2sccc21] | MS (ESI): m/z: 548 [M + H]+ |
| tert-butyl 4-[3-[[2-[(4-methylthieno[3,2-b]pyrrole-5-carbonyl)amino]phenyl]methoxy]phenoxy]piperidine-1-carboxylate | 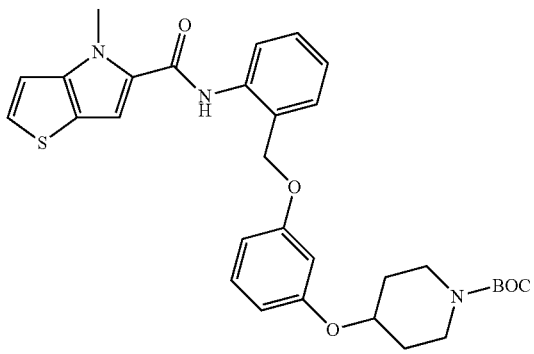 [SMILES: Cn1c(C(=O)Nc2ccccc2COc2cccc(OC3CCN(C(=O)OC(C)(C)C)CC3)c2)cc2sccc21] | 1H NMR (DMSO-d6) δ (ppm): 9.73 (s, 1 H), 7.56-7.47 (m, 3 H), 7.39-7.33 (m, 1 H), 7.28-7.21 (m, 3 H), 7.17-7.10 (m, 1 H), 6.58-6.49 (m, 3 H), 5.15 (s, 2 H), 4.51-4.43 (m, 1 H), 3.99 (s, 3 H), 3.66-3.55 (m, 2 H), 3.19-3.04 (m, 2 H), 1.88-1.77 (m, 2 H), 1.49-1.34 (m, 11 H); MS (ESI): m/z: 584 [M + Na]+ |
| tert-butyl (1S,5R)-3-[4-[[2-[(4-methylthieno[3,2-b]pyrrole-5-carbonyl)amino]phenyl]methoxy]phenoxy]-8-azabicyclo[3.2.1]octane-8-carboxylate | 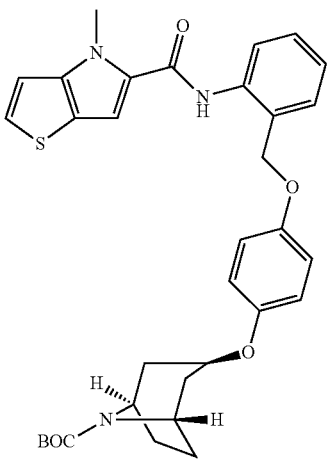 [SMILES: Cn1c(C(=O)Nc2ccccc2COc2ccc(O[C@@H]3C[C@H]4CC[C@@H](C3)N4C(=O)OC(C)(C)C)cc2)cc2sccc21] | MS (ESI): m/z: 588 [M + H]+ |

TABLE 1-continued

| Name | Structure | Analytical Data |
|---|---|---|
| tert-butyl (1S,5R)-3-[4-[[3-[(4-methylthieno[3,2-b]pyrrole-5-carbonyl)amino]phenyl]methoxy]phenoxy]-8-azabicyclo[3.2.1]octane-8-carboxylate | 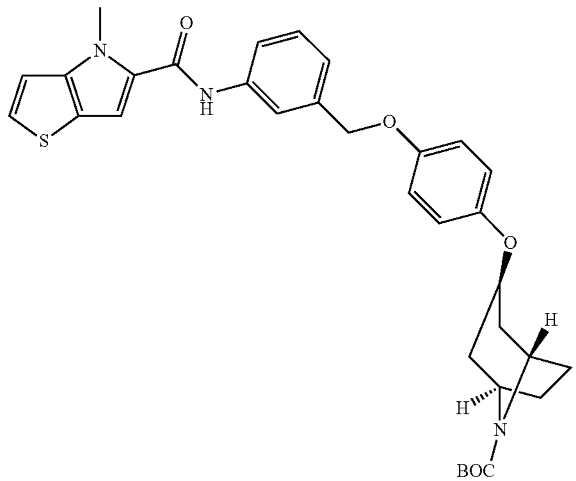 [SMILES: Cn1c(C(=O)Nc2cccc(COc3ccc(O[C@@H]4C[C@H]5CC[C@@H](C4)N5C(=O)OC(C)(C)C)cc3)c2)cc2sccc21] | MS (ESI): m/z: 588 [M + H]+ |
| tert-butyl 4-[[4-[[3-[(4-methylthieno[3,2-b]pyrrole-5-carbonyl)amino]phenyl]methoxy]phenoxy]methyl]piperidine-1-carboxylate | 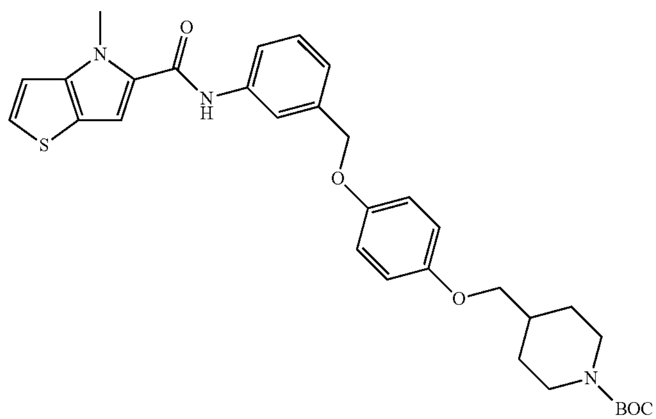 [SMILES: Cn1c(C(=O)Nc2cccc(COc3ccc(OCC4CCN(C(=O)OC(C)(C)C)CC4)cc3)c2)cc2sccc21] | MS (ESI): m/z: 598 [M + Na]+ |
| tert-butyl 3-[4-[[2-[(4-methylthieno[3,2-b]pyrrole-5-carbonyl)amino]phenyl]methoxy]phenoxy]piperidine-1-carboxylate | 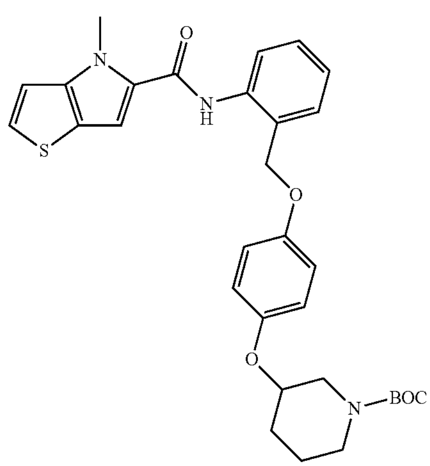 [SMILES: Cn1c(C(=O)Nc2ccccc2COc2ccc(OC3CCCN(C(=O)OC(C)(C)C)C3)cc2)cc2sccc21] | MS (ESI): m/z: 584 [M + Na]+ |

TABLE 1-continued

BOC Intermediates

| Name | Structure | Analytical Data |
| --- | --- | --- |
| tert-butyl 3-[4-[[3-[(4-methylthieno[3,2-b]pyrrole-5-carbonyl)amino]phenyl]methoxy]phenoxy]piperidine-1-carboxylate | 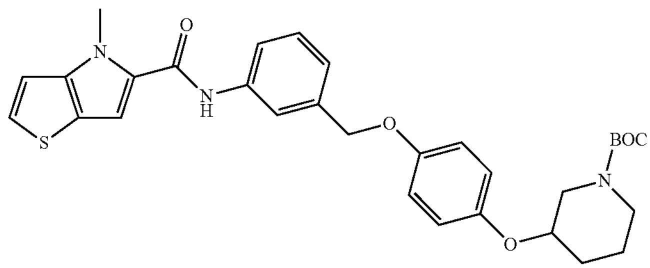 [SMILES: Cn1c(C(=O)Nc2cccc(COc3ccc(OC4CCCN(C(=O)OC(C)(C)C)C4)cc3)c2)cc2sccc21] | MS (ESI): m/z: 584 [M + Na]+ |
| tert-butyl N-[trans-4-[4-[[3-[(4-methylthieno[3,2-b]pyrrole-5-carbonyl)amino]phenyl]methoxy]phenoxy]cyclohexyl]carbamate | 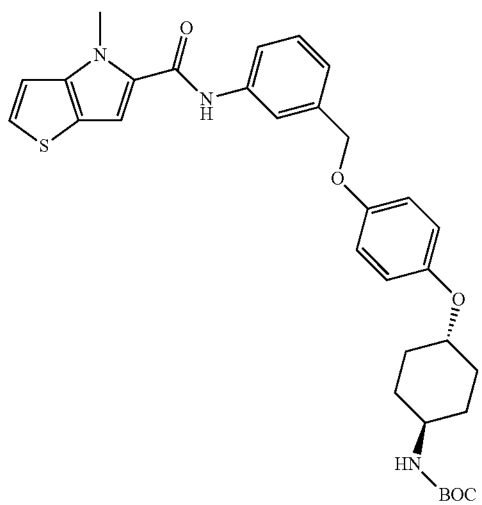 [SMILES: Cn1c(C(=O)Nc2cccc(COc3ccc(O[C@H]4CC[C@H](NC(=O)OC(C)(C)C)CC4)cc3)c2)cc2sccc21] | MS (ESI): m/z: 576 [M + H]+ |
| tert-butyl 3-[[4-[[3-[(4-methylthieno[3,2-b]pyrrole-5-carbonyl)amino]phenyl]methoxy]phenoxy]methyl]azetidine-1-carboxylate | 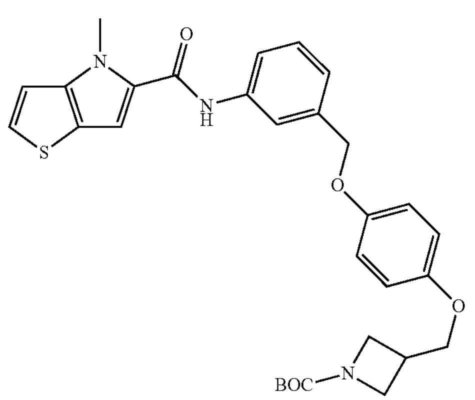 [SMILES: Cn1c(C(=O)Nc2cccc(COc3ccc(OCC4CN(C(=O)OC(C)(C)C)C4)cc3)c2)cc2sccc21] | MS (ESI): m/z: 548 [M + H]+ |

TABLE 1-continued

BOC Intermediates

| Name | Structure | Analytical Data |
|------|-----------|-----------------|
| tert-butyl N-methyl-N-[3-[4-[[2-[(4-methylthieno[3,2-b]pyrrole-5-carbonyl)amino]phenyl]methoxy]phenoxy]propyl]carbamate | 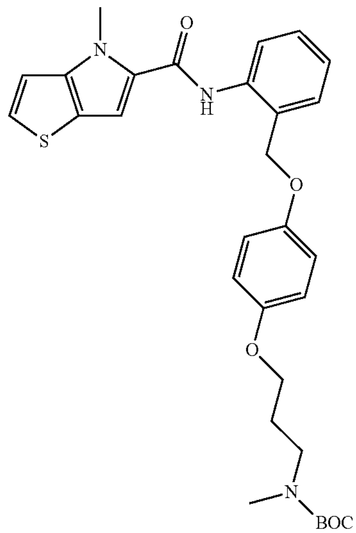 [SMILES: CN(CCCOc1ccc(OCc2ccccc2NC(=O)c2cc3sccc3n2C)cc1)C(=O)OC(C)(C)C] | 1H NMR (CDCl$_3$) δ (ppm): 9.09 (s, 1 H), 8.28 (d, J = 7.8 Hz, 1 H), 7.42 (t, J = 8.07 Hz, 1 H), 7.34-7.28 (m, 2 H), 7.13 (t, J = 7.58 Hz, 1 H), 7.02-6.95 (m, 3 H), 6.88-6.81 (m, 3 H), 5.14 (s, 2 H), 4.13 (s, 3 H), 3.94 (t, J = 6.11 Hz, 2 H), 3.41 (t, J = 7.09 Hz, 2 H), 2.89 (s, 3 H), 2.04-1.95 (m, 2 H), 1.44 (s, 9 H); MS (ESI): m/z: 550 [M + H]$^+$ |
| tert-butyl 3-[4-[[3-[(4-methylthieno[3,2-b]pyrrole-5-carbonyl)amino]phenyl]methoxy]phenoxy]pyrrolidine-1-carboxylate | 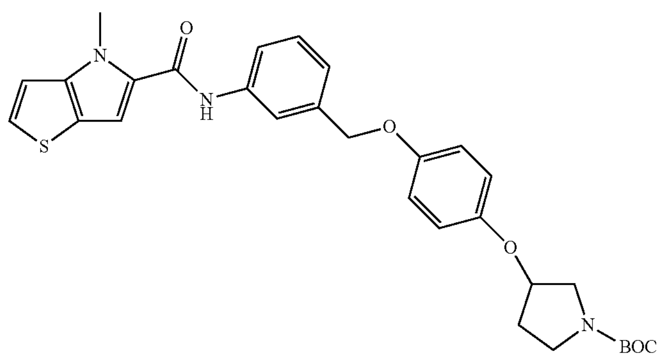 [SMILES: Cn1c(C(=O)Nc2cccc(COc3ccc(OC4CCN(C(=O)OC(C)(C)C)C4)cc3)c2)cc2sccc21] | 1H NMR (CDCl$_3$) δ (ppm): 7.76-7.72 (m, 1 H), 7.71-7.68 (m, 1 H), 7.59-7.55 (m, 1 H), 7.41-7.37 (m, 1 H), 7.33 (d, J = 5.38 Hz, 1 H), 7.23-7.19 (m, 1 H), 7.00 (d, J = 1.00 Hz, 1 H), 6.95 (s, 1 H), 6.94-6.90 (m, 2 H), 6.85-6.80 (m, 2 H), 5.05 (s, 2 H), 4.83-4.78 (m, 1 H), 4.12 (s, 3 H), 3.60-3.34 (m, 4 H), 2.21-1.89 (m, 2 H), 1.50-1.44 (m, 9 H); MS (ESI): m/z: 548 [M + H]+ |
| tert-butyl 4-[4-[[3-[(4-methylthieno[3,2-b]pyrrole-5-carbonyl)amino]phenyl]methoxy]phenoxy]azepane-1-carboxylate | 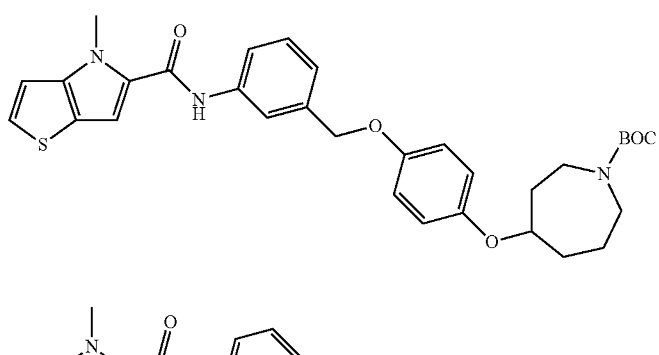 | 1H NMR (DMSO-d$_6$) δ (ppm): 10.03 (s, 1 H), 7.85 (s, 1 H), 7.68 (d, J = 7.83 Hz, 1 H), 7.52 (d, J = 5.38 Hz, 1 H), 7.37-7.30 (m, 2 H), 7.24 (d, J = 5.38 Hz, 1 H), 7.13 (d, J = 7.34 Hz, 1 H), 6.96-6.90 (m, 2 H), 6.88-6.81 (m, 2 H), 5.02 (s, 2 H), 4.36 (br. s., 1 H), 4.02 (s, 3 H), 3.42-3.33 (m, 2 H), 3.30 (br. s., 2 H), 1.97-1.50 (m, 6 H), 1.40 (s, 9 H); MS (ESI): m/z: 598 [M + Na]$^+$ |
| tert-butyl N-[cis-4-[4-[[3-[(4-methylthieno[3,2-b]pyrrole-5-carbonyl)amino]phenyl]methoxy]phenoxy]cyclohexyl]carbamate | 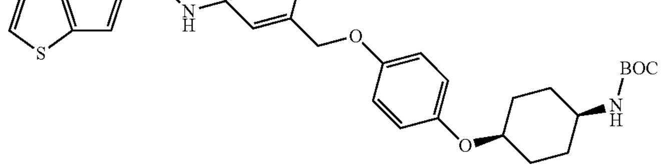 | 1H NMR (DMSO-d$_6$) δ (ppm): 7.75 (s, 1 H), 7.69 (s, 1 H), 7.57 (d, J = 8.31 Hz, 1 H), 7.39 (t, J = 7.83 Hz, 1 H), 7.33 (d, J = 5.38 Hz, 1 H), 7.21 (d, J = 7.34 Hz, 1 H), 6.99 (d, J = 5.38 Hz, 1 H), 6.95 (s, 1 H), 6.94-6.81 (m, 4 H), 5.05 (s, 2 H), 4.11 (s, 3 H), 3.92-3.83 (m, 2 H), 3.62-3.56 (m, 1 H), 3.51-3.45 (m, 1 H), 3.40-3.33 (m, 1 H), 3.23-3.17 (m, 1 H), 2.71-2.61 (m, 1 H), 2.11-2.03 (m, 1 H), 1.83-1.75 (m, 1 H), 1.48 (s, 9 H); MS (ESI): m/z: 598 [M + Na]$^+$ |

TABLE 1-continued

BOC Intermediates

| Name | Structure | Analytical Data |
|---|---|---|
| tert-butyl 3-[[4-[[3-[(4-methylthieno[3,2-b]pyrrole-5-carbonyl)amino]phenyl]methoxy]phenoxy]methyl]pyrrolidine-1-carboxylate | 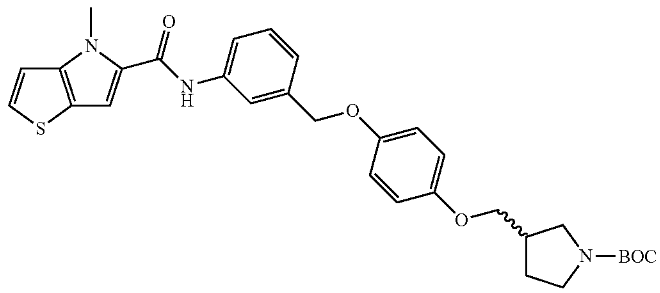 [SMILES: Cn1c(C(=O)Nc2cccc(COc3ccc(OCC4CCN(C(=O)OC(C)(C)C)C4)cc3)c2)cc2sccc21] | 1H NMR (CDCl$_3$) δ (ppm): 1.48 (s, 9 H) 1.75-1.83 (m, 1 H) 2.03-2.11 (m, 1 H) 2.61-2.71 (m, 1 H) 3.17-3.23 (m, 1 H) 3.33-3.40 (m, 1 H) 3.45-3.51 (m, 1 H) 3.56-3.62 (m, 1 H) 3.83-3.92 (m, 2 H) 4.11 (s, 3 H) 5.05 (s, 2 H) 6.81-6.94 (m, 4 H) 6.95 (s, 1 H) 6.99 (d, J = 5.38 Hz, 1 H) 7.21 (d, J = 7.34 Hz, 1 H) 7.33 (d, J = 5.38 Hz, 1 H) 7.39 (t, J = 7.83 Hz, 1 H) 7.57 (d, J = 8.31 Hz, 1 H) 7.69 (s, 1 H) 7.75 (s, 1 H); MS (ESI): m/z: 562 [M + H]$^+$ |
| tert-butyl 4-[4-[[2-[(4-methylthieno[3,2-b]pyrrole-5-carbonyl)amino]benzoyl]amino]phenoxy]piperidine-1-carboxylate | 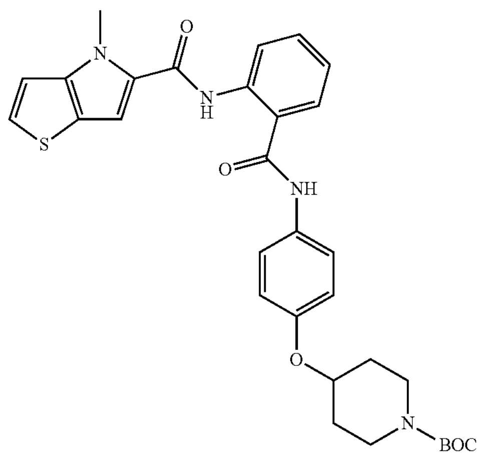 [SMILES: Cn1c(C(=O)Nc2ccccc2C(=O)Nc2ccc(OC3CCN(C(=O)OC(C)(C)C)CC3)cc2)cc2sccc21] | $^1$H NMR (DMSO-d$_6$) δ (ppm): 11.74 (s, 1 H), 10.44 (s, 1 H), 8.56-8.43 (m, 1 H), 7.99-7.85 (m, 1 H), 7.68-7.47 (m, 4 H), 7.31-6.90 (m, 5 H), 4.60-4.42 (m, 1 H), 4.04 (s, 3 H), 3.72-3.59 (m, 2 H), 3.27-3.09 (m, 2 H), 1.95-1.77 (m, 2 H), 1.60-1.45 (m, 2 H) 1.41 (s, 9 H); MS (ESI): m/z: 575 [M + H]$^+$ |
| tert-butyl 4-[4-[[2-[(4-methylthieno[3,2-b]pyrrole-5-carbonyl)amino]phenyl]methoxy]phenyl]piperazine-1-carboxylate | 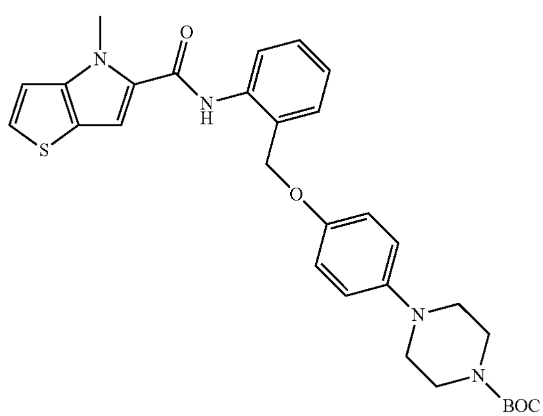 [SMILES: Cn1c(C(=O)Nc2ccccc2COc2ccc(N3CCN(C(=O)OC(C)(C)C)CC3)cc2)cc2sccc21] | $^1$H NMR (CDCl$_3$) δ (ppm): 9.05 (bs, 1 H), 8.30-8.21 (m, 1 H), 7.46-7.39 (m, 1 H), 7.36-7.28 (m, 2 H), 7.17-7.11 (m, 1 H), 7.08-6.87 (m, 5 H), 6.81 (s, 1 H), 5.15 (s, 2 H), 4.12 (s, 3 H), 3.71-3.47 (m, 4 H), 3.17-2.95 (m, 4 H), 1.50 (s, 9 H); MS (ESI): m/z: 547 [M + H]$^+$ |

TABLE 1-continued

| Name | Structure | Analytical Data |
|---|---|---|
| tert-butyl 4-[tert-butoxycarbonyl-[4-[[2-[(4-methylthieno[3,2-b]pyrrole-5-carbonyl)amino]phenyl]methoxy]phenyl]amino]piperidine-1-carboxylate | 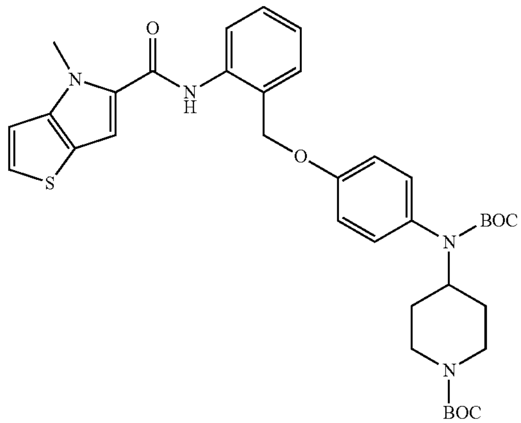 [SMILES: Cn1c(C(=O)Nc2ccccc2COc2ccc(N(C(=O)OC(C)(C)C)C3CCN(C(=O)OC(C)(C)C)CC3)cc2)cc2sccc21] | MS (ESI): m/z: 661 [M + H]+ |
| tert-butyl 3-[[4-[[2-[(4-methylthieno[3,2-b]pyrrole-5-carbonyl)amino]phenyl]methoxy]phenoxy]methyl]azetidine-1-carboxylate | 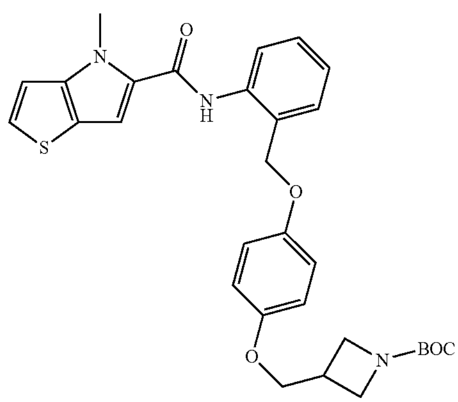 [SMILES: Cn1c(C(=O)Nc2ccccc2COc2ccc(OCC3CN(C(=O)OC(C)(C)C)C3)cc2)cc2sccc21] | 1H NMR (CDCl3) δ (ppm): 9.05 (s, 1 H), 8.33-8.18 (m, 1 H), 7.47-7.40 (m, 1 H), 7.35-7.29 (m, 2 H), 7.16-7.10 (m, 1 H), 7.02-6.95 (m, 3 H), 6.90-6.85 (m, 2 H), 6.82 (s, 1 H), 5.15 (s, 2 H), 4.13 (s, 3 H), 4.12-4.03 (m, 4 H), 3.83-3.76 (m, 2 H), 3.01-2.90 (m, 1 H), 1.46 (s, 9 H); MS (ESI): m/z: 548 [M + H]+ |
| tert-butyl 2-[[4-[[2-[(4-methylthieno[3,2-b]pyrrole-5-carbonyl)amino]phenyl]methoxy]phenyl]methyl]-2,8-diazaspiro[4.5]decane-8-carboxylate | 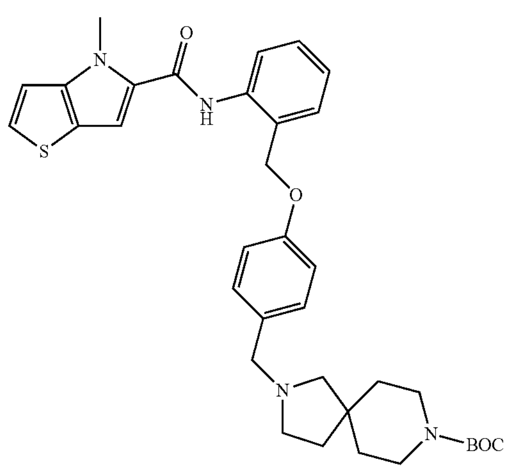 [SMILES: Cn1c(C(=O)Nc2ccccc2COc2ccc(CN3CCC4(CCN(C(=O)OC(C)(C)C)CC4)C3)cc2)cc2sccc21] | 1H NMR (DMSO-d6) δ (ppm): = 9.74 (s, 1 H), 7.54-7.48 (m, 3 H), 7.39-7.33 (m, 1 H), 7.29-7.21 (m, 3 H), 7.19-7.14 (m, 2 H), 6.93-6.88 (m, 2 H), 5.13 (s, 2 H), 4.00 (s, 3 H), 3.42 (s, 2 H), 3.31-3.24 (m, 2 H), 3.20-3.11 (m, 2 H), 2.46-2.41 (m, 2 H), 2.26 (s, 2 H), 1.58-1.50 (m, 2 H), 1.43-1.33 (m, 13 H). MS (ESI): m/z: 615 [M + H]+ |

TABLE 1-continued

BOC Intermediates

| Name | Structure | Analytical Data |
| --- | --- | --- |
| tert-butyl (3R)-3-[[4-[[2-amino-6-(methoxymethyl)phenyl]methoxy]phenoxy]methyl]pyrrolidine-1-carboxylate | 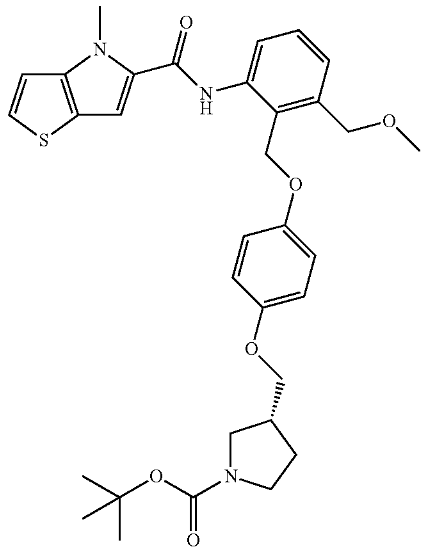 [SMILES: COCc1cccc(NC(=O)c2cc3sccc3n2C)c1COc1ccc(OC[C@@H]2CCN(C(=O)OC(C)(C)C)C2)cc1] | $^1$H NMR (DMSO-d$_6$) δ (ppm): 9.79 (s, 1 H), 7.50-7.48 (m, 1 H), 7.46-7.29 (m, 3 H), 7.23-7.20 (m, 1 H), 7.17 (s, 1 H), 6.91-6.80 (m, 4 H), 5.06 (s, 2 H), 4.55 (s, 2 H), 3.98 (s, 3 H), 3.89-3.74 (m, 2 H), 3.47-2.98 (m, 4 H), 3.29 (s, 3H), 2.62-2.50 (m, 1 H), 2.00-1.60 (m, 2 H), 1.38 (s, 9 H). MS (ESI): m/z: 606 [M + H]$^+$. |
| tert-butyl 4-[4-[[2-(methoxymethyl)-6-[(4-methylthieno[3,2-b]pyrrole-5-carbonyl)amino]phenyl]methoxy]phenoxy]piperidine-1-carboxylate | 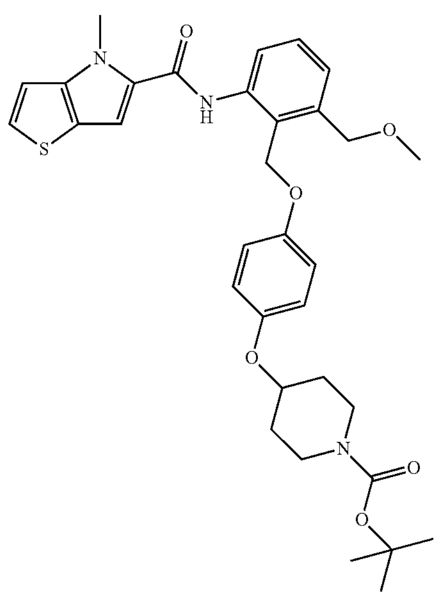 [SMILES: COCc1cccc(NC(=O)c2cc3sccc3n2C)c1COc1ccc(OC2CCN(C(=O)OC(C)(C)C)CC2)cc1] | $^1$H NMR (DMSO-d$_6$) δ (ppm): = 9.79 (s, 1 H), 7.52-7.48 (m, 1 H), 7.47-7.30 (m, 3 H), 7.25-7.20 (m, 1 H), 7.17 (s, 1 H), 6.92-6.84 (m, 4 H), 5.06 (s, 2 H), 4.56 (s, 2 H), 4.46-4.21 (m, 1 H), 3.98 (s, 3 H), 3.70-3.57 (m, 2 H), 3.30 (s, 3 H), 3.21-3.02 (m, 2 H), 1.88-1.41 (m, 4 H), 1.39 (s, 9 H). MS (ESI): m/z: 606 [M + H]$^+$. |

TABLE 1-continued

BOC Intermediates

| Name | Structure | Analytical Data |
|---|---|---|
| tert-butyl 4-[4-[[2-(methoxymethyl)-6-[(4-methylthieno[3,2-b]pyrrole-5-carbonyl)amino]phenyl]methoxy]phenoxy]azepane-1-carboxylate | 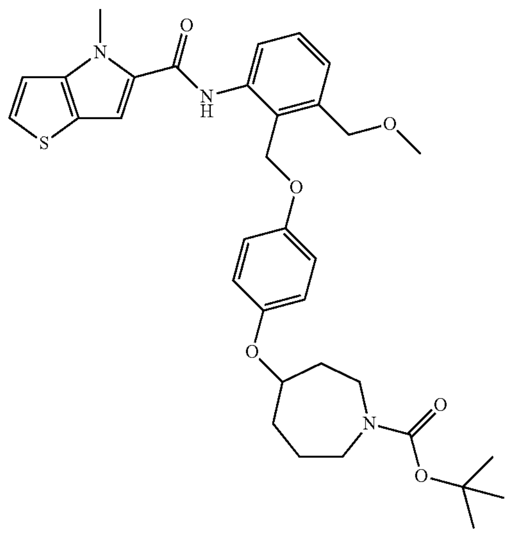 [SMILES: COCc1cccc(NC(=O)c2cc3sccc3n2C)c1COc1ccc(OC2CCCN(C(=O)OC(C)(C)C)CC2)cc1] | $^1$H NMR (DMSO-d$^6$) δ (ppm): 9.89 (s, 1 H), 7.53-7.48 (m, 1 H), 7.48-7.29 (m, 3 H), 7.24-7.20 (m, 1 H), 7.16 (s, 1 H), 6.91-6.78 (m, 4 H), 5.06 (s, 2 H), 4.56 (s, 2 H), 4.37-4.26 (m, 1 H), 3.97 (s, 3 H), 3.29 (s, 3H), 3.43-3.18 (m, 4 H), 1.97-1.46 (m, 6 H), 1.39 (s, 9 H). MS (ESI): m/z: 620 [M + H]$^+$. |
| tert-Butyl (3S)-3-[[4-[[2-(methoxymethyl)-6-[(4-methylthieno[3,2-b]pyrrole-5-carbonyl)amino]phenyl]methoxy]phenoxy]methyl]pyrrolidine-1-carboxylate | 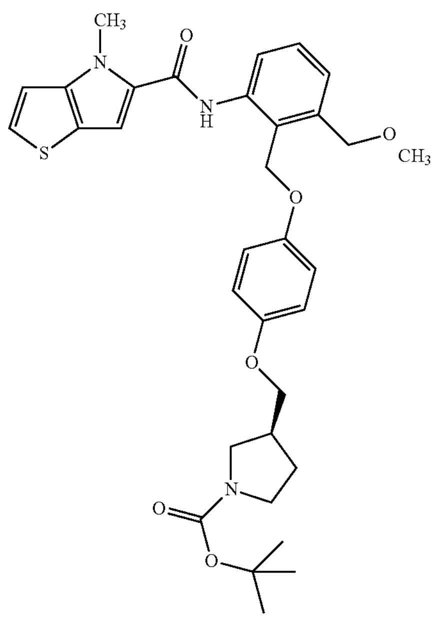 | $^1$H NMR (DMSO-d$_6$) δ (ppm): 9.83-9.75 (m, 1 H), 7.52-7.47 (m, 1 H), 7.46-7.29 (m, 3 H), 7.24-7.21 (m, 1 H), 7.17 (s, 1 H), 6.92-6.78 (m, 4 H), 5.06 (s, 2 H), 4.55 (s, 2 H), 3.98 (s, 3 H), 3.90-3.76 (m, 2 H), 3.46-2.96 (m, 4 H), 3.29 (s, 3H), 2.61-2.51 (m, 1 H), 1.98-1.60 (m, 2 H), 1.42-1.35 (m, 9 H); MS (ESI): m/z: 606 [M + H]$^+$ |

TABLE 1-continued

BOC Intermediates

| Name | Structure | Analytical Data |
| --- | --- | --- |
| tert-Butyl 4-[4-[[2-(ethoxymethyl)-6-[(4-methylthieno[3,2-b]pyrrole-5-carbonyl)amino]phenyl]methoxy]phenoxy]piperidine-1-carboxylate | 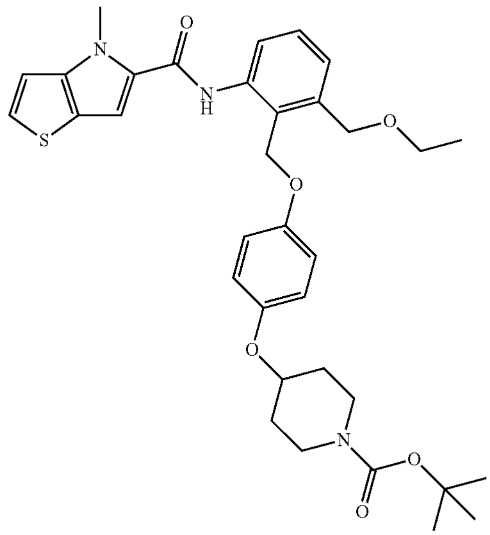 [SMILES: CCOCc1cccc(NC(=O)c2cc3sccc3n2C)c1COc1ccc(OC2CCN(C(=O)OC(C)(C)C)CC2)cc1] | $^1$H NMR (DMSO-$d_6$) δ (ppm): 9.78 (s, 1 H), 7.53-7.48 (m, 1 H), 7.46-7.29 (m, 3 H), 7.24-7.20 (m, 1 H), 7.17 (s, 1 H), 6.92-6.84 (m, 4 H), 5.07 (s, 2 H), 4.59 (s, 2 H), 4.40-4.30 (m, 1 H), 3.98 (s, 3 H), 3.67-3.57 (m, 2 H), 3.52-3.43 (m, 2 H), 3.20-3.01 (m, 2 H), 1.87-1.40 (m, 4H), 1.39 (s, 9 H), 1.15-1.10 (m, 3 H); MS (ESI): m/z: 620 [M + H]+ |
| tert-Butyl 4-[4-[[2-(isopropoxymethyl)-6-[(4-methylthieno[3,2-b]pyrrole-5-carbonyl)amino]phenyl]methoxy]phenoxy]piperidine-1-carboxylate | 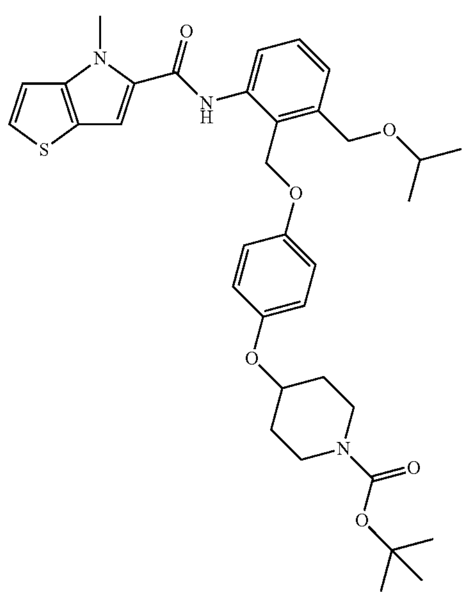 [SMILES: CC(C)OCc1cccc(NC(=O)c2cc3sccc3n2C)c1COc1ccc(OC2CCN(C(=O)OC(C)(C)C)CC2)cc1] | $^1$H NMR (DMSO-$d_6$) δ (ppm): 9.77 (s, 1 H), 7.53-7.47 (m, 1 H), 7.46-7.30 (m, 3 H), 7.24-7.20 (m, 1 H), 7.16 (s, 1 H), 6.91-6.84 (m, 4 H), 5.07 (s, 2 H), 4.59 (s, 2 H), 4.39-4.30 (m, 1 H), 3.98 (s, 3 H), 3.66-3.55 (m, 3 H), 3.20-3.03 (m, 2 H), 1.87-1.40 (m, 4H), 1.39 (s, 9 H), 1.13-1.09 (m, 6 H); MS (ESI): m/z: 634 [M + H]$^+$ |

TABLE 1-continued

BOC Intermediates

| Name | Structure | Analytical Data |
|---|---|---|
| tert-Butyl (3R)-3-[[4-[[2-(ethoxymethyl)-6-[(4-methylthieno[3,2-b]pyrrole-5-carbonyl)amino]phenyl]methoxy]phenoxy]methyl]pyrrolidine-1-carboxylate | 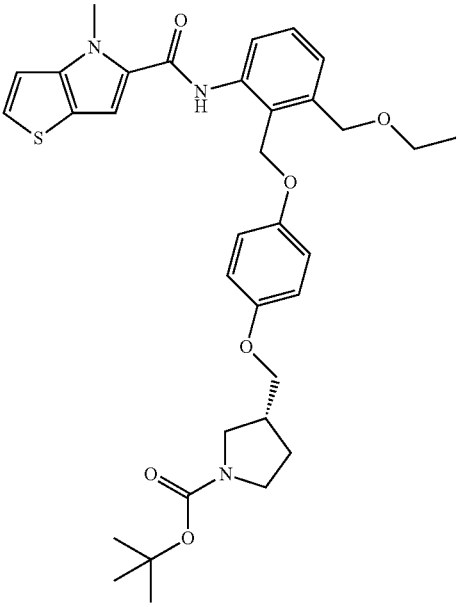 [SMILES: CCOCc1cccc(NC(=O)c2cc3sccc3n2C)c1COc1ccc(OC[C@@H]2CCN(C(=O)OC(C)(C)C)C2)cc1] | $^1$H NMR (DMSO-d$_6$) δ (ppm): 9.81-9.75 (bs, 1 H), 7.52-7.47 (m, 1 H), 7.46-7.29 (m, 3 H), 7.25-7.20 (m, 1 H), 7.18 (s, 1 H), 6.91-6.79 (m, 4 H), 5.07 (s, 2 H), 4.59 (s, 2 H), 3.98 (s, 3 H), 3.88-3.75 (m, 2 H), 3.54-2.97 (m, 6 H), 2.60-2.45 (m., 1 H), 2.02-1.91 (m, 1 H), 1.74-1.58 (m, 1 H), 1.38 (s, 9 H), 1.24-1.04 (m, 3 H); MS (ESI): m/z: 620 [M + H]$^+$ |
| tert-Butyl (3R)-3-[[4-[[2-[(4-ethylthieno[3,2-b]pyrrole-5-carbonyl)amino]-6-(methoxymethyl)phenyl]methoxy]phenoxy]methyl]pyrrolidine-1-carboxylate | 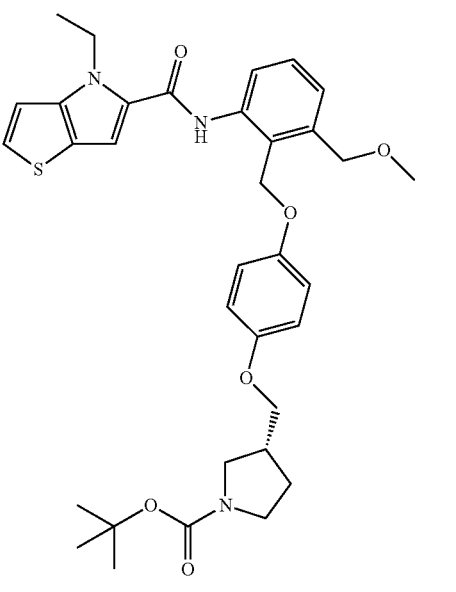 [SMILES: CCn1c(C(=O)Nc2cccc(COC)c2COc2ccc(OC[C@@H]3CCN(C(=O)OC(C)(C)C)C3)cc2)cc2sccc21] | $^1$H NMR (CDCl$_3$) δ (ppm): 9.10 (s, 1 H), 8.23 (d, J = 8.3 Hz, 1 H), 7.39 (t, J = 7.8 Hz, 1 H), 7.29 (d, J = 5.4 Hz, 1 H), 7.13 (d, J = 6.8 Hz, 1 H), 7.05-6.99 (m, 2 H), 6.97 (d, J = 4.9 Hz, 1 H), 6.90-6.84 (m, 2 H), 6.73 (s, 1 H), 5.23 (s, 2 H), 4.61 (q, J = 7.3 Hz, 2 H), 4.52 (s, 2 H), 3.95-3.85 (m, 2 H), 3.64-3.57 (m, 1 H), 3.53-3.46 (m, 1 H), 3.42-3.36 (m, 1 H), 3.34 (s, 3 H), 3.25-3.19 (m, 1 H), 2.72-2.64 (m, 1 H), 2.12-2.05 (m, 1 H), 1.85-1.76 (m, 1 H), 1.50-1.43 (m, 12 H); MS (ESI): m/z: 620 [M + H]$^+$ |

TABLE 1-continued

BOC Intermediates

| Name | Structure | Analytical Data |
|---|---|---|
| tert-Butyl 4-[4-[[2-[(4-methylthieno[3,2-b]pyrrole-5-carbonyl)amino]-6-(morpholinomethyl)phenyl]methoxy]phenoxy]piperidine-1-carboxylate | 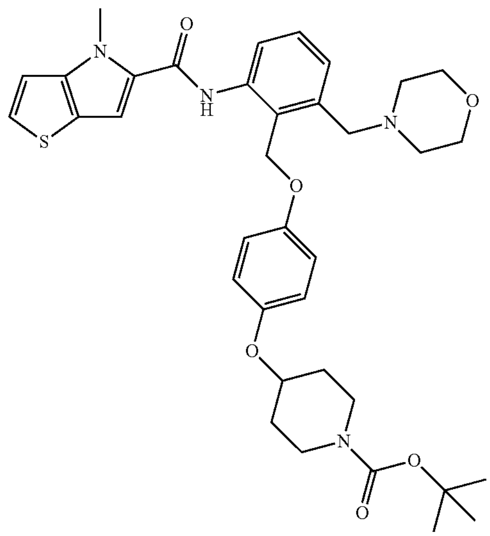 [SMILES: Cn1c(C(=O)Nc2cccc(CN3CCOCC3)c2COc2ccc(OC3CCN(C(=O)OC(C)(C)C)CC3)cc2)cc2sccc21] | $^1$H NMR (DMSO-d$_6$) δ (ppm): 9.70 (s, 1 H), 7.52-7.19 (m, 5 H), 7.15 (s, 1 H), 6.94-6.83 (m, 4 H), 5.19 (s, 2 H), 4.42-4.29 (m, 1 H), 3.97 (s, 3 H), 3.68-3.60 (m, 2 H), 3.57 (s, 2 H), 3.53-3.46 (m, 2 H), 3.18-3.01 (m, 4 H), 2.38-2.22 (m, 4 H), 1.86-1.41 (m, 4 H), 1.39 (s, 9 H); MS (ESI): m/z: 661 [M + H]$^+$ |
| tert-Butyl 3-[[4-[[4-methyl-2-[(4-methylthieno[3,2-b]pyrrole-5-carbonyl)amino]phenyl]methoxy]phenoxy]methyl]pyrrolidine-1-carboxylate | 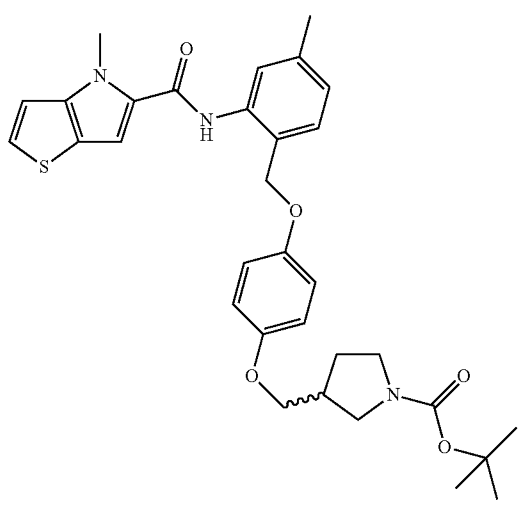 [SMILES: Cc1ccc(COc2ccc(OCC3CCN(C(=O)OC(C)(C)C)C3)cc2)c(NC(=O)c2cc3sccc3n2C)c1] | MS (ESI): m/z: 576 [M + H]$^+$ |

TABLE 1-continued

BOC Intermediates

| Name | Structure | Analytical Data |
|---|---|---|
| tert-Butyl 4-[[6-[[2-[(4-methylthieno[3,2-b]pyrrole-5-carbonyl)amino]phenyl]methoxy]-3-pyridyl]oxy]piperidine-1-carboxylate | 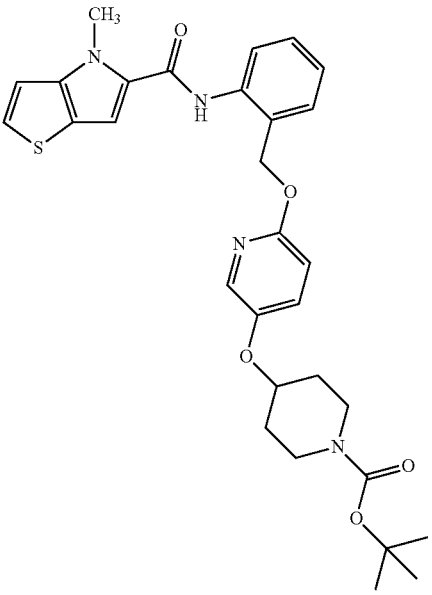 [SMILES: Cn1c(C(=O)Nc2ccccc2COc2ccc(OC3CCN(C(=O)OC(C)(C)C)CC3)cn2)cc2sccc21] | $^1$H NMR (DMSO-d$_6$) δ (ppm): 11.22 (s, 1 H), 7.94 (m, 1 H), 7.78 (m, 1 H), 7.41-7.64 (m, 4 H), 7.10-7.40 (m, 3 H), 6.54 (m, 1 H), 5.09 (s, 2 H), 4.18-4.34 (m, 1 H), 4.06 (s, 3 H), 3.62 (m, 2 H), 3.05-3.22 (m, 2 H), 1.75-1.95 (m, 2 H), 1.26-1.55 (m, 11 H); MS (ESI): m/z: 563 [M + H]$^+$ |
| tert-Butyl 4-[[2-[(4-methylthieno[3,2-b]pyrrole-5-carbonyl)amino]phenoxy]methyl]piperidine-1-carboxylate | 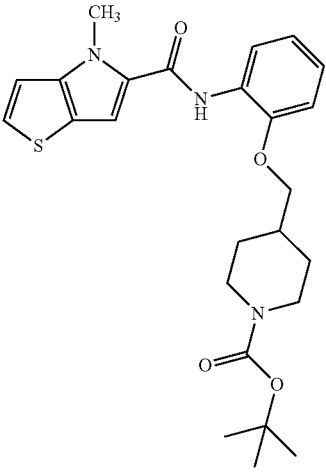 [SMILES: Cn1c(C(=O)Nc2ccccc2OCC2CCN(C(=O)OC(C)(C)C)CC2)cc2sccc21] | $^1$H NMR (CDCl$_3$) δ (ppm): 8.46-8.42 (m, 1 H), 8.39 (s, 1 H), 7.32 (d, J = 5.4 Hz, 1 H), 7.08-6.98 (m, 3 H), 6.93-6.90 (m, 1 H), 6.87 (s, 1 H), 4.24-4.15 (m, 2 H), 4.13 (s, 3 H), 3.95 (d, J = 6.8 Hz, 2 H), 2.85-2.74 (m, 2 H), 2.15-2.03 (m, 1 H), 1.90-1.82 (m, 2 H), 1.47 (s, 9 H), 1.39-1.26 (m, 2 H); MS (ESI): m/z: 470 [M + H]$^+$ |
| tert-Butyl 4-[3-[[3-[(4-methylthieno[3,2-b]pyrrole-5-carbonyl)amino]phenyl]methoxy]phenoxy]piperidine-1-carboxylate | 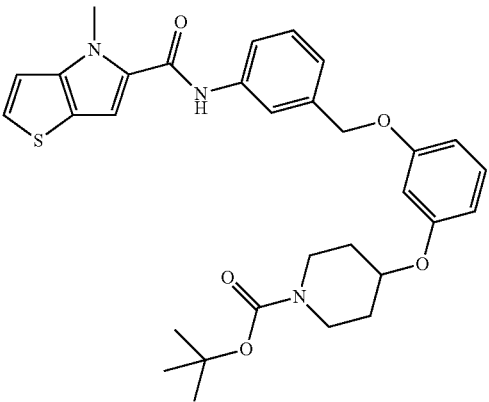 [SMILES: Cn1c(C(=O)Nc2cccc(COc3cccc(OC4CCN(C(=O)OC(C)(C)C)CC4)c3)c2)cc2sccc21] | $^1$H NMR (CDCl$_3$) δ (ppm): 7.75-7.70 (m, 2 H), 7.58-7.53 (m, 1 H), 7.42-7.36 (m, 1 H), 7.33 (d, J = 5.4 Hz, 1 H), 7.24-7.16 (m, 2 H), 6.99 (d, J = 5.4 Hz, 1 H), 6.95 (s, 1 H), 6.63-6.50 (m, 3 H), 5.07 (s, 2 H), 4.50-4.39 (m, 1 H), 4.11 (s, 3 H), 3.76-3.66 (m, 2 H), 3.39-3.25 (m, 2H), 1.98-1.86 (m, 2 H), 1.81-1.69 (m, 2 H), 1.47 (s, 9 H); MS (ESI): m/z: 584 [M + Na]$^+$ |

TABLE 1-continued

BOC Intermediates

| Name | Structure | Analytical Data |
| --- | --- | --- |
| tert-Butyl (NZ)-N-[(bis(tert-butoxycarbonyl)amino)-[tert-butoxycarbonyl-[[4-[[3-[(4-methylthieno[3,2-b]pyrrole-5-carbonyl)amino]phenyl]methoxy]phenyl]methyl]amino]methylene]carbamate | 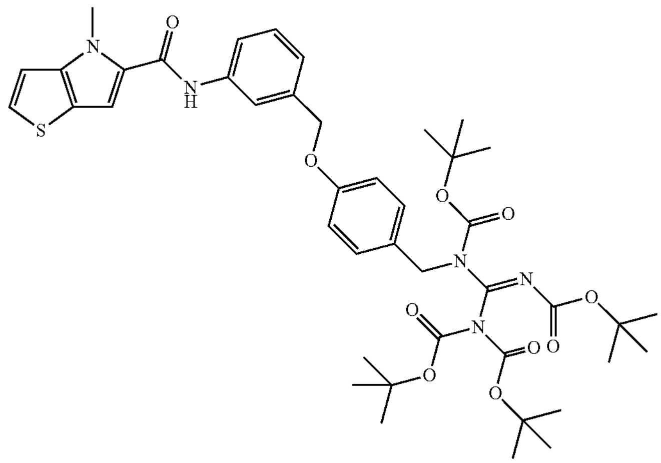 [SMILES: Cn1c(C(=O)Nc2cccc(COc3ccc(CN(C(=O)OC(C)(C)C)/C(=N/C(=O)OC(C)(C)C)N(C(=O)OC(C)(C)C)C(=O)OC(C)(C)C)cc3)c2)cc2sccc21] | $^1$H NMR (DMSO-d$_6$) δ (ppm): 10.03 (s, 1 H), 7.85 (s, 1 H), 7.68 (d, J = 8.3 Hz, 1 H), 7.52 (d, J = 5.9 Hz, 1 H), 7.36-7.30 (m, 2 H), 7.27-7.22 (m, 3 H), 7.13 (d, J = 6.8 Hz, 1 H), 6.96 (d, J = 8.3 Hz, 2 H), 5.08 (s, 2 H), 4.86 (s, 2 H), 4.01 (s, 3 H), 1.46-1.25 (m, 36 H); MS (ESI): m/z: 834 [M + H]$^+$ |
| tert-Butyl N-(N,N'-bis(tert-butoxycarbonyl)carbamimidoyl)-N-[[4-[[2-[(4-methylthieno[3,2-b]pyrrole-5-carbonyl)amino]phenyl]methoxy]phenyl]methyl]carbamate | 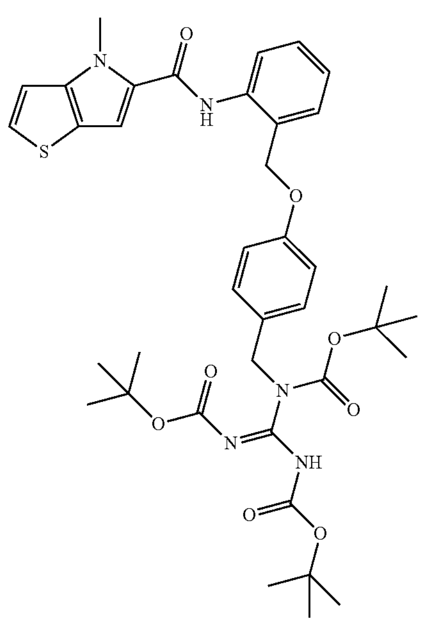 [SMILES: Cn1c(C(=O)Nc2ccccc2COc2ccc(CN(C(=O)OC(C)(C)C)/C(=N\C(=O)OC(C)(C)C)NC(=O)OC(C)(C)C)cc2)cc2sccc21] | $^1$H NMR (DMSO-d$_6$) δ (ppm): 10.25 (bs, 1 H), 9.78 (bs, 1 H), 7.53-7.46 (m, 3 H), 7.38-7.32 (m, 1 H), 7.28-7.21 (m, 3 H), 7.20-7.15 (m, 1 H), 6.94-6.87 (m, 1 H), 5.14 (s, 2 H), 4.62 (s, 2 H), 4.00 (s, 3 H), 1.49-1.29 (m, 27 H); MS (ESI): m/z: 734 [M + H]$^+$ |

TABLE 1-continued

BOC Intermediates

| Name | Structure | Analytical Data |
|---|---|---|
| tert-Butyl 4-[4-[2-[2-[(4-methylthieno[3,2-b]pyrrole-5-carbonyl)amino]phenyl]ethyl]phenoxy]piperidine-1-carboxylate | 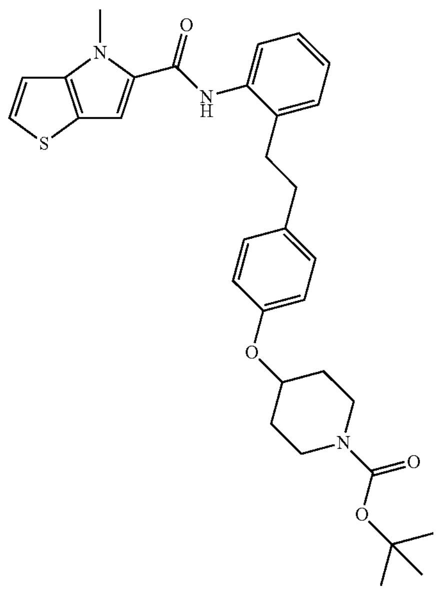 [SMILES: Cn1c(C(=O)Nc2ccccc2CCc2ccc(OC3CCN(C(=O)OC(C)(C)C)CC3)cc2)cc2sccc21] | $^1$H NMR (CDCl$_3$) δ (ppm): 7.76-7.71 (m, 1 H), 7.31 (d, J = 5.4 Hz, 1 H), 7.30-7.25 (m, 2 H), 7.22-7.17 (m, 1 H), 7.02-6.96 (m, 4 H), 6.84-6.80 (m, 2 H), 6.56 (s, 1 H), 4.44-4.34 (m, 1 H), 4.06 (s, 3 H), 3.74-3.64 (m, 2 H), 3.32-3.23 (m, 2 H), 2.95-2.86 (m, 4 H), 1.94-1.83 (m, 2 H), 1.77-1.65 (m, 2 H), 1.47 (s, 9 H); MS (ESI): m/z: 560 [M + H]$^+$ |
| tert-Butyl 4-[4-[2-[3-[(4-methylthieno[3,2-b]pyrrole-5-carbonyl)amino]phenyl]ethyl]phenoxy]piperidine-1-carboxylate | 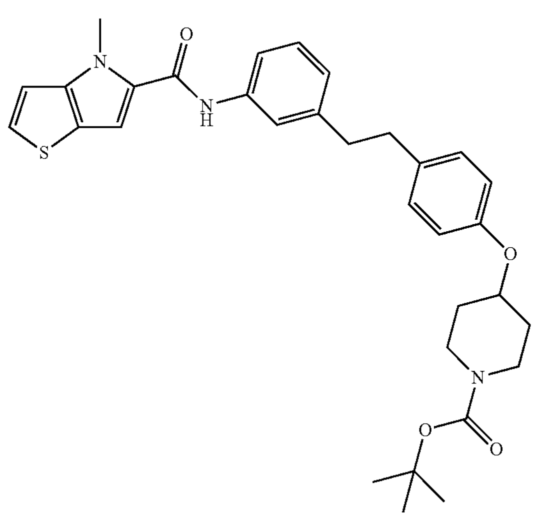 [SMILES: Cn1c(C(=O)Nc2cccc(CCc3ccc(OC4CCN(C(=O)OC(C)(C)C)CC4)cc3)c2)cc2sccc21] | $^1$H NMR (CDCl$_3$) δ (ppm): 7.66 (s, 1 H), 7.54-7.50 (m, 1 H), 7.40-7.36 (m, 1 H), 7.33 (d, J = 5.4 Hz, 1 H), 7.30-7.26 (m, 1 H), 7.14-7.09 (m, 2 H), 6.99 (d, J = 5.4 Hz, 1 H), 6.98-6.95 (m, 1 H), 6.94 (s, 1 H), 6.87-6.83 (m, 2 H), 4.48-4.38 (m, 1 H), 4.12 (s, 3 H), 3.76-3.67 (m, 2 H), 3.39-3.25 (m, 2 H), 2.97-2.84 (m, 4 H), 1.97-1.86 (m, 2 H), 1.80-1.69 (m, 2 H), 1.48 (s, 9 H); MS (ESI): m/z: 582 [M + Na]$^+$ |

TABLE 1-continued

BOC Intermediates

| Name | Structure | Analytical Data |
|---|---|---|
| tert-Butyl 4-[4-[tert-butoxycarbonyl-[[2-[(4-methylthieno[3,2-b]pyrrole-5-carbonyl)amino]phenyl]methyl]amino]phenoxy]piperidine-1-carboxylate | 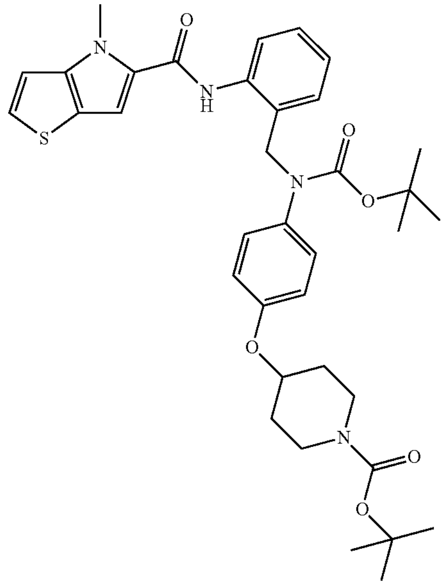 [SMILES: Cn1c(C(=O)Nc2ccccc2CN(C(=O)OC(C)(C)C)c2ccc(OC3CCN(C(=O)OC(C)(C)C)CC3)cc2)cc2sccc21] | $^1$H NMR (DMSO-d$_6$) δ (ppm): 9.75 (s, 1 H), 7.51 (d, J = 5.4 Hz, 1 H), 7.47-7.38 (m, 1 H), 7.31-7.15 (m, 5 H), 7.10-7.02 (m, 2 H), 6.87-6.80 (m, 2 H), 4.80 (s, 2 H), 4.48-4.38 (m, 1 H), 3.99 (s, 3 H), 3.68-3.57 (m, 2 H), 3.19-3.04 (m, 2 H), 1.91-1.78 (m, 2 H), 1.50-1.36 (m, 11 H), 1.29 (s, 9 H); MS (ESI): m/z: 661 [M + H]$^+$ |
| tert-Butyl 4-[3-[[2-[(6-methylthieno[2,3-b]pyrrole-5-carbonyl)amino]phenyl]methoxy]phenoxy]piperidine-1-carboxylate | 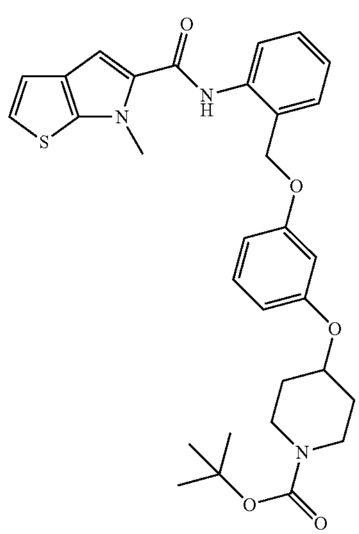 [SMILES: Cn1c(C(=O)Nc2ccccc2COc2cccc(OC3CCN(C(=O)OC(C)(C)C)CC3)c2)cc2ccsc21] | $^1$H NMR (CDCl$_3$) δ (ppm): 8.92 (s, 1 H), 8.31-8.15 (m, 1 H), 7.46-7.41 (m, 1 H), 7.35 (d, J = 6.4 Hz, 1 H), 7.26-7.21 (m, 1 H), 7.18-7.11 (m, 1 H), 6.95-6.89 (m, 2 H), 6.79 (s, 1 H), 6.71-6.66 (m, 1 H), 6.65-6.57 (m, 2 H), 5.16 (s, 2 H), 4.47-4.36 (m, 1 H), 4.09 (s, 3 H), 3.73-3.63 (m, 2 H), 3.35-3.22 (m, 2 H), 1.96-1.83 (m, 2 H), 1.79-1.65 (m, 2 H), 1.48 (s, 9 H); MS (ESI): m/z: 584 [M + Na]$^+$ |

TABLE 1-continued

BOC Intermediates

| Name | Structure | Analytical Data |
|---|---|---|
| tert-Butyl 4-[3-[[2-[(6-ethylthieno[2,3-b]pyrrole-5-carbonyl)amino]phenyl]methoxy]phenoxy]piperidine-1-carboxylate | 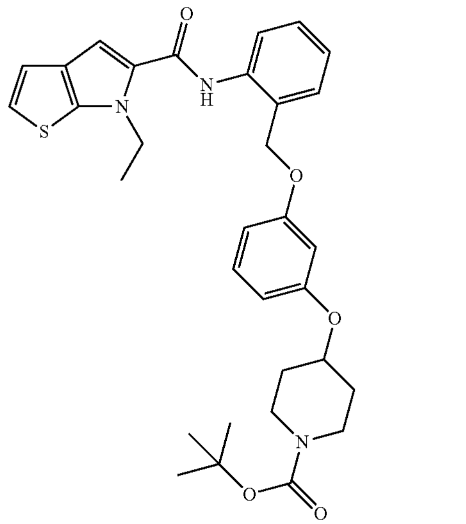 [SMILES: CCn1c(C(=O)Nc2ccccc2COc2cccc(OC3CCN(C(=O)OC(C)(C)C)CC3)c2)cc2ccsc21] | $^1$H NMR (CDCl$_3$) δ (ppm): 8.92 (s, 1 H), 8.31-8.18 (m, 1 H), 7.46-7.40 (m, 1 H), 7.35 (d, J = 7.3 Hz, 1 H), 7.26-7.21 (m, 1 H), 7.18-7.11 (m, 1 H), 6.95-6.88 (m, 2 H), 6.78 (s, 1 H), 6.71-6.66 (m, 1 H), 6.64-6.57 (m, 2 H), 5.17 (s, 2 H), 4.57 (q, J = 7.2 Hz, 2 H), 4.47-4.34 (m, 1 H), 3.73-3.62 (m, 2 H), 3.36-3.23 (m, 2 H), 1.95-1.82 (m, 2 H), 1.78-1.67 (m, 2 H), 1.53-1.46 (m, 12 H); MS (ESI): m/z: 598 [M + Na]$^+$ |
| tert-Butyl 4-[4-[[2-[(6-ethylthieno[2,3-b]pyrrole-5-carbonyl)amino]phenyl]methoxy]phenoxy]piperidine-1-carboxylate | | $^1$H NMR (CDCl$_3$) δ (ppm): 9.04 (s, 1 H), 8.27 (d, J = 8.3 Hz, 1 H), 7.46-7.39 (m, 1 H), 7.35-7.29 (m, J = 6.8 Hz, 1 H), 7.17-7.09 (m, 1 H), 7.03-6.97 (m, 2 H), 6.95-6.85 (m, 4 H), 6.84-6.79 (m, 1 H), 5.14 (s, 2 H), 4.57 (q, J = 7.2 Hz, 2 H), 4.39-4.31 (m, 1 H), 3.76-3.66 (m, 2 H), 3.35-3.27 (m, 2 H), 1.95-1.83 (m, 2 H), 1.79-1.68 (m, 2 H), 1.54-1.43 (m, 12 H) |
| tert-Butyl 4-[4-[[2-[(6-ethylthieno[2,3-b]pyrrole-5-carbonyl)amino]phenyl]methoxy]phenoxy]piperidine-1-carboxylate | | $^1$H NMR (CDCl$_3$) δ (ppm): 9.04 (s, 1 H), 8.29-8.24 (m, 1 H), 7.46-7.40 (m, 1 H), 7.34-7.30 (m, 1 H), 7.17-7.11 (m, 1 H), 7.02-6.97 (m, 2 H), 6.95-6.87 (m, 4 H), 6.83-6.80 (m, 1 H), 5.14 (s, 2 H), 4.38-4.33 (m, 1 H), 4.10 (s, 3 H), 3.75-3.69 (m, 2 H), 3.34-3.28 (m, 2 H), 1.93-1.87 (m, 2 H), 1.76-1.69 (m, 2 H), 1.48 (s, 9 H) |

TABLE 1-continued

BOC Intermediates

| Name | Structure | Analytical Data |
|---|---|---|
| tert-Butyl 3-[[4-[[2-[(6-methylthieno[2,3-b]pyrrole-5-carbonyl)amino]phenyl]methoxy]phenoxy]methyl]pyrrolidine-1-carboxylate | 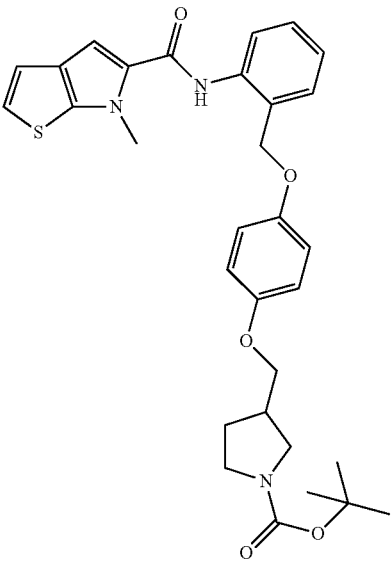 [SMILES: Cn1c(C(=O)Nc2ccccc2COc2ccc(OCC3CCN(C(=O)OC(C)(C)C)C3)cc2)cc2ccsc21] | $^1$H NMR (CDCl$_3$) δ (ppm): 9.05 (s, 1 H), 8.29-8.24 (m, 1 H), 7.45-7.39 (m, 1 H), 7.33-7.30 (m, 1 H), 7.15-7.10 (m, 1 H), 7.02-6.97 (m, 2 H), 6.96-6.91 (m, 2 H), 6.89-6.84 (m, 2 H), 6.83-6.80 (m, 1 H), 5.14 (s, 2 H), 4.10 (s, 3 H), 3.92-3.84 (m, 2 H), 3.63-3.57 (m, 1 H), 3.52-3.45 (m, 1 H), 3.41-3.34 (m, 1 H), 3.24-3.18 (m, 1 H), 2.70-2.63 (m, 1 H), 2.11-2.03 (m, 1 H), 1.83-1.75 (m, 1 H), 1.48 (s, 9 H) |

TABLE 2

Final Products

| Ex. | Name | Structure | Analytical Data |
|---|---|---|---|
| 4 | 4-methyl-N-[2-[[4-[[(3R)-pyrrolidin-3-yl]methoxy]phenoxy]methyl]phenyl]thieno[3,2-b]pyrrole-5-carboxamide | 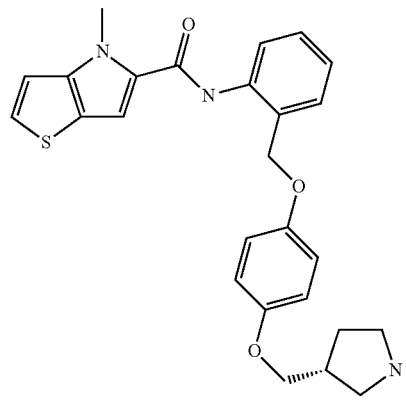 [SMILES: Cn1c(C(=O)Nc2ccccc2COc2ccc(OC[C@@H]3CCNC3)cc2)cc2sccc21] | $^1$H NMR (DMSO-d$_6$) δ (ppm): 9.73 (s, 1 H), 7.56-7.46 (m, 3 H), 7.39-7.33 (m, 1 H), 7.28-7.20 (m, 3 H), 6.94-6.78 (m, 4 H), 5.09 (s, 2 H), 4.00 (s, 3 H), 3.82-3.68 (m, 2 H), 2.90-2.77 (m, 2 H), 2.73-2.66 (m, 1 H), 2.60-2.54 (m, 1 H), 2.41-2.33 (m, 1 H), 1.85-1.75 (m, 1 H), 1.43-1.30 (m, 1 H); MS (ESI): m/z: 462 [M + H]$^+$ |
| 5 | 4-methyl-N-[2-[[4-(pyrrolidin-3-ylmethoxy)phenoxy]methyl]phenyl]thieno[3,2-b]pyrrole-5-carboxamide | 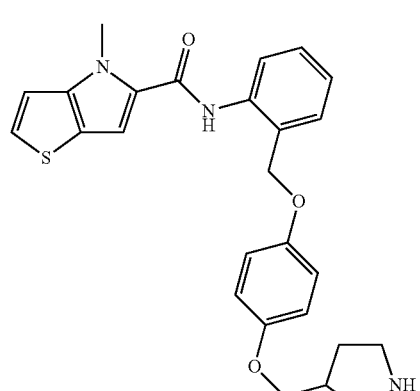 | $^1$H NMR (DMSO-d$_6$) δ (ppm): 9.73 (s, 1 H), 7.57-7.46 (m, 3 H), 7.40-7.31 (m, 1 H), 7.29-7.18 (m, 3 H), 6.95-6.75 (m, 4 H), 5.09 (s, 2 H), 4.00 (s, 3 H), 3.81-3.68 (m, 2 H), 2.88-2.74 (m, 2 H), 2.72-2.61 (m, 1 H), 2.59-2.53 (m, 1 H), 2.43-2.30 (m, 1 H), 1.85-1.73 (m, 1 H), 1.42-1.29 (m, 1 H); MS (ESI): m/z: 462 [M + H]$^+$ |

TABLE 2-continued

Final Products

| Ex. | Name | Structure | Analytical Data |
|---|---|---|---|
| 6 | 4-ethyl-N-[3-[[4-(4-piperidyloxy)phenoxy]methyl]phenyl]thieno[3,2-b]pyrrole-5-carboxamide | 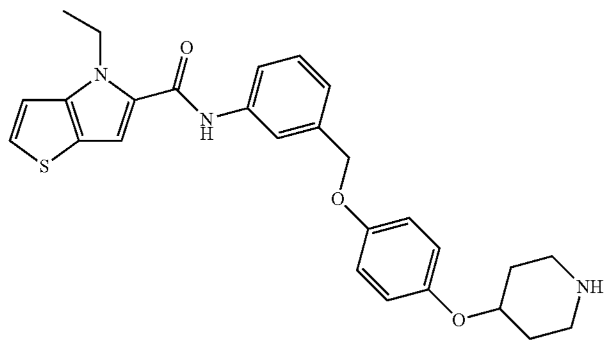 [SMILES: CCn1c(C(=O)Nc2cccc(COc3ccc(OC4CCNCC4)cc3)c2)cc2sccc21] | $^1$H NMR (DMSO-d$_6$) δ (ppm): 10.04 (s, 1 H), 7.88-7.82 (m, 1 H), 7.71-7.64 (m, 1 H), 7.52 (d, J = 5.4 Hz, 1 H), 7.37-7.31 (m, 2 H), 7.26 (d, J = 5.4 Hz, 1 H), 7.16-7.10 (m, 1 H), 6.95-6.84 (m, 4 H), 5.02 (s, 2 H), 4.53 (q, J = 7.0 Hz, 2 H), 4.28-4.19 (m, 1 H), 2.98-2.86 (m, 2 H), 2.58-2.50 (m, 2 H), 1.92-1.80 (m, 2 H), 1.45-1.36 (m, 2 H), 1.31 (t, J = 7.1 Hz, 3 H); MS (ESI): m/z: 476 [M + H]$^+$ |
| 7 | N-[2-[[4-(azepan-4-yloxy)phenoxy]methyl]phenyl]-4-methyl-thieno[3,2-b]pyrrole-5-carboxamide hydrochloride | 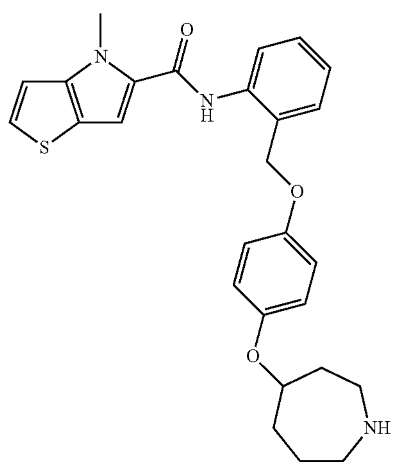 [SMILES: Cn1c(C(=O)Nc2ccccc2COc2ccc(OC3CCCNCC3)cc2)cc2sccc21] | $^1$H NMR (DMSO-d$_6$) δ (ppm): 9.75 (s, 1 H), 8.86 (bs, 2 H), 7.21-7.55 (m, 7 H), 6.82-6.94 (m, 4 H), 5.10 (s, 2 H), 4.51 (dt, J = 7.09, 3.30 Hz, 1 H), 4.00 (s, 3 H), 3.01-3.23 (m, 4 H), 1.63-2.14 (m, 6 H); MS (ESI): m/z: 476 [M + H]$^+$ |
| 8 | 4-ethyl-N-[2-[[4-(4-piperidyloxy)phenoxy]methyl]phenyl]thieno[3,2-b]pyrrole-5-carboxamide | 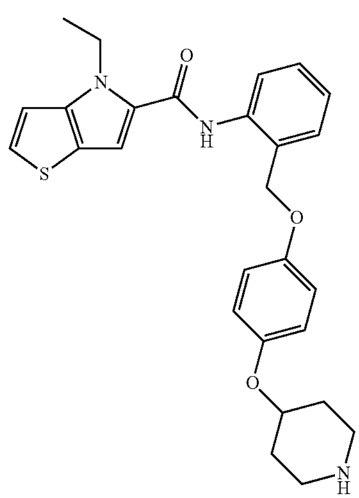 [SMILES: CCn1c(C(=O)Nc2ccccc2COc2ccc(OC3CCNCC3)cc2)cc2sccc21] | $^1$H NMR (DMSO-d$_6$) δ (ppm): 9.73 (s, 1 H), 7.58-7.46 (m, 3 H), 7.41-7.31 (m, 1 H), 7.29-7.17 (m, 3 H), 6.91-6.77 (m, 4 H), 5.09 (s, 2 H), 4.52 (q, J = 6.8 Hz, 2 H), 4.24-4.14 (m, 1 H), 2.95-2.84 (m, 2 H), 2.48-2.44 (m, 2 H), 1.87-1.79 (m, 2 H), 1.41-1.32 (m, 2 H), 1.29 (t, J = 7.1 Hz, 3 H); MS (ESI): m/z: 476 [M + H]$^+$ |

TABLE 2-continued

Final Products

| Ex. | Name | Structure | Analytical Data |
|---|---|---|---|
| 9 | N-[2-[[4-(cis-4-aminocyclohexoxy)phenoxy]methyl]phenyl]4-methylthieno[3,2-b]pyrrole-5-carboxamide | 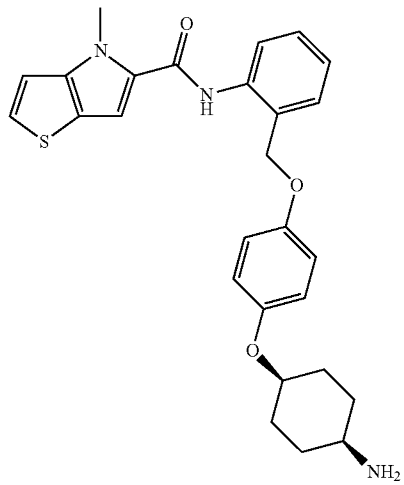 [SMILES: Cn1c(C(=O)Nc2ccccc2COc2ccc(O[C@H]3CC[C@@H](N)CC3)cc2)cc2sccc21] | $^1$H NMR (DMSO-d$_6$) δ (ppm): 9.73 (s, 1 H), 7.59-7.47 (m, 3 H), 7.42-7.32 (m, 1 H), 7.29-7.15 (m, 3 H), 6.95-6.76 (m, 4 H), 5.09 (s, 2 H), 4.29 (bs, 1 H), 4.00 (s, 3 H), 2.67 (bs, 1 H), 1.93-1.30 (m, 8 H); MS (ESI): m/z: 476 [M + H]$^+$ |
| 10 | 4-methyl-N-[3-[[4-(4-piperidyloxy)phenoxy]methyl]phenyl]thieno[3,2-b]pyrrole-5-carboxamide | 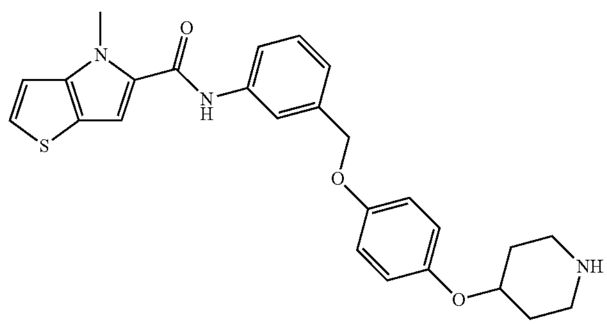 [SMILES: Cn1c(C(=O)Nc2cccc(COc3ccc(OC4CCNCC4)cc3)c2)cc2sccc21] | $^1$H NMR (DMSO-d$_6$) δ (ppm): 10.03 (s, 1 H), 7.90-7.79 (m, 1 H), 7.71-7.65 (m, 1 H), 7.52 (d, J = 5.4 Hz, 1 H), 7.36-7.30 (m, 2 H), 7.24 (d, J = 5.4 Hz, 1 H), 7.15-7.09 (m, 1 H), 6.95-6.83 (m, 4 H), 5.02 (s, 2 H), 4.28-4.17 (m, 1 H), 4.02 (s, 3 H), 2.97-2.87 (m, 2 H), 2.57-2.50 (m, 2 H), 1.92-1.79 (m, 2 H), 1.46-1.32 (m, 2 H); MS (ESI): m/z: 462 [M + H]$^+$ |
| 11 | 4-methyl-N-[2-[[4-[[(3S)-pyrrolidin-3-yl]methoxy]phenoxy]methyl]phenyl]thieno[3,2-b]pyrrole-5-carboxamide | 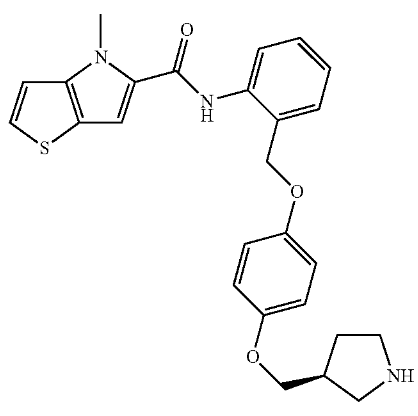 [SMILES: Cn1c(C(=O)Nc2ccccc2COc2ccc(OC[C@H]3CCNC3)cc2)cc2sccc21] | $^1$H NMR (DMSO-d$_6$) δ (ppm): 9.73 (s, 1 H), 7.55-7.47 (m, 3 H), 7.39-7.32 (m, 1 H), 7.28-7.20 (m, 3 H), 6.93-6.78 (m, 4 H), 5.10 (s, 2 H), 4.02-3.97 (m, 3 H), 3.83-3.71 (m, 2 H), 2.96-2.83 (m, 2 H), 2.80-2.72 (m, 1 H), 2.67-2.59 (m, 1 H), 2.46-2.38 (m, 1 H), 1.89-1.78 (m, 1 H), 1.48-1.36 (m, 1 H); MS (ESI): m/z: 462 [M + H]$^+$ |

TABLE 2-continued

Final Products

| Ex. | Name | Structure | Analytical Data |
|---|---|---|---|
| 12 | 4-ethyl-N-[2-[[4-[(1-methyl-4-piperidyl)oxy]phenoxy]methyl]phenyl]thieno[3,2-b]pyrrole-5-carboxamide | 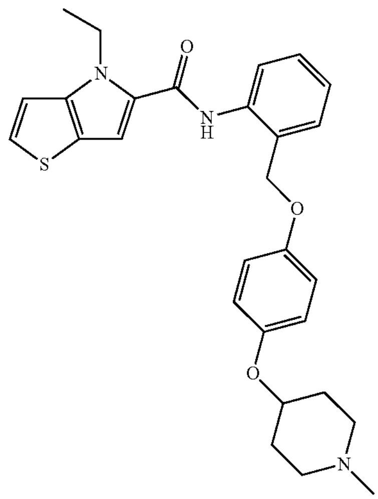 [SMILES: CCn1c(C(=O)Nc2ccccc2COc2ccc(OC3CCN(C)CC3)cc2)cc2sccc21] | $^1$H NMR (DMSO-d$_6$) δ (ppm): 9.74 (s, 1 H), 7.57-7.46 (m, 3 H), 7.40-7.31 (m, 1 H), 7.29-7.19 (m, 3 H), 6.91-6.79 (m, 4 H), 5.09 (s, 2 H), 4.52 (q, J = 6.8 Hz, 2 H), 4.23-4.11 (m, 1 H), 2.64-2.52 (m, 2 H), 2.19-2.03 (m, 5 H), 1.90-1.78 (m, 2 H), 1.61-1.49 (m, 2 H), 1.29 (t, J = 6.8 Hz, 3 H); MS (ESI): m/z: 490 [M + H |
| 13 | 4-methyl-N-[2-[[4-[(1-methyl-4-piperidyl)oxy]phenoxy]methyl]phenyl]thieno[3,2-b]pyrrole-5-carboxamide | 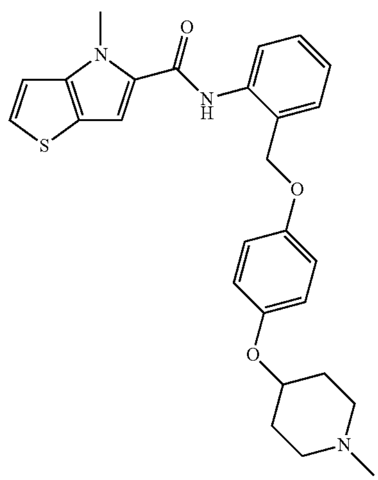 [SMILES: CN1CCC(Oc2ccc(OCc3ccccc3NC(=O)c3cc4sccc4n3C)cc2)CC1] | $^1$H NMR (DMSO-d$_6$) δ (ppm): 9.72 (s, 1 H), 7.55-7.48 (m, 3 H), 7.39-7.33 (m, 1 H), 7.28-7.21 (m, 3 H), 6.91-6.80 (m, 4 H), 5.09 (s, 2 H), 4.22-4.11 (m, 1 H), 4.00 (s, 3 H), 2.61-2.52 (m, 2 H), 2.14 (s, 3 H), 2.12-2.05 (m, 2 H), 1.88-1.79 (m, 2 H), 1.61-1.48 (m, 2 H); MS (ESI): m/z: 476 [M + H]$^+$ |
| 14 | N-[2-[[4-(trans-4-aminocyclohexoxy)phenoxy]methyl]phenyl]-4-methyl-thieno[3,2-b]pyrrole-5-carboxamide | 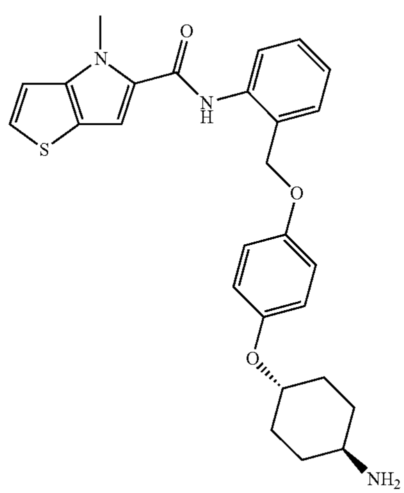 [SMILES: Cn1c(C(=O)Nc2ccccc2COc2ccc(O[C@H]3CC[C@H](N)CC3)cc2)cc2sccc21] | $^1$H NMR (DMSO-d$_6$) δ (ppm): 9.72 (s, 1 H), 7.57-7.46 (m, 3 H), 7.40-7.32 (m, 1 H), 7.28-7.19 (m, 3 H), 6.92-6.74 (m, 4 H), 5.09 (s, 2 H), 4.12-4.02 (m, 1 H), 4.00 (s, 3 H), 2.67-2.54 (m, 1 H), 2.11-1.02 (m, 8 H); MS (ESI): m/z: 476 [M + H]$^+$ |

TABLE 2-continued

Final Products

| Ex. | Name | Structure | Analytical Data |
|---|---|---|---|
| 15 | 4-methyl-N-[3-[[4-[(1-methyl-4-piperidyl)oxy]phenoxy]methyl]phenyl]thieno[3,2-b]pyrrole-5-carboxamide | 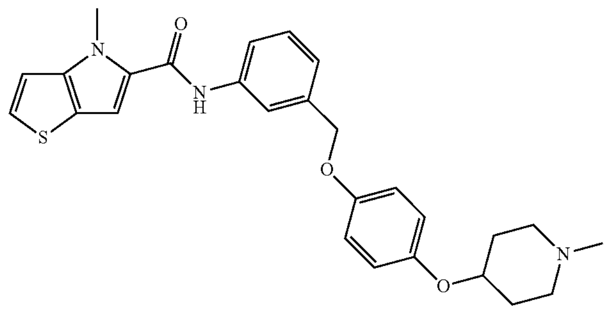 [SMILES: CN1CCC(Oc2ccc(OCc3cccc(NC(=O)c4cc5sccc5n4C)c3)cc2)CC1] | $^1$H NMR (DMSO-d$_6$) δ (ppm): 10.03 (s, 1 H), 7.88-7.81 (m, 1 H), 7.72-7.65 (m, 1 H), 7.52 (d, J = 5.4 Hz, 1 H), 7.37-7.30 (m, 2 H), 7.24 (d, J = 5.4 Hz, 1 H), 7.15-7.10 (m, 1 H), 6.96-6.84 (m, 4 H), 5.02 (s, 2 H), 4.26-4.14 (m, 1 H), 4.01 (s, 3 H), 2.65-2.53 (m, 2 H), 2.21-2.06 (m, 5 H), 1.91-1.79 (m, 2 H), 1.65-1.50 (m, 2 H); MS (ESI): m/z: 476 [M + H]$^+$ |
| 16 | 4-methyl-N-[2-[(4-pyrrolidin-3-yloxyphenoxy)methyl]phenyl]thieno[3,2-b]pyrrole-5-carboxamide | 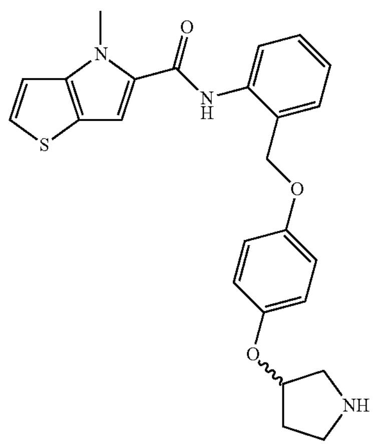 [SMILES: Cn1c(C(=O)Nc2ccccc2COc2ccc(OC3CCNC3)cc2)cc2sccc21] | $^1$H NMR (DMSO-d$_6$) δ (ppm): 9.73 (s, 1 H), 7.56-7.46 (m, 3 H), 7.40-7.31 (m, 1 H), 7.29-7.18 (m, 3 H), 6.93-6.74 (m, 4 H), 5.09 (s, 2 H), 4.79-4.66 (m, 1 H), 4.00 (s, 3 H), 3.04-2.94 (m, 1 H), 2.92-2.69 (m, 3 H), 1.99-1.85 (m, 1 H), 1.76-1.63 (m, 1 H); MS (ESI): m/z: 448 [M + H]$^+$ |
| 17 | 4-methyl-N-[2-[[3-[(1-methyl-4-piperidyl)oxy]phenoxy]methyl]phenyl]thieno[3,2-b]pyrrole-5-carboxamide | 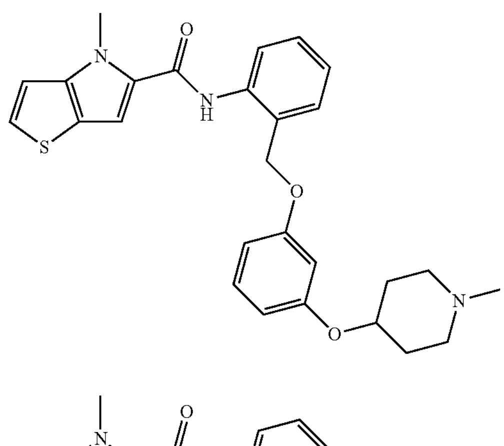 | $^1$H NMR (DMSO-d$_6$) δ (ppm): 9.73 (s, 1 H), 7.56-7.47 (m, 3 H), 7.40-7.33 (m, 1 H), 7.29-7.21 (m, 3 H), 7.16-7.09 (m, 1 H), 6.56-6.46 (m, 3 H), 5.15 (s, 2 H), 4.30-4.21 (m, 1 H), 4.00 (s, 3 H), 2.60-2.51 (m, 2 H), 2.13 (s, 3 H), 2.11-2.03 (m, 2 H), 1.88-1.78 (m, 2 H), 1.61-1.47 (m, 2 H); MS (ESI): m/z: 476 [M + H]$^+$ |
| 18 | 4-methyl-N-[2-[[3-(4-piperidyloxy)phenoxy]methyl]phenyl]thieno[3,2-b]pyrrole-5-carboxamide | 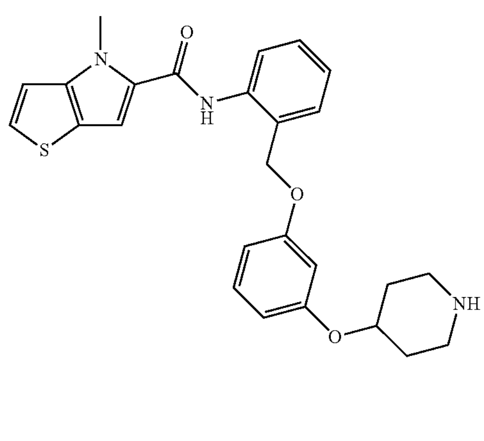 [SMILES: Cn1c(C(=O)Nc2ccccc2COc2cccc(OC3CCNCC3)c2)cc2sccc21] | $^1$H NMR (DMSO-d$_6$) δ (ppm): 9.72 (s, 1 H), 7.56-7.46 (m, 3 H), 7.40-7.32 (m, 1 H), 7.28-7.20 (m, 3 H), 7.16-7.06 (m, 1 H), 6.57-6.45 (m, 3 H), 5.15 (s, 2 H), 4.35-4.24 (m, 1 H), 4.00 (s, 3 H), 2.93-2.82 (m, 2 H), 2.55-2.50 (m, 2 H), 1.87-1.76 (m, 2 H), 1.43-1.30 (m, 2 H); MS (ESI): m/z: 462 [M + H]$^+$ |

TABLE 2-continued

Final Products

| Ex. | Name | Structure | Analytical Data |
|---|---|---|---|
| 19 | 4-methyl-N-[3-[(1-methyl-3-piperidyl)methoxy]phenyl]thieno[3,2-b]pyrrole-5-carboxamide | 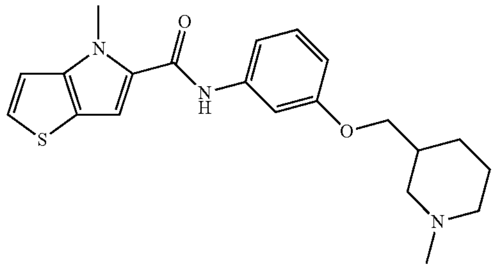 [SMILES: CN1CCCC(COc2cccc(NC(=O)c3cc4sccc4n3C)c2)C1] | ¹H NMR (DMSO-d₆) δ (ppm): 9.93 (s, 1 H), 7.52 (d, J = 5.4 Hz, 1 H), 7.46-7.41 (m, 1 H), 7.33-7.28 (m, 2 H), 7.26-7.23 (m, 1 H), 7.23-7.18 (m, 1 H), 6.66-6.60 (m, 1 H), 4.01 (s, 3 H), 3.88-3.76 (m, 2 H), 2.86-2.75 (m, 1 H), 2.67-2.57 (m, 1 H), 2.15 (s, 3 H), 2.04-1.96 (m, 1 H), 1.95-1.86 (m, 1 H), 1.85-1.75 (m, 1 H), 1.75-1.59 (m, 2 H), 1.55-1.42 (m, 1 H), 1.14-0.99 (m, 1 H); MS (ESI): m/z: 384 [M + H]⁺ |
| 20 | 4-methyl-N-[2-[[4-[(4-methylpiperazin-1-yl)methyl]phenoxy]methyl]phenyl]thieno[3,2-b]pyrrole-5-carboxamide | 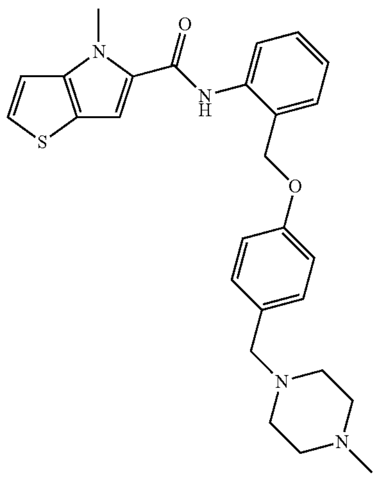 | ¹H NMR (DMSO-d₆) δ (ppm): 9.75 (s, 1 H), 7.56-7.49 (m, 3 H), 7.40-7.33 (m, 1 H), 7.29-7.21 (m, 3 H), 7.19-7.13 (m, 2 H), 6.94-6.88 (m, 2 H), 5.14 (s, 2 H), 3.99 (s, 3 H), 3.35 (s, 2 H), 2.47-2.06 (m, 11 H); MS (ESI): m/z: 475 [M + H]⁺ |
| 21 | 4-methyl-N-[3-(4-pyridylmethoxy)phenyl]thieno[3,2-b]pyrrole-5-carboxamide | 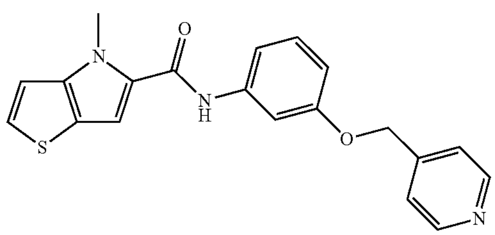 | ¹H NMR (DMSO-d₆) δ (ppm): 9.99 (s, 1 H), 8.62-8.54 (m, 2 H), 7.57-7.54 (m, 1 H), 7.52 (d, J = 5.4 Hz, 1 H), 7.47-7.43 (m, 2 H), 7.35-7.30 (m, 2 H), 7.27-7.21 (m, 2 H), 6.75-6.70 (m, 1 H), 5.18 (s, 2 H), 4.01 (s, 3 H); MS (ESI): m/z: 364 [M + H]⁺ |
| 22 | 4-methyl-N-[3-(4-pyridyloxymethyl)phenyl]thieno[3,2-b]pyrrole-5-carboxamide | 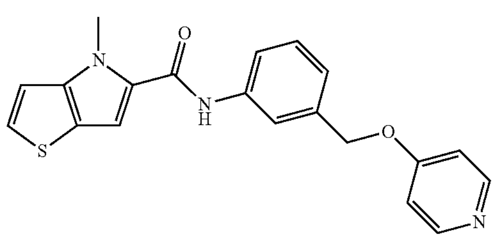 [SMILES: Cn1c(C(=O)Nc2cccc(COc3ccncc3)c2)cc2sccc21] | ¹H NMR (DMSO-d₆) δ (ppm): 10.07 (s, 1 H), 7.76-7.71 (m, 2 H), 7.71-7.66 (m, 2 H), 7.52 (d, J = 5.4 Hz, 1 H), 7.37-7.33 (m, 1 H), 7.31 (s, 1 H), 7.24 (d, J = 5.4 Hz, 1 H), 7.01-6.97 (m, 1 H), 6.15-6.07 (m, 2 H), 5.08 (s, 2 H), 4.00 (s, 3 H) ); MS (ESI): m/z: 364 [M + H]⁺ |
| 23 | 4-methyl-N-[4-[[4-[(1-methyl-4-piperidyl)oxy]phenoxy]methyl]phenyl]thieno[3,2-b]pyrrole-5-carboxamide | 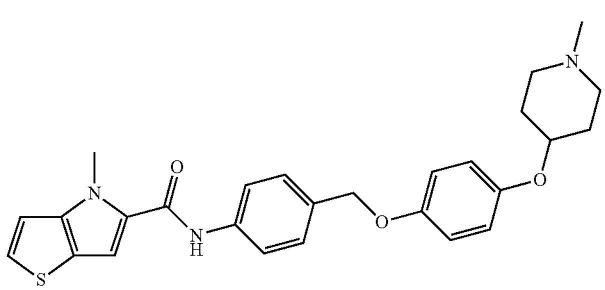 [SMILES: CN1CCC(Oc2ccc(OCc3ccc(NC(=O)c4cc5sccc5n4C)cc3)cc2)CC1] | ¹H NMR (DMSO-d₆) δ (ppm): 10.03 (s, 1 H), 7.78-7.70 (m, 2 H), 7.52 (d, J = 5.4 Hz, 1 H), 7.42-7.35 (m, 2 H), 7.32 (s, 1 H), 7.24 (d, J = 5.4 Hz, 1 H), 6.94-6.82 (m, 4 H), 4.97 (s, 2 H), 4.25-4.13 (m, 1 H), 4.02 (s, 3 H), 2.64-2.54 (m, 2 H), 2.20-2.04 (m, 5 H), 1.92-1.80 (m, 2 H), 1.63-1.50 (m, 2 H) ); MS (ESI): m/z: 476 [M + H]⁺ |

TABLE 2-continued

Final Products

| Ex. | Name | Structure | Analytical Data |
|---|---|---|---|
| 24 | N-[2-[[4-[[(1S,5R)-8-azabicyclo[3.2.1]octan-3-yl]oxy]phenoxy]methyl]phenyl]-4-methyl-thieno[3,2-b]pyrrole-5-carboxamide | 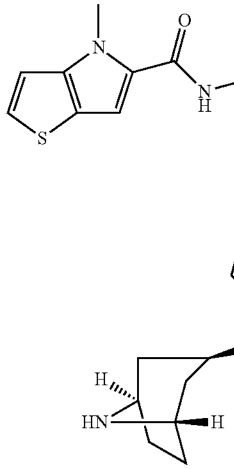 | $^1$H NMR (DMSO-d$_6$) δ (ppm): 9.72 (s, 1 H), 7.56-7.47 (m, 3 H), 7.40-7.32 (m, 1 H), 7.29-7.19 (m, 3 H), 6.91-6.78 (m, 4 H), 5.09 (s, 2 H), 4.45-4.33 (m, 1 H), 4.00 (s, 3 H), 3.45-3.39 (m, 2 H), 1.98-1.34 (m, 8 H); MS (ESI): m/z: 488 [M + H]$^+$ |
| 25 | N-[3-[[4-[[(1S,5R)-8-azabicyclo[3.2.1]octan-3-yl]oxy]phenoxy]methyl]phenyl]-4-methyl-thieno[3,2-b]pyrrole-5-carboxamide | 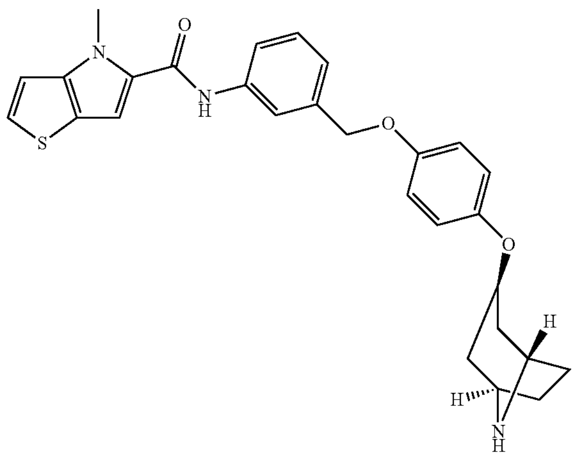 [SMILES: Cn1c(C(=O)Nc2cccc(COc3ccc(O[C@@H]4C[C@H]5CC[C@@H](C4)N5)cc3)c2)cc2sccc21] | $^1$H NMR (DMSO-d$_6$) δ (ppm): 10.03 (s, 1 H), 7.84 (s, 1 H), 7.71-7.65 (m, 1 H), 7.52 (d, J = 5.4 Hz, 1 H), 7.37-7.30 (m, 2 H), 7.24 (d, J = 5.4 Hz, 1 H), 7.15-7.09 (m, 1 H), 6.93-6.83 (m, 4 H), 5.02 (s, 2 H), 4.48-4.34 (m, 1 H), 4.01 (s, 3 H), 3.49-3.40 (m, 2 H), 2.02-1.37 (m, 8 H); MS (ESI): m/z: 488 [M + H]$^+$ |
| 26 | 4-methyl-N-[3-[[4-(4-piperidylmethoxy)phenoxy]methyl]phenyl]thieno[3,2-b]pyrrole-5-carboxamide | 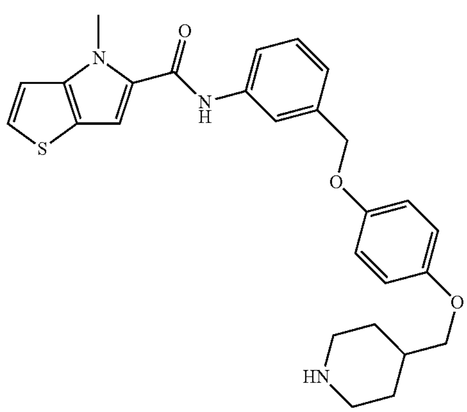 [SMILES: Cn1c(C(=O)Nc2cccc(COc3ccc(OCC4CCNCC4)cc3)c2)cc2sccc21] | $^1$H NMR (DMSO-d$_6$) δ (ppm): 10.04 (s, 1 H), 7.84 (s, 1 H), 7.72-7.65 (m, 1 H), 7.52 (d, J = 5.4 Hz, 1 H), 7.37-7.30 (m, 2 H), 7.24 (d, J = 4.9 Hz, 1 H), 7.16-7.09 (m, 1 H), 6.96-6.81 (m, 4 H), 5.02 (s, 2 H), 4.01 (s, 3 H), 3.71 (d, J = 6.4 Hz, 2 H), 3.00-2.89 (m, 2 H), 2.49-2.41 (m, 2 H), 1.81-1.71 (m, 1 H), 1.69-1.62 (m, 2 H), 1.19-1.06 (m, 2 H); MS (ESI): m/z: 476 [M + H]$^+$ |

TABLE 2-continued

Final Products

| Ex. | Name | Structure | Analytical Data |
|---|---|---|---|
| 27 | 4-methyl-N-[2-[[4-(3-piperidyloxy)phenoxy]methyl]phenyl]thieno[3,2-b]pyrrole-5-carboxamide | 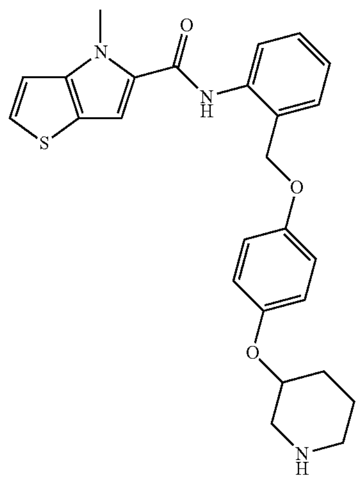 [SMILES: Cn1c(C(=O)Nc2ccccc2COc2ccc(OC3CCCNC3)cc2)cc2sccc21] | $^1$H NMR (DMSO-d$_6$) δ (ppm): 9.72 (s, 1 H), 7.56-7.47 (m, 3 H), 7.40-7.32 (m, 1 H), 7.29-7.19 (m, 3 H), 6.93-6.78 (m, 4 H), 5.09 (s, 2 H), 4.09-4.02 (m, 1 H), 4.00 (s, 3 H), 3.07-2.97 (m, 1 H), 2.77-2.67 (m, 1 H), 2.46-2.38 (m, 2 H), 2.01-1.91 (m, 1 H), 1.67-1.57 (m, 1 H), 1.46-1.33 (m, 2 H); MS (ESI): m/z: 462 [M + H]$^+$ |
| 28 | 4-methyl-N-[3-[[4-(3-piperidyloxy)phenoxy]methyl]phenyl]thieno[3,2-b]pyrrole-5-carboxamide | 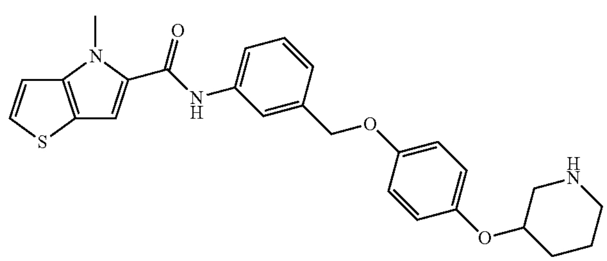 [SMILES: Cn1c(C(=O)Nc2cccc(COc3ccc(OC4CCCNC4)cc3)c2)cc2sccc21] | $^1$H NMR (DMSO-d$_6$) δ (ppm): 10.04 (s, 1 H), 7.84 (s, 1 H), 7.72-7.63 (m, 1 H), 7.52 (d, J = 5.4 Hz, 1 H), 7.37-7.30 (m, 2 H), 7.25 (d, J = 4.9 Hz, 1 H), 7.16-7.09 (m, 1 H), 6.96-6.82 (m, 4 H), 5.02 (s, 2 H), 4.13-4.04 (m, 1 H), 4.01 (s, 3 H), 3.08-2.98 (m, 1 H), 2.78-2.70 (m, 1 H), 2.46-2.39 (m, 2 H), 2.20 (bs, 1 H), 2.04-1.94 (m, 1 H), 1.69-1.57 (m, 1 H), 1.51-1.31 (m, 2 H); MS (ESI): m/z: 462 [M + H]$^+$ |
| 29 | N-[3-[[4-(trans-4-aminocyclohexoxy)phenoxy]methyl]phenyl]-4-methyl-thieno[3,2-b]pyrrole-5-carboxamide | 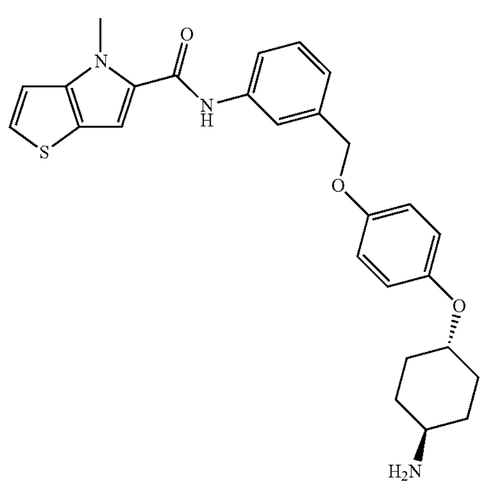 [SMILES: Cn1c(C(=O)Nc2cccc(COc3ccc(O[C@H]4CC[C@H](N)CC4)cc3)c2)cc2sccc21] | $^1$H NMR (DMSO-d$_6$) δ (ppm): 10.04 (s, 1 H), 7.85 (s, 1 H), 7.72-7.64 (m, 1 H), 7.52 (d, J = 5.4 Hz, 1 H), 7.38-7.31 (m, 2 H), 7.25 (d, J = 5.4 Hz, 1 H), 7.16-7.09 (m, 1 H), 6.97-6.81 (m, 4 H), 5.02 (s, 2 H), 4.14-4.05 (m, 1 H), 4.02 (s, 3 H), 2.63-2.55 (m, 1 H), 2.03-1.06 (m, 8 H); MS (ESI): m/z: 476 [M + H]$^+$ |

TABLE 2-continued

Final Products

| Ex. | Name | Structure | Analytical Data |
|---|---|---|---|
| 30 | N-[3-[[4-(azetidin-3-ylmethoxy)phenoxy]methyl]phenyl]-4-methyl-thieno[3,2-b]pyrrole-5-carboxamide | 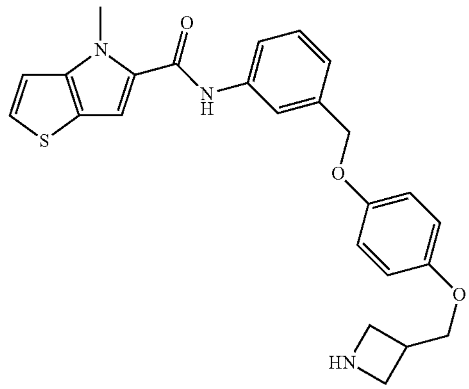 [SMILES: Cn1c(C(=O)Nc2cccc(COc3ccc(OCC4CNC4)cc3)c2)cc2sccc21] | $^1$H NMR (acetonitrile-d$_3$) δ (ppm): 8.63 (s, 1 H), 7.85 (s, 1 H), 7.69-7.62 (m, 1 H), 7.46-7.36 (m, 2 H), 7.24-7.16 (m, 2 H), 7.12 (d, J = 5.4 Hz, 1 H), 7.00-6.84 (m, 4 H), 5.09 (s, 2 H), 4.13-4.01 (m, 5 H), 3.74-3.62 (m, 2 H), 3.48-3.36 (m, 2 H), 3.12-2.97 (m, 1 H); MS (ESI): m/z: 448 [M + H]$^+$ |
| 31 | 4-methyl-N-[2-[[4-(3-methylaminopropoxy)phenoxy]methyl]phenyl]thieno[3,2-b]pyrrole-5-carboxamide hydrochloride | 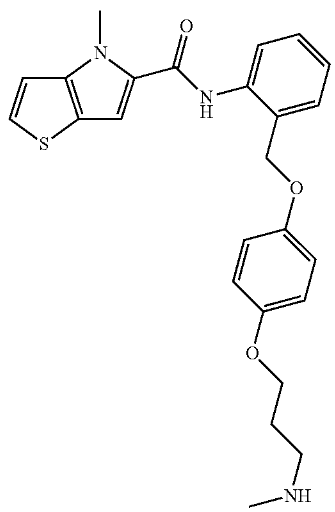 [SMILES: CNCCCOc1ccc(OCc2ccccc2NC(=O)c2cc3sccc3n2C)cc1] | $^1$H NMR (CDCl$_3$) δ (ppm): 9.65 (bs, 2 H), 9.01 (s, 1 H), 8.25 (d, J = 7.8 Hz, 1 H), 7.41 (t, J = 7.8 Hz, 1 H), 7.32-7.28 (m, 2 H), 7.12 (t, J = 7.3 Hz, 1 H), 7.00-6.92 (m, 3 H), 6.89-6.84 (m, 2 H), 6.80 (s, 1 H), 5.10 (s, 2 H), 4.12 (s, 3 H), 4.07-4.01 (m, 2 H), 3.26-3.16 (m, 2 H), 2.74 (s, 3 H), 2.43-2.32 (m, 2 H); MS (ESI): m/z: 450 [M + H]$^+$ |
| 32 | 4-methyl-N-[3-[(4-pyrrolidin-3-yloxyphenoxy)methyl]phenyl]thieno[3,2-b]pyrrole-5-carboxamide hydrochloride | 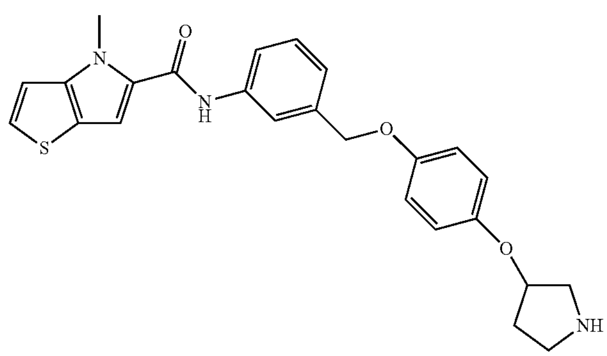 [SMILES: Cn1c(C(=O)Nc2cccc(COc3ccc(OC4CCNC4)cc3)c2)cc2sccc21] | $^1$H NMR (DMSO-d$_6$) δ (ppm): 10.08 (s, 1 H), 9.56-9.30 (m, 2 H), 7.88 (s, 1 H), 7.69 (d, J = 8.3 Hz, 1 H), 7.53 (d, J = 4.9 Hz, 1 H), 7.39-7.32 (m, 2 H), 7.25 (d, J = 5.4 Hz, 1 H), 7.14 (d, J = 7.3 Hz, 1 H), 7.01-6.90 (m, 4 H), 5.09-5.00 (m, 3 H), 4.02 (s, 3 H), 3.44-3.20 (m, 4 H), 2.18-2.06 (m, 2 H); MS (ESI): m/z: 448 [M + H]$^+$ |
| 33 | N-[3-[[4-(azepan-4-yloxy)phenoxy]methyl]phenyl]-4-methyl-thieno[3,2-b]pyrrole-5-carboxamide | 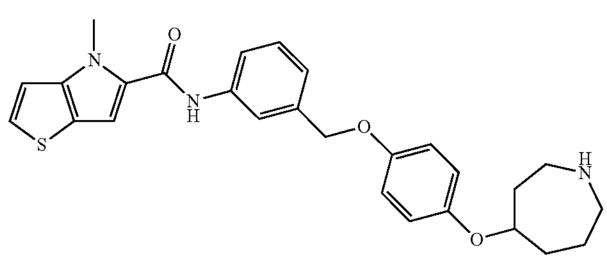 [SMILES: Cn1c(C(=O)Nc2cccc(COc3ccc(OC4CCCNCC4)cc3)c2)cc2sccc21] | $^1$H NMR (DMSO-d$_6$) δ (ppm). 10.04 (s, 1 H), 7.84 (s, 1 H), 7.68 (d, J = 8.3 Hz, 1 H), 7.52 (d, J = 5.4 Hz, 1 H), 7.37-7.30 (m, 2 H), 7.24 (d, J = 5.4 Hz, 1 H), 7.13 (d, J = 7.3 Hz, 1 H), 6.96-6.88 (m, 2 H), 6.85-6.79 (m, 2 H), 5.02 (s, 2 H), 4.46-4.38 (m, 1 H), 4.02 (s, 3 H), 2.83-2.61 (m, 4 H), 2.02-1.42 (m, 6 H); MS (ESI): m/z: 476 [M + H]$^+$ |

TABLE 2-continued

Final Products

| Ex. | Name | Structure | Analytical Data |
|---|---|---|---|
| 34 | N-[3-[[4-(cis-4-aminocyclohexoxy)phenoxy]methyl]phenyl]-4-methyl-thieno[3,2-b]pyrrole-5-carboxamide | 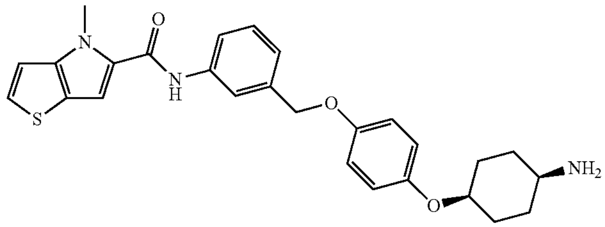 [SMILES: Cn1c(C(=O)Nc2cccc(COc3ccc(O[C@H]4CC[C@@H](N)CC4)cc3)c2)cc2sccc21] | $^1$H NMR (DMSO-d$_6$) δ (ppm): 10.05 (s, 1 H), 7.86 (s, 1 H), 7.69 (d, J = 8.3 Hz, 1 H), 7.52 (d, J = 4.9 Hz, 1 H), 7.38-7.31 (m, 2 H), 7.25 (d, J = 5.4 Hz, 1 H), 7.14 (d, J = 7.3 Hz, 1 H), 6.96-6.84 (m, 4 H), 5.03 (s, 2 H), 4.33 (bs, 1 H), 4.02 (s, 3 H), 2.75-2.67 (m, 1 H), 1.89-1.78 (m, 2 H), 1.59-1.35 (m, 6 H); MS (ESI): m/z: 476 [M + H]$^+$ |
| 35 | 4-methyl-N-[3-[[4-(pyrrolidin-3-ylmethoxy)phenoxy]methyl]phenyl]thieno[3,2-b]pyrrole-5-carboxamide hydrochloride | 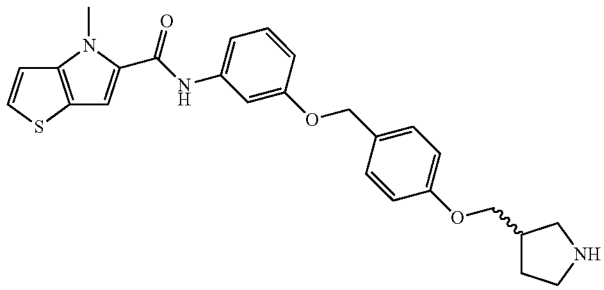 [SMILES: Cn1c(C(=O)Nc2cccc(OCc3ccc(OCC4CCNC4)cc3)c2)cc2sccc21] | $^1$H NMR (DMSO-d$_6$) δ (ppm): 10.06 (s, 1 H), 8.92 (bs, 2 H), 7.87 (s, 1 H) 7.67 (d, J = 7.34 Hz, 1 H) 7.53 (d, J = 5.38 Hz, 1 H) 7.31-7.37 (m, 2 H), 7.25 (d, J = 5.38 Hz, 1 H), 7.13 (d, J = 7.83 Hz, 1 H), 6.85-6.99 (m, 4 H), 5.04 (s, 2 H), 4.02 (s, 3 H) 3.86-3.99 (m, 2 H) 2.95-3.03 (m, 1 H), 3.11-3.33 (m, 3 H), 2.63-2.74 (m, 1 H), 2.03-2.12 (m, 1 H) 1.67-1.78 (m, 1 H); MS (ESI): m/z: 462 [M + H]$^+$ |
| 36 | 4-methyl-N-[2-[[4-(4-piperidyloxy)phenyl]carbamoyl]phenyl]thieno[3,2-b]pyrrole-5-carboxamide | 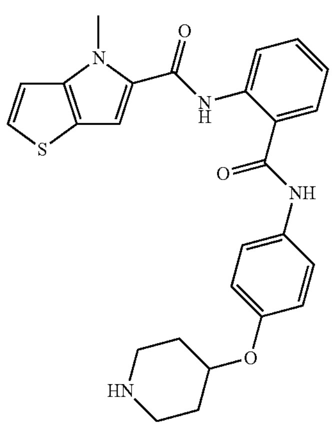 [SMILES: Cn1c(C(=O)Nc2ccccc2C(=O)Nc2ccc(OC3CCNCC3)cc2)cc2sccc21] | $^1$H NMR (DMSO-d$_6$) δ (ppm): 11.76 (bs, 1 H), 10.43 (bs, 1 H), 8.60-8.38 (m, 1 H), 8.01-7.80 (m, 1 H), 7.71-7.51 (m, 4 H), 7.31-6.87 (m, 5 H), 4.36 (bs, 1 H), 4.04 (s, 3 H), 3.02-2.88 (m, 2 H), 2.64-2.52 (m, 3 H), 1.98-1.82 (m, 2 H), 1.53-1.36 (m, 2 H); MS (ESI): m/z: 475 [M + H]$^+$. |
| 37 | 4-methyl-N-[2-[(4-piperazin-1-ylphenoxy)methyl]phenyl]thieno[3,2-b]pyrrole-5-carboxamide | 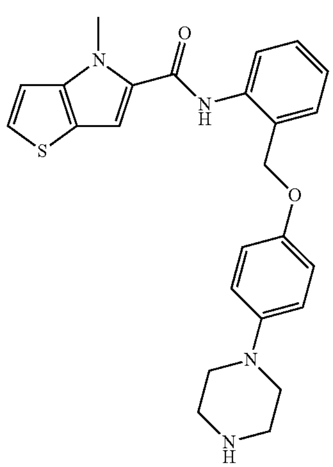 [SMILES: Cn1c(C(=O)Nc2ccccc2COc2ccc(N3CCNCC3)cc2)cc2sccc21] | $^1$H NMR (DMSO-d$_6$) δ (ppm): 9.06 (s, 1 H), 8.27 (d, J = 7.8 Hz, 1 H), 7.45-7.39 (m, 1 H), 7.35-7.28 (m, 2 H), 7.16-7.11 (m, 1 H), 7.03-6.90 (m, 5 H), 6.81 (s, 1 H), 5.14 (s, 2 H), 4.13 (s, 3 H), 3.19-3.10 (m, 8 H); MS (ESI): m/z: 447 [M + H]$^+$. |

TABLE 2-continued

Final Products

| Ex. | Name | Structure | Analytical Data |
|---|---|---|---|
| 38 | 4-methyl-N-[2-[[4-[(1-methyl-4-piperidyl)oxy]phenyl]methoxy]phenyl]thieno[3,2-b]pyrrole-5-carboxamide | 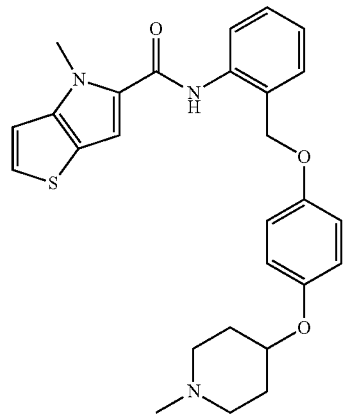 [SMILES: CN1CCC(Oc2ccc(OCc3ccccc3NC(=O)c3cc4sccc4n3C)cc2)CC1] | ¹H NMR (DMSO-d₆) δ (ppm): 9.08 (s, 1 H), 7.85-7.73 (m, 1 H), 7.56-7.47 (m, 1 H), 7.45-7.35 (m, 2 H), 7.28-7.20 (m, 1 H), 7.19-7.08 (m, 3 H), 7.00-6.84 (m, 3 H), 5.10 (s, 2 H), 4.41-4.27 (m, 1 H), 4.00 (s, 3 H), 2.60 (bs, 2 H), 2.24-2.07 (m, 5 H), 1.98-1.47 (m, 4 H); MS (ESI): m/z: 476 [M + H]⁺. |
| 39 | 4-methyl-N-[2-[[4-(4-piperidylamino)phenoxy]methyl]phenyl]thieno[3,2-b]pyrrole-5-carboxamide; 2,2,2-trifluoroacetic acid | 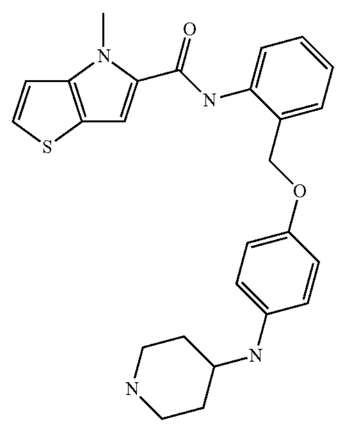 [SMILES: Cn1c(C(=O)Nc2ccccc2COc2ccc(NC3CCNCC3)cc2)cc2sccc21] | ¹H NMR (DMSO-d₆) δ (ppm): 10.35 (s, 1 H), 9.19-8.84 (m, 2 H), 8.47-8.34 (m, 1 H), 8.05-7.89 (m, 1 H), 7.75 (d, J = 7.8 Hz, 1 H), 7.54 (d, J = 4.9 Hz, 1 H), 7.34-7.13 (m, 4 H), 7.05 (t, J = 7.6 Hz, 1 H), 6.83 (d, J = 8.3 Hz, 2 H), 6.59 (d, J = 8.8 Hz, 2 H), 4.33 (s, 2 H), 4.03 (s, 3 H), 3.64-3.52 (m, 1 H), 3.33-3.21 (m, 2 H), 2.99-2.86 (m, 2 H), 2.00-1.88 (m, 2 H), 1.59-1.44 (m, 2 H); MS (ESI): m/z: 461 [M + H]⁺. |
| 40 | N-[2-[[4-(azetidin-3-ylmethoxy)phenoxy]methyl]phenyl]-4-methyl-thieno[3,2-b]pyrrole-5-carboxamide; 2,2,2-trifluoroacetic acid | 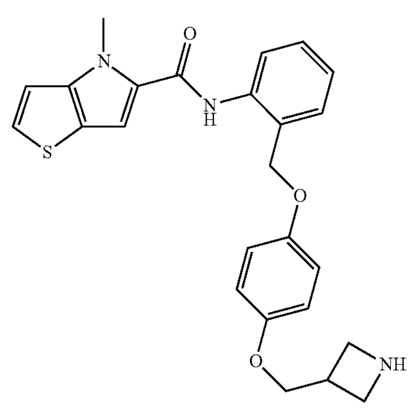 [SMILES: Cn1c(C(=O)Nc2ccccc2COc2ccc(OCC3CNC3)cc2)cc2sccc21] | ¹H NMR (DMSO-d₆) δ (ppm): 9.74 (s, 1 H), 8.52 (bs, 2 H), 7.56-7.47 (m, 3 H), 7.40-7.31 (m, 1 H), 7.29-7.21 (m, 3 H), 6.97-6.83 (m, 4 H), 5.11 (s, 2 H), 4.09-3.96 (m, 7 H), 3.85-3.76 (m, 2 H), 3.21-3.07 (m, 1 H); MS (ESI): m/z: 448 [M + H]⁺. |

TABLE 2-continued

Final Products

| Ex. | Name | Structure | Analytical Data |
|---|---|---|---|
| 41 | N-[2-[[4-(2,8-diazaspiro[4.5]decan-2-ylmethyl)phenoxy]methyl]phenyl]-4-methyl-thieno[3,2-b]pyrrole-5-carboxamide | 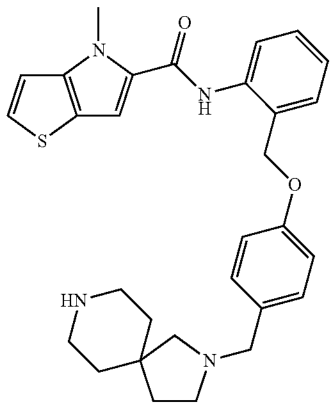 [SMILES: Cn1c(C(=O)Nc2ccccc2COc2ccc(CN3CCC4(CCNCC4)C3)cc2)cc2sccc21] | $^1$H NMR (DMSO-d$_6$) δ (ppm): 10.87 (bs, 1 H), 9.83 (s, 1 H), 8.59 (bs, 2 H), 7.55-7.46 (m, 5 H), 7.41-7.34 (m, 1 H), 7.31-7.22 (m, 3 H), 7.06-7.00 (m, 2 H), 5.18 (s, 2 H), 4.32-4.14 (m, 2 H), 4.00 (s, 3 H), 3.43-3.35 (m, 1 H), 3.30-3.12 (m, 2 H), 3.08-2.89 (m, 5 H), 2.06-1.65 (m, 6 H); MS (ESI): m/z: 515 [M + H]$^+$. |
| 42 | N-[3-(methoxymethyl)-2-[[4-[[(3R)-pyrrolidin-3-yl]methoxy]phenoxy]methyl]phenyl]-4-methyl-thieno[3,2-b]pyrrole-5-carboxamide hydrochloride | 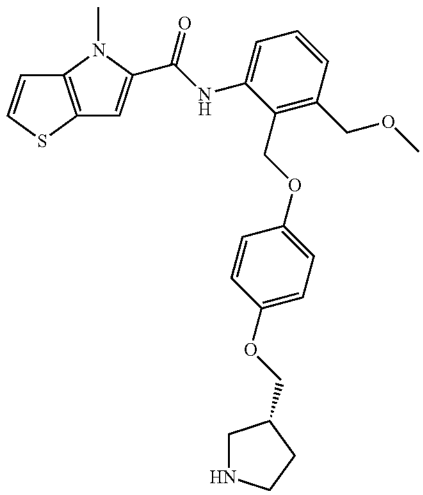 [SMILES: COCc1cccc(NC(=O)c2cc3sccc3n2C)c1COc1ccc(OC[C@@H]2CCNC2)cc1] | $^1$H NMR (DMSO-d$_6$) δ (ppm): 9.81 (s, 1 H), 8.92-8.49 (bs, 2 H), 7.51-7.48 (m, 1 H), 7.46-7.29 (m, 3 H), 7.24-7.21 (m, 1 H), 7.19 (s, 1 H), 6.94-6.81 (m, 4 H), 5.06 (s, 2 H), 4.55 (s, 2 H), 3.98 (s, 3 H), 3.94-3.79 (m, 2 H), 3.36-3.30 (m, 1 H), 3.29 (s, 3 H), 3.26-3.09 (m, 2 H), 3.00-2.93 (m, 1 H), 2.71-2.60 (m, 1 H), 2.10-2.00 (m, 1H), 1.65-1.75 (m, 1 H). MS (ESI): m/z: 506 [M + H]$^+$. |
| 43 | N-[3-(methoxymethyl)-2-[[4-(4-piperidyloxy)phenoxy]methyl]phenyl]-4-methyl-thieno[3,2-b]pyrrole-5-carboxamide hydrochloride | 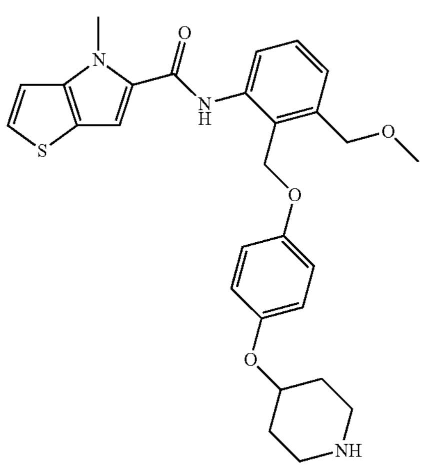 [SMILES: COCc1cccc(NC(=O)c2cc3sccc3n2C)c1COc1ccc(OC2CCNCC2)cc1] | $^1$H NMR (DMSO-d$_6$) δ (ppm): 9.81 (s, 1 H), 8.63-8.34 (m, 2 H), 7.52-7.49 (m, 1 H), 7.47-7.29 (m, 3 H), 7.24-7.21 (m, 1 H), 7.19 (s, 1 H), 6.95-6.97 (m, 4 H), 5.07 (s, 2 H), 4.56 (s, 2 H), 4.51-4.40 (m, 1 H), 3.98 (s, 3 H), 3.30 (s, 3 H), 3.25-2.96 (m, 4 H), 2.07-1.69 (m, 4 H). MS (ESI): m/z: 506 [M + H]$^+$. |

TABLE 2-continued

Final Products

| Ex. | Name | Structure | Analytical Data |
|---|---|---|---|
| 44 | N-[2-[[4-(azepan-4-yloxy)phenoxy]methyl]-3-(methoxymethyl)phenyl]-4-methyl-thieno[3,2-b]pyrrole-5-carboxamide hydrochloride | 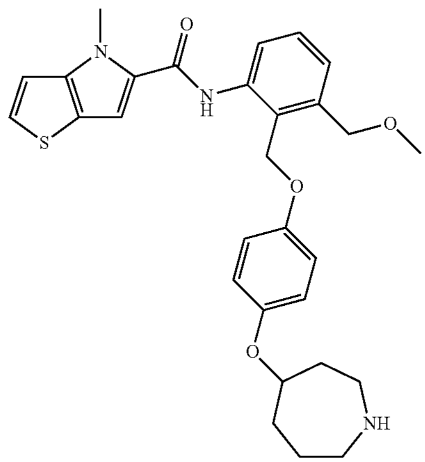 [SMILES: COCc1cccc(NC(=O)c2cc3sccc3n2C)c1COc1ccc(OC2CCCNCC2)cc1] | ¹H NMR (DMSO-d₆) δ (ppm): 9.80 (s, 1 H), 8.66-8.32 (m, 2 H), 7.53-7.48 (m, 1 H), 7.46-7.29 (m, 3 H), 7.25-7.21 (m, 1 H), 7.18 (s, 1 H), 6.82-6.92 (m, 4 H), 5.06 (s, 2 H), 4.56 (s, 2 H), 4.52-4.47 (m, 1 H), 3.98 (s, 3 H), 3.29 (s, 3 H), 3.23-2.99 (m, 4 H), 2.15-1.59 (m, 6 H). MS (ESI): m/z: 520 [M + H]⁺. |
| 45 | 4-ethyl-N-[3-(methoxymethyl)phenyl]thieno[3,2-b]pyrrole-5-carboxamide | 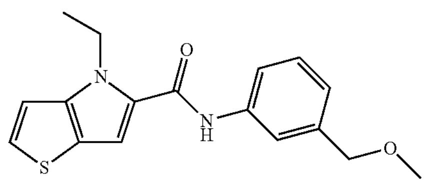 [SMILES: CCn1c(C(=O)Nc2cccc(COC)c2)cc2sccc21] | ¹H NMR (DMSO-d₆) δ (ppm): 10.00 (s, 1 H), 6.84-7.82 (m, 7 H), 4.54 (q, J = 6.85 Hz, 2 H), 4.40 (s, 2 H), 3.30 (s, 3 H) 1.32 (t, J = 7.09 Hz, 3 H); MS (ESI): m/z: 315 [M + H]⁺ |
| 46 | 4-methyl-N-[3-(methylsulfanylmethyl)phenyl]thieno[3,2-b]pyrrole-5-carboxamide | 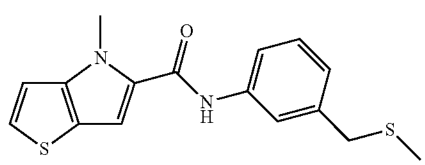 [SMILES: CSCc1cccc(NC(=O)c2cc3sccc3n2C)c1] | MS (ESI): m/z: 316 [M + H]⁺ |
| 47 | 4-methyl-N-[3-(methoxymethyl)phenyl]thieno[3,2-b]pyrrole-5-carboxamide | 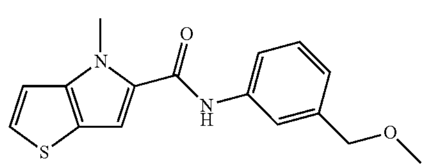 [SMILES: COCc1cccc(NC(=O)c2cc3sccc3n2C)c1] | MS (ESI): m/z: 301 [M + H]⁺ |
| 48 | N-[3-(methoxymethyl)phenyl]-6-methyl-thieno[2,3-b]pyrrole-5-carboxamide | 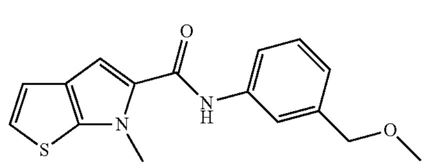 [SMILES: COCc1cccc(NC(=O)c2cc3ccsc3n2C)c1] | ¹H NMR (CDCl₃) δ (ppm): 7.68 (bs, 1 H), 7.60-7.52 (m, 2 H), 7.40-7.32 (m, 1 H), 7.16-7.09 (m, 1 H), 7.05-7.00 (m, 1 H), 6.98-6.93 (m, 1 H), 6.92-6.89 (m, 1 H), 4.49 (s, 2 H), 4.09 (s, 3 H), 3.43 (s, 3 H); MS (ESI): m/z: 301 [M + H]+ |

TABLE 2-continued

Final Products

| Ex. | Name | Structure | Analytical Data |
|---|---|---|---|
| 49 | N-[3-(Methoxymethyl)-2-[[4-[[(3S)-pyrrolidin-3-yl]methoxy]phenoxy]methyl]phenyl]-4-methyl-thieno[3,2-b]pyrrole-5-carboxamide hydrochloride | 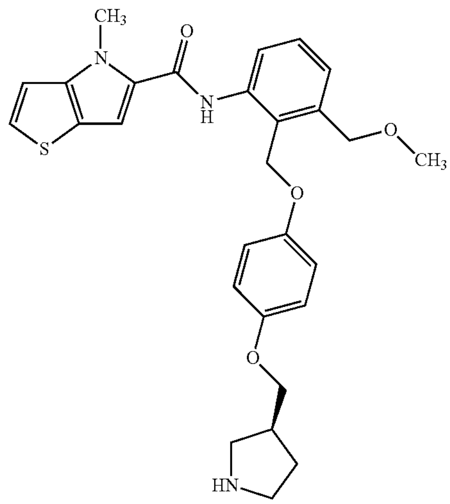 [SMILES: COCc1cccc(NC(=O)c2cc3sccc3n2C)c1COc1ccc(OC[C@H]2CCNC2)cc1] | $^1$H NMR (DMSO-d$_6$) δ (ppm): 9.81 (bs, 1 H), 8.88-8.57 (bs, 2 H), 7.52-7.49 (m, 1 H), 7.47-7.29 (m, 3 H), 7.25-7.22 (m, 1 H), 7.19 (s, 1 H), 6.95-6.79 (m, 4 H), 5.06 (s, 2 H), 4.55 (s, 2 H), 3.98 (s, 3 H), 3.93-3.82 (m, 2H), 3.34-2.93 (m, 4 H), 3.29 (s, 3H), 2.72-2.60 (m, 1 H), 2.12-1.65 (m, 2 H); MS (ESI): m/z: 506 [M + H]$^+$ |
| 50 | N-[3-(Ethoxymethyl)-2-[[4-(4-piperidyloxy)phenoxy]methyl]phenyl]-4-methyl-thieno[3,2-b]pyrrole-5-carboxamide hydrochloride | 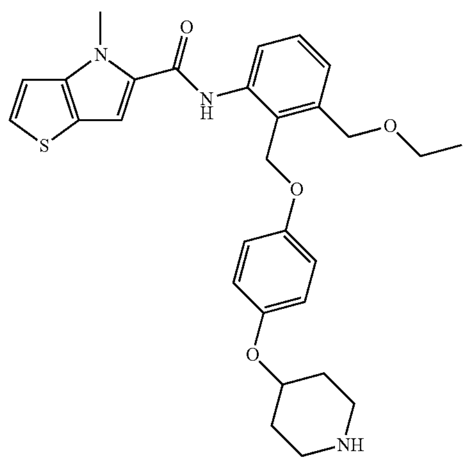 [SMILES: CCOCc1cccc(NC(=O)c2cc3sccc3n2C)c1COc1ccc(OC2CCNCC2)cc1] | $^1$H NMR (DMSO-d$_6$) δ (ppm): 9.80 (s, 1 H), 8.30 (bs, 2 H), 7.51-7.48 (m, 1 H), 7.47-7.30 (m, 3 H), 7.25-7.21 (m, 1 H), 7.19 (s, 1 H), 6.93-6.87 (m, 4 H), 5.07 (s, 2 H), 4.59 (s, 2 H), 4.48-4.40 (m, 1 H), 3.98 (s, 3 H), 3.50-3.44 (m, 2 H), 3.23-2.92 (m, 4 H), 2.04-1.66 (m, 4 H), 1.15-1.10 (m, 3 H); MS (ESI): m/z: 520 [M + H]$^+$ |
| 51 | N-[3-(Isopropoxymethyl)-2-[[4-(4-piperidyloxy)phenoxy]methyl]phenyl]-4-methyl-thieno[3,2-b]pyrrole-5-carboxamide | 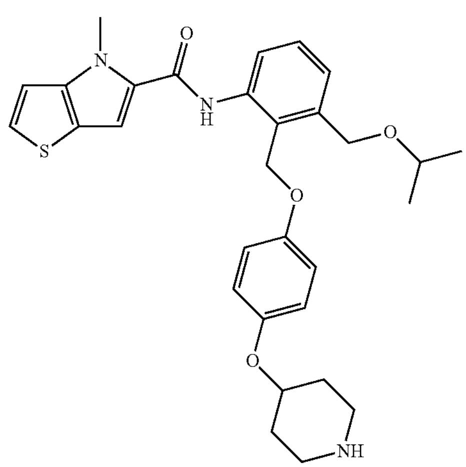 [SMILES: CC(C)OCc1cccc(NC(=O)c2cc3sccc3n2C)c1COc1ccc(OC2CCNCC2)cc1] | $^1$H NMR (CDCl$_3$) δ (ppm): 9.12 (s, 1 H), 8.23-8.17 (m, 1 H), 7.41-7.34 (m, 1 H), 7.32-7.25 (m, 1 H), 7.16-7.11 (m, 1 H), 7.04-6.99 (m, 2 H), 6.98-6.94 (m, 1 H), 6.93-6.88 (m, 2 H), 6.75 (s, 1 H), 5.25 (s, 2 H), 4.56 (s, 2 H), 4.36-4.27 (m, 1 H), 4.12 (s, 3 H), 3.71-3.61 (m, 1 H), 3.25-2.73 (m, 4 H), 2.10-1.64 (m, 4 H), 1.20-1.15 (m, 6 H); MS (ESI): m/z: 534 [M + H]$^+$ |

TABLE 2-continued

Final Products

| Ex. | Name | Structure | Analytical Data |
|---|---|---|---|
| 52 | N-[3-(Ethoxymethyl)-2-[[4-[[(3R)-pyrrolidin-3-yl]methoxy]phenoxy]methyl]phenyl]-4-methyl-thieno[3,2-b]pyrrole-5-carboxamide hydrochloride | 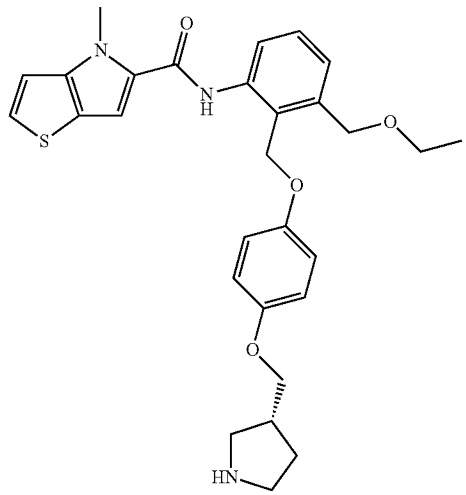 [SMILES: CCOCc1cccc(NC(=O)c2cc3sccc3n2C)c1COc1ccc(OC[C@@H]2CCNC2)cc1] | $^1$H NMR (DMSO-d$_6$) δ (ppm): 9.8 (s, 1 H), 8.84-8.56 (bs, 2 H), 7.53-7.48 (m, 1 H), 7.46-7.27 (m, 3 H), 7.26-7.22 (m, 1 H), 7.19 (s, 1 H), 6.93-6.81 (m, 4 H), 5.07 (s, 2 H), 4.59 (s, 2 H), 3.98 (s, 3 H), 3.94-3.80 (m, 2 H), 3.52-3.42 (m, 2 H), 3.33-2.93 (m, 4 H), 2.71-2.59 (m, 1 H), 2.12-1.64 (m, 2 H), 1.16-1.10 (m, 3 H); MS (ESI): m/z: 520 [M + H]$^+$ |
| 53 | 4-Ethyl-N-[3-(methoxymethyl)-2-[[4-[[(3R)-pyrrolidin-3-yl]methoxy]phenoxy]methyl]phenyl]thieno[3,2-b]pyrrole-5-carboxamide; trifluoroacetic acid | 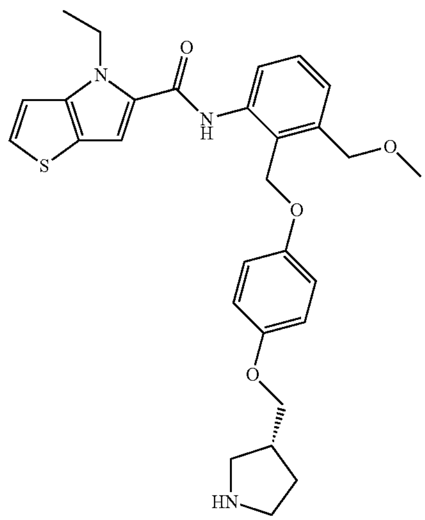 [SMILES: CCn1c(C(=O)Nc2cccc(COC)c2COc2ccc(OC[C@@H]3CCNC3)cc2)cc2sccc21] | $^1$H NMR (DMSO-d$_6$) δ (ppm): 9.81 (s, 1 H), 8.72-8.55 (m, 2 H), 7.50 (d, J = 5.5 Hz, 1 H), 7.47-7.43 (m, 1 H), 7.39 (t, J = 7.7 Hz, 1 H), 7.35-7.29 (m, 1 H), 7.24 (d, J = 5.5 Hz, 1 H), 7.19 (s, 1 H), 6.94-6.87 (m, 2 H), 6.86-6.80 (m, 2 H), 5.07 (s, 2 H), 4.58-4.45 (m, 4 H), 3.93-3.88 (m, 1 H), 3.87-3.80 (m, 1 H), 3.36-3.27 (m, 4 H), 3.26-3.20 (m, 1 H), 3.19-3.11 (m, 1 H), 3.02-2.93 (m, 1 H), 2.71-2.61 (m, 1 H), 2.11-2.01 (m, 1 H), 1.75-1.65 (m, 1 H), 1.27 (t, J = 7.1 Hz, 3 H); MS (ESI): m/z: 520 [M + H]$^+$ |
| 54 | 4-Methyl-N-[3-(morpholinomethyl)-2-[[4-(4-piperidyloxy)phenoxy]methyl]phenyl]thieno[3,2-b]pyrrole-5-carboxamide dihydrochloride | 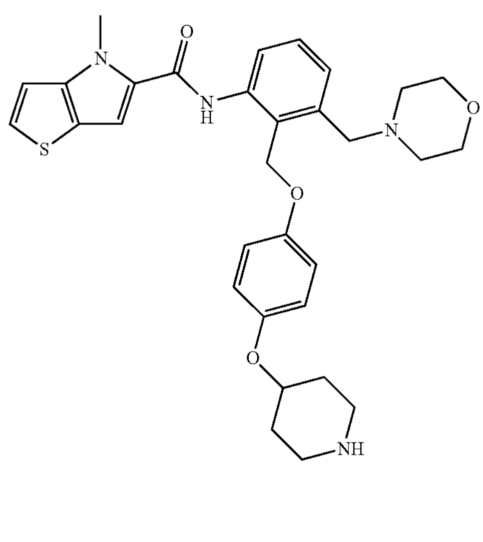 [SMILES: Cn1c(C(=O)Nc2cccc(CN3CCOCC3)c2COc2ccc(OC3CCNCC3)cc2)cc2sccc21] | $^1$H NMR (D$_2$O) δ (ppm): 7.52-7.35 (m, 3 H), 7.30-7.26 (m, 1 H), 6.93-6.90 (m, 1 H), 6.81-6.67 (m, 5 H), 5.10 (s, 2 H), 4.48 (s, 2 H), 4.28-4.20 (m, 1 H), 3.99-3.85 (m, 2 H), 3.65 (s, 3 H), 3.66-3.56 (m, 2H), 3.46-3.32 (m, 2 H), 3.27-3.11 (m, 4 H), 2.99-2.89 (m, 2 H), 1.87-1.61 (m, 4 H); MS (ESI): m/z: 561 [M + H]$^+$ |

TABLE 2-continued

Final Products

| Ex. | Name | Structure | Analytical Data |
|---|---|---|---|
| 55 | 4-Methyl-N-[5-methyl-2-[[4-(pyrrolidin-3-ylmethoxy)phenoxy]methyl]phenyl]thieno[3,2-b]pyrrole-5-carboxamide | 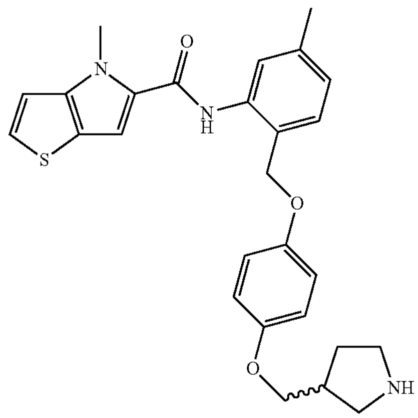 [SMILES: Cc1ccc(COc2ccc(OCC3CCNC3)cc2)c(NC(=O)c2cc3sccc3n2C)c1] | ¹H NMR (DMSO-d₆) δ (ppm): 9.66 (s, 1 H), 7.51 (d, J = 5.4 Hz, 1 H), 7.39-7.34 (m, 2 H), 7.23 (d, J = 5.4 Hz, 1 H), 7.20 (s, 1 H), 7.07-7.03 (m, 1 H), 6.90-6.84 (m, 2 H), 6.83-6.78 (m, 2 H), 5.05 (s, 2 H), 3.99 (s, 3 H), 3.79-3.69 (m, 2 H), 2.88-2.76 (m, 2 H), 2.72-2.64 (m, 1 H), 2.59-2.53 (m, 1 H), 2.41-2.33 (m, 1 H), 2.32 (s, 3 H), 1.84-1.74 (m, 1 H), 1.39-1.31 (m, 1 H); MS (ESI): m/z: 476 [M + H]⁺ |
| 56 | 4-Methyl-N-[2-[[5-(4-piperidyloxy)-2-pyridyl]oxymethyl]phenyl]thieno[3,2-b]pyrrole-5-carboxamide hydrochloride | 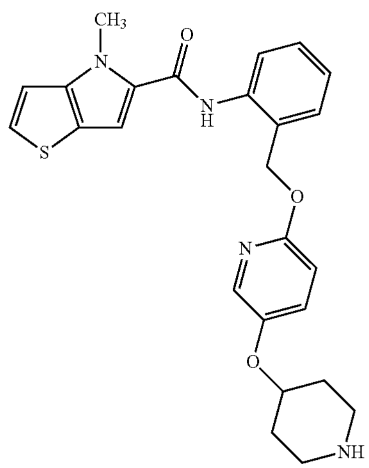 [SMILES: Cn1c(C(=O)Nc2ccccc2COc2ccc(OC3CCNCC3)cn2)cc2sccc21] | ¹H NMR (DMSO-d₆) δ (ppm): 11.19 (s, 1 H), 8.58 (bs, 2 H), 7.98 (m, 1 H), 7.81-6.92 (m, 8 H), 6.57 (m, 1 H), 5.09 (s, 2 H), 4.29-4.41 (m, 1 H), 4.06 (s, 3 H), 3.16 (s, 4 H), 1.71-2.12 (m, 4 H); MS (ESI): m/z: 463 [M + H]⁺ |
| 57 | 4-Methyl-N-[2-(4-piperidylmethoxy)phenyl]thieno[3,2-b]pyrrole-5-carboxamide hydrochloride | 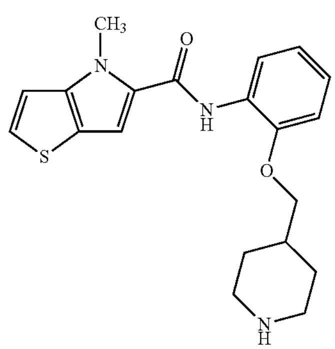 [SMILES: Cn1c(C(=O)Nc2ccccc2OCC2CCNCC2)cc2sccc21] | ¹H NMR (DMSO-d₆) δ (ppm): 9.07 (s, 1 H), 8.60 (bs, 1 H), 8.30 (bs, 1 H), 7.85-7.71 (m, 1 H), 7.52 (d, J = 5.9 Hz, 1 H), 7.27-7.22 (m, 2 H), 7.18-7.08 (m, 2 H), 7.00-6.93 (m, 1 H), 4.01 (s, 3 H), 3.93 (d, J = 6.4 Hz, 2 H), 3.30-3.22 (m, 2 H), 2.95-2.82 (m, 2 H), 2.17-2.05 (m, 1 H), 1.99-1.91 (m, 2 H), 1.51-1.37 (m, 2 H); MS (ESI): m/z: 370 [M + H]⁺ |
| 58 | 4-Methyl-N-[3-[[3-(4-piperidyloxy)phenoxy]methyl]phenyl]thieno[3,2-b]pyrrole-5-carboxamide hydrochloride | 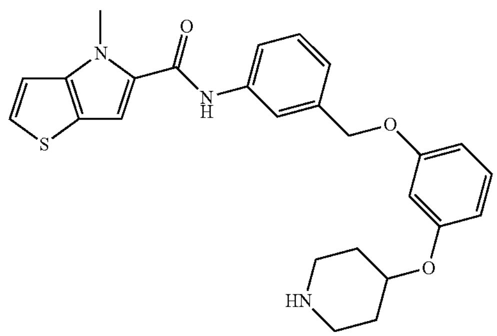 [SMILES: Cn1c(C(=O)Nc2cccc(COc3cccc(OC4CCNCC4)c3)c2)cc2sccc21] | ¹H NMR (DMSO-d₆) δ (ppm): 10.07 (s, 1 H), 8.51 (bs, 2 H), 7.92-7.85 (m, 1 H), 7.69-7.63 (m, 1 H), 7.52 (d, J = 5.4 Hz, 1 H), 7.38-7.31 (m, 2 H), 7.25 (d, J = 5.4 Hz, 1 H), 7.23-7.17 (m, 1 H), 7.16-7.12 (m, 1 H), 6.67-6.56 (m, 3 H), 5.07 (s, 2 H), 4.68-4.56 (m, 1 H), 4.01 (s, 3 H), 3.27-3.17 (m, 2 H), 3.11-2.99 (m, 2 H), 2.12-2.01 (m, 2 H), 1.84-1.71 (m, 2 H); MS (ESI): m/z: 462 [M + H]⁺ |

TABLE 2-continued

Final Products

| Ex. | Name | Structure | Analytical Data |
|---|---|---|---|
| 59 | N-[3-[[4-(Guanidinomethyl)phenoxy]methyl]phenyl]-4-methyl-thieno[3,2-b]pyrrole-5-carboxamide; trifluoroacetic acid | 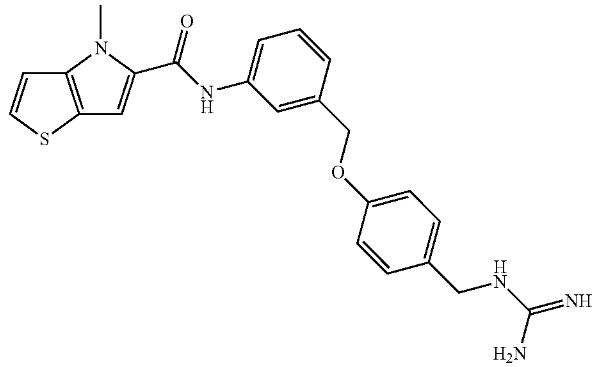 [SMILES: Cn1c(C(=O)Nc2cccc(COc3ccc(CNC(=N)N)cc3)c2)cc2sccc21] | $^1$H NMR (DMSO-d$_6$) δ (ppm): 10.05 (s, 1 H), 7.88 (s, 1 H), 7.82-7.76 (m, 1 H), 7.68-7.63 (m, 1 H), 7.53 (d, J = 5.5 Hz, 1 H), 7.37-7.31 (m, 2 H), 7.26-7.21 (m, 3 H), 7.16-7.11 (m, 1 H), 7.04 (d, J = 8.2 Hz, 2 H), 5.11 (s, 2 H), 4.27 (d, J = 6.0 Hz, 2 H), 4.01 (s, 3 H); MS (ESI): m/z: 434 [M + H]$^+$ |
| 60 | N-[2-[[4-(Guanidinomethyl)phenoxy]methyl]phenyl]-4-methyl-thieno[3,2-b]pyrrole-5-carboxamide; trifluoroacetic acid | 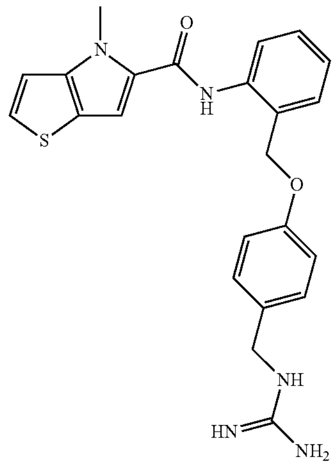 [SMILES: Cn1c(C(=O)Nc2ccccc2COc2ccc(CNC(=N)N)cc2)cc2sccc21] | $^1$H NMR (DMSO-d$_6$) δ (ppm): 9.80 (s, 1 H), 7.77 (t, J = 5.8 Hz, 1 H), 7.55-7.45 (m, 3 H), 7.39-7.33 (m, 1 H), 7.30-7.23 (m, 3 H), 7.20 (d, J = 8.2 Hz, 2 H), 6.98 (d, J = 8.2 Hz, 2 H), 5.16 (s, 2 H), 4.24 (d, J = 6.0 Hz, 2 H), 4.00 (s, 3 H); MS (ESI): m/z: 434 [M + H]$^+$ |
| 61 | 4-Methyl-N-[2-[2-[4-(4-piperidyloxy)phenyl]ethyl]phenyl]thieno[3,2-b]pyrrole-5-carboxamide hydrochloride | 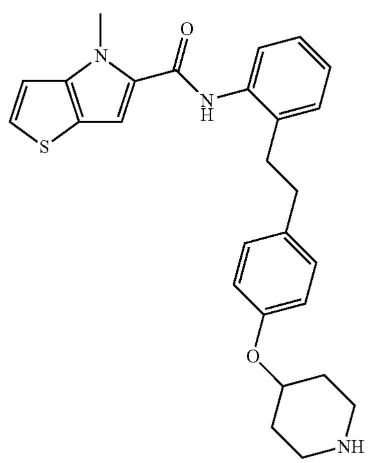 [SMILES: Cn1c(C(=O)Nc2ccccc2CCc2ccc(OC3CCNCC3)cc2)cc2sccc21] | $^1$H NMR (DMSO-d$_6$) δ (ppm): 9.67 (s, 1 H), 8.51 (bs, 2 H), 7.51 (d, J = 5.4 Hz, 1 H), 7.33-7.27 (m, 3 H), 7.26-7.17 (m, 3 H), 7.10-7.05 (m, 2 H), 6.87-6.82 (m, 2 H), 4.59-4.49 (m, 1 H), 4.00 (s, 3 H), 3.24-3.15 (m, 2 H), 3.10-2.99 (m, 2 H), 2.89-2.72 (m, 4 H), 2.07-1.96 (m, 2 H), 1.81-1.70 (m, 2 H); MS (ESI): m/z: 460 [M + H]$^+$ |
| 62 | 4-Methyl-N-[3-[2-[4-(4-piperidyloxy)phenyl]ethyl]phenyl]thieno[3,2-b]pyrrole-5-carboxamide hydrochloride | 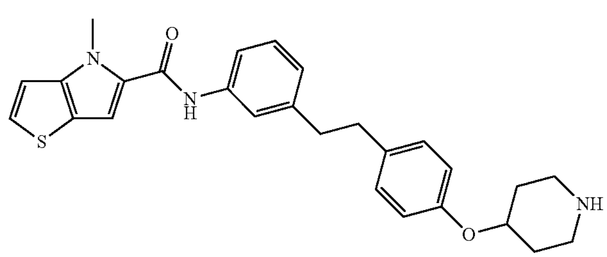 [SMILES: Cn1c(C(=O)Nc2cccc(CCc3ccc(OC4CCNCC4)cc3)c2)cc2sccc21] | $^1$H NMR (DMSO-d$_6$) δ (ppm): 9.93 (s, 1 H), 8.53 (bs, 2 H), 7.67 (s, 1 H), 7.56-7.47 (m, 2 H), 7.32 (s, 1 H), 7.26-7.20 (m, 2 H), 7.20-7.14 (m, 2 H), 6.96-6.88 (m, 3 H), 4.63-4.52 (m, 1 H), 4.02 (s, 3 H), 3.27-3.15 (m, 2 H), 3.11-2.99 (m, 2 H), 2.83 (s, 4 H), 2.12-1.98 (m, 2 H), 1.84-1.71 (m, 2 H); MS (ESI): m/z: 460 [M + H]$^+$ |

TABLE 2-continued

Final Products

| Ex. | Name | Structure | Analytical Data |
|---|---|---|---|
| 63 | 4-Methyl-N-[2-[[4-(4-piperidyloxy)anilino]methyl]phenyl]thieno[3,2-b]pyrrole-5-carboxamide dihydrochloride | 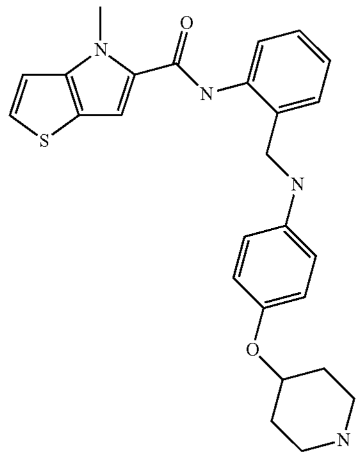 [SMILES: Cn1c(C(=O)Nc2ccccc2CNc2ccc(OC3CCNCC3)cc2)cc2sccc21] | $^1$H NMR (D$_2$O) δ (ppm): 7.47-7.43 (m, 1 H), 7.42-7.37 (m, 1 H), 7.35 (d, J = 5.4 Hz, 1 H), 7.33-7.27 (m, 2 H), 7.00 (d, J = 5.4 Hz, 1 H), 6.95-6.89 (m, 2 H), 6.82 (s, 1 H), 6.77-6.72 (m, 2 H), 4.47 (s, 2 H), 4.31-4.23 (m, 1 H), 3.77 (s, 3 H), 3.22-3.08 (m, 2 H), 3.00-2.85 (m, 2 H), 1.89-1.78 (m, 2 H), 1.73-1.61 (m, 2 H); MS (ESI): m/z: 461 [M + H]$^+$ |
| 64 | 6-Methyl-N-[2-[[3-(4-piperidyloxy)phenoxy]methyl]phenyl]thieno[2,3-b]pyrrole-5-carboxamide | 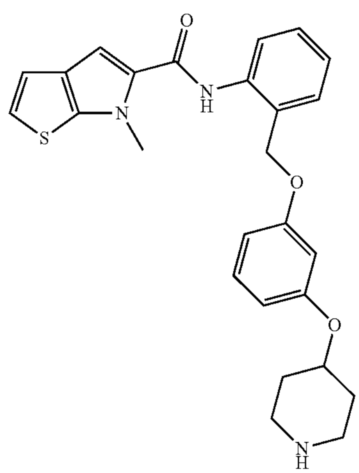 [SMILES: Cn1c(C(=O)Nc2ccccc2COc2cccc(OC3CCNCC3)c2)cc2ccsc21] | $^1$H NMR (DMSO-d$_6$) δ (ppm): 9.70 (s, 1 H), 7.56-7.47 (m, 2 H), 7.39-7.32 (m, 1 H), 7.29-7.22 (m, 1 H), 7.20 (s, 1 H), 7.17 (d, J = 5.4 Hz, 1 H), 7.15-7.10 (m, 1 H), 7.06 (d, J = 5.4 Hz, 1 H), 6.55-6.47 (m, 3 H), 5.15 (s, 2 H), 4.39-4.27 (m, 1 H), 3.96 (s, 3 H), 2.97-2.86 (m, 2 H), 2.61-2.52 (m, 2 H), 1.88-1.78 (m, 2 H), 1.47-1.34 (m, 2 H); MS (ESI): m/z: 462 [M + H]$^+$ |
| 65 | 6-Ethyl-N-[2-[[3-(4-piperidyloxy)phenoxy]methyl]phenyl]thieno[2,3-b]pyrrole-5-carboxamide | 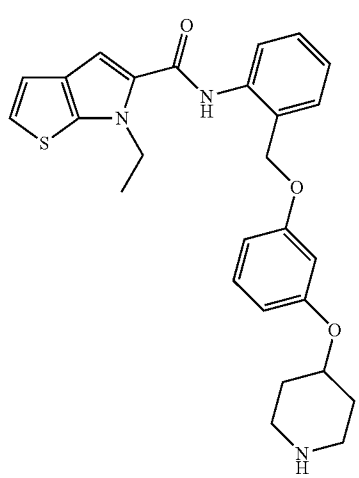 [SMILES: CCn1c(C(=O)Nc2ccccc2COc2cccc(OC3CCNCC3)c2)cc2ccsc21] | $^1$H NMR (DMSO-d$_6$) δ (ppm): 9.72 (s, 1 H), 7.55-7.47 (m, 2 H), 7.40-7.33 (m, 1 H), 7.28-7.23 (m, 1 H), 7.20 (s, 1 H), 7.16 (d, J = 5.4 Hz, 1 H), 7.15-7.10 (m, 1 H), 7.06 (d, J = 4.9 Hz, 1 H), 6.57-6.47 (m, 3 H), 5.15 (s, 2 H), 4.45 (q, J = 6.8 Hz, 2 H), 4.39-4.29 (m, 1 H), 2.98-2.89 (m, 2 H), 2.67-2.56 (m, 2H), 1.89-1.81 (m, 2 H), 1.49-1.38 (m, 2 H), 1.33 (t, J = 7.1 Hz, 3 H); MS (ESI): m/z: 476 [M + H]$^+$ |

TABLE 2-continued

Final Products

| Ex. | Name | Structure | Analytical Data |
|---|---|---|---|
| 66 | 6-Ethyl-N-[2-[[4-(4-piperidyloxy)phenoxy]methyl]phenyl]thieno[2,3-b]pyrrole-5-carboxamide hydrochloride | 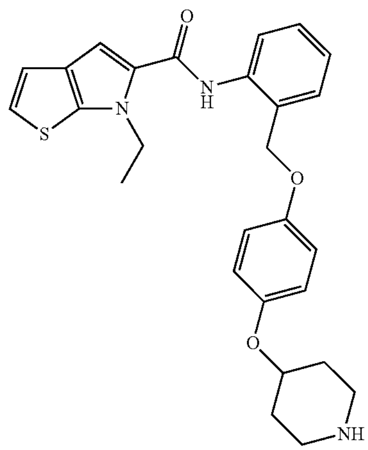 [SMILES: CCn1c(C(=O)Nc2ccccc2COc2ccc(OC3CCNCC3)cc2)cc2ccsc21] | $^1$H NMR (DMSO-d$_6$) δ (ppm). 9.74 (s, 1 H), 8.55 (bs, 2 H), 7.54-7.48 (m, 2 H), 7.39-7.33 (m, 1 H), 7.28-7.23 (m, 1 H), 7.23-7.20 (m, 1 H), 7.17 (d, J = 5.4 Hz, 1 H), 7.08 (d, J = 5.4 Hz, 1 H), 6.90 (s, 4 H), 5.10 (s, 2 H), 4.49-4.41 (m, 3 H), 3.24-3.15 (m, 2 H), 3.06-2.98 (m, 2 H), 2.05-1.96 (m, 2 H), 1.79-1.70 (m, 2 H), 1.33 (t, J = 7.1 Hz, 3 H); MS (ESI): m/z: 476 [M + H]$^+$ |
| 67 | 6-Methyl-N-[2-[[4-(4-piperidyloxy)phenoxy]methyl]phenyl]thieno[2,3-b]pyrrole-5-carboxamide | 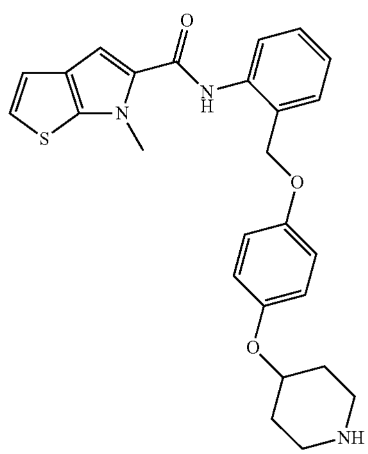 [SMILES: Cn1c(C(=O)Nc2ccccc2COc2ccc(OC3CCNCC3)cc2)cc2ccsc21] | $^1$H NMR (DMSO-d$_6$) δ (ppm): 9.72 (s, 1 H), 7.54-7.47 (m, 2 H), 7.39-7.33 (m, 1 H), 7.28-7.22 (m, 1 H), 7.22-7.14 (m, 2 H), 7.09-7.05 (m, 1 H), 6.92-6.83 (m, 4 H), 5.10 (s, 2 H), 4.37-4.30 (m, 1 H), 3.96 (s, 3 H), 3.10-3.02 (m, 2 H), 2.82-2.73 (m, 2 H), 1.97-1.88 (m, 2 H), 1.62-1.51 (m, 2 H); MS (ESI): m/z: 462 [M + H]$^+$ |
| 68 | 6-Methyl-N-[2-[[4-(pyrrolidin-3-ylmethoxy)phenoxy]methyl]phenyl]thieno[2,3-b]pyrrole-5-carboxamide hydrochloride | 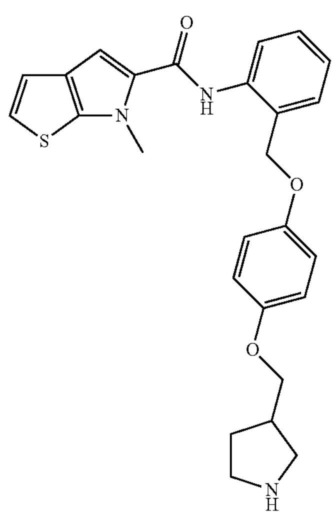 [SMILES: Cn1c(C(=O)Nc2ccccc2COc2ccc(OCC3CCNC3)cc2)cc2ccsc21] | $^1$H NMR (DMSO-d$_6$) δ (ppm): 9.73 (s, 1 H), 8.90 (bs, 2 H), 7.53-7.47 (m, 2 H), 7.38-7.33 (m, 1 H), 7.28-7.15 (m, 3 H), 7.10-7.06 (m, 1 H), 6.94-6.82 (m, 4 H), 5.10 (s, 2 H), 4.00-3.81 (m, 5 H), 3.30-3.27 (m, 1 H), 3.26-3.19 (m, 1 H), 3.17-3.09 (m, 1 H), 3.01-2.92 (m, 1 H), 2.70-2.62 (m, 1 H), 2.10-2.01 (m, 1 H), 1.75-1.65 (m, 1 H); MS (ESI): m/z: 462 [M + H]$^+$ |

Example 69: 4-Methyl-N-[4-[[4-(4-piperidyloxy)phenyl]carbamoyl]-2-pyridyl]thieno[3,2-b]pyrrole-5-carboxamide hydrochloride

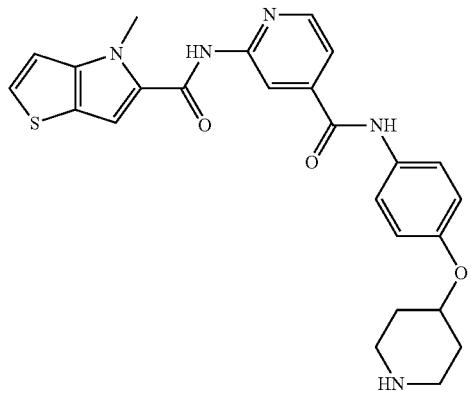 [SMILES: Cn1c(C(=O)Nc2cc(C(=O)Nc3ccc(OC4CCNCC4)cc3)ccn2)cc2sccc21]

4-Methyl-N-[4-[[4-(4-piperidyloxy)phenyl]carbamoyl]-2-pyridyl]thieno[3,2-b]pyrrole-5-carboxamide hydrochloride 0.037 g (99%) of 4-methyl-N-[4-[[4-(4-piperidyloxy)phenyl]carbamoyl]-2-pyridyl]thieno[3,2-b]pyrrole-5-carboxamide hydrochloride was obtained starting from 0.042 g (0.073 mmol) of tert-butyl 4-[4-[[2-[(4-methylthieno[3,2-b]pyrrole-5-carbonyl)amino]pyridine-4-carbonyl]amino]phenoxy]piperidine-1-carboxylate (Intermediate 35) according to the procedure described for Example 1, step 2. $^1$H NMR (DMSO-d$_6$) δ (ppm): 10.75 (s, 1H), 10.45 (s, 1H), 8.77-8.59 (m, 2H), 8.59-8.56 (m, 1H), 8.55-8.52 (m, 1H), 7.72-7.67 (m, 2H), 7.60 (s, 1H), 7.60-7.56 (m, 1H), 7.58 (d, J=5.4 Hz, 1H), 7.26 (d, J=5.4 Hz, 1H), 7.05-7.00 (m, 2H), 4.66-4.57 (m, 1H), 4.05 (s, 3H), 3.30-3.18 (m, 2H), 3.13-3.01 (m, 2H), 2.14-2.03 (m, 2H), 1.88-1.77 (m, 2H); MS (ESI): m/z: 476 [M+H]$^+$.

Example 2: Biological Testing

2.1 Assay of Enzyme Inhibition of KDM1A (LSD1)

The KDM1A inhibiting activity was determined using a TR-FRET assay (time resolved fluorescence resonance energy transfer, Lance® Ultra Demethylase technology (Perkin Elmer, Waltham, Mass., USA)), which comprises a Europium chelate donor dye (TRF0404, Perkin Elmer, Waltham, Mass., USA) together with ULight™ (TR0102, Perkin Elmer, Waltham, Mass., USA), a small molecular weight acceptor dye with a red-shifted fluorescent emission, and a biotinylated 21 aminoacids histone H3-derived monomethylated peptide (H3K4me) [Lys(Mel)4]-Histone H3 (1-21)-GGK(biotin), (64355, Anaspec, Fremont, Calif., USA) as substrate. The intensity of the light emission is proportional to the level of biotinylated reaction product. The complex of human recombinant KDM1A/CoREST protein was produced in *E. coli* as separate proteins and co-purified as previously described. (Forneris, F. et al. Trends Biochem, Sci, 2008, 33, 181-189) (Forneris, F. et al. J. Biol. Chem. 2007, 282, 20070-20074).

Demethylase Assay Conditions:

0.25 nM KDM1A/CoREST protein and compound in 100% DMSO were added in a final volume of 48 µL assay buffer (Tris HCl 50 mM pH 8.8, NaCl 50 mM, DTT 1 mM, Tween-20 0.01%) to each well of a 96 well half area flat bottom white plate (3693 Costar, Sigma-Aldrich, St. Louis, M, USA).

Demethylase reaction was started by the addition of 50 nM histone H3K4 monomethylated. After 20 min at RT, 300 µM tranylcypromine (P8511-1G, Sigma-Aldrich, St. Louis, Mo. 63103) was added to stop the reaction.

Detection Step Conditions:

10 µL of the assay mixture was transferred from the original plate into a 384 well white plate (6007290 OptiPlate™, Perkin Elmer, Waltham, Mass., USA) and 10 µL of the detection Mix containing 2 nM Eu-antibody and 10 nM U-Light-Streptavidin in 1× Lance Detection Buffer (TRF0404, TR0102, CR97100, Perkin Elmer, Waltham, Mass., USA). The resulting mixture was incubated in the dark for 1 h at RT. Then, TR-FRET signal was read by a fluorimeter (Infinite® F200, Tecan, Miinnedorf, Swirzerland) (Excitation 320 nm, Emission 665 nm and 620 nm, delay time 50 µs, window time 100 µs).

IC$_{50}$ Determination:

The inhibitor concentrations ranged from 0.025 to 500 µM (serial 1:3 dilutions). The IC$_{50}$ was calculated using GraphPad Software.

Compounds 1-46, 49-55, and 58-68 exhibit IC$_{50}$ values of less than 10 µM, examples 47, 48, and 56 exhibit IC$_{50}$ values of less than 25 µM, example 57 exhibits an IC$_{50}$ value of less than 50 µM.

2.2 Cell Growth

CellTiter-Flor® (Promega) is as a nonlytic, single-reagent-addition fluorescence assay that measures the relative number of living cells in a culture population after experimental manipulation. The CellTiter-Fluor™ Cell Viability Assay measures the conserved and constitutive protease activity within live cells and therefore acts as a marker for cell viability.

Human leukemia MV4-11 cells, (obtained from the Deutsche Sammlung von Mikroorganismen und Zellkulturen, ACC 102) or NB4 cells, (obtained from the Deutsche Sammlung von Mikroorganismen und Zellkulturen) in exponential growth, were incubated for 48 h with different concentrations of the inhibitors. After 48 h a volume of CellTiter-Fluor® Reagent equal to one fifth of volume of cell culture medium was added. The content was mixed and incubates for at least 90 min at 37° C. degree to obtain a stable signal. The fluorescence was recorded using an excitation wavelength of 360 nm and an emission at 535 nm. The IC$_{50}$ was calculated using GraphPad Software.

Compounds 1-21, 49-55 and 61-63 exhibit IC$_{50}$ values of less than 10 M against human leukemia MV4-11 cells and IC$_{50}$ values of less than 20 µM against human leukemia NB4 cells.

2.3 Bioluminescent-Coupled Assay for Monoamine Oxidases (MAO-Glo Assay)

The MAO Glo Assay from Promega (cat. V1402, Promega, Madison, Wis.) was used to measure the effect of inhibitors on MAO A and MAO B activity. Human recombinant MAO A and MAO B were expressed in *Pichia pastoris* and purified as published (Binda C. et al. Proc. Natl. Acad. Sci. USA, 2003, 9750-9755). The assay was performed at RT in 50 µL (25 µL reaction solution+25 µL detection reagent) in 96 well half area white plates (cat. 3693, Corning, Corning, N.Y.). Luminescence was measured after 20 min incubation in the dark using a microplate reader (Infinite F200, Tecan Group, Switzerland) with an integration time of 0.25 s per well. 50 nM MAO A or 125 nM MAO B were incubated with five different inhibitor concentrations (from 0.004 M to 100 µM) for 15 min at RT in Promega MAO Buffer or Promega MAO B Buffer (MAO Glo Assay kit, catalogue number V1402, Promega, Madison, Wis.). After 30 min of incubation the reaction was stopped with the Promega detection reagent. All compounds were tested twice and IC$_{50}$ values were calculated using GraphPad Prism version 4.0 (GraphPad Software, San Diego, Calif.).

Compounds 1-17, 19, 22, 26, 38, 42-45, 50, 52-53, 55, 61-62, 66 and 68 were at least 10 times more active against KDM1A (LSD1) compared to both MAO A and MAO B, compounds 18, 20-21, 30, 35, 46-48 were at least 5 times more active against KDM1A (LSD1) compared to both MAO A and MAO B.

The invention claimed is:
1. A compound of formula (Ia)

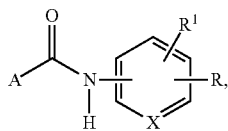

(Ia)

or a stereoisomer or pharmaceutically acceptable salt thereof,
wherein:
A is

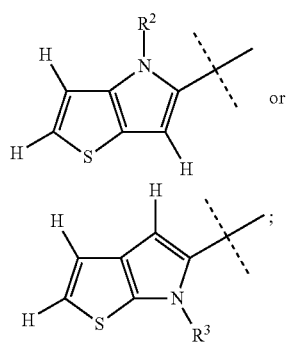

X is CH or N;
R is L$^1$-R$^4$;
IV is H, halogen, C1-C6-alkyl, C1-C6-alkoxy, —CH2-Z—R$^5$, or —Z—CH2-R$^6$;
R$^2$ and R$^3$ are each C1-C4-alkyl;
L$^1$ is —(CH2)j-Y—, —Y—(CH2)k-, —CH2-CH2- or —CO—NH—;
j and k are, independently, each an integer from 1 to 6;
Y is oxygen, sulphur, NH or N(C1-C6-alkyl);
Z is a bond, oxygen, sulphur, NH or N(C1-C6-alkyl);
R$^4$ is aryl, or heteroaryl, wherein the aryl or heteroaryl are optionally substituted by halogen, C1-C6-alkyl, or L$^2$-R$^7$; or heterocyclyl, wherein the heterocyclyl is optionally substituted by C1-C6-alkyl;
R$^5$ and R$^6$ are each, independently, C1-C6-alkyl; aryl, or heteroaryl, wherein the aryl or heteroaryl are optionally substituted by halogen, C1-C6-alkyl, or L$^2$-R$^7$; or heterocyclyl, wherein the heterocyclyl is optionally substituted by C1-C6-alkyl;
L$^2$ is —(CH2)m- or —(CH2)n-W—(CH2)o-;
R$^7$ is C1-C6-alkylamino, C3-C7 cycloalkyl or heterocyclyl, wherein the C3-C7 cycloalkyl or heterocyclyl are optionally substituted by C1-C6-alkyl, or NH2; or guanidine;
m, n, o are, independently, each zero or an integer from 1 to 6;
W is oxygen, sulphur, NH, or CH2;
wherein aryl is a mono or bicyclic aromatic ring system of 6 or 9 or 10 atoms; heteroaryl is a mono or bicyclic heteroaromatic ring system of 5 to 10 members, which contains one, two, three or four heteroatoms selected from nitrogen, oxygen and sulphur, and one to nine carbon atoms; and
heterocyclyl is a mono, bicyclic or a spirocyclic saturated or partially saturated non-aromatic ring system of 4 to 12 members, which contains one, two, or three heteroatoms selected from nitrogen, oxygen, and sulphur, and three to eleven carbon atoms;
provided that when A is 4H-thieno[3,2-b]pyrrole-5-yl, R$^2$ is methyl, ethyl or isopropyl, and X is CH, then R is other than 4-benzyloxy or 3-phenoxymethylene.

2. The compound of claim 1, wherein R$^2$ and R$^3$ are each methyl or ethyl.
3. The compound of claim 1, wherein X is CH.
4. The compound of claim 1, wherein L$^1$ is —CH2-O—, —CH2-NH—, —O—CH2, —CH2-CH2- or —CO—NH—.
5. The compound of claim 1 selected from the group consisting of:
4-methyl-N-[2-[[4-(4-piperidyloxy)phenoxy]methyl]phenyl]thieno[3,2-b]pyrrole-5-carboxamide;
4-methyl-N-[2-[[4-(4-piperidylmethoxy)phenoxy]methyl]phenyl]thieno-[3,2-b]pyrrole-5-carboxamide;
N-[2-[[4-[(1-ethyl-4-piperidyl)oxy]phenoxy]methyl]phenyl]-4-methyl-thieno[3,2-b]pyrrole-5-carboxamide;
4-methyl-N-[2-[[4-[[(3R)-pyrrolidin-3-yl]methoxy]phenoxy]methyl]phenyl]thieno[3,2-b]pyrrole-5-carboxamide;
4-methyl-N-[2-[[4-(pyrrolidin-3-ylmethoxy)phenoxy]methyl]phenyl]thieno[3,2-b]pyrrole-5-carboxamide;
4-ethyl-N-[3-[[4-(4-piperidyloxy)phenoxy]methyl]phenyl]thieno[3,2-b]pyrrole-5-carboxamide;
N-[2-[[4-(azepan-4-yloxy)phenoxy]methyl]phenyl]-4-methyl-thieno[3,2-b]pyrrole-5-carboxamide;
4-ethyl-N-[2-[[4-(4-piperidyloxy)phenoxy]methyl]phenyl]thieno[3,2-b]pyrrole-5-carboxamide;
N-[2-[[4-(cis-4-aminocyclohexoxy)phenoxy]methyl]phenyl]-4-methyl-thieno[3,2-b]pyrrole-5-carboxamide;
4-methyl-N-[3-[[4-(4-piperidyloxy)phenoxy]methyl]phenyl]thieno[3,2-b]pyrrole-5-carboxamide;
4-methyl-N-[2-[[4-[[(3 S)-pyrrolidin-3-yl]methoxy]phenoxy]methyl]phenyl]thieno[3,2-b]pyrrole-5-carboxamide;
4-ethyl-N-[2-[[4-[(1-methyl-4-piperidyl)oxy]phenoxy]methyl]phenyl]thieno[3,2-b]pyrrole-5-carboxamide;
4-methyl-N-[2-[[4-[(1-methyl-4-piperidyl)oxy]phenoxy]methyl]phenyl]thieno[3,2-b]pyrrole-5-carboxamide;
N-[2-[[4-(trans-4-aminocyclohexoxy)phenoxy]methyl]phenyl]-4-methyl-thieno[3,2-b]pyrrole-5-carboxamide;
4-methyl-N-[3-[4-[(1-methyl-4-piperidyl)oxy]phenoxy]methyl]phenyl]thieno[3,2-b]pyrrole-5-carboxamide;
4-methyl-N-[2-[(4-pyrrolidin-3-yloxyphenoxy)methyl]phenyl]thieno[3,2-b]pyrrole-5-carboxamide;
4-methyl-N-[2-[[3-[(1-methyl-4-piperidyl)oxy]phenoxy]methyl]phenyl]thieno[3,2-b]pyrrole-5-carboxamide;
4-methyl-N-[2-[[3-(4-piperidyloxy)phenoxy]methyl]phenyl]thieno[3,2-b]pyrrole-5-carboxamide;
4-methyl-N-[3-[(1-methyl-3-piperidyl)methoxy]phenyl]thieno[3,2-b]pyrrole-5-carboxamide;

4-methyl-N-[2-[[4-[(4-methylpiperazin-1-yl)methyl]phenoxy]methyl]phenyl]thieno[3,2-b]pyrrole-5-carboxamide;
4-methyl-N-[3-(4-pyridylmethoxy)phenyl]thieno[3,2-b]pyrrole-5-carboxamide;
4-methyl-N-[3-(4-pyridyloxymethyl)phenyl]thieno[3,2-b]pyrrole-5-carboxamide;
4-methyl-N-[4-[[4-[(1-methyl-4-piperidyl)oxy]phenoxy]methyl]phenyl]thieno[3,2-b]pyrrole-5-carboxamide;
N-[2-[[4-[[(1 S,5R)-8-azabicyclo[3.2.1]octan-3-yl]oxy]phenoxy]methyl]phenyl]-4-methyl-thieno[3,2-b]pyrrole-5-carboxamide;
N-[3-[[4-[[(1 S,5R)-8-azabicyclo[3.2.1]octan-3-yl]oxy]phenoxy]methyl]phenyl]-4-methyl-thieno[3,2-b]pyrrole-5-carboxamide;
4-methyl-N-[3-[[4-(4-piperidylmethoxy)phenoxy]methyl]phenyl]thieno[3,2-b]pyrrole-5-carboxamide;
4-methyl-N-[2-[[4-(3-piperidyloxy)phenoxy]methyl]phenyl]thieno[3,2-b]pyrrole-5-carboxamide;
4-methyl-N-[3-[[4-(3-piperidyloxy)phenoxy]methyl]phenyl]thieno[3,2-b]pyrrole-5-carboxamide;
N-[3-[[4-(trans-4-aminocyclohexoxy)phenoxy]methyl]phenyl]-4-methyl-thieno[3,2-b]pyrrole-5-carboxamide;
N-[3-[[4-(azetidin-3-ylmethoxy)phenoxy]methyl]phenyl]-4-methyl-thieno[3,2-b]pyrrole-5-carboxamide;
4-methyl-N-[2-[[4-(3-methylaminopropoxy)phenoxy]methyl]phenyl]thieno[3,2-b]pyrrole-5-carboxamide;
4-methyl-N-[3-[(4-pyrrolidin-3-yloxyphenoxy)methyl]phenyl]thieno[3,2-b]pyrrole-5-carboxamide;
N-[3-[[4-(azepan-4-yloxy)phenoxy]methyl]phenyl]-4-methyl-thieno[3,2-b]pyrrole-5-carboxamide;
N-[3-[[4-(cis-4-aminocyclohexoxy)phenoxy]methyl]phenyl]-4-methyl-thieno[3,2-b]pyrrole-5-carboxamide;
4-methyl-N-[3-[[4-(pyrrolidin-3-ylmethoxy)phenoxy]methyl]phenyl]thieno[3,2-b]pyrrole-5-carboxamide;
4-methyl-N-[2-[[4-(4-piperidyloxy)phenyl]carbamoyl]phenyl]thieno[3,2-b]pyrrole-5-carboxamide;
4-methyl-N-[2-[(4-piperazin-1-ylphenoxy)methyl]phenyl]thieno[3,2-b]pyrrole-5-carboxamide;
4-methyl-N-[2-[[4-[(1-methyl-4-piperidyl)oxy]phenyl]methoxy]phenyl]thieno[3,2-b]pyrrole-5-carboxamide;
4-methyl-N-[2-[[4-(4-piperidylamino)phenoxy]methyl]phenyl]thieno[3,2-b]pyrrole-5-carboxamide;
N-[2-[[4-(azetidin-3-ylmethoxy)phenoxy]methyl]phenyl]-4-methyl-thieno[3,2-b]pyrrole-5-carboxamide;
N-[2-[[4-(2,8-diazaspiro[4.5]decan-2-ylmethyl)phenoxy]methyl]phenyl]-4-methyl-thieno[3,2-b]pyrrole-5-carboxamide;
N-[3-(methoxymethyl)-2-[[4-[[(3R)-pyrrolidin-3-yl]methoxy]phenoxy]methyl]phenyl]-4-methyl-thieno[3,2-b]pyrrole-5-carboxamide;
N-[3-(methoxymethyl)-2-[[4-(4-piperidyloxy)phenoxy]methyl]phenyl]-4-methyl-thieno[3,2-b]pyrrole-5-carboxamide;
N-[2-[[4-(azepan-4-yloxy)phenoxy]methyl]-3-(methoxymethyl)phenyl]-4-methyl-thieno[3,2-b]pyrrole-5-carboxamide;
N-[3-(methoxymethyl)-2-[[4-[[(3 S)-pyrrolidin-3-yl]methoxy]phenoxy]methyl]phenyl]-4-methyl-thieno[3,2-b]pyrrole-5-carboxamide;
N-[3-(ethoxymethyl)-2-[[4-(4-piperidyloxy)phenoxy]methyl]phenyl]-4-methyl-thieno[3,2-b]pyrrole-5-carboxamide;
N-[3-(isopropoxymethyl)-2-[[4-(4-piperidyloxy)phenoxy]methyl]phenyl]-4-methyl-thieno[3,2-b]pyrrole-5-carboxamide;
N-[3-(ethoxymethyl)-2-[[4-[[(3R)-pyrrolidin-3-yl]methoxy]phenoxy]methyl]phenyl]-4-methyl-thieno[3,2-b]pyrrole-5-carboxamide;
4-ethyl-N-[3-(methoxymethyl)-2-[[4-[[(3R)-pyrrolidin-3-yl]methoxy]phenoxy]methyl]phenyl]thieno[3,2-b]pyrrole-5-carboxamide;
4-methyl-N-[3-(morpholinomethyl)-2-[[4-(4-piperidyloxy)phenoxy]methyl]phenyl]thieno[3,2-b]pyrrole-5-carboxamide;
4-methyl-N-[5-methyl-2-[[4-(pyrrolidin-3-ylmethoxy)phenoxy]methyl]phenyl]thieno[3,2-b]pyrrole-5-carboxamide;
4-methyl-N-[2-[[5-(4-piperidyloxy)-2-pyridyl]oxymethyl]phenyl]thieno[3,2-b]pyrrole-5-carboxamide;
4-methyl-N-[2-(4-piperidylmethoxy)phenyl]thieno[3,2-b]pyrrole-5-carboxamide;
4-methyl-N-[3-[[3-(4-piperidyloxy)phenoxy]methyl]phenyl]thieno[3,2-b]pyrrole-5-carboxamide;
N-[3-[[4-(guanidinomethyl)phenoxy]methyl]phenyl]-4-methyl-thieno[3,2-b]pyrrole-5-carboxamide;
N-[2-[[4-(guanidinomethyl)phenoxy]methyl]phenyl]-4-methyl-thieno[3,2-b]pyrrole-5-carboxamide;
4-methyl-N-[2-[2-[4-(4-piperidyloxy)phenyl]ethyl]phenyl]thieno[3,2-b]pyrrole-5-carboxamide;
4-methyl-N-[3-[2-[4-(4-piperidyloxy)phenyl]ethyl]phenyl]thieno[3,2-b]pyrrole-5-carboxamide;
4-methyl-N-[2-[[4-(4-piperidyloxy)anilino]methyl]phenyl]thieno[3,2-b]pyrrole-5-carboxamide;
6-methyl-N-[2-[[3-(4-piperidyloxy)phenoxy]methyl]phenyl]thieno[2,3-b]pyrrole-5-carboxamide;
6-ethyl-N-[2-[[3-(4-piperidyloxy)phenoxy]methyl]phenyl]thieno[2,3-b]pyrrole-5-carboxamide;
6-ethyl-N-[2-[[4-(4-piperidyloxy)phenoxy]methyl]phenyl]thieno[2,3-b]pyrrole-5-carboxamide;
6-methyl-N-[2-[[4-(4-piperidyloxy)phenoxy]methyl]phenyl]thieno[2,3-b]pyrrole-5-carboxamide;
6-methyl-N-[2-[[4-(pyrrolidin-3-ylmethoxy)phenoxy]methyl]phenyl]thieno[2,3-b]pyrrole-5-carboxamide; and
4-methyl-N-[4-[[4-(4-piperidyloxy)phenyl]carbamoyl]-2-pyridyl]thieno[3,2-b]pyrrole-5-carboxamide;
or a stereoisomer or pharmaceutically acceptable salt thereof.

6. A method of inhibiting KDM1 comprising administering to a subject a therapeutically effective amount of a compound of claim 1.

7. The method of claim 6, wherein the compound is a reversible KDM1 inhibitor.

8. A method of treating a cancer, an infectious disease, or a disease characterized by aberration of cellular energy metabolism, comprising administering to a subject a therapeutically effective amount of a compound of claim 1.

9. The method of claim 8, wherein the cancer is leukemia, non-small cell lung cancer, hepatocellular carcinoma, or glioblastoma.

10. The method of claim 8, wherein the disease characterized by aberration of cellular energy metabolism is obesity.

11. A pharmaceutical composition comprising a compound of claim 1 together with a pharmaceutically acceptable excipient and/or diluent.

12. The pharmaceutical composition of claim 11 further comprising at least one therapeutic agent selected from the group consisting of a histone deacetylase inhibitor, a retinoid receptor modulator, an antiproliferative/antineoplastic agent, a cytostatic agent, an agent which inhibits cancer cell invasion, an inhibitor of growth factor function, an antiangiogenic agent, a cell cycle inhibitor, a proteasome inhibitor, a HSP90 inhibitor, a selective COX-2 inhibitor, and a chemotherapeutic agent.

13. The pharmaceutical composition of claim 11, wherein the composition is in the form of a tablet, capsule, oral preparation, powder, granule, pill, injectable or infusible liquid, solution, suspension, emulsion, suppository, ointment, cream, lotion, gel, paste, or transdermal delivery device.

14. A method of treating a cancer, an infectious disease, or a disease characterized by aberration of cellular energy metabolism, comprising administering to a subject a therapeutically effective amount of a compound of formula (I)

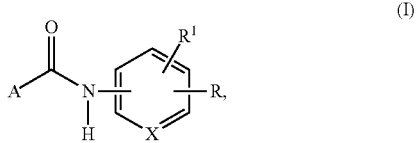

or a stereoisomer or pharmaceutically acceptable salt thereof,
wherein:
A is

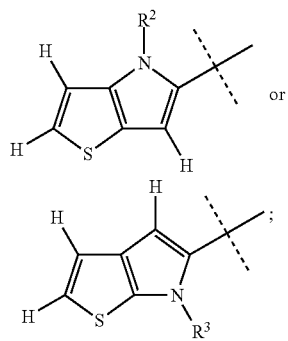

X is CH or N;
R is $L^1$-$R^4$;
$R^1$ is H, halogen, C1-C6-alkyl, C1-C6-alkoxy, —CH2-Z—$R^5$, or —Z—CH2-$R^6$;
$R^2$ and $R^3$ are each C1-C4-alkyl;
$L^1$ is —(CH2)j-Y—, —Y—(CH2)k-, —CH2-CH2- or —CO—NH—;
j and k are, independently, each an integer from 1 to 6;
Y is oxygen, sulphur, NH, or N(C1-C6-alkyl);
Z is a bond, oxygen, sulphur, NH or N(C1-C6-alkyl);
$R^4$, $R^5$, and $R^6$ are each, independently, C1-C6-alkyl, aryl, heteroaryl, wherein the aryl or heteroaryl are optionally substituted by halogen, C1-C6-alkyl, or $L^2$-$R^7$; or heterocyclyl, wherein the heterocyclyl is optionally substituted by C1-C6-alkyl;
$L^2$ is —(CH2)m- or —(CH2)n-W—(CH2)o-;
$R^7$ is C1-C6-alkylamino, C3-C7 cycloalkyl or heterocyclyl, wherein the C3-C7 cycloalkyl or heterocyclyl are optionally substituted by C1-C6-alkyl, or NH2; or guanidine;
m, n, and o are, independently, each zero or an integer from 1 to 6;
W is oxygen, sulphur, NH, or CH2;
wherein aryl is a mono or bicyclic aromatic ring system of 6 or 9 or 10 atoms; heteroaryl is a mono or bicyclic heteroaromatic ring system of 5 to 10 members, which contains one, two, three or four heteroatoms selected from nitrogen, oxygen and sulphur, and one to nine carbon atoms; and
heterocyclyl is a mono, bicyclic or a spirocyclic saturated or partially saturated non-aromatic ring system of 4 to 12 members, which contains one, two, or three heteroatoms selected from nitrogen, oxygen, and sulphur, and three to eleven carbon atoms.

15. The method of claim 14, wherein the compound is selected from the group consisting of:
methyl-N-[2-[[4-(4-piperidyloxy)phenoxy]methyl]phenyl]thieno[3,2-b]pyrrole-5-carboxamide;
4-methyl-N-[2-[[4-(4-piperidylmethoxy)phenoxy]methyl]phenyl]thieno-[3,2-b]pyrrole-5-carboxamide;
N-[2-[[4-[(1-ethyl-4-piperidyl)oxy]phenoxy]methyl]phenyl]-4-methyl-thieno[3,2-b]pyrrole-5-carboxamide;
4-methyl-N-[2-[[4-[[(3R)-pyrrolidin-3-yl]methoxy]phenoxy]methyl]phenyl]thieno[3,2-b]pyrrole-5-carboxamide;
4-methyl-N-[2-[[4-(pyrrolidin-3-ylmethoxy)phenoxy]methyl]phenyl]thieno[3,2-b]pyrrole-5-carboxamide;
4-ethyl-N-[3-[[4-(4-piperidyloxy)phenoxy]methyl]phenyl]thieno[3,2-b]pyrrole-5-carboxamide;
N-[2-[[4-(azepan-4-yloxy)phenoxy]methyl]phenyl]-4-methyl-thieno[3,2-b]pyrrole-5-carboxamide 4-ethyl-N-[2-[[4-(4-piperidyloxy)phenoxy]methyl]phenyl]thieno[3,2-b]pyrrole-5-carboxamide;
N-[2-[[4-(cis-4-aminocyclohexoxy)phenoxy]methyl]phenyl]-4-methyl-thieno[3,2-b]pyrrole-5-carboxamide;
4-methyl-N-[3-[[4-(4-piperidyloxy)phenoxy]methyl]phenyl]thieno[3,2-b]pyrrole-5-carboxamide;
4-methyl-N-[2-[[4-[[(3 S)-pyrrolidin-3-yl]methoxy]phenoxy]methyl]phenyl]thieno[3,2-b]pyrrole-5-carboxamide;
4-ethyl-N-[2-[[4-[(1-methyl-4-piperidyl)oxy]phenoxy]methyl]phenyl]thieno[3,2-b]pyrrole-5-carboxamide;
4-methyl-N-[2-[[4-[(1-methyl-4-piperidyl)oxy]phenoxy]methyl]phenyl]thieno[3,2-b]pyrrole-5-carboxamide;
N-[2-[[4-(trans-4-aminocyclohexoxy)phenoxy]methyl]phenyl]-4-methyl-thieno[3,2-b]pyrrole-5-carboxamide;
4-methyl-N-[3-[[4-[(1-methyl-4-piperidyl)oxy]phenoxy]methyl]phenyl]thieno[3,2-b]pyrrole-5-carboxamide;
4-methyl-N-[2-[(4-pyrrolidin-3-yloxyphenoxy)methyl]phenyl]thieno[3,2-b]pyrrole-5-carboxamide;
4-methyl-N-[2-[[3-[(1-methyl-4-piperidyl)oxy]phenoxy]methyl]phenyl]thieno[3,2-b]pyrrole-5-carboxamide;
4-methyl-N-[2-[[3-(4-piperidyloxy)phenoxy]methyl]phenyl]thieno[3,2-b]pyrrole-5-carboxamide;
4-methyl-N-[3-[(1-methyl-3-piperidyl)methoxy]phenyl]thieno[3,2-b]pyrrole-5-carboxamide;
4-methyl-N-[2-[[4-[(4-methylpiperazin-1-yl)methyl]phenoxy]methyl]phenyl]thieno[3,2-b]pyrrole-5-carboxamide;
4-methyl-N-[3-(4-pyridylmethoxy)phenyl]thieno[3,2-b]pyrrole-5-carboxamide;
4-methyl-N-[3-(4-pyridyloxymethyl)phenyl]thieno[3,2-b]pyrrole-5-carboxamide;
4-methyl-N-[4-[[4-[(1-methyl-4-piperidyl)oxy]phenoxy]methyl]phenyl]thieno[3,2-b]pyrrole-5-carboxamide;
N-[2-[[4-[[(1S,5R)-8-azabicyclo[3.2.1]octan-3-yl]oxy]phenoxy]methyl]phenyl]-4-methyl-thieno[3,2-b]pyrrole-5-carboxamide;
N-[3-[[4-[[(1S,5R)-8-azabicyclo[3.2.1]octan-3-yl]oxy]phenoxy]methyl]phenyl]-4-methyl-thieno[3,2-b]pyrrole-5-carboxamide;

4-methyl-N-[3-[[4-(4-piperidylmethoxy)phenoxy]
methyl]phenyl]thieno[3,2-b]pyrrole-5-carboxamide;
4-methyl-N-[2-[[4-(3-piperidyloxy)phenoxy]methyl]phe-
nyl]thieno[3,2-b]pyrrole-5-carboxamide;
4-methyl-N-[3-[[4-(3-piperidyloxy)phenoxy]methyl]phe-
nyl]thieno[3,2-b]pyrrole-5-carboxamide;
N-[3-[[4-(trans-4-aminocyclohexoxy)phenoxy]methyl]
phenyl]-4-methyl-thieno[3,2-b]pyrrole-5-carboxam-
ide;
N-[3-[[4-(azetidin-3-ylmethoxy)phenoxy]methyl]phe-
nyl]-4-methyl-thieno[3,2-b]pyrrole-5-carboxamide;
4-methyl-N-[2-[[4-(3-methylaminopropoxy)phenoxy]
methyl]phenyl]thieno[3,2-b]pyrrole-5-carboxamide;
4-methyl-N-[3-[(4-pyrrolidin-3-yloxyphenoxy)methyl]
phenyl]thieno[3,2-b]pyrrole-5-carboxamide;
N-[3-[[4-(azepan-4-yloxy)phenoxy]methyl]phenyl]-4-
methyl-thieno[3,2-b]pyrrole-5-carboxamide;
N-[3-[[4-(cis-4-aminocyclohexoxy)phenoxy]methyl]phe-
nyl]-4-methyl-thieno[3,2-b]pyrrole-5-carboxamide;
4-methyl-N-[3-[[4-(pyrrolidin-3-ylmethoxy)phenoxy]
methyl]phenyl]thieno[3,2-b]pyrrole-5-carboxamide;
4-methyl-N-[2-[[4-(4-piperidyloxy)phenyl]carbamoyl]
phenyl]thieno[3,2-b]pyrrole-5-carboxamide;
4-methyl-N-[2-[(4-piperazin-1-ylphenoxy)methyl]phe-
nyl]thieno[3,2-b]pyrrole-5-carboxamide;
4-methyl-N-[2-[[4-[(1-methyl-4-piperidyl)oxy]phenyl]
methoxy]phenyl]thieno[3,2-b]pyrrole-5-carboxamide;
4-methyl-N-[2-[[4-(4-piperidylamino)phenoxy]methyl]
phenyl]thieno[3,2-b]pyrrole-5-carboxamide;
N-[2-[[4-(azetidin-3-ylmethoxy)phenoxy]methyl]phe-
nyl]-4-methyl-thieno[3,2-b]pyrrole-5-carboxamide;
N-[2-[[4-(2,8-diazaspiro[4.5]decan-2-ylmethyl)phenoxy]
methyl]phenyl]-4-methyl-thieno[3,2-b]pyrrole-5-car-
boxamide;
N-[3-(methoxymethyl)-2-[[4-[[(3R)-pyrrolidin-3-yl]
methoxy]phenoxy]methyl]phenyl]-4-methyl-thieno[3,
2-b]pyrrole-5-carboxamide;
N-[3-(methoxymethyl)-2-[[4-(4-piperidyloxy)phenoxy]
methyl]phenyl]-4-methyl-thieno[3,2-b]pyrrole-5-car-
boxamide;
N-[2-[[4-(azepan-4-yloxy)phenoxy]methyl]-3-
(methoxymethyl)phenyl]-4-methyl-thieno[3,2-b]pyr-
role-5-carboxamide;
4-ethyl-N-[3-(methoxymethyl)phenyl]thieno[3,2-b]pyr-
role-5-carboxamide;
4-methyl-N-[3-(methylsulfanylmethyl)phenyl]thieno[3,
2-b]pyrrole-5-carboxamide;
4-methyl-N-[3-(methoxymethyl)phenyl]thieno[3,2-b]
pyrrole-5-carboxamide;
N-[3-(methoxymethyl)phenyl]-6-methyl-thieno[2,3-b]
pyrrole-5-carboxamide;
N-[3-(methoxymethyl)-2-[[4-[[(3 S)-pyrrolidin-3-yl]
methoxy]phenoxy]methyl]phenyl]-4-methyl-thieno[3,
2-b]pyrrole-5-carboxamide;
N-[3-(ethoxymethyl)-2-[[4-(4-piperidyloxy)phenoxy]
methyl]phenyl]-4-methyl-thieno[3,2-b]pyrrole-5-car-
boxamide;
N-[3-(isopropoxymethyl)-2-[[4-(4-piperidyloxy)phe-
noxy]methyl]phenyl]-4-methyl-thieno[3,2-b]pyrrole-
5-carboxamide;
N-[3-(ethoxymethyl)-2-[[4-[[(3R)-pyrrolidin-3-yl]
methoxy]phenoxy]methyl]phenyl]-4-methyl-thieno[3,
2-b]pyrrole-5-carboxamide;
4-ethyl-N-[3-(methoxymethyl)-2-[[4-[[(3R)-pyrrolidin-3-
yl]methoxy]phenoxy]methyl]phenyl]thieno[3,2-b]pyr-
role-5-carboxamide;

4-methyl-N-[3-(morpholinomethyl)-2-[[4-(4-piperidy-
loxy)phenoxy]methyl]phenyl]thieno[3,2-b]pyrrole-5-
carboxamide;
4-methyl-N-[5-methyl-2-[[4-(pyrrolidin-3-ylmethoxy)
phenoxy]methyl]phenyl]thieno[3,2-b]pyrrole-5-car-
boxamide;
4-methyl-N-[2-[[5-(4-piperidyloxy)-2-pyridyl]oxym-
ethyl]phenyl]thieno[3,2-b]pyrrole-5-carboxamide;
4-methyl-N-[2-(4-piperidylmethoxy)phenyl]thieno[3,2-
b]pyrrole-5-carboxamide;
4-methyl-N-[3-[[3-(4-piperidyloxy)phenoxy]methyl]phe-
nyl]thieno[3,2-b]pyrrole-5-carboxamide;
N-[3-[[4-(guanidinomethyl)phenoxy]methyl]phenyl]-4-
methyl-thieno[3,2-b]pyrrole-5-carboxamide;
N-[2-[[4-(guanidinomethyl)phenoxy]methyl]phenyl]-4-
methyl-thieno[3,2-b]pyrrole-5-carboxamide;
4-methyl-N-[2-[2-[4-(4-piperidyloxy)phenyl]ethyl]phe-
nyl]thieno[3,2-b]pyrrole-5-carboxamide;
4-methyl-N-[3-[2-[4-(4-piperidyloxy)phenyl]ethyl]phe-
nyl]thieno[3,2-b]pyrrole-5-carboxamide;
4-methyl-N-[2-[[4-(4-piperidyloxy)anilino]methyl]phe-
nyl]thieno[3,2-b]pyrrole-5-carboxamide;
6-methyl-N-[2-[[3-(4-piperidyloxy)phenoxy]methyl]phe-
nyl]thieno[2,3-b]pyrrole-5-carboxamide;
6-ethyl-N-[2-[[3-(4-piperidyloxy)phenoxy]methyl]phe-
nyl]thieno[2,3-b]pyrrole-5-carboxamide;
6-ethyl-N-[2-[[4-(4-piperidyloxy)phenoxy]methyl]phe-
nyl]thieno[2,3-b]pyrrole-5-carboxamide;
6-methyl-N-[2-[[4-(4-piperidyloxy)phenoxy]methyl]phe-
nyl]thieno[2,3-b]pyrrole-5-carboxamide;
6-methyl-N-[2-[[4-(pyrrolidin-3-ylmethoxy)phenoxy]
methyl]phenyl]thieno[2,3-b]pyrrole-5-carboxamide;
and
4-methyl-N-[4-[[4-(4-piperidyloxy)phenyl]carbamoyl]-
2-pyridyl]thieno[3,2-b]pyrrole-5-carboxamide;
or a stereoisomer or pharmaceutically acceptable salt
thereof.

16. The method of claim 14, wherein the cancer is leukemia, non-small cell lung cancer, hepatocellular carcinoma, or glioblastoma.

17. The method of claim 14, wherein the disease characterized by aberration of cellular energy metabolism is obesity.

18. A method of inhibiting KDM1 comprising administering to a subject a therapeutically effective amount of a compound of formula (I)

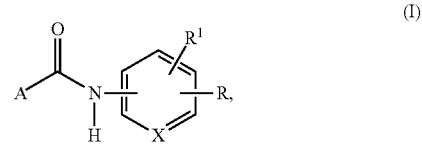

or a stereoisomer or pharmaceutically acceptable salt thereof,
wherein:
A is

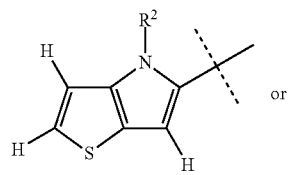

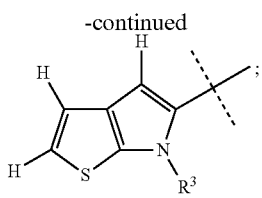

X is CH or N;
R is L¹-R⁴;
R¹ is H, halogen, C1-C6-alkyl, C1-C6-alkoxy, —CH2-Z—R⁵, or —Z—CH2-R⁶;
R² and R³ are each C1-C4-alkyl;
L¹ is —(CH2)j-Y—, —Y—(CH2)k-, —CH2-CH2- or —CO—NH—;
j and k are, independently, each an integer from 1 to 6;
Y is oxygen, sulphur, NH, or N(C1-C6-alkyl);
Z is a bond, oxygen, sulphur, NH or N(C1-C6-alkyl);
R⁴, R⁵, and R⁶ are each, independently, C1-C6-alkyl, aryl, heteroaryl, wherein the aryl or heteroaryl are optionally substituted by halogen, C1-C6-alkyl, or L²-R⁷; or heterocyclyl, wherein the heterocyclyl is optionally substituted by C1-C6-alkyl;
L² is —(CH2)m- or —(CH2)n-W—(CH2)o-;
R⁷ is C1-C6-alkylamino, C3-C7 cycloalkyl or heterocyclyl, wherein the C3-C7 cycloalkyl or heterocyclyl are optionally substituted by C1-C6-alkyl, or NH2; or guanidine;
m, n, and o are, independently, each zero or an integer from 1 to 6;
W is oxygen, sulphur, NH, or CH2;
wherein aryl is a mono or bicyclic aromatic ring system of 6 or 9 or 10 atoms; heteroaryl is a mono or bicyclic heteroaromatic ring system of 5 to 10 members, which contains one, two, three or four heteroatoms selected from nitrogen, oxygen and sulphur, and one to nine carbon atoms; and
heterocyclyl is a mono, bicyclic or a spirocyclic saturated or partially saturated non-aromatic ring system of 4 to 12 members, which contains one, two, or three heteroatoms selected from nitrogen, oxygen, and sulphur, and three to eleven carbon atoms.

19. The method of claim 18, wherein the compound is selected from the group consisting of:

methyl-N-[2-[[4-(4-piperidyloxy)phenoxy]methyl]phenyl]thieno[3,2-b]pyrrole-5-carboxamide;
4-methyl-N-[2-[[4-(4-piperidylmethoxy)phenoxy]methyl]phenyl]thieno-[3,2-b]pyrrole-5-carboxamide;
N-[2-[[4-[(1-ethyl-4-piperidyl)oxy]phenoxy]methyl]phenyl]-4-methyl-thieno[3,2-b]pyrrole-5-carboxamide;
4-methyl-N-[2-[[4-[[(3R)-pyrrolidin-3-yl]methoxy]phenoxy]methyl]phenyl]thieno[3,2-b]pyrrole-5-carboxamide;
4-methyl-N-[2-[[4-(pyrrolidin-3-ylmethoxy)phenoxy]methyl]phenyl]thieno[3,2-b]pyrrole-5-carboxamide;
4-ethyl-N-[3-[[4-(4-piperidyloxy)phenoxy]methyl]phenyl]thieno[3,2-b]pyrrole-5-carboxamide;
N-[2-[[4-(azepan-4-yloxy)phenoxy]methyl]phenyl]-4-methyl-thieno[3,2-b]pyrrole-5-carboxamide 4-ethyl-N-[2-[[4-(4-piperidyloxy)phenoxy]methyl]phenyl]thieno[3,2-b]pyrrole-5-carboxamide;
N-[2-[[4-(cis-4-aminocyclohexoxy)phenoxy]methyl]phenyl]-4-methyl-thieno[3,2-b]pyrrole-5-carboxamide;
4-methyl-N-[3-[[4-(4-piperidyloxy)phenoxy]methyl]phenyl]thieno[3,2-b]pyrrole-5-carboxamide;
4-methyl-N-[2-[[4-[[(3S)-pyrrolidin-3-yl]methoxy]phenoxy]methyl]phenyl]thieno[3,2-b]pyrrole-5-carboxamide;
4-ethyl-N-[2-[[4-[(1-methyl-4-piperidyl)oxy]phenoxy]methyl]phenyl]thieno[3,2-b]pyrrole-5-carboxamide;
4-methyl-N-[2-[[4-[(1-methyl-4-piperidyl)oxy]phenoxy]methyl]phenyl]thieno[3,2-b]pyrrole-5-carboxamide;
N-[2-[[4-(trans-4-aminocyclohexoxy)phenoxy]methyl]phenyl]-4-methyl-thieno[3,2-b]pyrrole-5-carboxamide;
4-methyl-N-[3-[[4-[(1-methyl-4-piperidyl)oxy]phenoxy]methyl]phenyl]thieno[3,2-b]pyrrole-5-carboxamide;
4-methyl-N-[2-[(4-pyrrolidin-3-yloxyphenoxy)methyl]phenyl]thieno[3,2-b]pyrrole-5-carboxamide;
4-methyl-N-[2-[[3-[(1-methyl-4-piperidyl)oxy]phenoxy]methyl]phenyl]thieno[3,2-b]pyrrole-5-carboxamide;
4-methyl-N-[2-[[3-(4-piperidyloxy)phenoxy]methyl]phenyl]thieno[3,2-b]pyrrole-5-carboxamide;
4-methyl-N-[3-[(1-methyl-3-piperidyl)methoxy]phenyl]thieno[3,2-b]pyrrole-5-carboxamide;
4-methyl-N-[2-[[4-[(4-methylpiperazin-1-yl)methyl]phenoxy]methyl]phenyl]thieno[3,2-b]pyrrole-5-carboxamide;
4-methyl-N-[3-(4-pyridylmethoxy)phenyl]thieno[3,2-b]pyrrole-5-carboxamide;
4-methyl-N-[3-(4-pyridyloxymethyl)phenyl]thieno[3,2-b]pyrrole-5-carboxamide;
4-methyl-N-[4-[[4-[(1-methyl-4-piperidyl)oxy]phenoxy]methyl]phenyl]thieno[3,2-b]pyrrole-5-carboxamide;
N-[2-[[4-[[(1S,5R)-8-azabicyclo[3.2.1]octan-3-yl]oxy]phenoxy]methyl]phenyl]-4-methyl-thieno[3,2-b]pyrrole-5-carboxamide;
N-[3-[[4-[[(1S,5R)-8-azabicyclo[3.2.1]octan-3-yl]oxy]phenoxy]methyl]phenyl]-4-methyl-thieno[3,2-b]pyrrole-5-carboxamide;
4-methyl-N-[3-[[4-(4-piperidylmethoxy)phenoxy]methyl]phenyl]thieno[3,2-b]pyrrole-5-carboxamide;
4-methyl-N-[2-[[4-(3-piperidyloxy)phenoxy]methyl]phenyl]thieno[3,2-b]pyrrole-5-carboxamide;
4-methyl-N-[3-[[4-(3-piperidyloxy)phenoxy]methyl]phenyl]thieno[3,2-b]pyrrole-5-carboxamide;
N-[3-[[4-(trans-4-aminocyclohexoxy)phenoxy]methyl]phenyl]-4-methyl-thieno[3,2-b]pyrrole-5-carboxamide;
N-[3-[[4-(azetidin-3-ylmethoxy)phenoxy]methyl]phenyl]-4-methyl-thieno[3,2-b]pyrrole-5-carboxamide;
4-methyl-N-[2-[[4-(3-methylaminopropoxy)phenoxy]methyl]phenyl]thieno[3,2-b]pyrrole-5-carboxamide;
4-methyl-N-[3-[(4-pyrrolidin-3-yloxyphenoxy)methyl]phenyl]thieno[3,2-b]pyrrole-5-carboxamide;
N-[3-[[4-(azepan-4-yloxy)phenoxy]methyl]phenyl]-4-methyl-thieno[3,2-b]pyrrole-5-carboxamide;
N-[3-[[4-(cis-4-aminocyclohexoxy)phenoxy]methyl]phenyl]-4-methyl-thieno[3,2-b]pyrrole-5-carboxamide;
4-methyl-N-[3-[[4-(pyrrolidin-3-ylmethoxy)phenoxy]methyl]phenyl]thieno[3,2-b]pyrrole-5-carboxamide;
4-methyl-N-[2-[[4-(4-piperidyloxy)phenyl]carbamoyl]phenyl]thieno[3,2-b]pyrrole-5-carboxamide;
4-methyl-N-[2-[(4-piperazin-1-ylphenoxy)methyl]phenyl]thieno[3,2-b]pyrrole-5-carboxamide;
4-methyl-N-[2-[[4-[(1-methyl-4-piperidyl)oxy]phenyl]methoxy]phenyl]thieno[3,2-b]pyrrole-5-carboxamide;
4-methyl-N-[2-[[4-(4-piperidylamino)phenoxy]methyl]phenyl]thieno[3,2-b]pyrrole-5-carboxamide;
N-[2-[[4-(azetidin-3-ylmethoxy)phenoxy]methyl]phenyl]-4-methyl-thieno[3,2-b]pyrrole-5-carboxamide;

N-[2-[[4-(2,8-diazaspiro[4.5]decan-2-ylmethyl)phenoxy]methyl]phenyl]-4-methyl-thieno[3,2-b]pyrrole-5-carboxamide;
N-[3-(methoxymethyl)-2-[[4-[[(3R)-pyrrolidin-3-yl]methoxy]phenoxy]methyl]phenyl]-4-methyl-thieno[3,2-b]pyrrole-5-carboxamide;
N-[3-(methoxymethyl)-2-[[4-(4-piperidyloxy)phenoxy]methyl]phenyl]-4-methyl-thieno[3,2-b]pyrrole-5-carboxamide;
N-[2-[[4-(azepan-4-yloxy)phenoxy]methyl]-3-(methoxymethyl)phenyl]-4-methyl-thieno[3,2-b]pyrrole-5-carboxamide;
4-ethyl-N-[3-(methoxymethyl)phenyl]thieno[3,2-b]pyrrole-5-carboxamide;
4-methyl-N-[3-(methylsulfanylmethyl)phenyl]thieno[3,2-b]pyrrole-5-carboxamide;
4-methyl-N-[3-(methoxymethyl)phenyl]thieno[3,2-b]pyrrole-5-carboxamide;
N-[3-(methoxymethyl)phenyl]-6-methyl-thieno[2,3-b]pyrrole-5-carboxamide;
N-[3-(methoxymethyl)-2-[[4-[[(3 S)-pyrrolidin-3-yl]methoxy]phenoxy]methyl]phenyl]-4-methyl-thieno[3,2-b]pyrrole-5-carboxamide;
N-[3-(ethoxymethyl)-2-[[4-(4-piperidyloxy)phenoxy]methyl]phenyl]-4-methyl-thieno[3,2-b]pyrrole-5-carboxamide;
N-[3-(isopropoxymethyl)-2-[[4-(4-piperidyloxy)phenoxy]methyl]phenyl]-4-methyl-thieno[3,2-b]pyrrole-5-carboxamide;
N-[3-(ethoxymethyl)-2-[[4-[[(3R)-pyrrolidin-3-yl]methoxy]phenoxy]methyl]phenyl]-4-methyl-thieno[3,2-b]pyrrole-5-carboxamide;
4-ethyl-N-[3-(methoxymethyl)-2-[[4-[[(3R)-pyrrolidin-3-yl]methoxy]phenoxy]methyl]phenyl]thieno[3,2-b]pyrrole-5-carboxamide;
4-methyl-N-[3-(morpholinomethyl)-2-[[4-(4-piperidyloxy)phenoxy]methyl]phenyl]thieno[3,2-b]pyrrole-5-carboxamide;
4-methyl-N-[5-methyl-2-[[4-(pyrrolidin-3-ylmethoxy)phenoxy]methyl]phenyl]thieno[3,2-b]pyrrole-5-carboxamide;
4-methyl-N-[2-[[5-(4-piperidyloxy)-2-pyridyl]oxymethyl]phenyl]thieno[3,2-b]pyrrole-5-carboxamide;
4-methyl-N-[2-(4-piperidylmethoxy)phenyl]thieno[3,2-b]pyrrole-5-carboxamide;
4-methyl-N-[3-[[3-(4-piperidyloxy)phenoxy]methyl]phenyl]thieno[3,2-b]pyrrole-5-carboxamide;
N-[3-[[4-(guanidinomethyl)phenoxy]methyl]phenyl]-4-methyl-thieno[3,2-b]pyrrole-5-carboxamide;
N-[2-[[4-(guanidinomethyl)phenoxy]methyl]phenyl]-4-methyl-thieno[3,2-b]pyrrole-5-carboxamide;
4-methyl-N-[2-[2-[4-(4-piperidyloxy)phenyl]ethyl]phenyl]thieno[3,2-b]pyrrole-5-carboxamide;
4-methyl-N-[3-[2-[4-(4-piperidyloxy)phenyl]ethyl]phenyl]thieno[3,2-b]pyrrole-5-carboxamide;
4-methyl-N-[2-[[4-(4-piperidyloxy)anilino]methyl]phenyl]thieno[3,2-b]pyrrole-5-carboxamide;
6-methyl-N-[2-[[3-(4-piperidyloxy)phenoxy]methyl]phenyl]thieno[2,3-b]pyrrole-5-carboxamide;
6-ethyl-N-[2-[[3-(4-piperidyloxy)phenoxy]methyl]phenyl]thieno[2,3-b]pyrrole-5-carboxamide;
6-ethyl-N-[2-[[4-(4-piperidyloxy)phenoxy]methyl]phenyl]thieno[2,3-b]pyrrole-5-carboxamide;
6-methyl-N-[2-[[4-(4-piperidyloxy)phenoxy]methyl]phenyl]thieno[2,3-b]pyrrole-5-carboxamide;
6-methyl-N-[2-[[4-(pyrrolidin-3-ylmethoxy)phenoxy]methyl]phenyl]thieno[2,3-b]pyrrole-5-carboxamide; and
4-methyl-N-[4-[[4-(4-piperidyloxy)phenyl]carbamoyl]-2-pyridyl]thieno[3,2-b]pyrrole-5-carboxamide;
or a stereoisomer or pharmaceutically acceptable salt thereof.

20. The method of claim 18, wherein the compound is a reversible KDM1 inhibitor.

21. A pharmaceutical composition comprising a compound of formula (I)

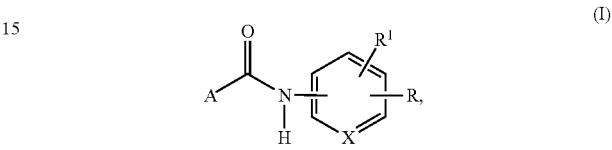

or a stereoisomer or pharmaceutically acceptable salt thereof, together with a pharmaceutically acceptable excipient and/or diluent, wherein:

A is

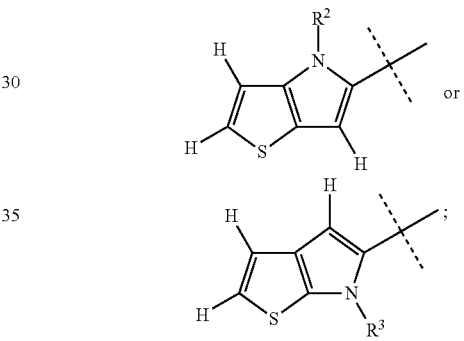

X is CH or N;
R is $L^1$-$R^4$;
$R^1$ is H, halogen, C1-C6-alkyl, C1-C6-alkoxy, —CH2-Z—$R^5$, or —Z—CH2-$R^6$;
$R^2$ and $R^3$ are each C1-C4-alkyl;
$L^1$ is —(CH2)j-Y—, —Y—(CH2)k-, —CH2-CH2- or —CO—NH—;
j and k are, independently, each an integer from 1 to 6;
Y is oxygen, sulphur, NH, or N(C1-C6-alkyl);
Z is a bond, oxygen, sulphur, NH or N(C1-C6-alkyl);
$R^4$, $R^5$, and $R^6$ are each, independently, C1-C6-alkyl, aryl, heteroaryl, wherein the aryl or heteroaryl are optionally substituted by halogen, C1-C6-alkyl, or $L^2$-$R^7$; or heterocyclyl, wherein the heterocyclyl is optionally substituted by C1-C6-alkyl;
$L^2$ is —(CH2)m- or —(CH2)n-W—(CH2)o-;
$R^7$ is C1-C6-alkylamino, C3-C7 cycloalkyl or heterocyclyl, wherein the C3-C7 cycloalkyl or heterocyclyl are optionally substituted by C1-C6-alkyl, or NH2; or guanidine;
m, n, and o are, independently, each zero or an integer from 1 to 6;
W is oxygen, sulphur, NH, or CH2;
wherein aryl is a mono or bicyclic aromatic ring system of 6 or 9 or 10 atoms; heteroaryl is a mono or bicyclic heteroaromatic ring system of 5 to 10 members, which contains one, two, three or four heteroatoms selected from nitrogen, oxygen and sulphur, and one to nine carbon atoms; and heterocyclyl is a mono, bicyclic or a spirocyclic saturated or partially saturated non-aromatic ring system of 4 to 12 members, which contains one, two, or three heteroatoms selected from nitrogen, oxygen, and sulphur, and three to eleven carbon atoms.

22. The pharmaceutical composition of claim 21, wherein the compound is selected from the group consisting of:

methyl-N-[2-[[4-(4-piperidyloxy)phenoxy]methyl]phenyl]thieno[3,2-b]pyrrole-5-carboxamide;
4-methyl-N-[2-[[4-(4-piperidylmethoxy)phenoxy]methyl]phenyl]thieno-[3,2-b]pyrrole-5-carboxamide;
N-[2-[[4-[(1-ethyl-4-piperidyl)oxy]phenoxy]methyl]phenyl]-4-methyl-thieno[3,2-b]pyrrole-5-carboxamide;
4-methyl-N-[2-[[4-[[(3R)-pyrrolidin-3-yl]methoxy]phenoxy]methyl]phenyl]thieno[3,2-b]pyrrole-5-carboxamide;
4-methyl-N-[2-[[4-(pyrrolidin-3-ylmethoxy)phenoxy]methyl]phenyl]thieno[3,2-b]pyrrole-5-carboxamide;
4-ethyl-N-[3-[[4-(4-piperidyloxy)phenoxy]methyl]phenyl]thieno[3,2-b]pyrrole-5-carboxamide;
N-[2-[[4-(azepan-4-yloxy)phenoxy]methyl]phenyl]-4-methyl-thieno[3,2-b]pyrrole-5-carboxamide 4-ethyl-N-[2-[[4-(4-piperidyloxy)phenoxy]methyl]phenyl]thieno[3,2-b]pyrrole-5-carboxamide;
N-[2-[[4-(cis-4-aminocyclohexoxy)phenoxy]methyl]phenyl]-4-methyl-thieno[3,2-b]pyrrole-5-carboxamide;
4-methyl-N-[3-[[4-(4-piperidyloxy)phenoxy]methyl]phenyl]thieno[3,2-b]pyrrole-5-carboxamide;
4-methyl-N-[2-[[4-[[(3 S)-pyrrolidin-3-yl]methoxy]phenoxy]methyl]phenyl]thieno[3,2-b]pyrrole-5-carboxamide;
4-ethyl-N-[2-[[4-[(1-methyl-4-piperidyl)oxy]phenoxy]methyl]phenyl]thieno[3,2-b]pyrrole-5-carboxamide;
4-methyl-N-[2-[[4-[(1-methyl-4-piperidyl)oxy]phenoxy]methyl]phenyl]thieno[3,2-b]pyrrole-5-carboxamide;
N-[2-[[4-(trans-4-aminocyclohexoxy)phenoxy]methyl]phenyl]-4-methyl-thieno[3,2-b]pyrrole-5-carboxamide;
4-methyl-N-[3-[[4-[(1-methyl-4-piperidyl)oxy]phenoxy]methyl]phenyl]thieno[3,2-b]pyrrole-5-carboxamide;
4-methyl-N-[2-[(4-pyrrolidin-3-yloxyphenoxy)methyl]phenyl]thieno[3,2-b]pyrrole-5-carboxamide;
4-methyl-N-[2-[[3-[(1-methyl-4-piperidyl)oxy]phenoxy]methyl]phenyl]thieno[3,2-b]pyrrole-5-carboxamide;
4-methyl-N-[2-[[3-(4-piperidyloxy)phenoxy]methyl]phenyl]thieno[3,2-b]pyrrole-5-carboxamide;
4-methyl-N-[3-[(1-methyl-3-piperidyl)methoxy]phenyl]thieno[3,2-b]pyrrole-5-carboxamide;
4-methyl-N-[2-[[4-[(4-methylpiperazin-1-yl)methyl]phenoxy]methyl]phenyl]thieno[3,2-b]pyrrole-5-carboxamide;
4-methyl-N-[3-(4-pyridylmethoxy)phenyl]thieno[3,2-b]pyrrole-5-carboxamide;
4-methyl-N-[3-(4-pyridyloxymethyl)phenyl]thieno[3,2-b]pyrrole-5-carboxamide;
4-methyl-N-[4-[[4-[(1-methyl-4-piperidyl)oxy]phenoxy]methyl]phenyl]thieno[3,2-b]pyrrole-5-carboxamide;
N-[2-[[4-[[(1S,5R)-8-azabicyclo[3.2.1]octan-3-yl]oxy]phenoxy]methyl]phenyl]-4-methyl-thieno[3,2-b]pyrrole-5-carboxamide;
N-[3-[[4-[[(1S,5R)-8-azabicyclo[3.2.1]octan-3-yl]oxy]phenoxy]methyl]phenyl]-4-methyl-thieno[3,2-b]pyrrole-5-carboxamide;
4-methyl-N-[3-[[4-(4-piperidylmethoxy)phenoxy]methyl]phenyl]thieno[3,2-b]pyrrole-5-carboxamide;
4-methyl-N-[2-[[4-(3-piperidyloxy)phenoxy]methyl]phenyl]thieno[3,2-b]pyrrole-5-carboxamide;
4-methyl-N-[3-[[4-(3-piperidyloxy)phenoxy]methyl]phenyl]thieno[3,2-b]pyrrole-5-carboxamide;
N-[3-[[4-(trans-4-aminocyclohexoxy)phenoxy]methyl]phenyl]-4-methyl-thieno[3,2-b]pyrrole-5-carboxamide;
N-[3-[[4-(azetidin-3-ylmethoxy)phenoxy]methyl]phenyl]-4-methyl-thieno[3,2-b]pyrrole-5-carboxamide;
4-methyl-N-[2-[[4-(3-methylaminopropoxy)phenoxy]methyl]phenyl]thieno[3,2-b]pyrrole-5-carboxamide;
4-methyl-N-[3-[(4-pyrrolidin-3-yloxyphenoxy)methyl]phenyl]thieno[3,2-b]pyrrole-5-carboxamide;
N-[3-[[4-(azepan-4-yloxy)phenoxy]methyl]phenyl]-4-methyl-thieno[3,2-b]pyrrole-5-carboxamide;
N-[3-[[4-(cis-4-aminocyclohexoxy)phenoxy]methyl]phenyl]-4-methyl-thieno[3,2-b]pyrrole-5-carboxamide;
4-methyl-N-[3-[[4-(pyrrolidin-3-ylmethoxy)phenoxy]methyl]phenyl]thieno[3,2-b]pyrrole-5-carboxamide;
4-methyl-N-[2-[[4-(4-piperidyloxy)phenyl]carbamoyl]phenyl]thieno[3,2-b]pyrrole-5-carboxamide;
4-methyl-N-[2-[(4-piperazin-1-ylphenoxy)methyl]phenyl]thieno[3,2-b]pyrrole-5-carboxamide;
4-methyl-N-[2-[[4-[(1-methyl-4-piperidyl)oxy]phenyl]methoxy]phenyl]thieno[3,2-b]pyrrole-5-carboxamide;
4-methyl-N-[2-[[4-(4-piperidylamino)phenoxy]methyl]phenyl]thieno[3,2-b]pyrrole-5-carboxamide;
N-[2-[[4-(azetidin-3-ylmethoxy)phenoxy]methyl]phenyl]-4-methyl-thieno[3,2-b]pyrrole-5-carboxamide;
N-[2-[[4-(2,8-diazaspiro[4.5]decan-2-ylmethyl)phenoxy]methyl]phenyl]-4-methyl-thieno[3,2-b]pyrrole-5-carboxamide;
N-[3-(methoxymethyl)-2-[[4-[[(3R)-pyrrolidin-3-yl]methoxy]phenoxy]methyl]phenyl]-4-methyl-thieno[3,2-b]pyrrole-5-carboxamide;
N-[3-(methoxymethyl)-2-[[4-(4-piperidyloxy)phenoxy]methyl]phenyl]-4-methyl-thieno[3,2-b]pyrrole-5-carboxamide;
N-[2-[[4-(azepan-4-yloxy)phenoxy]methyl]-3-(methoxymethyl)phenyl]-4-methyl-thieno[3,2-b]pyrrole-5-carboxamide;
4-ethyl-N-[3-(methoxymethyl)phenyl]thieno[3,2-b]pyrrole-5-carboxamide;
4-methyl-N-[3-(methyl sulfanylmethyl)phenyl]thieno[3,2-b]pyrrole-5-carboxamide;
4-methyl-N-[3-(methoxymethyl)phenyl]thieno[3,2-b]pyrrole-5-carboxamide;
N-[3-(methoxymethyl)phenyl]-6-methyl-thieno[2,3-b]pyrrole-5-carboxamide;
N-[3-(methoxymethyl)-2-[[4-[[(3 S)-pyrrolidin-3-yl]methoxy]phenoxy]methyl]phenyl]-4-methyl-thieno[3,2-b]pyrrole-5-carboxamide;
N-[3-(ethoxymethyl)-2-[[4-(4-piperidyloxy)phenoxy]methyl]phenyl]-4-methyl-thieno[3,2-b]pyrrole-5-carboxamide;
N-[3-(isopropoxymethyl)-2-[[4-(4-piperidyloxy)phenoxy]methyl]phenyl]-4-methyl-thieno[3,2-b]pyrrole-5-carboxamide;
N-[3-(ethoxymethyl)-2-[[4-[[(3R)-pyrrolidin-3-yl]methoxy]phenoxy]methyl]phenyl]-4-methyl-thieno[3,2-b]pyrrole-5-carboxamide;
4-ethyl-N-[3-(methoxymethyl)-2-[[4-[[(3R)-pyrrolidin-3-yl]methoxy]phenoxy]methyl]phenyl]thieno[3,2-b]pyrrole-5-carboxamide;

4-methyl-N-[3-(morpholinomethyl)-2-[[4-(4-piperidy-loxy)phenoxy]methyl]phenyl]thieno[3,2-b]pyrrole-5-carboxamide;
4-methyl-N-[5-methyl-2-[[4-(pyrrolidin-3-ylmethoxy)phenoxy]methyl]phenyl]thieno[3,2-b]pyrrole-5-carboxamide;
4-methyl-N-[2-[[5-(4-piperidyloxy)-2-pyridyl]oxymethyl]phenyl]thieno[3,2-b]pyrrole-5-carboxamide;
4-methyl-N-[2-(4-piperidylmethoxy)phenyl]thieno[3,2-b]pyrrole-5-carboxamide;
4-methyl-N-[3-[[3-(4-piperidyloxy)phenoxy]methylphenyl]thieno[3,2-b]pyrrole-5-carboxamide;
N-[3-[[4-(guanidinomethyl)phenoxy]methyl]phenyl]-4-methyl-thieno[3,2-b]pyrrole-5-carboxamide;
N-[2-[[4-(guanidinomethyl)phenoxy]methyl]phenyl]-4-methyl-thieno[3,2-b]pyrrole-5-carboxamide;
4-methyl-N-[2-[2-[4-(4-piperidyloxy)phenyl]ethyl]phenyl]thieno[3,2-b]pyrrole-5-carboxamide;
4-methyl-N-[3-[2-[4-(4-piperidyloxy)phenyl]ethyl]phenyl]thieno[3,2-b]pyrrole-5-carboxamide;
4-methyl-N-[2-[[4-(4-piperidyloxy)anilino]methyl]phenyl]thieno[3,2-b]pyrrole-5-carboxamide;
6-methyl-N-[2-[[3-(4-piperidyloxy)phenoxy]methyl]phenyl]thieno[2,3-b]pyrrole-5-carboxamide;
6-ethyl-N-[2-[[3-(4-piperidyloxy)phenoxy]methyl]phenyl]thieno[2,3-b]pyrrole-5-carboxamide;
6-ethyl-N-[2-[[4-(4-piperidyloxy)phenoxy]methyl]phenyl]thieno[2,3-b]pyrrole-5-carboxamide;
6-methyl-N-[2-[[4-(4-piperidyloxy)phenoxy]methyl]phenyl]thieno[2,3-b]pyrrole-5-carboxamide;
6-methyl-N-[2-[[4-(pyrrolidin-3-ylmethoxy)phenoxy]methyl]phenyl]thieno[2,3-b]pyrrole-5-carboxamide; and
4-methyl-N-[4-[[4-(4-piperidyloxy)phenyl]carbamoyl]-2-pyridyl]thieno[3,2-b]pyrrole-5-carboxamide;
or a stereoisomer or pharmaceutically acceptable salt thereof.

23. The pharmaceutical composition of claim 21, further comprising at least one therapeutic agent selected from the group consisting of a histone deacetylase inhibitor, a retinoid receptor modulator, an antiproliferative/antineoplastic agent, a cytostatic agent, an agent which inhibits cancer cell invasion, an inhibitor of growth factor function, an antiangiogenic agent, a cell cycle inhibitor, a proteasome inhibitor, a HSP90 inhibitor, a selective COX-2 inhibitor and a chemotherapeutic agent.

24. The pharmaceutical composition of claim 21, wherein the composition is in the form of a tablet, capsule, oral preparation, powder, granule, pill, injectable or infusible liquid, solution, suspension, emulsion, suppository, ointment, cream, lotion, gel, paste, or transdermal delivery device.

25. A process for obtaining a compound of claim 1, the process comprising:
   a. the preparation of a compound of formula A3 or A4 by reaction of a compound of formula A1 or A2 with the suitable alkyl halide of formula $R^2$-LG or $R^3$-LG and in presence of a base;
   b. the hydrolysis of a compound of formula A3 or A4 to the corresponding carboxylic acid of formula A5 or A6; and
   c. the condensation of a compound of formula A5 or A6 with an amine of formula A7 to obtain a compound of formula (Ia), represented as follows:

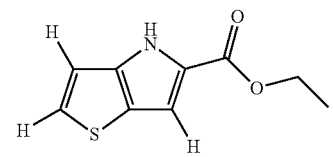
A1

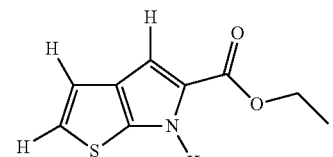
A2

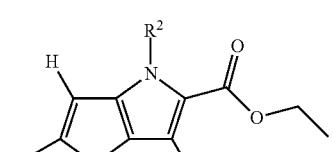
A3

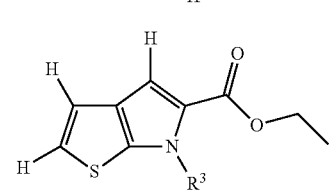
A4

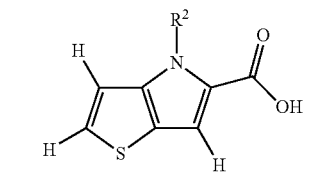
A5

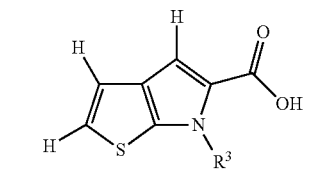
A6

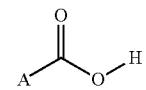
A5 or A6

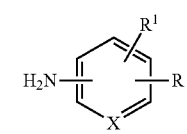
A7

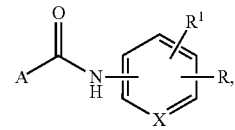
Ia wherein LG is bromide or iodide.

26. A process for obtaining a compound of claim 1, the process comprising;
   a. the reaction of a compound of formula A5 or A6 with an amine of formula B1 to obtain a hydroxyl derivative of formula B2; and b. the treatment of the hydroxyl derivative of formula B2 with an alcohol of formula B3 to obtain a compound of formula (Ia), represented as follows:
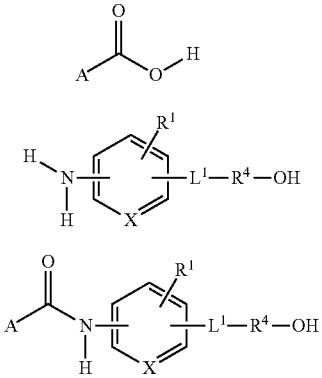
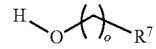
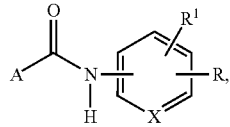
wherein R⁴ is aryl or heteroaryl.
27. The method of claim 8, wherein the cancer is acute myeloid leukemia.
28. The method of claim 14, wherein the cancer is acute myeloid leukemia.
* * * * *

UNITED STATES PATENT AND TRADEMARK OFFICE
CERTIFICATE OF CORRECTION

PATENT NO. : 10,183,952 B2
APPLICATION NO. : 15/508816
DATED : January 22, 2019
INVENTOR(S) : Paola Vianello et al.

It is certified that error appears in the above-identified patent and that said Letters Patent is hereby corrected as shown below:

In the Claims

At Column 151, Claim number 1, Line number 47:
"IV is H, halogen, C1-C6-alkyl, C1-C6-alkoxy, -CH2-Z-"
Should read:
-- $R_1$ is H, halogen, C1-C6-alkyl, C1-C6-alkoxy, -CH2-Z- --

At Column 152, Claim number 4, Line numbers 22-23:
"4. The compound of claim 1, wherein $L^1$ is –CH2-O- CH2-NH-, -O-CH2, -CH2-CH2- or -CO-NH-."
Should read:
-- 4. The compound of claim 1, wherein $L^1$ is –$CH_2$-O- $CH_2$-NH-, -O-$CH_2$, -$CH_2$-$CH_2$- or -CO-NH-." --

At Column 156, Claim number 15, Line number 12:
"methyl-N-[2-[[4-(4-piperidyloxy)phenoxy]methyl]phe-"
Should read:
-- 4-methyl-N-[2-[[4-(4-piperidyloxy)phenoxy]methyl]phe- --

At Column 159, Claim number 19, Line number 46:
"methyl-N-[2-[[4-(4-piperidyloxy)phenoxy]methyl]phe-"
Should read:
-- 4-methyl-N-[2-[[4-(4-piperidyloxy)phenoxy]methyl]phe- --

At Column 163, Claim number 22, Line number 11:
"methyl-N-[2-[[4-(4-piperidyloxy)phenoxy]methyl]phe-"
Should read:
-- 4-methyl-N-[2-[[4-(4-piperidyloxy)phenoxy]methyl]phe- --

Signed and Sealed this
Sixteenth Day of April, 2019

Andrei Iancu
*Director of the United States Patent and Trademark Office*

At Column 165, Claim number 23, Line number 47:
"a HSP90 inhibitor, a selective COX-2 inhibitor and a che-"
Should read:
-- a HSP90 inhibitor, a selective COX-2 inhibitor, and a che- --